(12) United States Patent
Lee et al.

(10) Patent No.: US 10,633,583 B2
(45) Date of Patent: Apr. 28, 2020

(54) ORGANIC ELECTROLUMINESCENT COMPOUNDS AND AN ORGANIC ELECTROLUMINESCENT DEVICE COMPRISING THE SAME

(71) Applicant: Rohm and Haas Electronic Materials Korea Ltd., Cheonan (KR)

(72) Inventors: Su-Hyun Lee, Suwon (KR); Hee-Choon Ahn, Seoul (KR); Young-Mook Lim, Cheonan (KR); Bitnari Kim, Cheonan (KR); Tae-Jin Lee, Seoul (KR)

(73) Assignee: Rohm and Haas Electronic Materials Korea Ltd., Seoul (KR)

( * ) Notice: Subject to any disclaimer, the term of this patent is extended or adjusted under 35 U.S.C. 154(b) by 0 days.

(21) Appl. No.: 15/518,276

(22) PCT Filed: Oct. 22, 2015

(86) PCT No.: PCT/KR2015/011220
§ 371 (c)(1),
(2) Date: Apr. 11, 2017

(87) PCT Pub. No.: WO2016/064227
PCT Pub. Date: Apr. 28, 2016

(65) Prior Publication Data
US 2017/0305854 A1   Oct. 26, 2017

(30) Foreign Application Priority Data

Oct. 23, 2014  (KR) .................. 10-2014-0144063
Oct. 21, 2015  (KR) .................. 10-2015-0146568

(51) Int. Cl.
| | | |
|---|---|---|
| C07D 209/86 | (2006.01) | |
| C09K 11/06 | (2006.01) | |
| H01L 51/00 | (2006.01) | |
| H01L 51/50 | (2006.01) | |

(52) U.S. Cl.
CPC ............ C09K 11/06 (2013.01); C07D 209/86 (2013.01); H01L 51/0052 (2013.01); H01L 51/0058 (2013.01); H01L 51/0067 (2013.01); H01L 51/0072 (2013.01); H01L 51/0085 (2013.01); *C09K 2211/1007* (2013.01); *C09K 2211/1011* (2013.01); *C09K 2211/1014* (2013.01); *C09K 2211/1029* (2013.01); *C09K 2211/1033* (2013.01); *C09K 2211/1037* (2013.01); *C09K 2211/1044* (2013.01); *C09K 2211/1059* (2013.01); *C09K 2211/1088* (2013.01); *C09K 2211/1092* (2013.01); *C09K 2211/185* (2013.01); *H01L 51/0074* (2013.01); *H01L 51/5016* (2013.01); *H01L 51/5064* (2013.01); *H01L 2251/5384* (2013.01)

(58) Field of Classification Search
CPC .................................................. C07D 209/86
See application file for complete search history.

(56) References Cited

U.S. PATENT DOCUMENTS

| | | |
|---|---|---|
| 2010/0066241 A1 | 3/2010 | Cho et al. |
| 2015/0021576 A1 | 1/2015 | Itoi |
| 2015/0179949 A1 | 6/2015 | Miyata |
| 2017/0170408 A1 | 6/2017 | Park et al. |
| 2017/0213985 A1 | 7/2017 | Lee et al. |
| 2017/0256722 A1 | 9/2017 | Shim et al. |
| 2017/0279056 A1 | 9/2017 | Kim et al. |

FOREIGN PATENT DOCUMENTS

| | | |
|---|---|---|
| CN | 104628623 A | 5/2015 |
| CN | 104818014 A | 8/2015 |
| JP | 2009029725 A | 2/2009 |
| JP | 2009029726 A | 2/2009 |
| JP | 2009057307 A | 3/2009 |
| JP | 2009073803 A | 4/2009 |
| JP | 2009120582 A | 6/2009 |
| JP | 2009123976 A | 6/2009 |
| JP | 2009194042 A | 8/2009 |
| JP | 2010195708 A | 9/2010 |
| JP | 2011195708 A | 10/2011 |
| JP | 2014068427 A | 4/2014 |
| JP | 2014086427 A | 5/2014 |
| KR | 20150012835 A | 2/2015 |
| WO | 2011155742 A2 | 12/2011 |
| WO | 2013146942 A1 | 10/2013 |
| WO | 2015080404 A1 | 6/2015 |
| WO | 2015088183 A1 | 6/2015 |
| WO | 2015/099507 A1 | 7/2015 |
| WO | 2015115756 A1 | 8/2015 |

(Continued)

OTHER PUBLICATIONS

Hayakawa, et al. Document No. 153:419133, retrieved from STN; Sep. 9, 2010.*
Cho, et al. Document No. 152:132309, retrieved from STN; Dec. 30, 2009.*
Tamano, et al. Document No. 151:325021, retrieved from STN; Aug. 28, 2009.*
Hayakawa, et al. Document No. 150:575549, retrieved from STN; Jun. 4, 2009.*
Toba, et al. Document No. 150:362399, retrieved from STN; Mar. 19, 2009.*

(Continued)

*Primary Examiner* — Shawquia Jackson

(74) *Attorney, Agent, or Firm* — S. Matthew Cairns

(57) ABSTRACT

The present disclosure relates to novel organic electroluminescent compounds and an organic electroluminescent device comprising the same. By using the organic electroluminescent compound of the present disclosure, the organic electroluminescent device may improve driving lifespan while maintaining equal or greater efficiency compared to conventional devices.

6 Claims, No Drawings

(56) References Cited

FOREIGN PATENT DOCUMENTS

WO  2015160224 A1  10/2015

OTHER PUBLICATIONS

Tamano, et al. Document No. 150:226162, retrieved from STN; Feb. 12, 2009.*
Notice of Reasons for Refusal for Japanese application No. 2017-519669; dated Oct. 22, 2015.
Chinese Search Report for Patent application No. 201580055365.7; dated Oct. 22, 2015.

* cited by examiner

ORGANIC ELECTROLUMINESCENT COMPOUNDS AND AN ORGANIC ELECTROLUMINESCENT DEVICE COMPRISING THE SAME

TECHNICAL FIELD

The present disclosure relates to novel organic electroluminescent compounds and an organic electroluminescent device comprising the same.

BACKGROUND ART

An electroluminescent device (EL device) is a self-light-emitting device which has advantages in that it provides a wider viewing angle, a greater contrast ratio, and a faster response time. The first organic EL device was developed by Eastman Kodak, by using small aromatic diamine molecules, and aluminum complexes as materials for forming a light-emitting layer [Appl. Phys. Lett. 51, 913, 1987].

An organic EL device (OLED) is a device changing electrical energy to light by applying electricity to an organic electroluminescent material, and generally has a structure comprising an anode, a cathode, and an organic layer between the anode and the cathode. The organic layer of an organic EL device may be comprised of a hole injection layer, a hole transport layer, an electron blocking layer, a light-emitting layer (which comprises host and dopant materials), an electron buffer layer, a hole blocking layer, an electron transport layer, an electron injection layer, etc., and the materials used for the organic layer are categorized by their functions in hole injection material, hole transport material, electron blocking material, light-emitting material, electron buffer material, hole blocking material, electron transport material, electron injection material, etc. In the organic EL device, due to an application of a voltage, holes are injected from the anode to the light-emitting layer, electrons are injected from the cathode to the light-emitting layer, and excitons of high energies are formed by a recombination of the holes and the electrons. By this energy, luminescent organic compounds reach an excited state, and light emission occurs by emitting light from energy due to the excited state of the luminescent organic compounds returning to a ground state.

The most important factor determining luminous efficiency in an organic EL device is light-emitting materials. A light-emitting material must have high quantum efficiency, high electron and hole mobility, and the formed light-emitting material layer must be uniform and stable. Light-emitting materials are categorized into blue, green, and red light-emitting materials dependent on the color of the light emission, and additionally yellow or orange light-emitting materials. In addition, light-emitting materials can also be categorized into host and dopant materials according to their functions. Recently, the development of an organic EL device providing high efficiency and long lifespan is an urgent issue. In particular, considering EL characteristic requirements for a middle or large-sized panel of OLED, materials showing better characteristics than conventional ones must be urgently developed. The host material, which acts as a solvent in a solid state and transfers energy, needs to have high purity and a molecular weight appropriate for vacuum deposition. Furthermore, the host material needs to have high glass transition temperature and high thermal degradation temperature to achieve thermal stability, high electro-chemical stability to achieve a long lifespan, ease of forming an amorphous thin film, good adhesion to materials of adjacent layers, and non-migration to other layers.

Iridium(III) complexes have been widely known as phosphorescent materials, including (acac)Ir(btp)$_2$ (bis(2-(2'-benzothienyl)-pyridinato-N,C3')iridium(acetylacetonate)), Ir(ppy)$_3$ (tris(2-phenylpyridine)iridium) and Firpic (bis(4,6-difluorophenylpyridinato-N,C2)picolinato iridium) as red-, green- and blue-emitting materials, respectively.

A light-emitting material can be used as a combination of a host and a dopant to improve color purity, luminous efficiency, and stability. Since host materials greatly influence the efficiency and lifespan of the EL device when using a dopant/host material system as a light-emitting material, their selection is important. At present, 4,4'-N,N'-dicarbazol-biphenyl (CBP) is the most widely known as phosphorescent host materials. Recently, Pioneer (Japan) et al., developed a high performance organic EL device using bathocuproine (BCP) and aluminum(III) bis(2-methyl-8-quinolinate)(4-phenylphenolate) (BAlq), etc., as host materials, which were known as hole blocking materials.

Although these materials provide good luminous characteristics, they have the following disadvantages: (1) Due to their low glass transition temperature and poor thermal stability, their degradation may occur during a high-temperature deposition process in a vacuum. (2) The power efficiency of the organic EL device is given by [(Tr/voltage)×luminous efficiency], and the power efficiency is inversely proportional to the voltage. Although the organic EL device comprising phosphorescent host materials provides higher luminous efficiency (cd/A) than one comprising fluorescent materials, a significantly high driving voltage is necessary. Thus, there is no merit in terms of power efficiency (lm/W). (3) Furthermore, the operational lifespan of the organic EL device is short, and luminous efficiency is still necessary to improve.

Thus, in order to embody excellent properties of the organic EL device, materials constituting the organic layers in the device, in particular host or dopant materials constituting a light-emitting material, should be suitably selected. In this regard, WO 2013/146942 A1 discloses the compounds linked with two carbazoles via arylene group, as a host material. However, the organic EL devices comprising the compounds recited in the above publication still does not satisfy efficiency, lifespan, etc.

In this regard, the present inventors have tried to find host compounds that can provide superior efficiency and long lifespan compared to the conventional host materials, and have found that the compounds of the present disclosure provide a device with high luminous efficiency and long lifespan.

DISCLOSURE OF THE INVENTION

Problems to be Solved

The object of the present disclosure is, firstly, to provide organic electroluminescent compounds having high luminous efficiency, and secondly, to provide an organic electroluminescent device comprising the organic electroluminescent compounds in a light-emitting layer, which is improved long lifespan.

Solution to Problems

The present inventors found that the above objective can be achieved by an organic electroluminescent compound represented by the following formula 1:

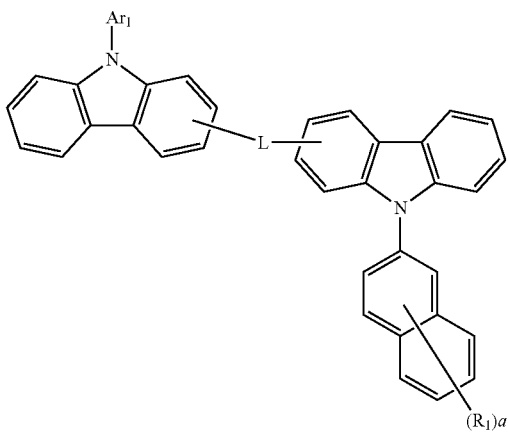

(1)

wherein

Ar₁ represents a substituted or unsubstituted (C6-C30) aryl;

L represents a substituted or unsubstituted (C6-C30) arylene;

R₁ represents hydrogen, deuterium, a halogen, a cyano, a substituted or unsubstituted (C1-C30)alkyl, or a substituted or unsubstituted (C6-C30)aryl;

a represents an integer of 0 to 4; where a represents an integer of 2 or more, each of R₁ may be the same or different.

Effects of the Invention

The organic electroluminescent compounds of the present disclosure could provide an organic electroluminescent device having high efficiency and improved lifespan.

EMBODIMENTS OF THE INVENTION

Hereinafter, the present disclosure will be described in detail. However, the following description is intended to explain the disclosure, and is not meant in any way to restrict the scope of the disclosure.

The present disclosure relates to an organic electroluminescent compound represented by formula 1, an organic electroluminescent material comprising the organic electroluminescent compound, and an organic electroluminescent device comprising the organic electroluminescent material.

In formula 1, preferably, Ar₁ represents a substituted or unsubstituted (C6-C15)aryl, L represents a substituted or unsubstituted (C6-C15)arylene, R₁ represents hydrogen, a substituted or unsubstituted (C1-C10)alkyl, or a substituted or unsubstituted (C6-C15)aryl.

In formula 1, more preferably, Ar₁ represents (C6-C15) aryl unsubstituted or substituted with a (C1-C10)alkyl, a halogen, a cyano or deuterium; L represents an unsubstituted (C6-C15)arylene; R₁ represents hydrogen, or an unsubstituted (C6-C15)aryl.

Herein, "(C1-C30)alkyl" is meant to be a linear or branched alkyl having 1 to 30 carbon atoms constituting the chain, in which the number of carbon atoms is preferably 1 to 20, more preferably 1 to 10, and includes methyl, ethyl, n-propyl, isopropyl, n-butyl, isobutyl, tert-butyl, etc.; "(C2-C30)alkenyl" is meant to be a linear or branched alkenyl having 2 to 30 carbon atoms constituting the chain, in which the number of carbon atoms is preferably 2 to 20, more preferably 2 to 10, and includes vinyl, 1-propenyl, 2-propenyl, 1-butenyl, 2-butenyl, 3-butenyl, 2-methylbut-2-enyl, etc.; "(C2-C30)alkynyl" is meant to be a linear or branched alkynyl having 2 to 30 carbon atoms constituting the chain, in which the number of carbon atoms is preferably 2 to 20, more preferably 2 to 10, and includes ethynyl, 1-propynyl, 2-propynyl, 1-butynyl, 2-butynyl, 3-butynyl, 1-methylpent-2-ynyl, etc.; "(C1-C30)alkoxy" is meant to be a linear or branched alkoxy having 1 to 30 carbon atoms constituting the chain, in which the number of carbon atoms is preferably 1 to 20, more preferably 1 to 10, and includes methoxy, ethoxy, propoxy, isopropoxy, 1-ethylpropoxy, etc.; "(C3-C30)cycloalkyl" is a mono- or polycyclic hydrocarbon having 3 to 30 ring backbone carbon atoms, in which the number of carbon atoms is preferably 3 to 20, more preferably 3 to 7, and includes cyclopropyl, cyclobutyl, cyclopentyl, cyclohexyl, etc.; "5- to 7-membered heterocycloalkyl" is a cycloalkyl having 5 to 7 ring backbone atoms, including at least one heteroatom selected from B, N, O, S, Si, and P, preferably O, S, and N, and includes pyrrolidine, thiolan, tetrahydropyran, etc.; "(C6-C30)aryl(ene)" is a monocyclic or fused ring derived from an aromatic hydrocarbon having 6 to 30 ring backbone carbon atoms, in which the number of carbon atoms is preferably 6 to 20, more preferably 6 to 15, and includes phenyl, biphenyl, terphenyl, naphthyl, fluorenyl, phenanthrenyl, anthracenyl, indenyl, triphenylenyl, pyrenyl, tetracenyl, perylenyl, chrysenyl, naphthacenyl, fluoranthenyl, etc.; "3- to 30-membered heteroaryl(ene)" is an aryl having 3 to 30 ring backbone atoms, preferably 3 to 20 ring backbone atoms, and more preferably 3 to 15 ring backbone atoms, including at least one, preferably 1 to 4 heteroatoms selected from the group consisting of B, N, O, S, Si, and P; is a monocyclic ring, or a fused ring condensed with at least one benzene ring; may be partially saturated; may be one formed by linking at least one heteroaryl or aryl group to a heteroaryl group via a single bond(s); and includes a monocyclic ring-type heteroaryl including furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl including benzofuranyl, benzothiophenyl, isobenzofuranyl, dibenzofuranyl, dibenzothiophenyl, benzimidazolyl, benzothiazolyl, benzoisothiazolyl, benzoisoxazolyl, benzoxazolyl, isoindolyl, indolyl, indazolyl, benzothiadiazolyl, quinolyl, isoquinolyl, cinnolinyl, quinazolinyl, quinoxalinyl, carbazolyl, phenoxazinyl, phenanthridinyl, benzodioxolyl, etc. Further, "halogen" includes F, Cl, Br, and I.

Herein, "substituted" in the expression "substituted or unsubstituted" means that a hydrogen atom in a certain functional group is replaced with another atom or group, i.e. a substituent. The substituents of the substituted alkyl, the substituted alkenyl, the substituted alkynyl, the substituted alkoxy, the substituted cycloalkyl, the substituted aryl(ene), the substituted heteroaryl, the substituted mono- or polycyclic, alicyclic or aromatic ring in the formulas each independently are at least one selected from the group consisting of deuterium, a halogen, a cyano, a carboxyl, a nitro, a hydroxyl, a (C1-C30)alkyl, a halo(C1-C30)alkyl, a (C2-C30) alkenyl, a (C2-C30) alkynyl, a (C1-C30)alkoxy, a (C1-C30)alkylthio, a (C3-C30)cycloalkyl, a (C3-C30)cycloalkenyl, a 3- to 7-membered heterocycloalkyl, a (C6-C30)aryloxy, a (C6-C30)arylthio, a 3- to 30-membered heteroaryl unsubstituted or substituted with a (C6-C30)aryl, a (C6-C30)aryl unsubstituted or substituted with a 3- to 30-membered heteroaryl, a cyano or (C1-C30)alkyl, a tri (C1-C30)alkylsilyl, a tri(C6-C30)arylsilyl, a di(C1-C30)alkyl(C6-C30)arylsilyl, a (C1-C30)alkyldi(C6-C30)arylsilyl, an amino, a mono- or di-(C1-C30)alkylamino, a mono- or di-(C6-C30)arylamino, a (C1-C30)alkyl(C6-C30)arylamino, a (C1-C30)alkylcarbonyl, a (C1-C30)alkoxycarbonyl, a (C6-C30)arylcarbonyl, a di(C6-C30)arylboronyl, a di(C1-C30)alkylboronyl, a (C1-C30)alkyl(C6-C30)arylboronyl, a (C6-C30)aryl(C1-C30)alkyl, and a (C1-C30)alkyl(C6-C30)aryl.

The organic electroluminescent compound according to the present disclosure includes the following compounds, but is not limited thereto:

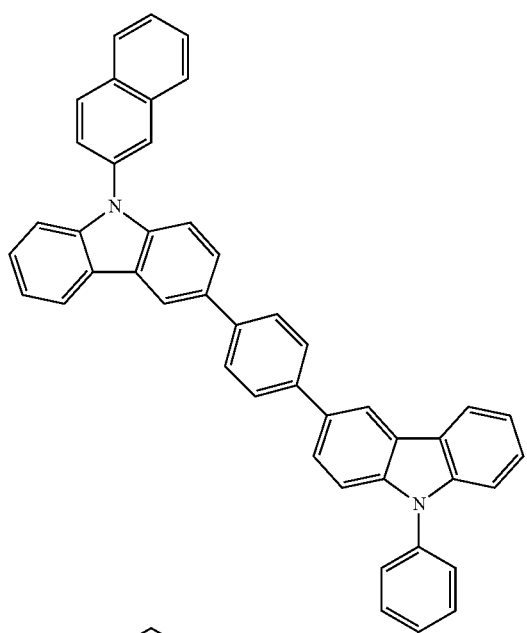

H-1

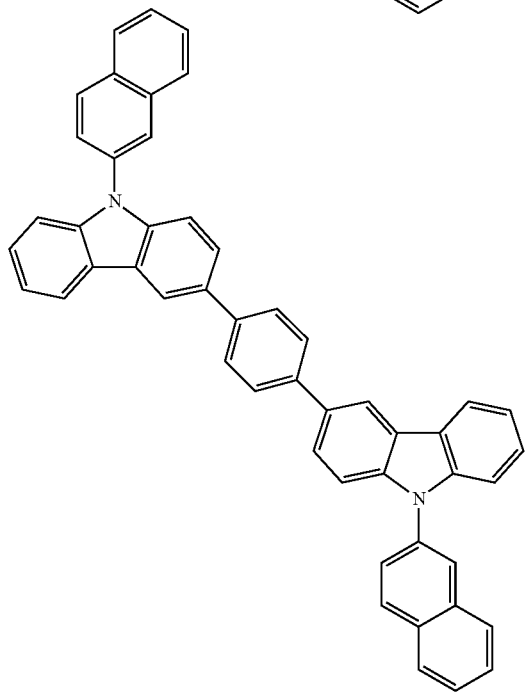

H-2

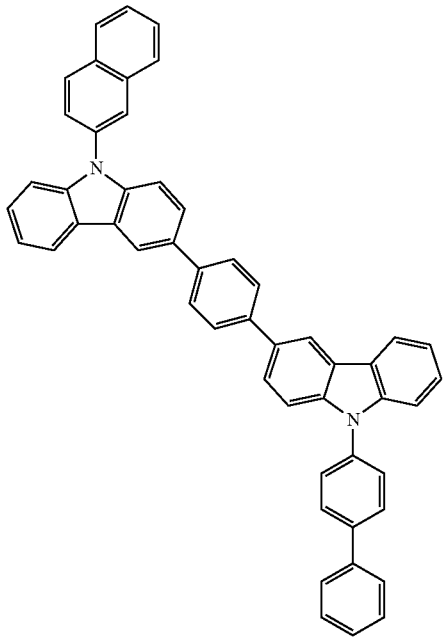

H-3

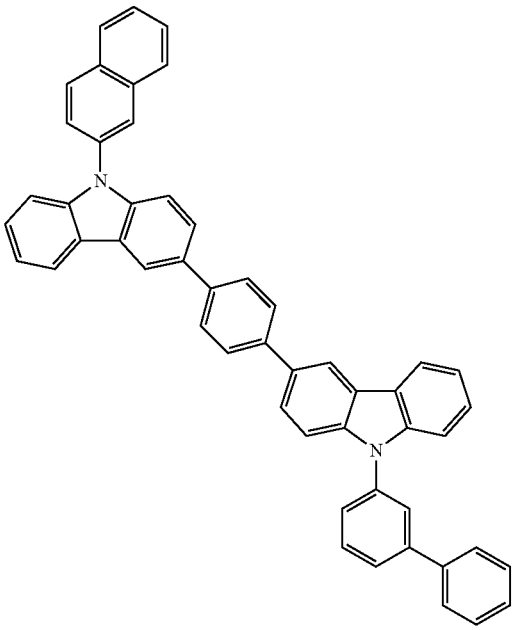

H-4

H-5
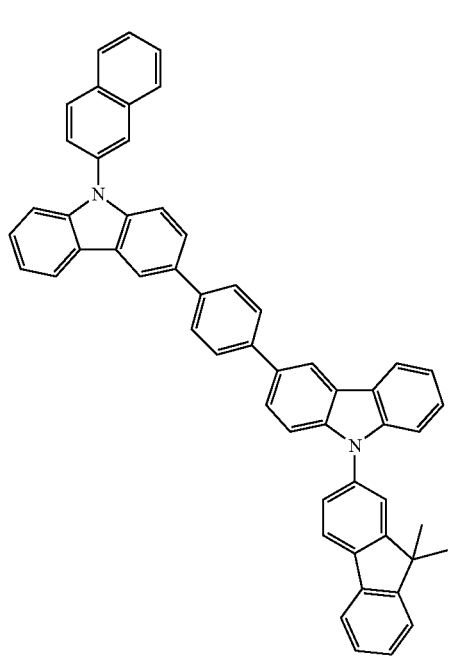
H-7
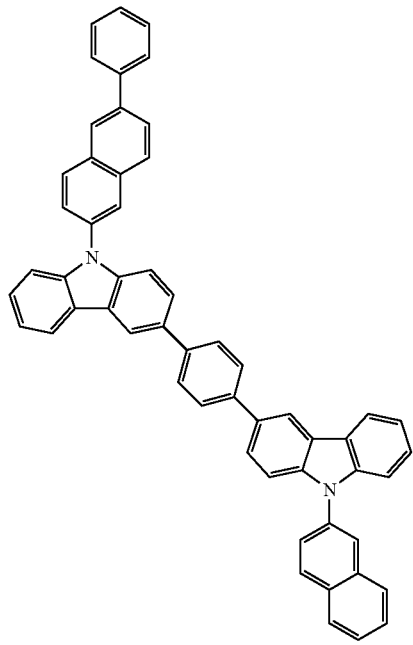
H-6
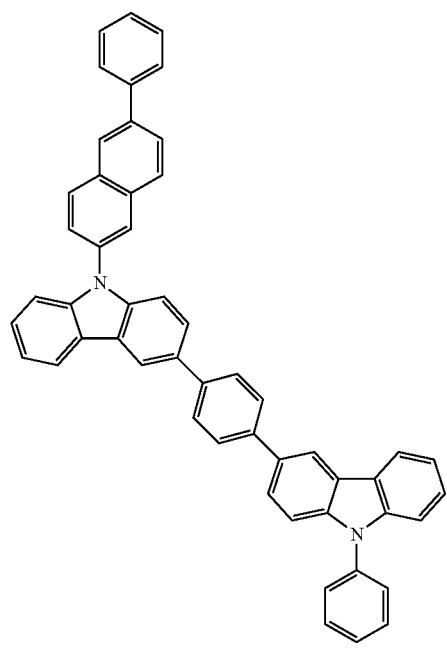
H-8
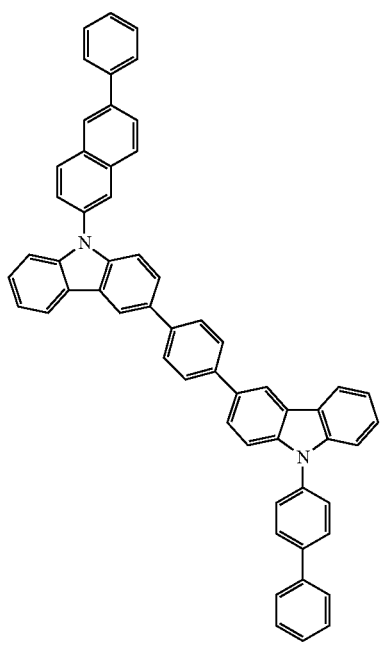

H-9
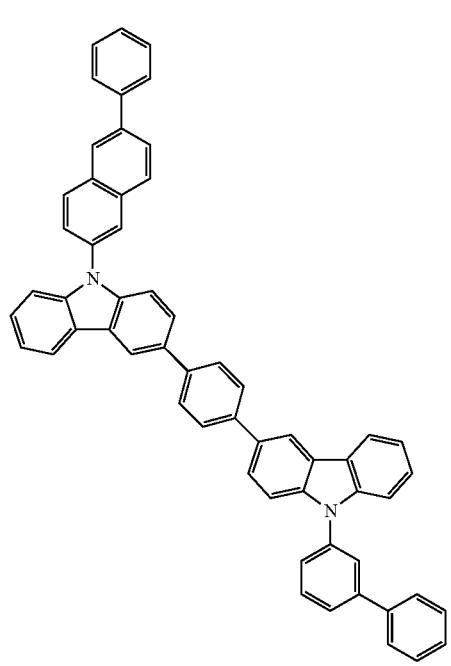
H-10
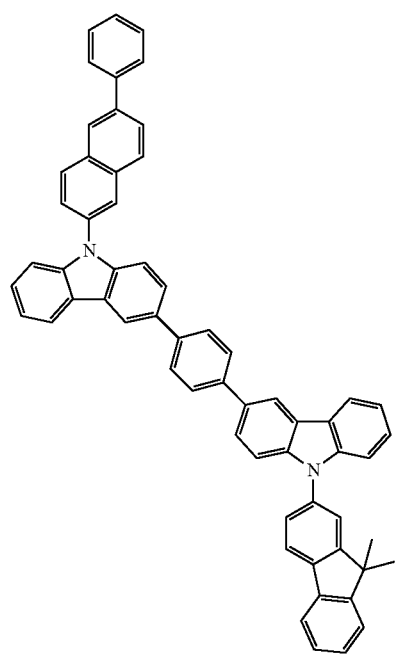
H-11
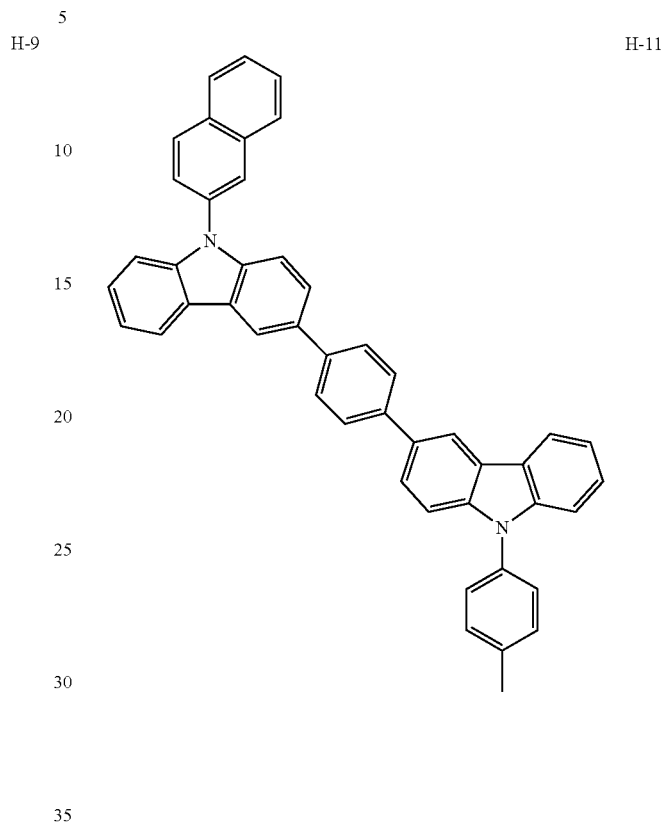
H-12
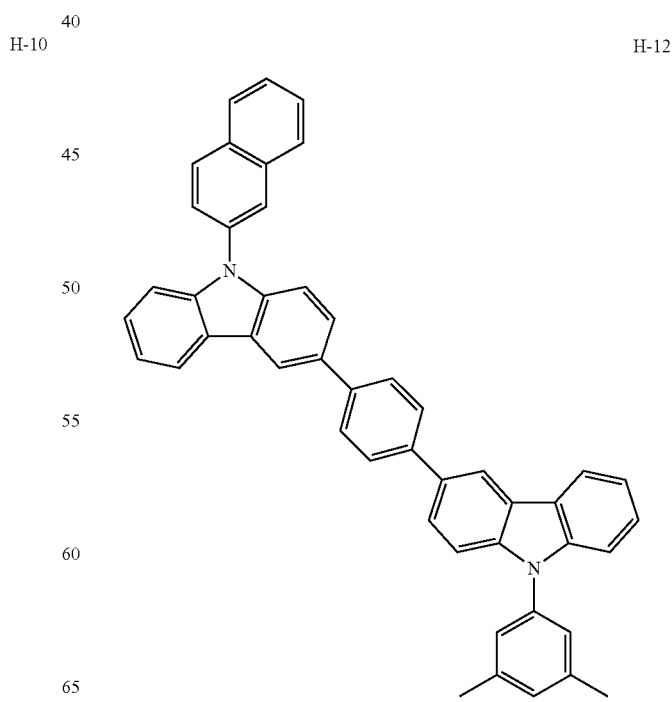

H-13
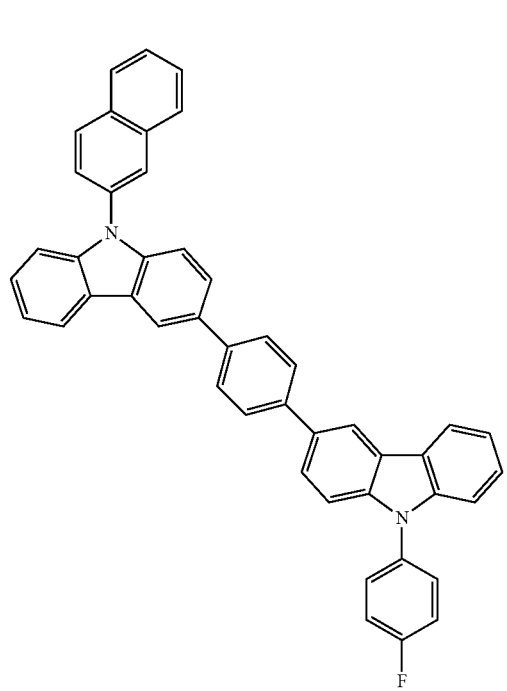
H-14
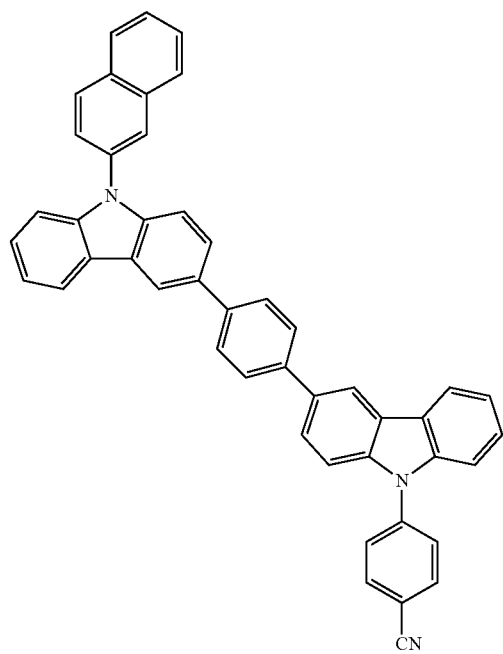
H-15
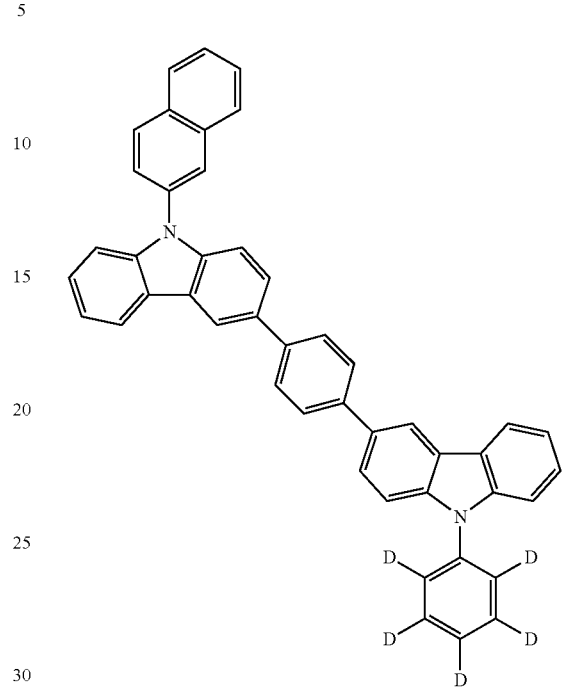
H-16
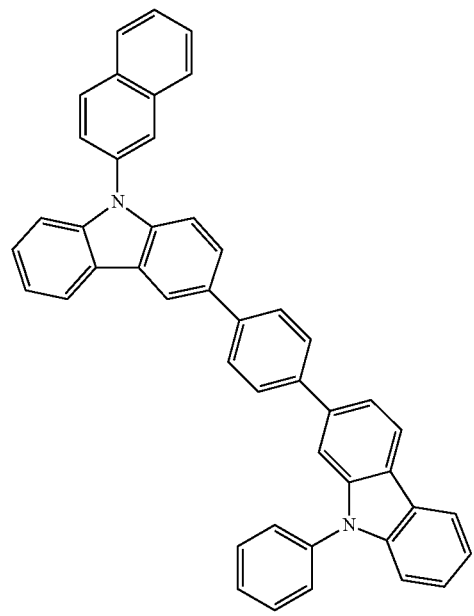

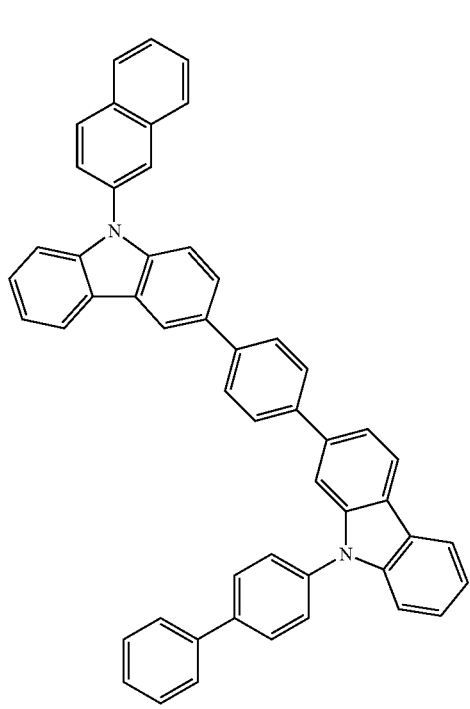
H-17
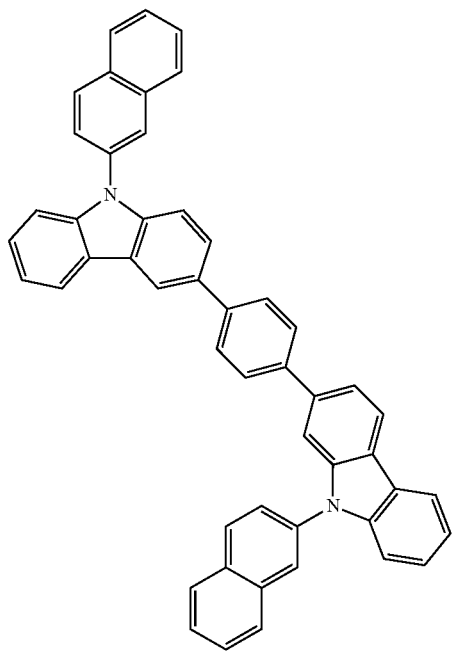
H-19
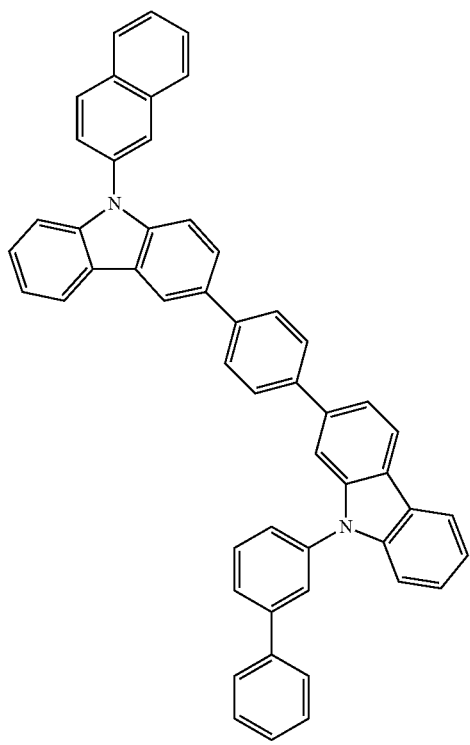
H-18
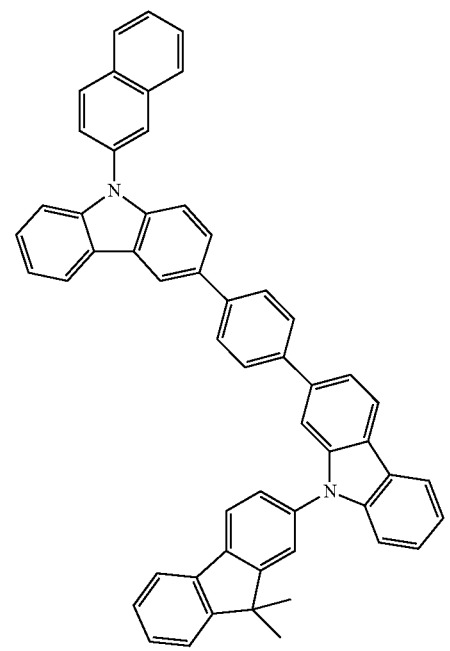
H-20

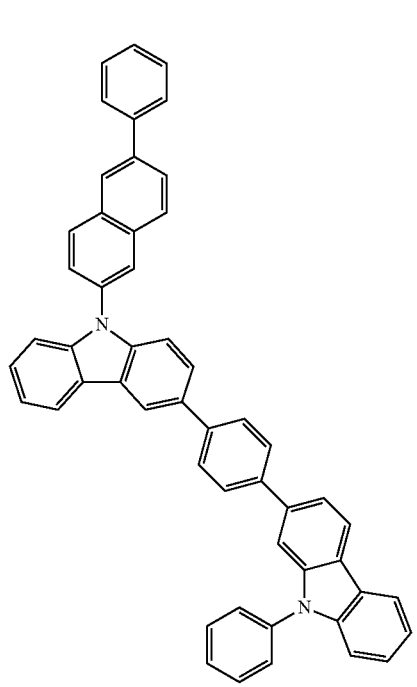
H-21
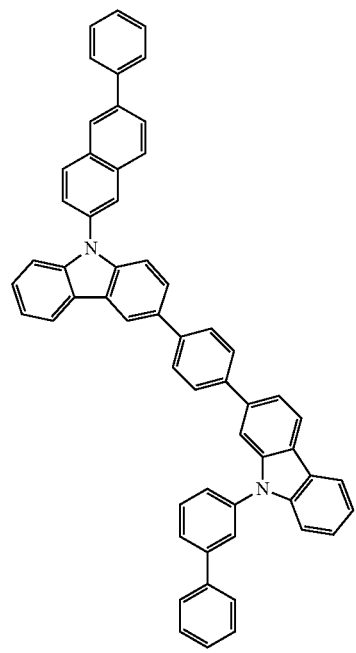
H-23
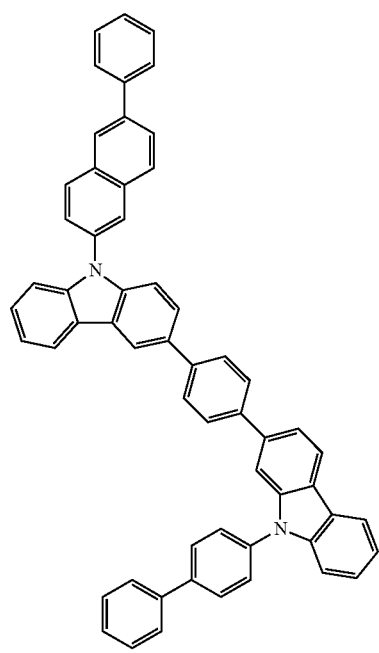
H-22
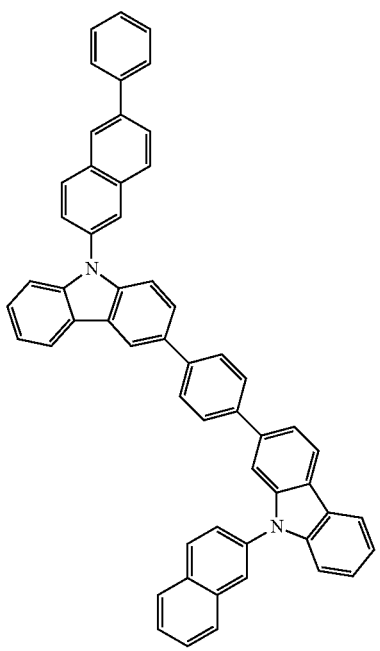
H-24

-continued
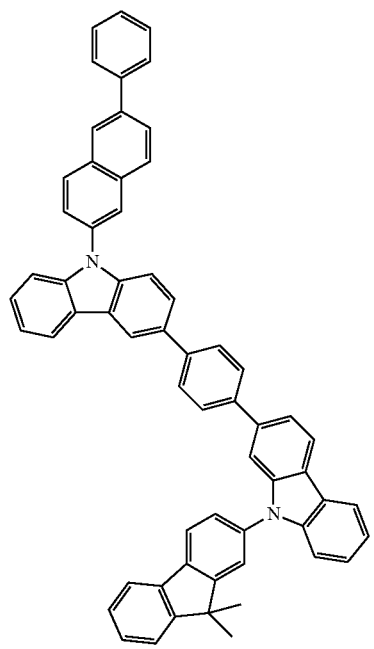
H-25
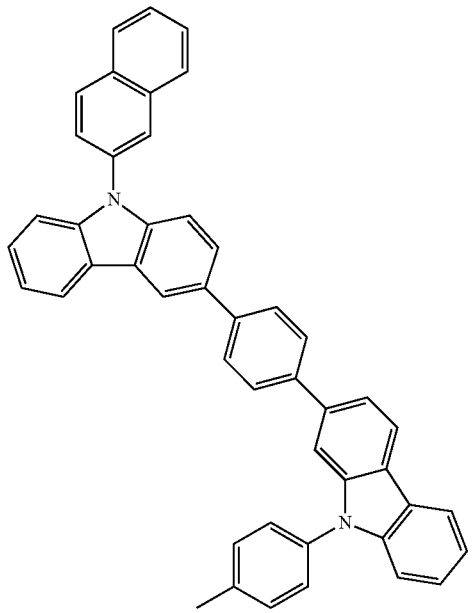
H-27
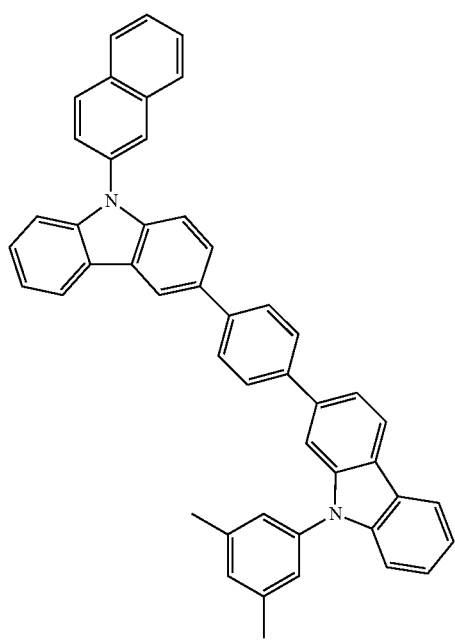
H-26
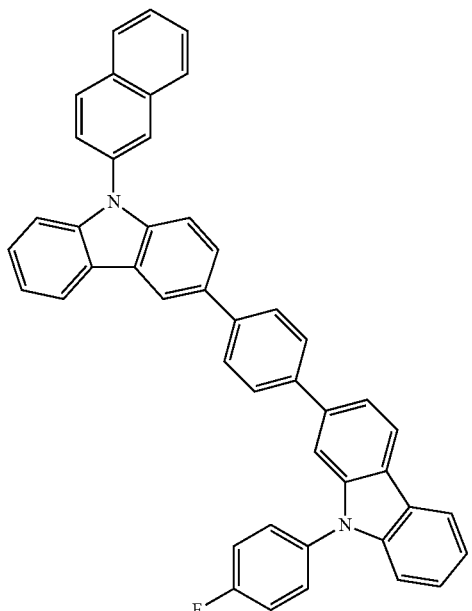
H-28

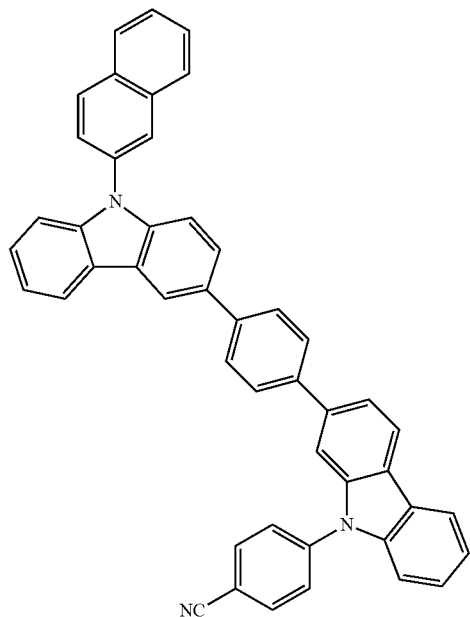
H-29
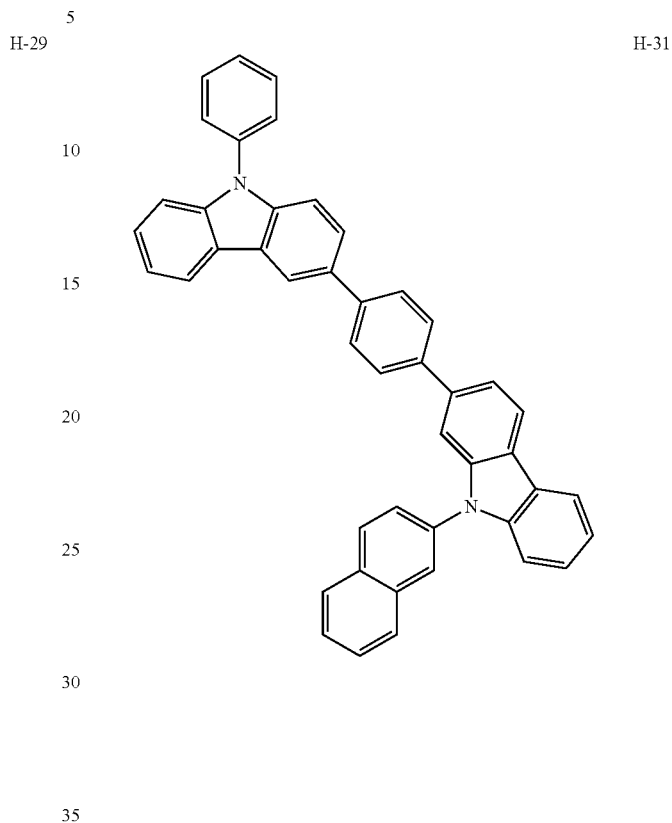
H-31
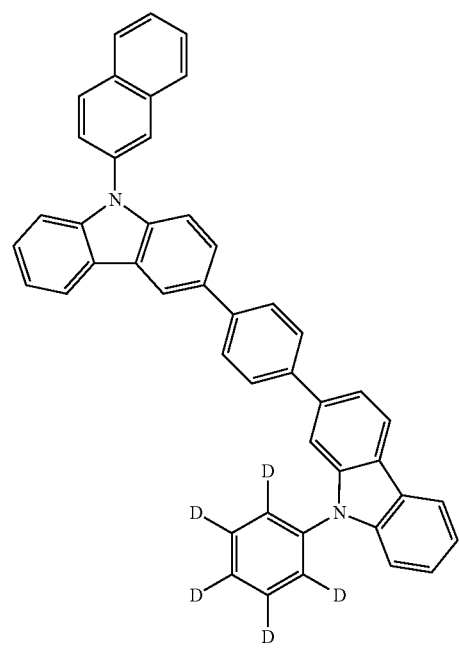
H-30
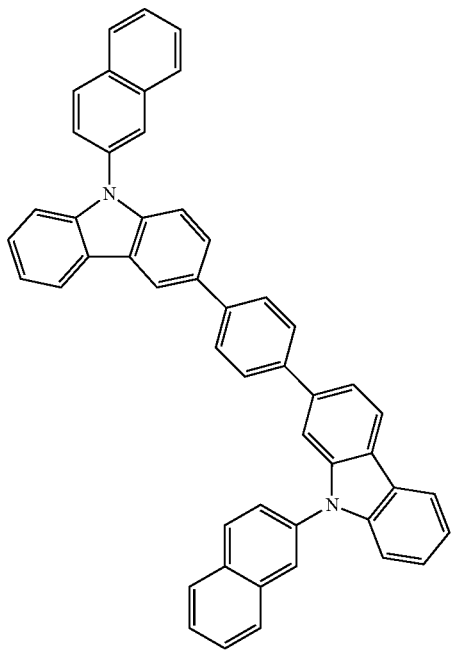
H-32

-continued
H-33
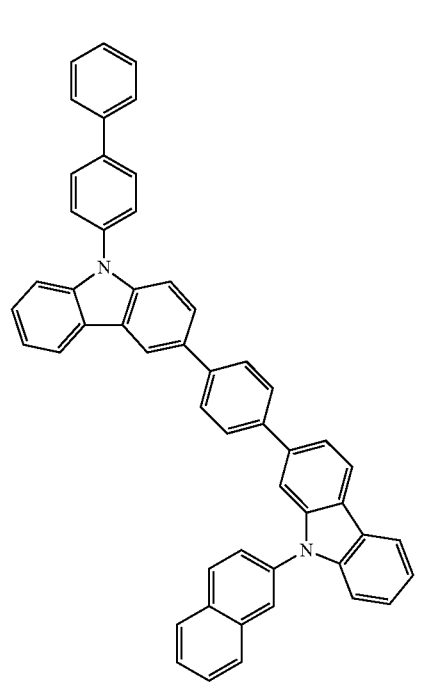
H-35
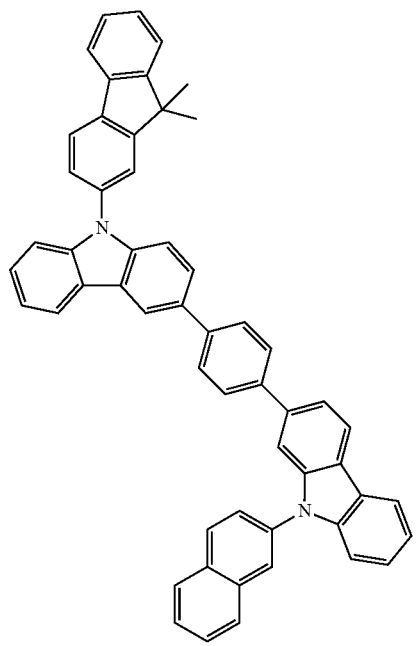
H-34
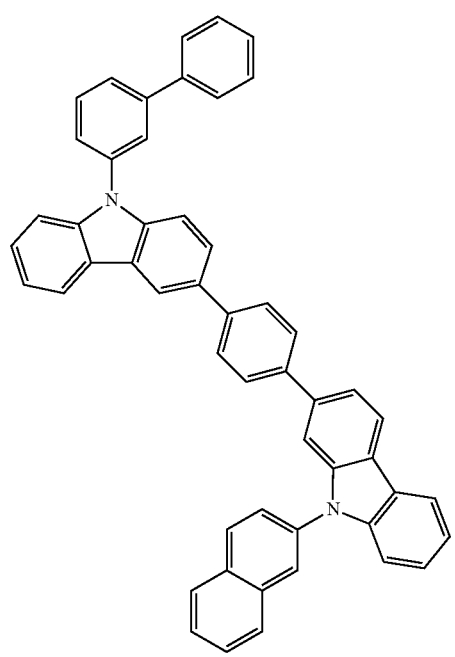
H-36
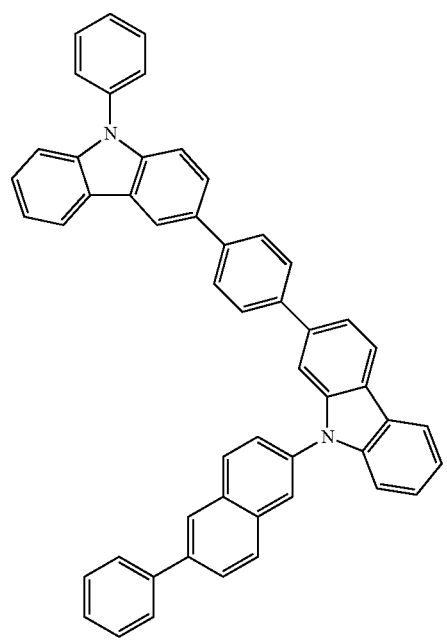

H-37
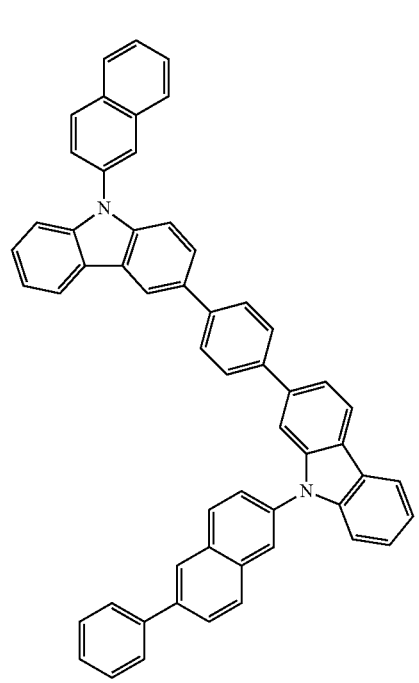
H-38
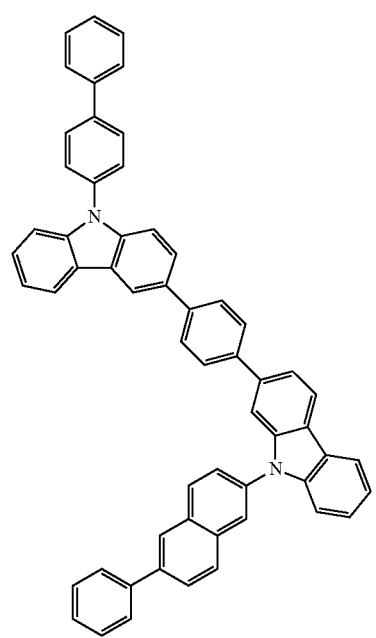
H-39
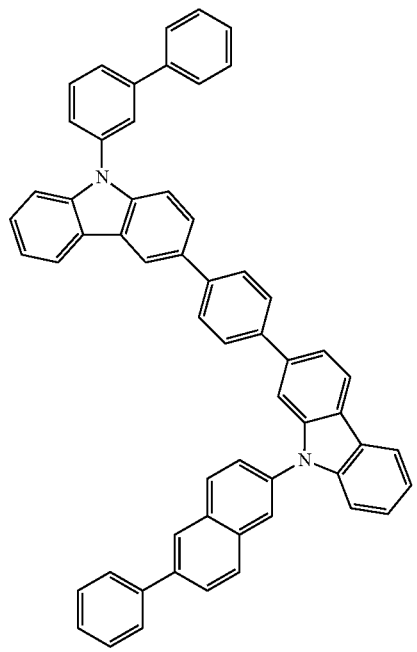
H-40
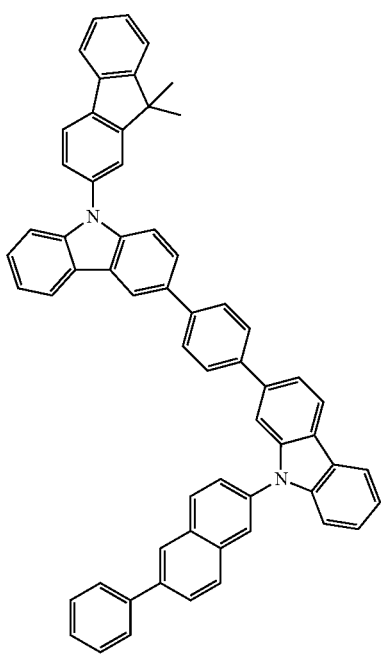

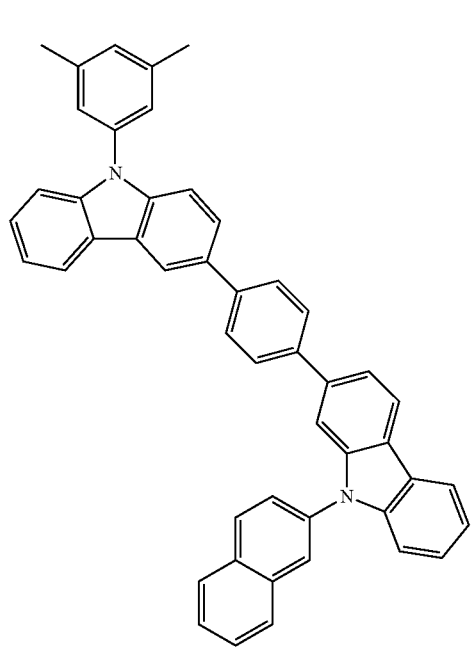
H-41
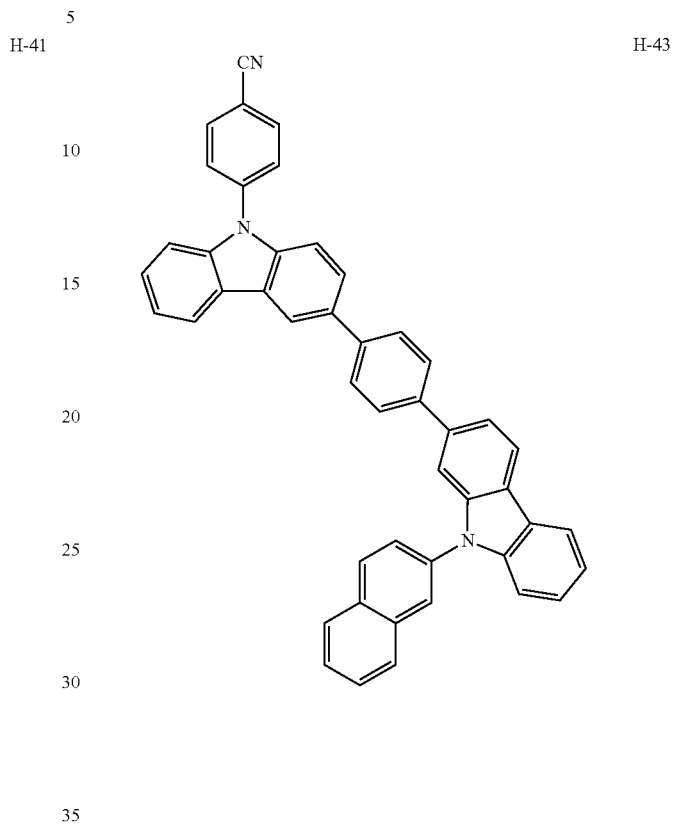
H-43
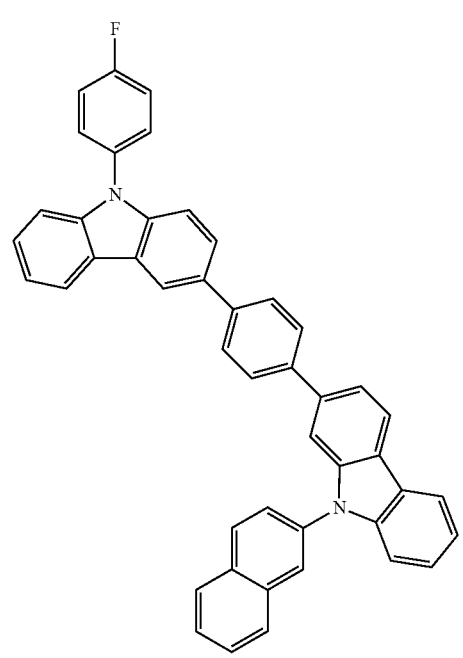
H-42
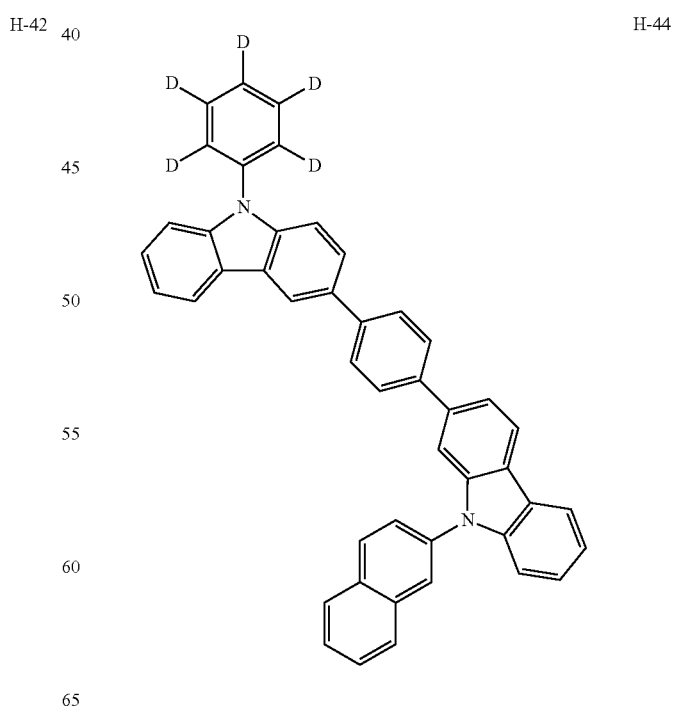
H-44

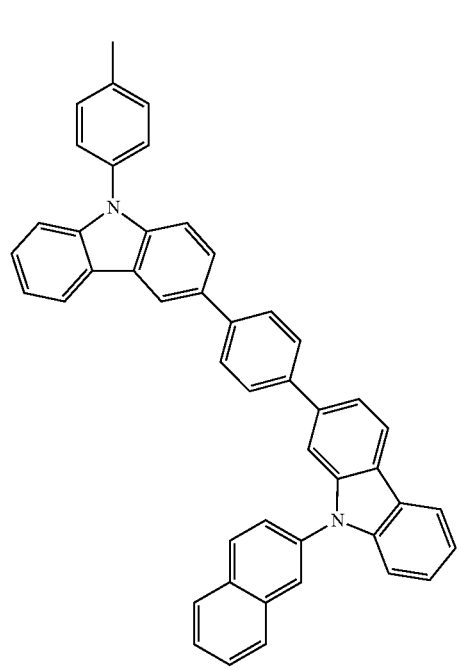 H-45
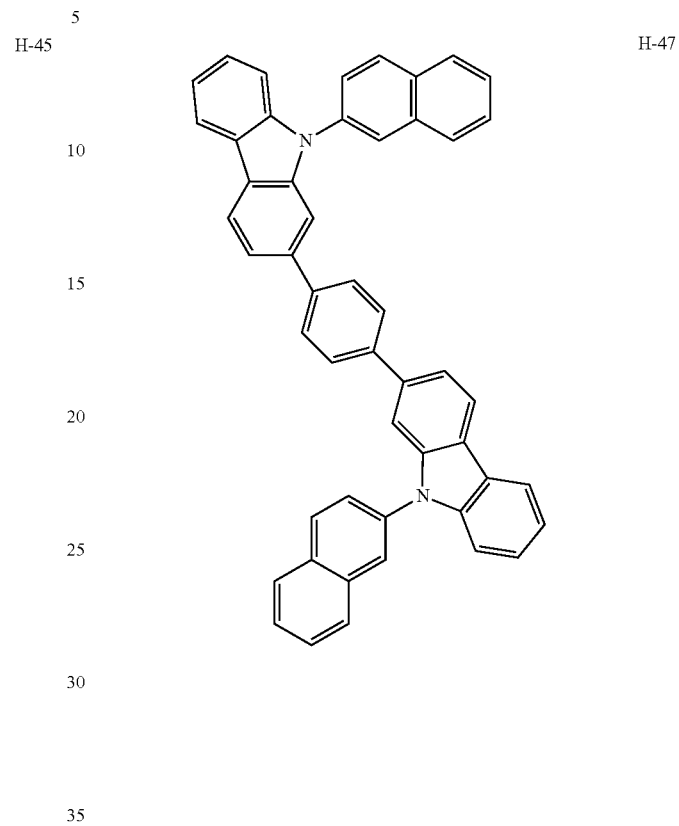 H-47
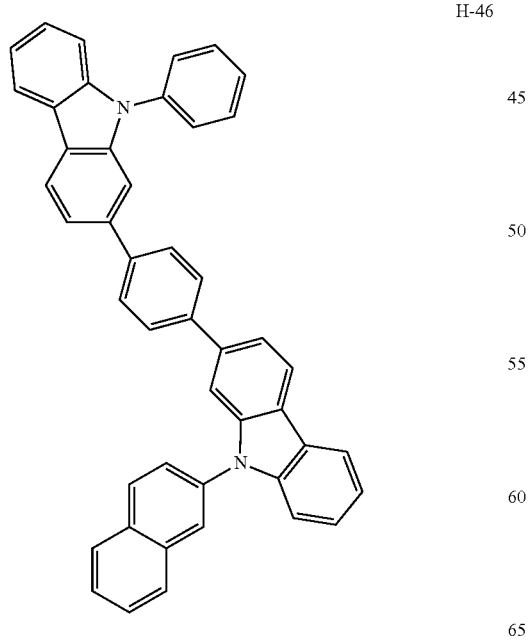 H-46
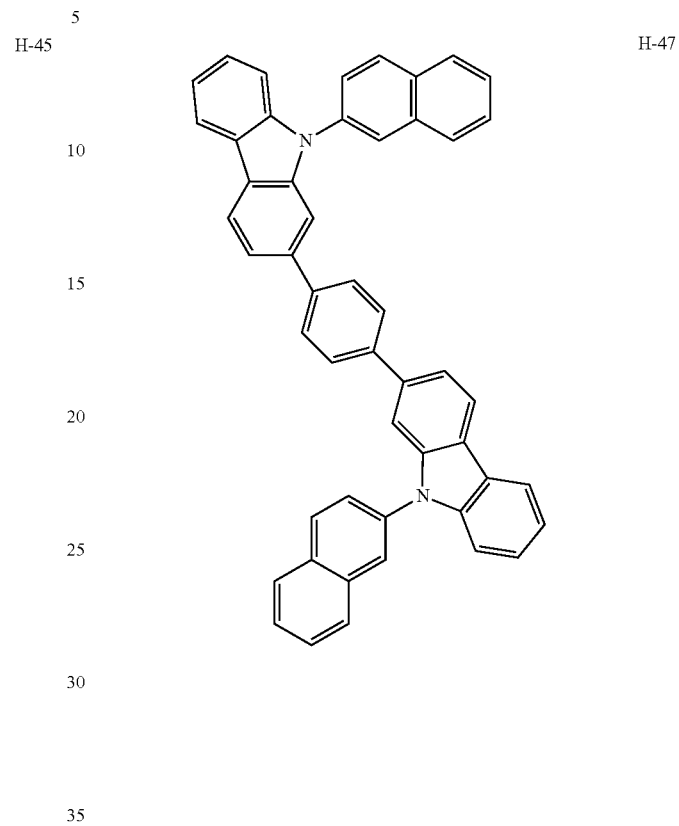 H-48

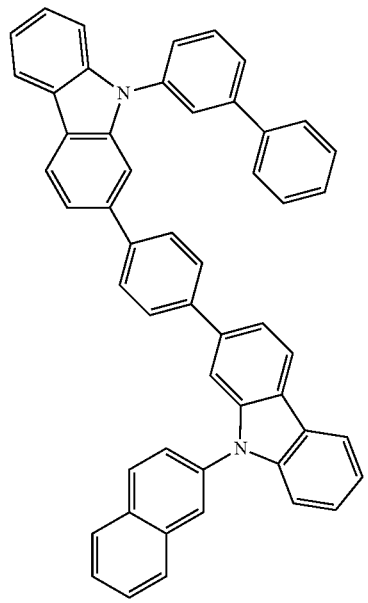
H-49
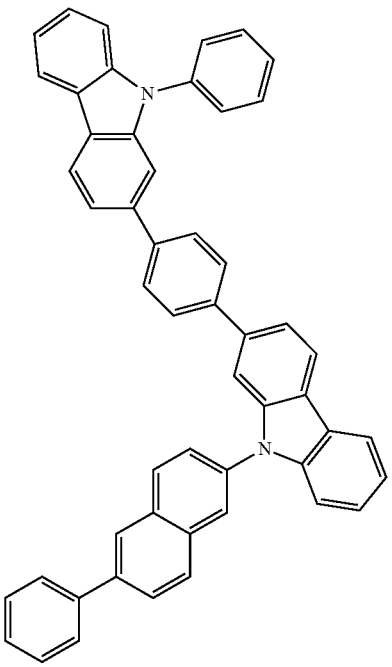
H-51
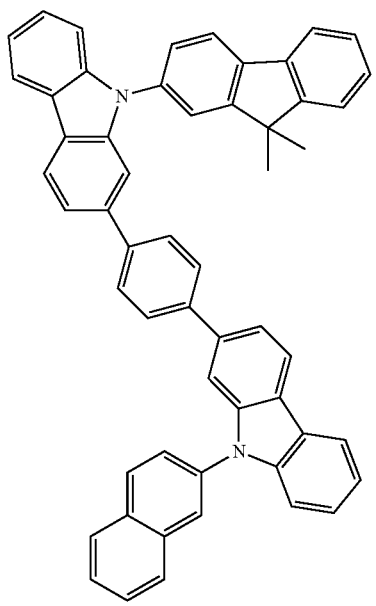
H-50
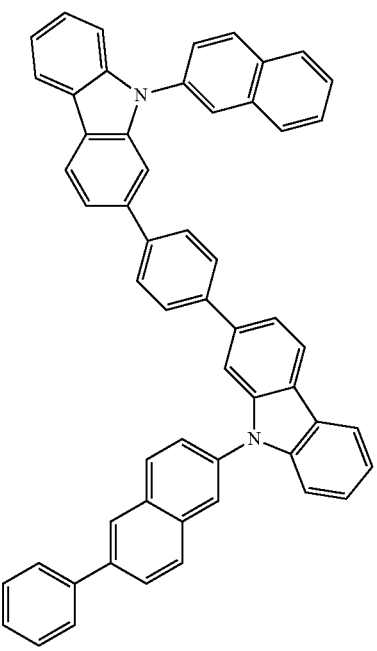
H-52

-continued
H-53
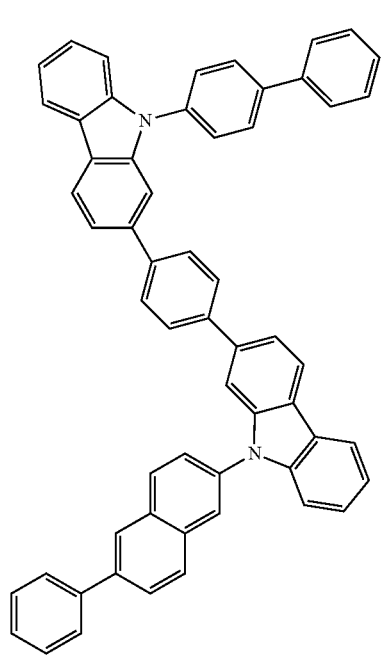
H-54
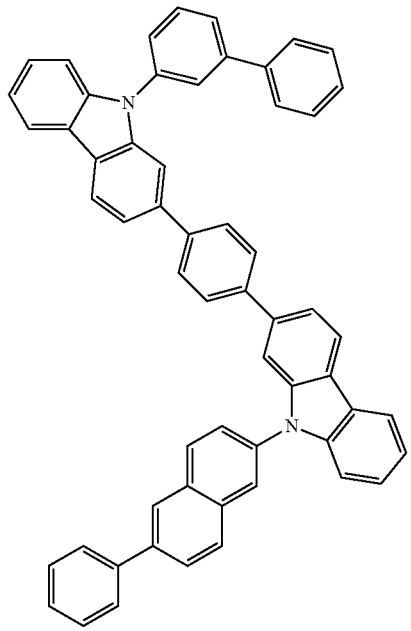
-continued
H-55
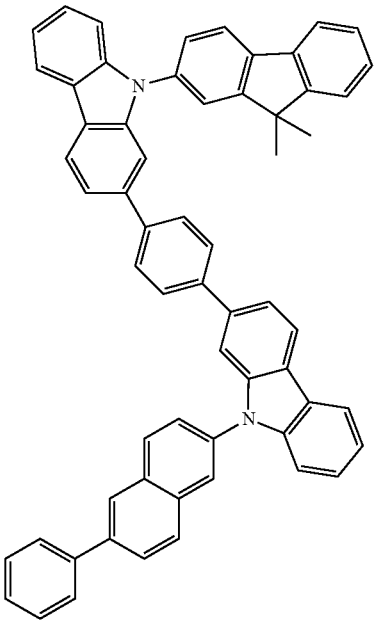
H-56
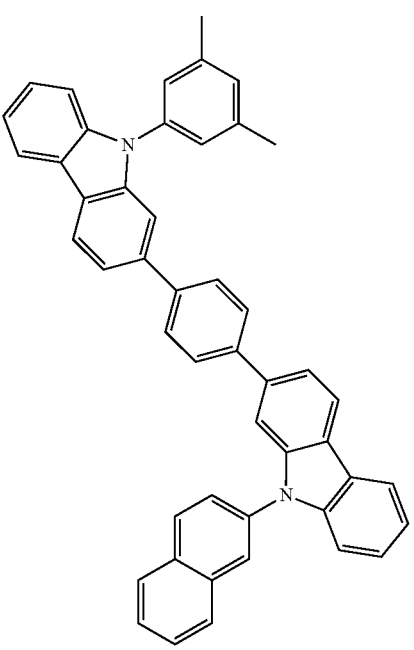

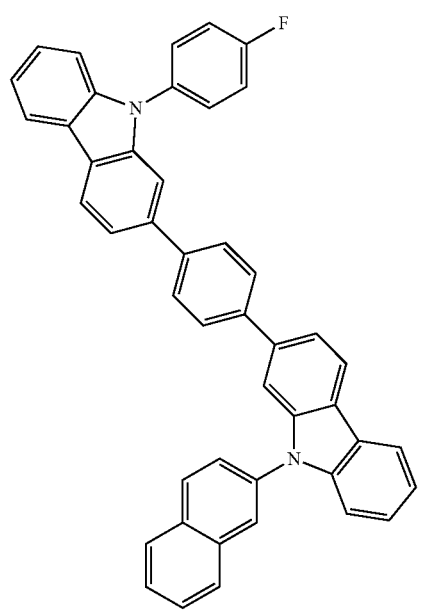
H-57
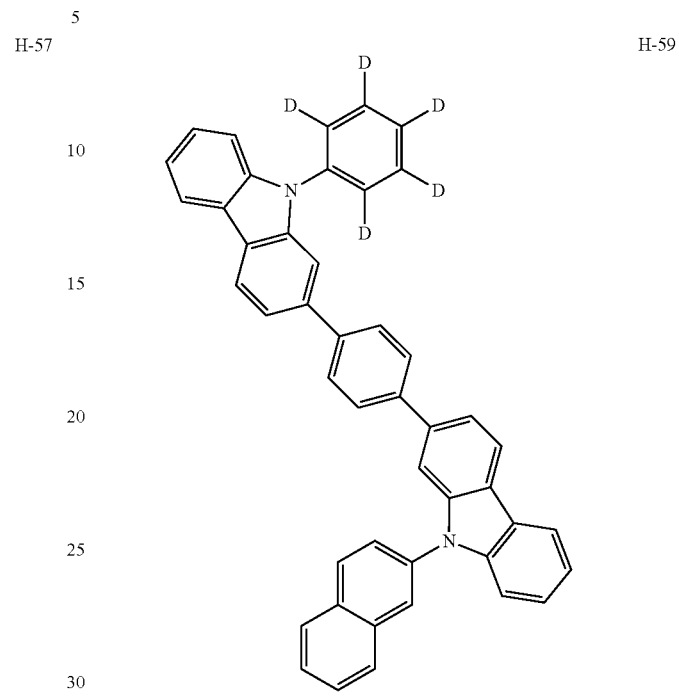
H-59
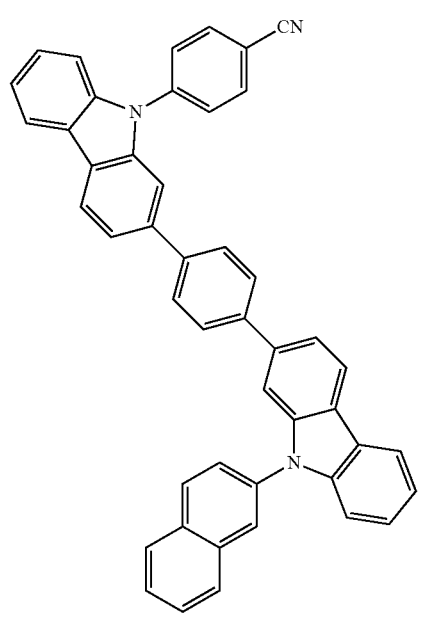
H-58
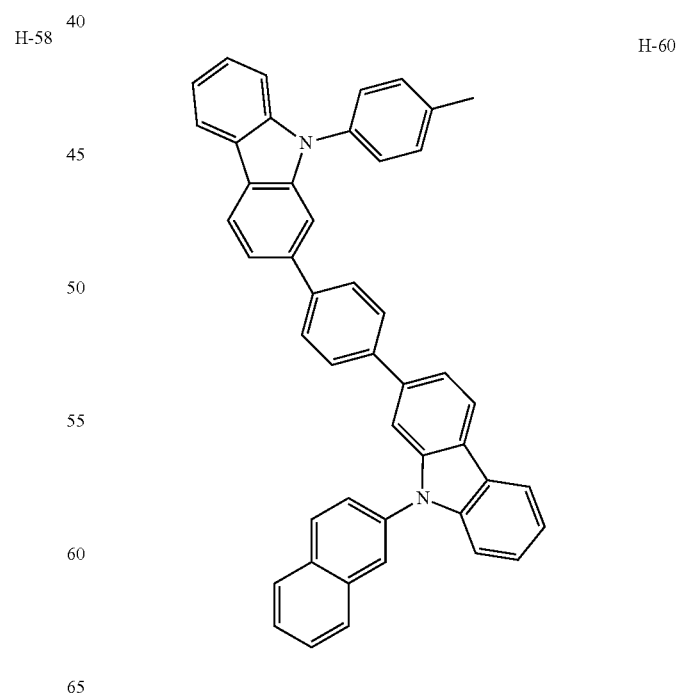
H-60

H-61
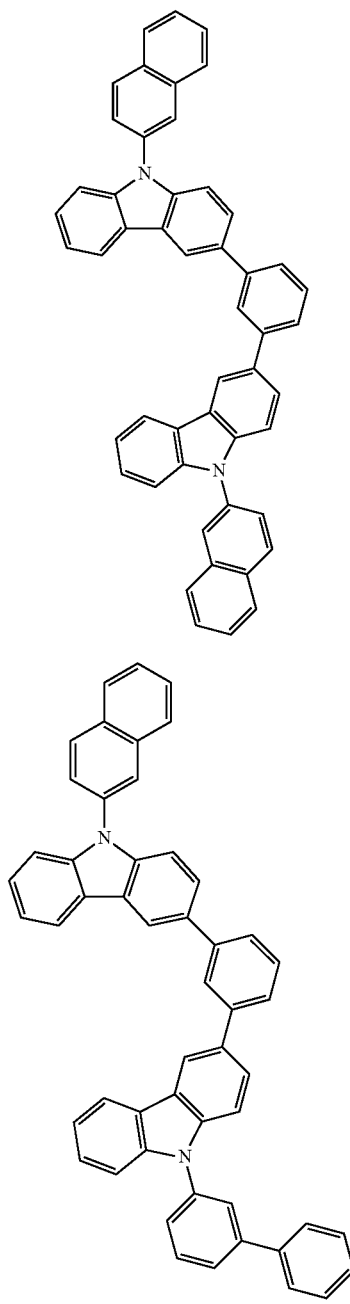
H-62
The organic electroluminescent compound according to the present disclosure can be prepared by known methods to one skilled in the art, and can be prepared, for example, according to the following reaction scheme 1:
Reaction scheme 1
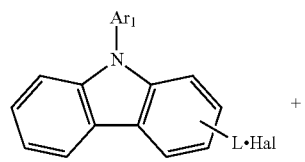
+
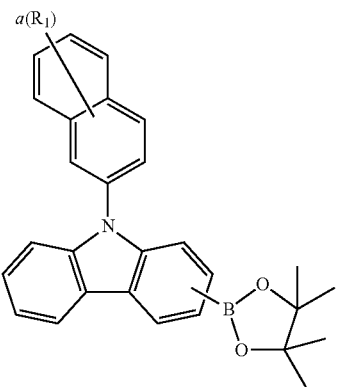
→
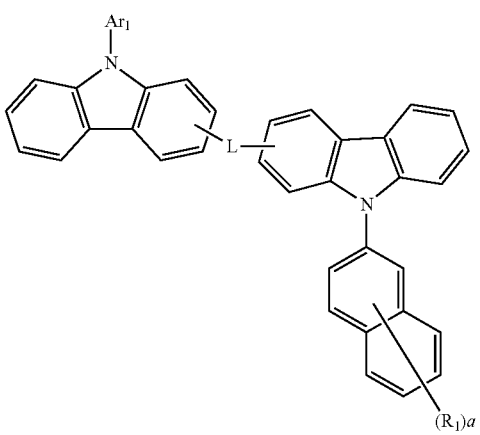
Reaction scheme 2
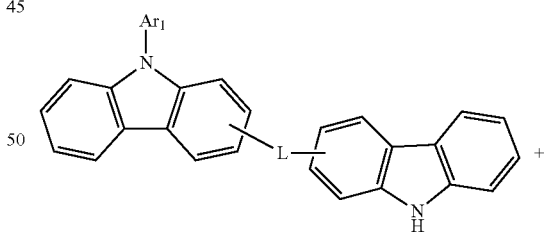
+
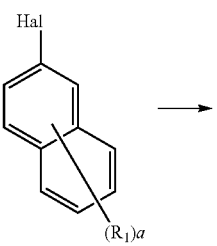
→

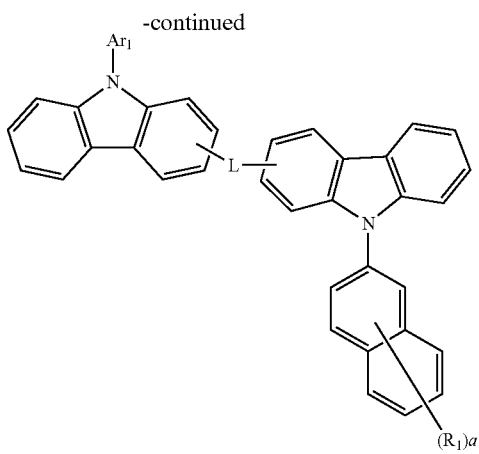

Reaction scheme 3

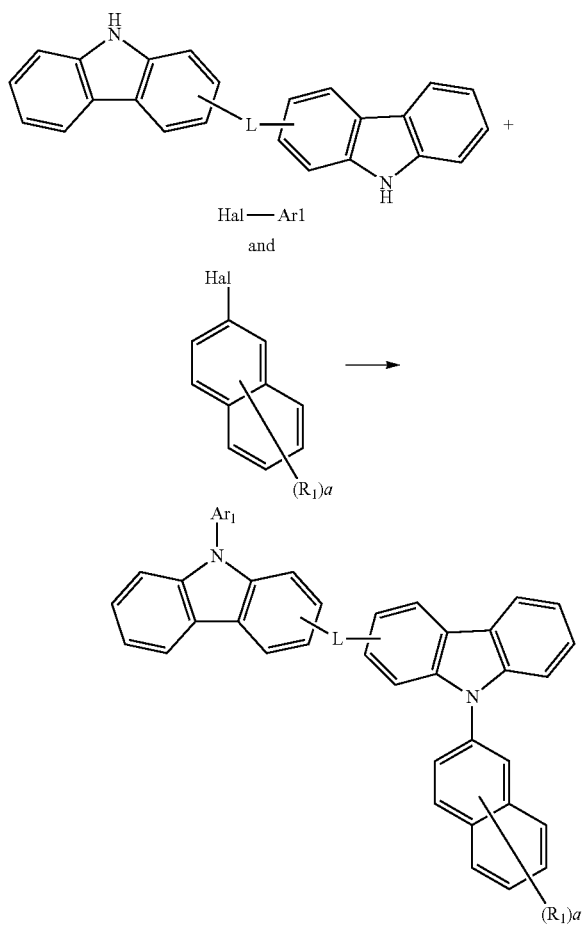

wherein $Ar_1$, L, $R_1$, and a are as defined in formula 1; and Hal represents a halogen.

The present disclosure further provides an organic electroluminescent material comprising the organic electroluminescent compound of formula 1, and an organic electroluminescent device comprising the organic electroluminescent material. The organic electroluminescent material can be comprised of the organic electroluminescent compound of the present disclosure alone, or can further include conventional materials generally used in organic electroluminescent materials.

The organic electroluminescent device of the present disclosure may comprise a first electrode, a second electrode, and at least one organic layer between the first and second electrodes. The organic layer may comprise at least one compound of formula 1.

One of the first and second electrodes may be an anode, and the other may be a cathode. The organic layer may comprise a light-emitting layer, and may further comprise at least one layer selected from a hole injection layer, a hole transport layer, an electron transport layer, an electron injection layer, an interlayer, a hole blocking layer, an electron buffer layer, and an electron blocking layer.

The organic electroluminescent compound of the present disclosure may be comprised in the light-emitting layer. When used in the light-emitting layer, the organic electroluminescent compound of the present disclosure may be comprised as a host material.

The organic electroluminescent device comprising the organic electroluminescent compound of the present disclosure may further comprise one or more compounds other than the compound of formula 1, and may further comprise at least one dopant.

When the organic electroluminescent compound of the present disclosure is comprised as a host material (a first host material) in the light-emitting layer, another compounds may be further comprised as a second host material, in which the weight ratio of the first host material to the second host material may be in the range of 1:99 to 99:1.

The second host material can be any known phosphorescent host material and preferably, is selected from the group consisting of the compounds of the following formula 2 in view of luminous efficiency.

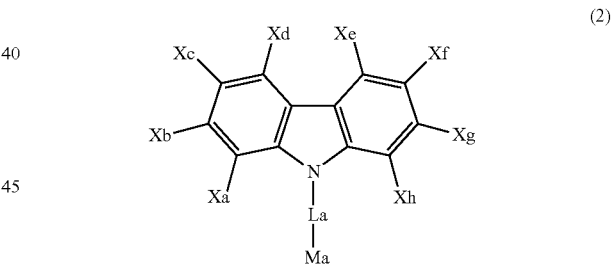

(2)

wherein

Ma represents a substituted or unsubstituted 5- to 11-membered nitrogen-containing heteroaryl;

La represents a single bond, or a substituted or unsubstituted (C6-C30)arylene;

Xa to Xh each independently represent hydrogen, deuterium, a halogen, a cyano, a substituted or unsubstituted (C1-C30)alkyl, a substituted or unsubstituted (C2-C30)alkenyl, a substituted or unsubstituted (C2-C30)alkynyl, a substituted or unsubstituted (C3-C30)cycloalkyl, a substituted or unsubstituted (C6-C60)aryl, a substituted or unsubstituted 3- to 30-membered heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, or a substituted or unsubstituted mono- or di-(C6-C30)arylamino; or are linked to each other to form a substituted or unsubstituted mono- or polycyclic, (C3-C30) alicyclic or aromatic ring, whose carbon atom(s) may be replaced with at least one hetero atom selected from nitrogen, oxygen, and sulfur; and
the heteroaryl contains at least one hetero atom selected from B, N, O, S, Si, and P.
Specifically, the second host material preferably includes the following:
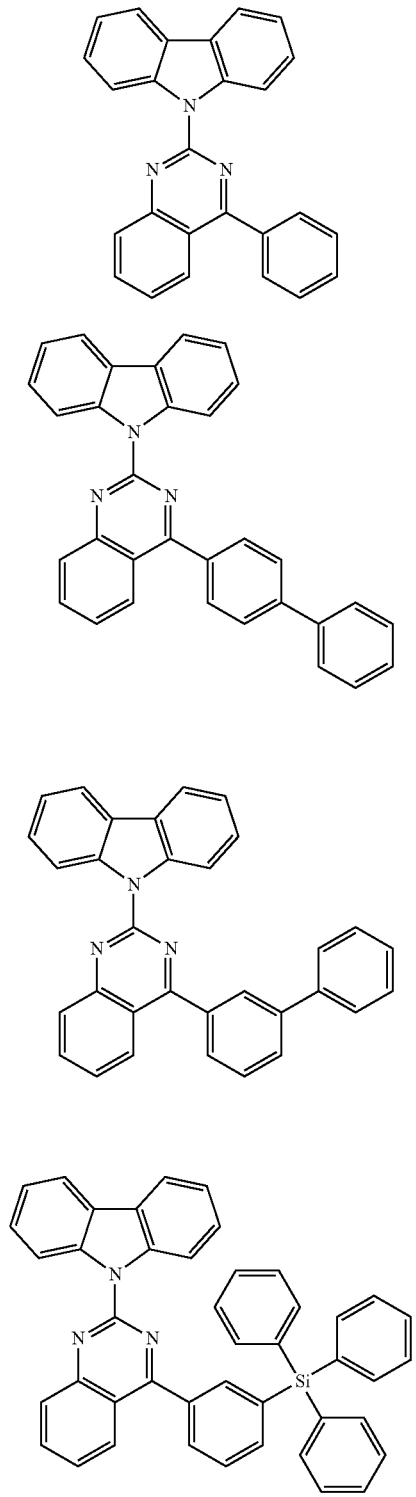
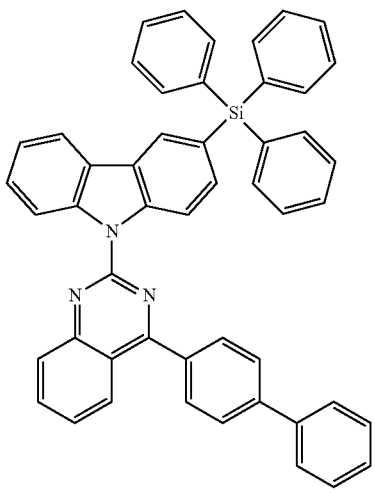
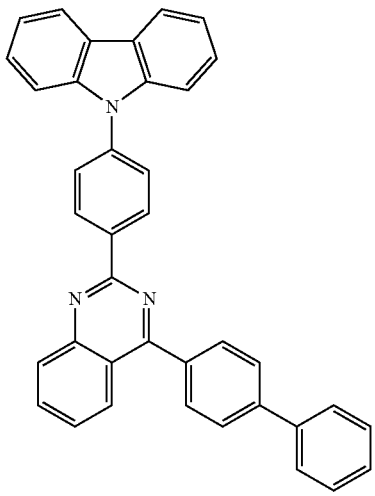
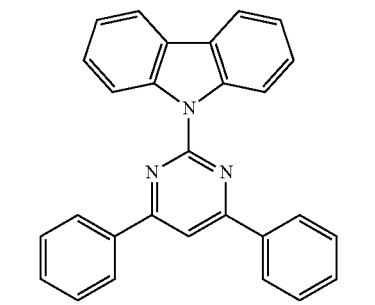
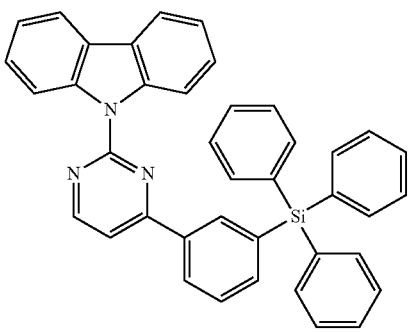

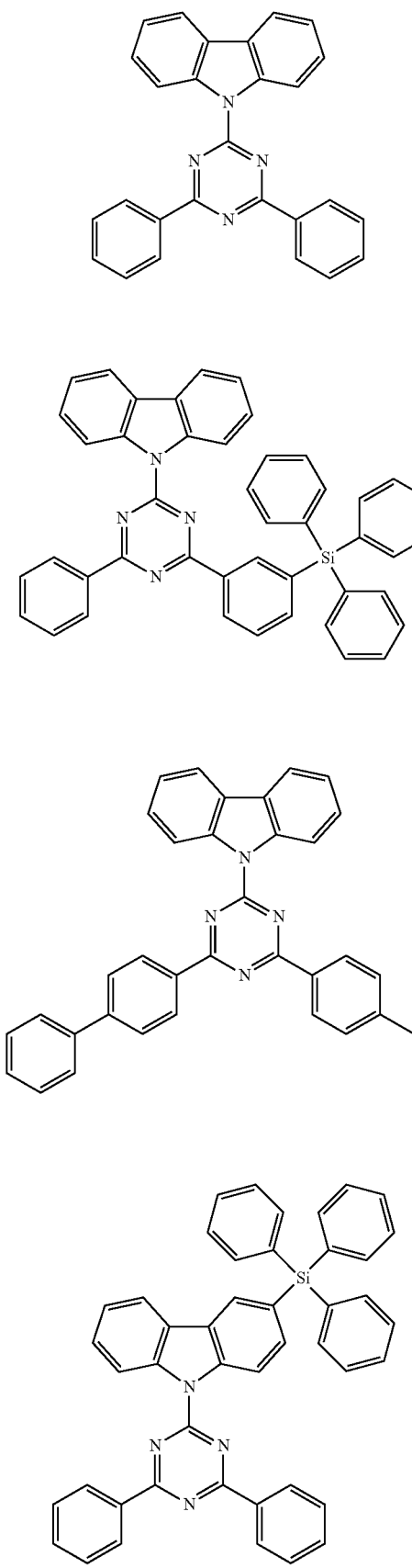

H2-16
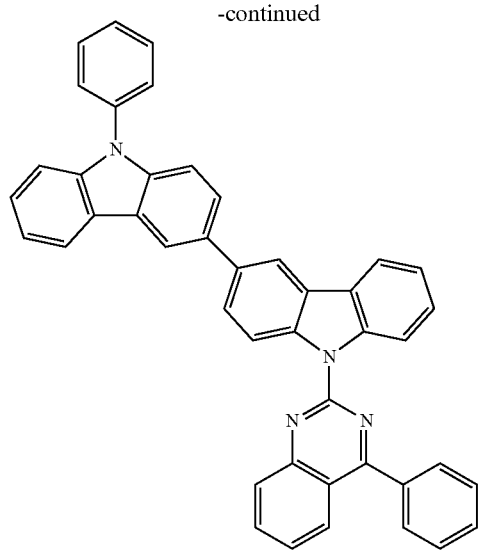
H2-17
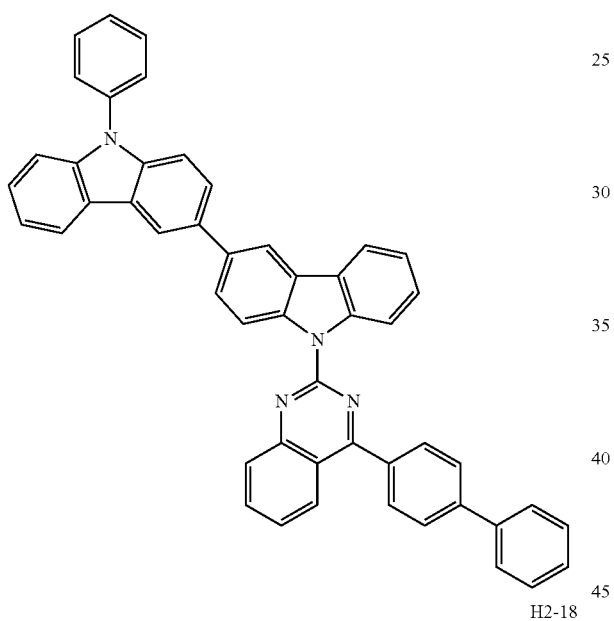
H2-18
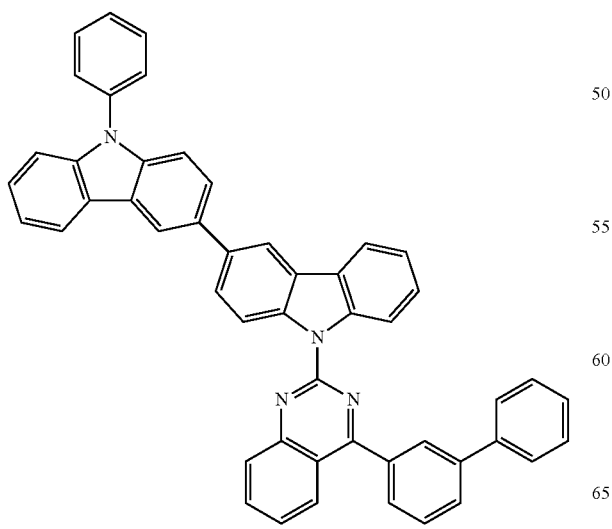
H2-19
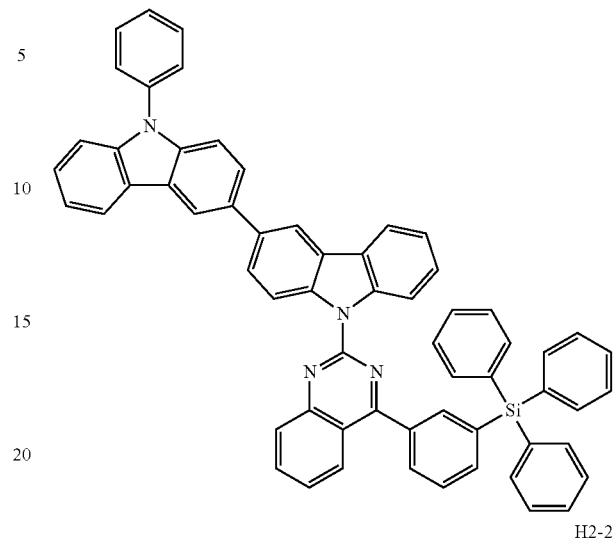
H2-20
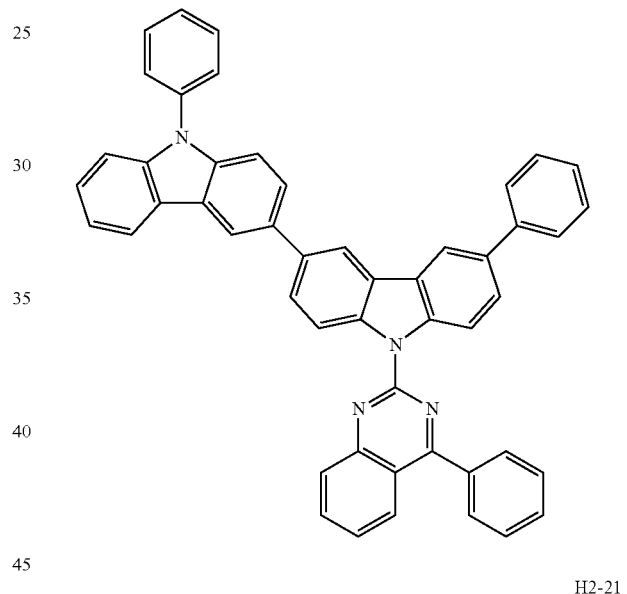
H2-21
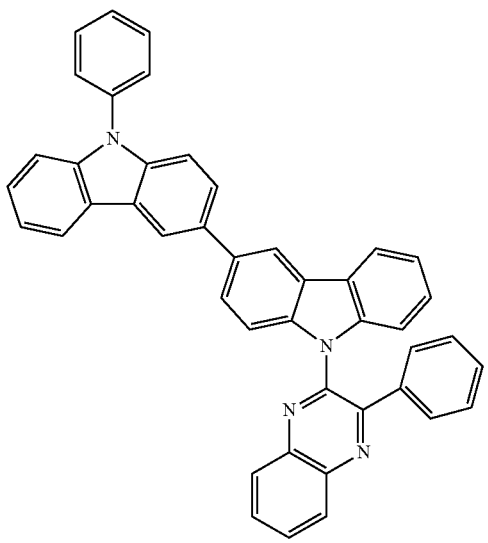

H2-22
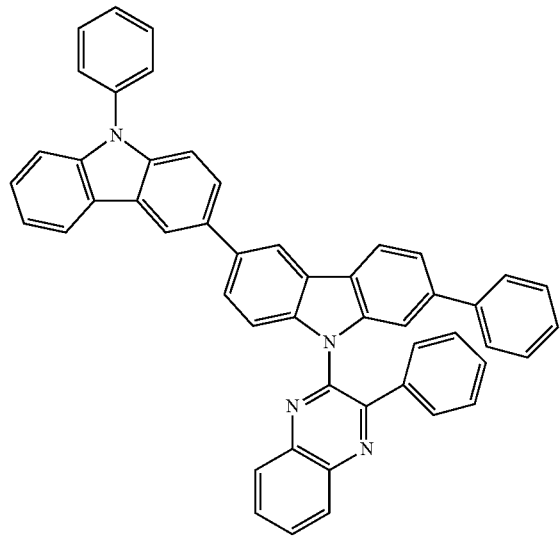
H2-23
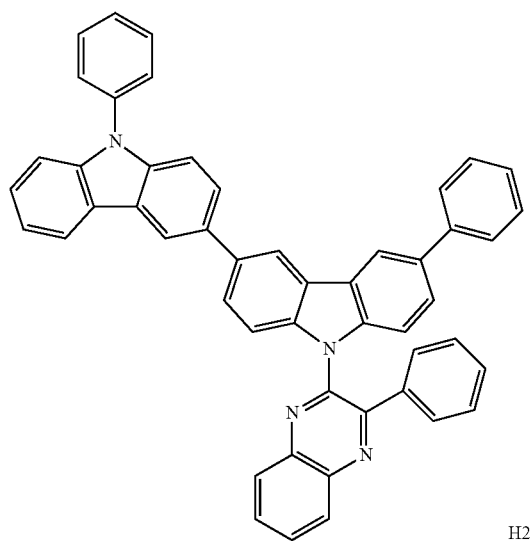
H2-24
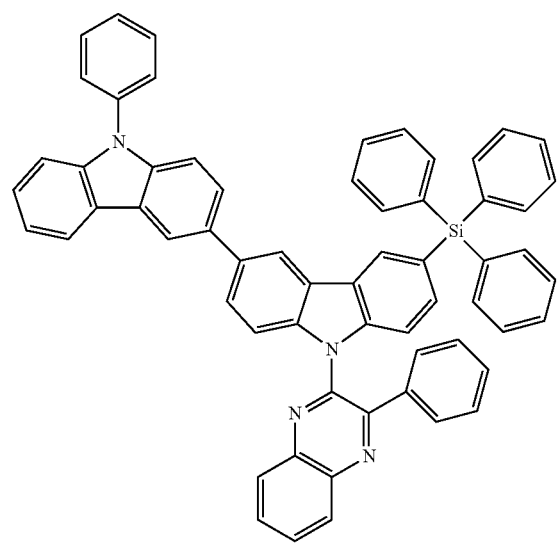
H2-25
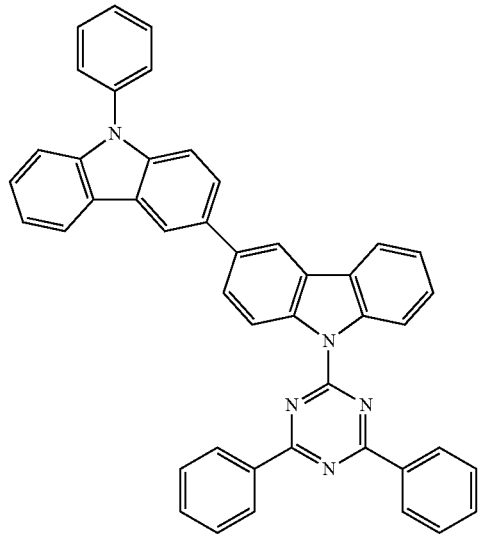
H2-26
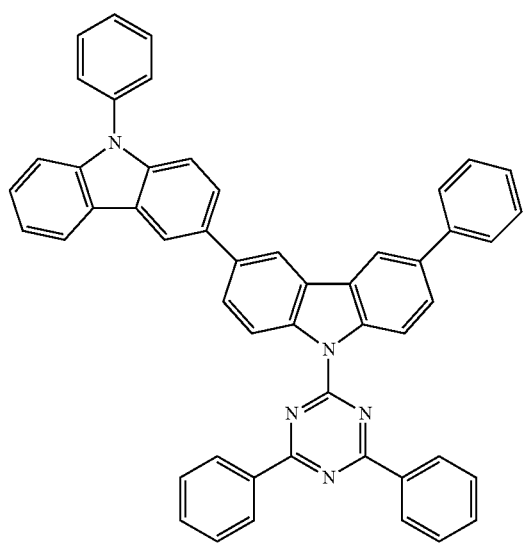
H2-27
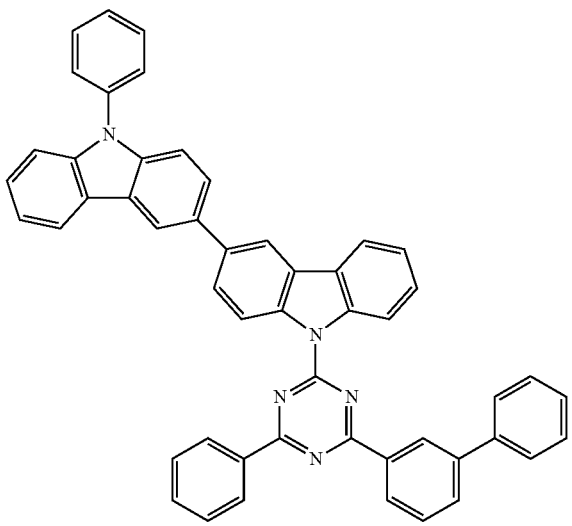

H2-28
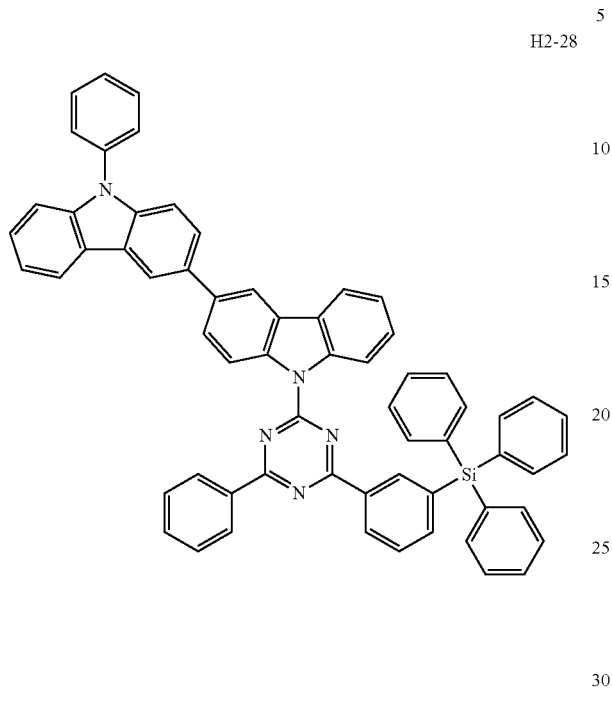
H2-29
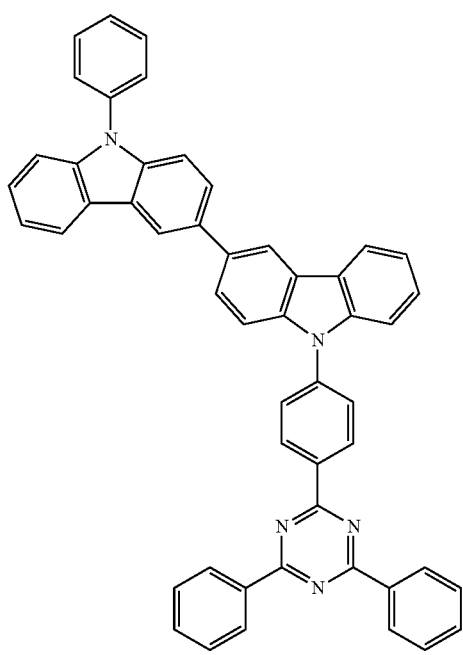
H2-30
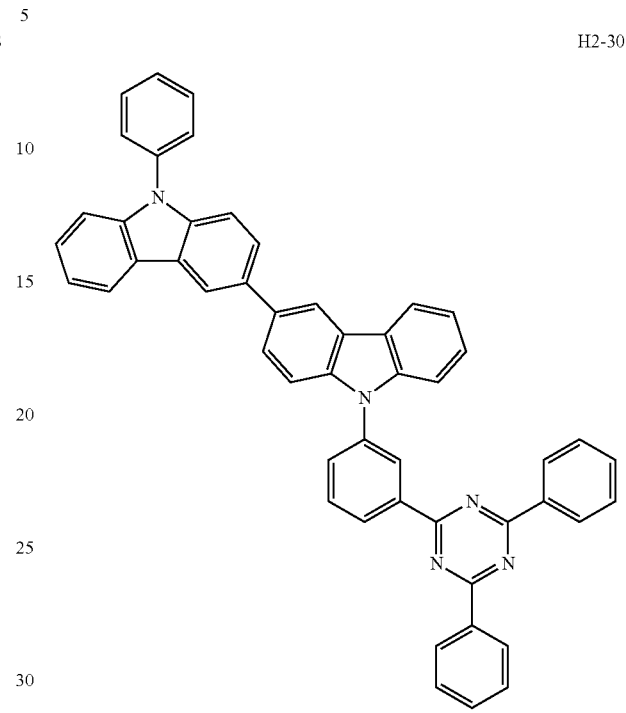
H2-31
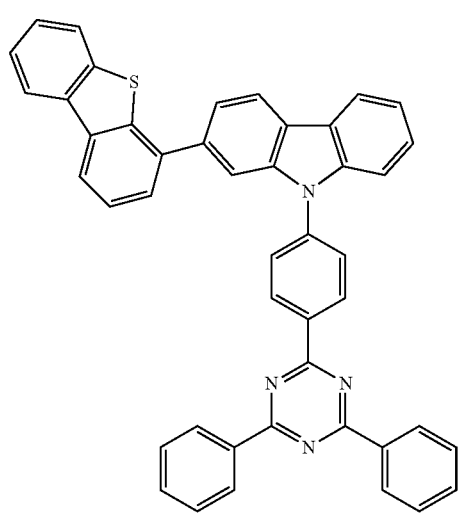

H2-32
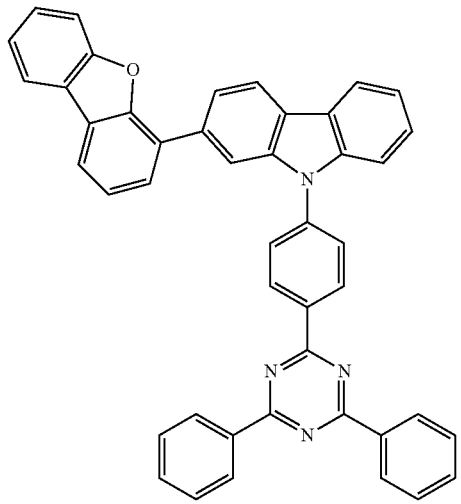
H2-33
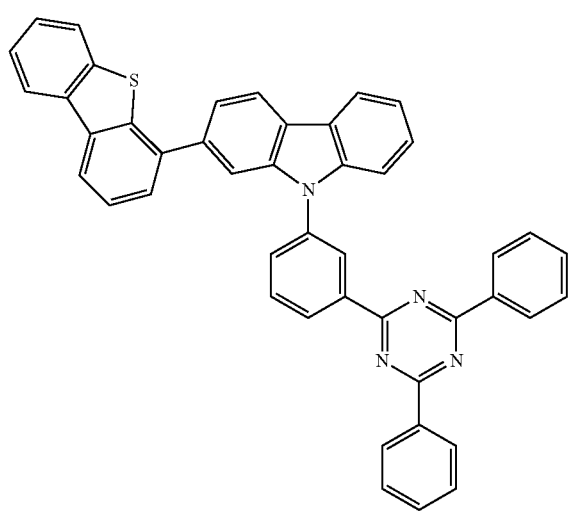
H2-34
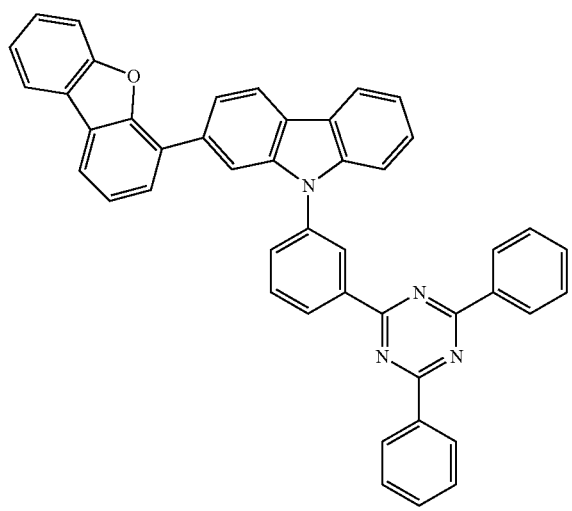
H2-35
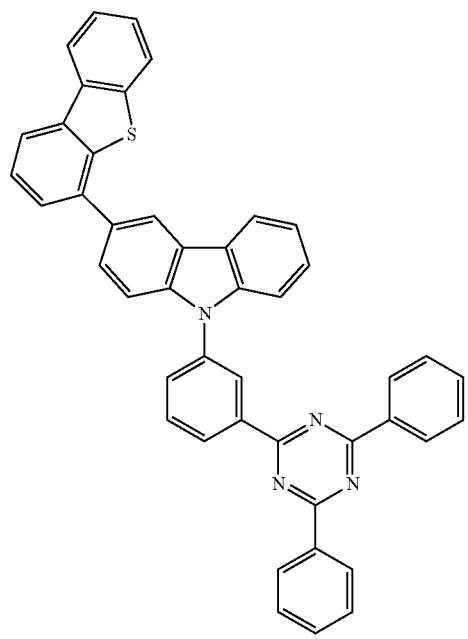
H2-36
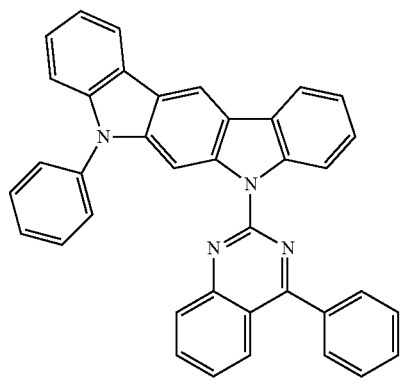
H2-37
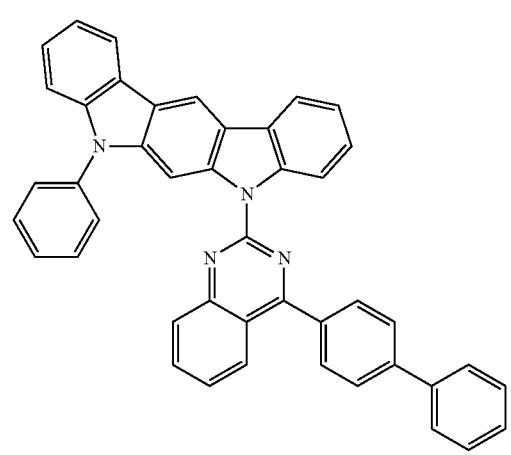

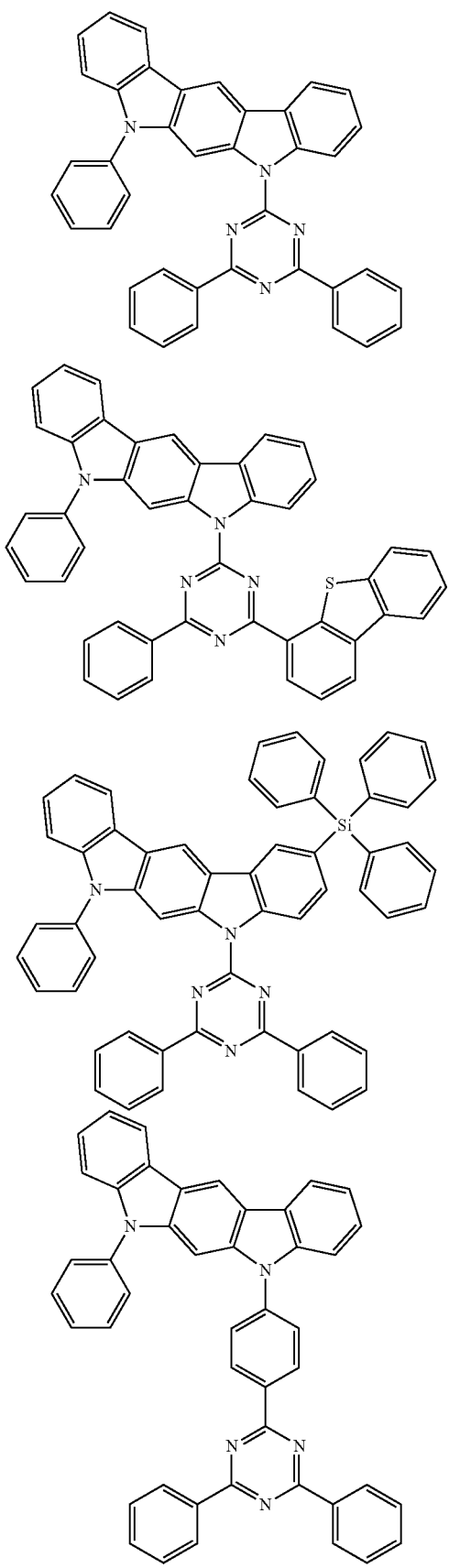
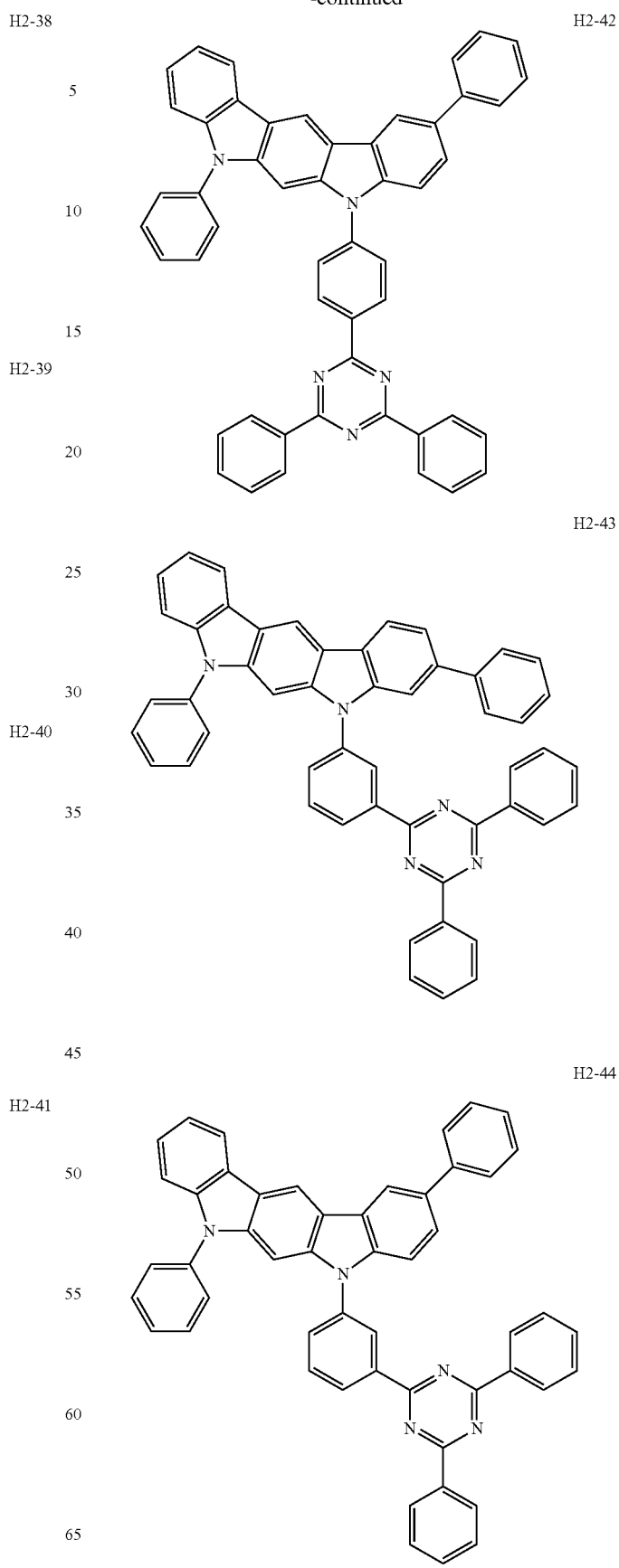

H2-45
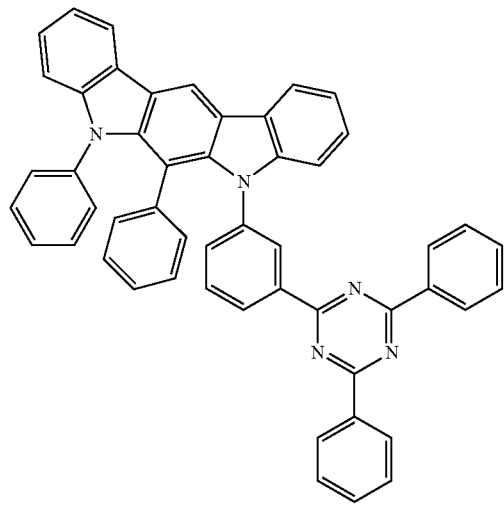
H2-46
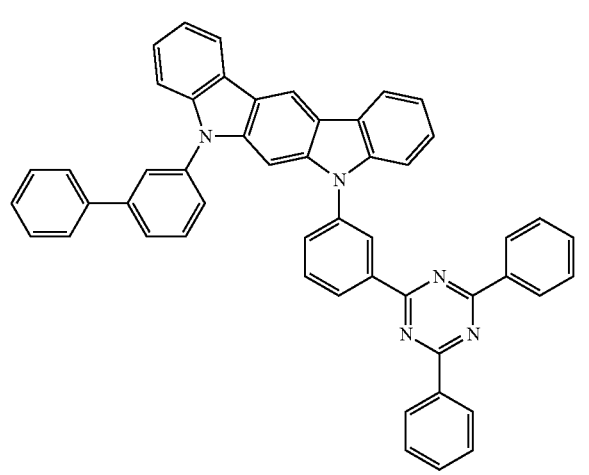
H2-47
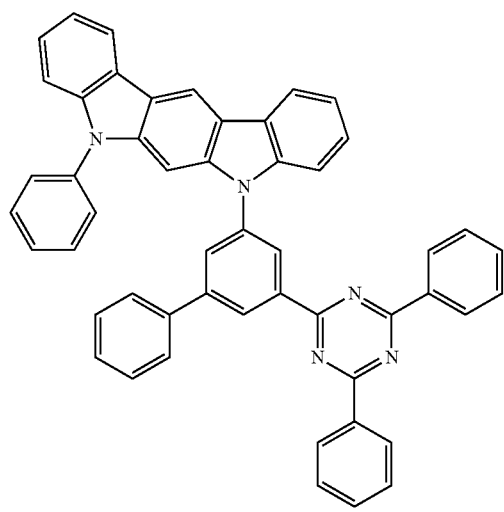
H2-48
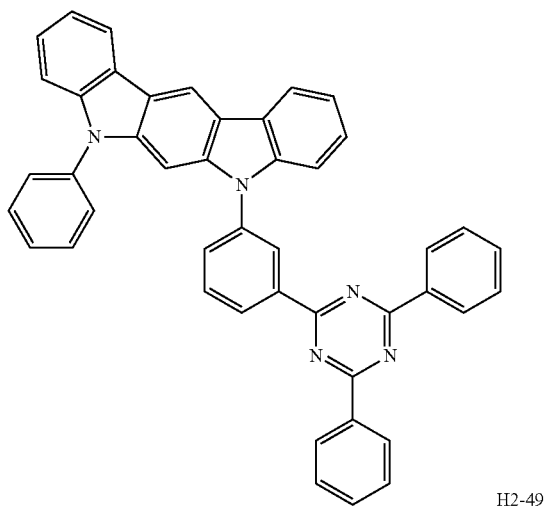
H2-49
H2-50
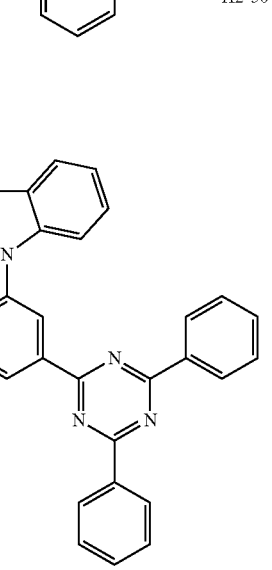

H2-51
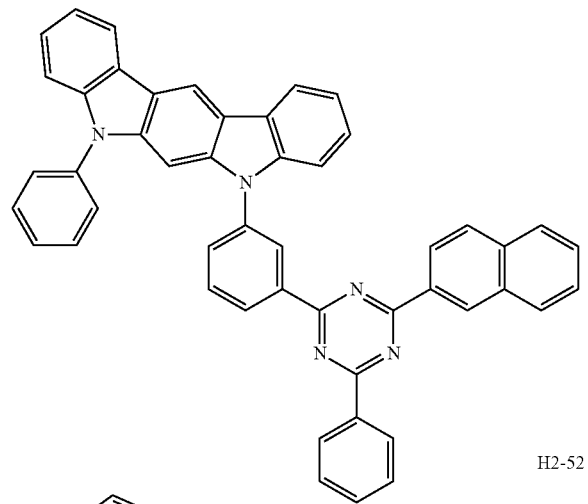
H2-52
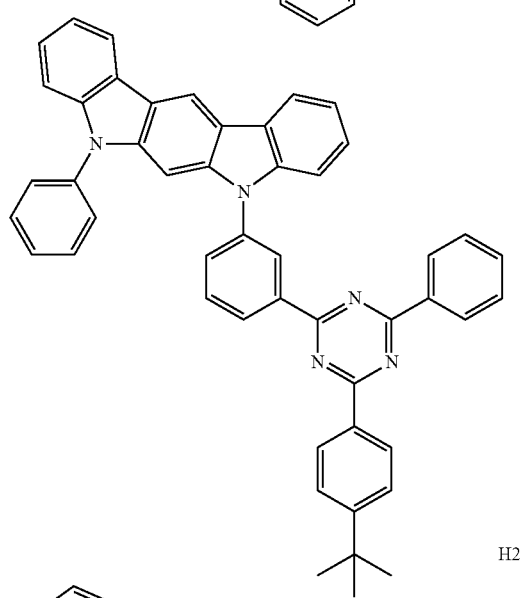
H2-53
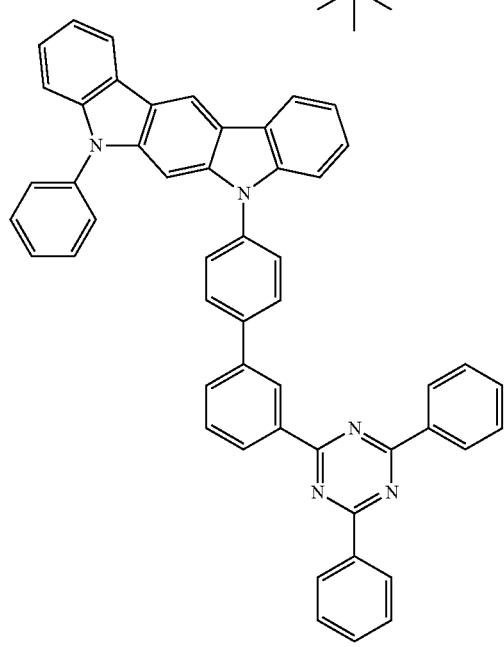
H2-54
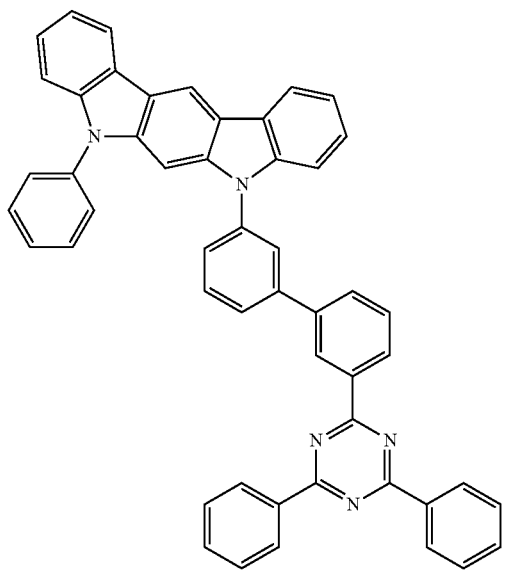
H2-55
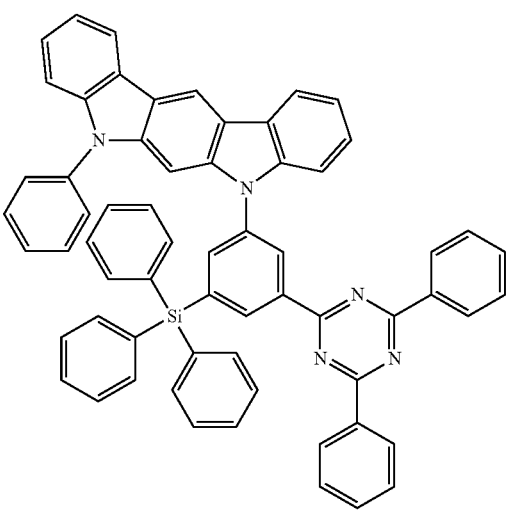
H2-56
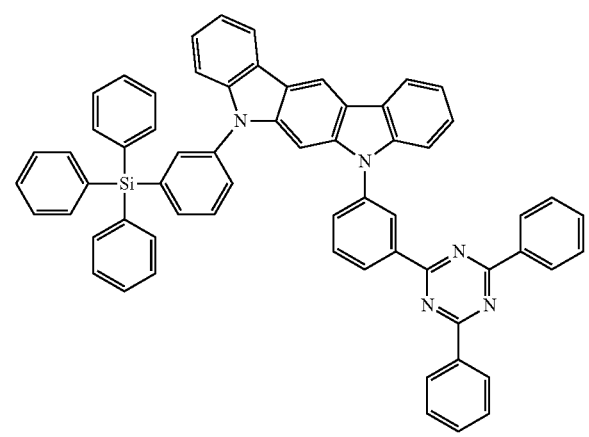

H2-57
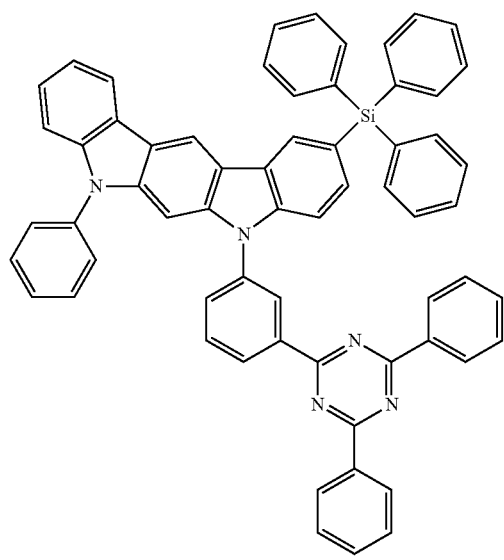
H2-58
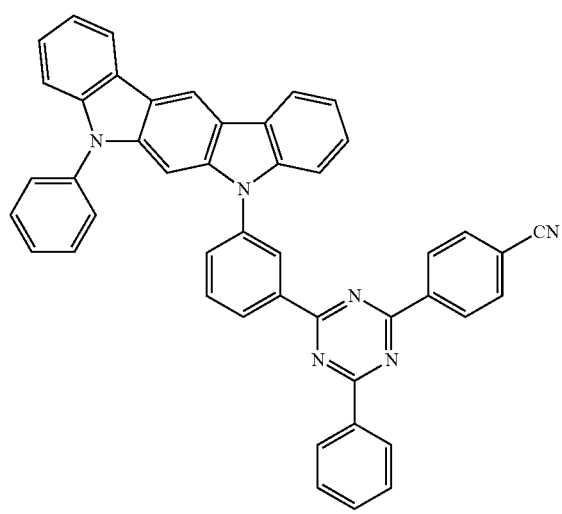
H2-59
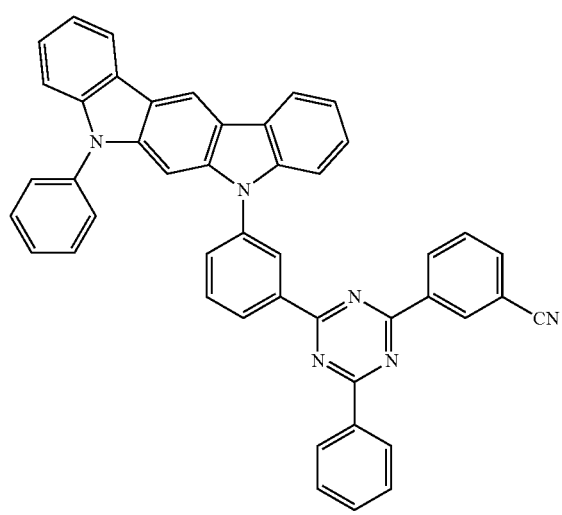
H2-60
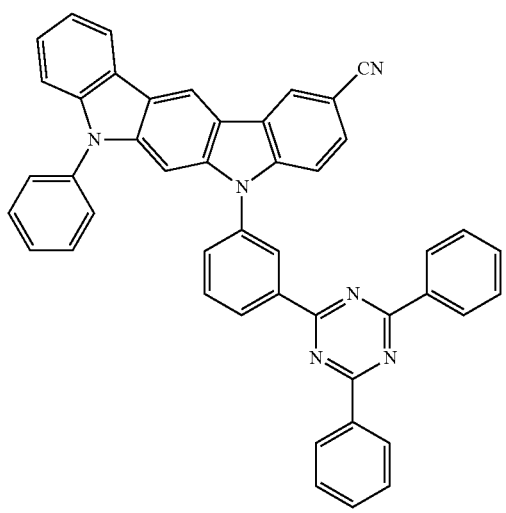
H2-61
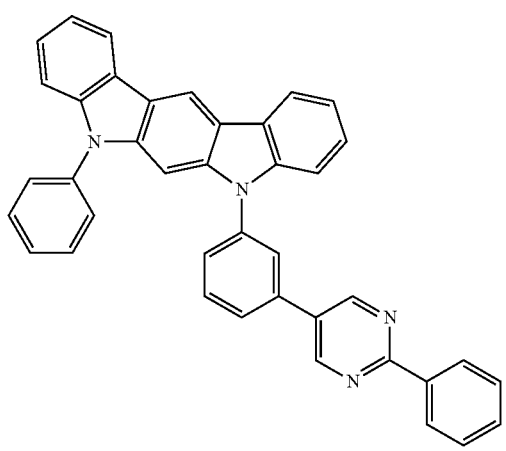
H2-62
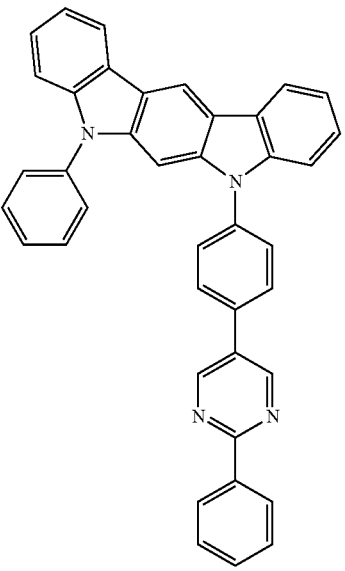

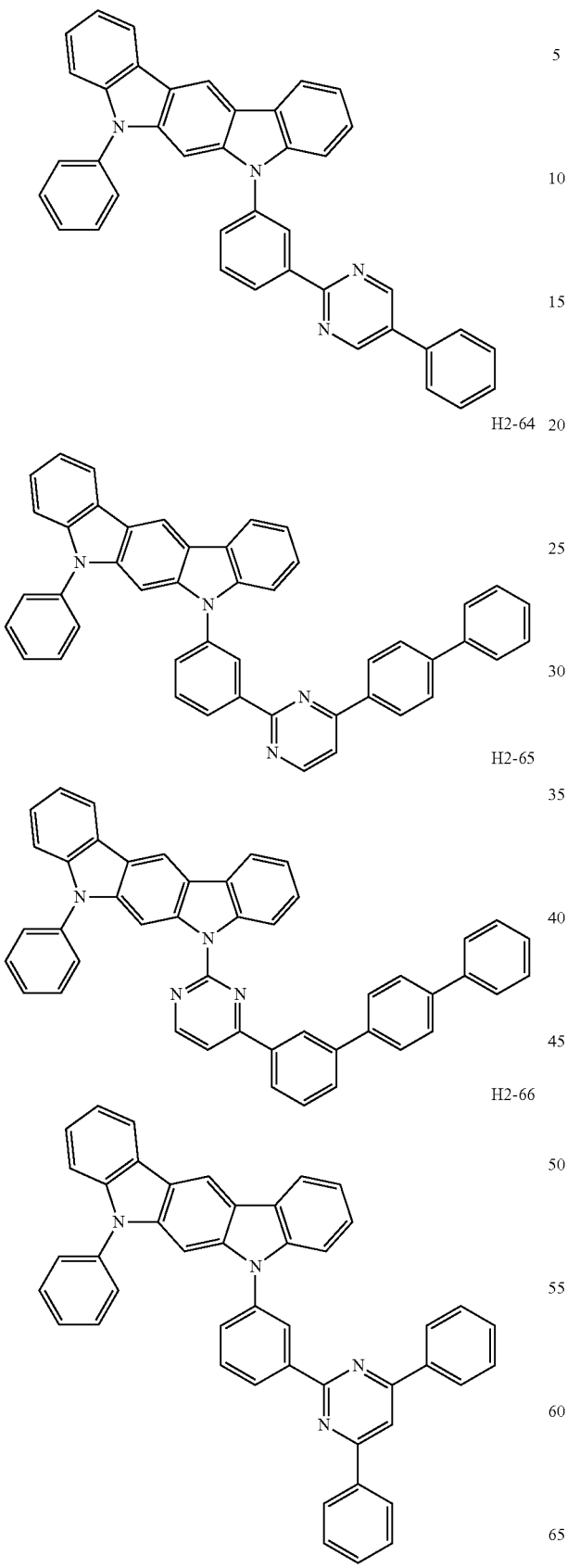
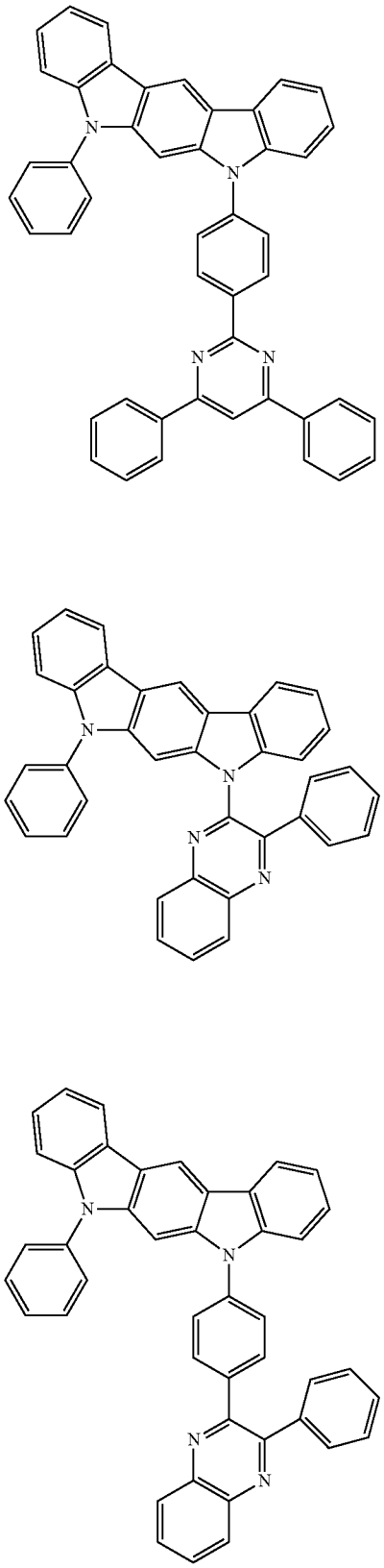

-continued
H2-70
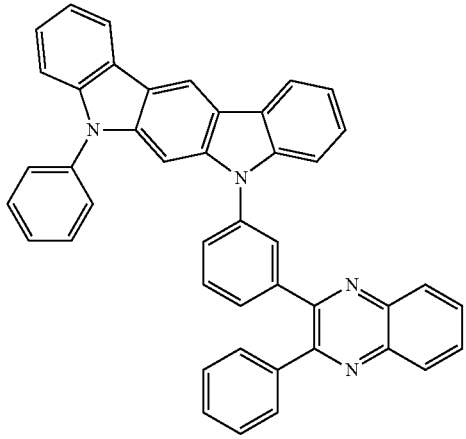
H2-71
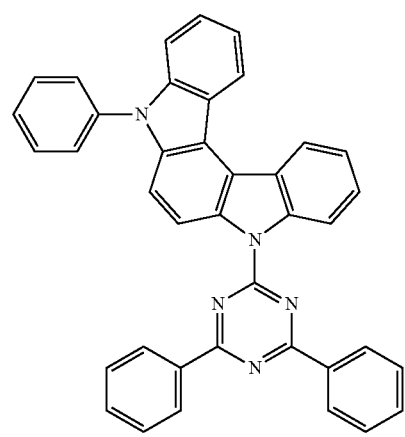
H2-72
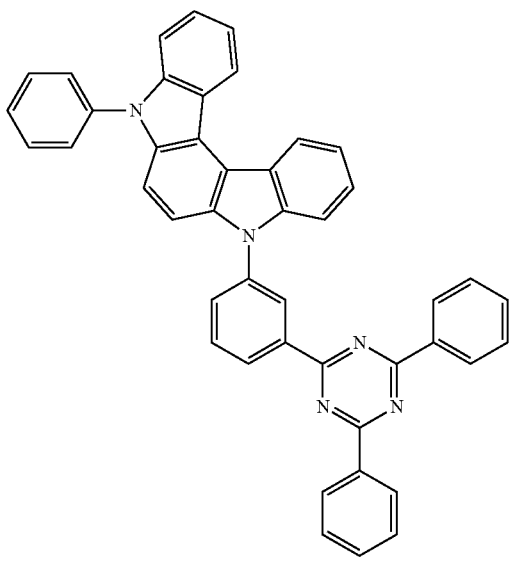
-continued
H2-73
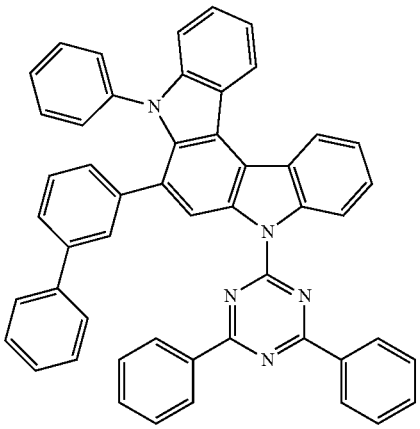
H2-74
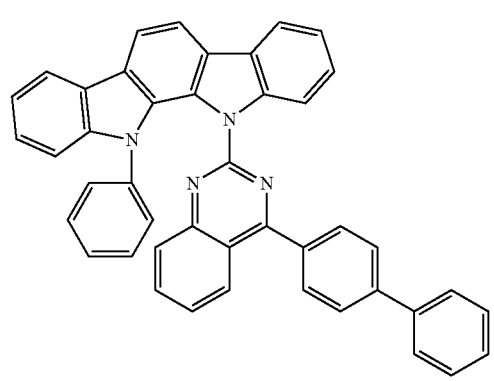
H2-75
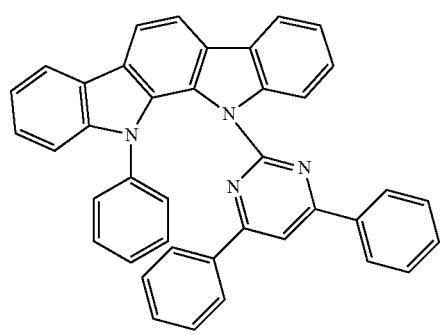
H2-76
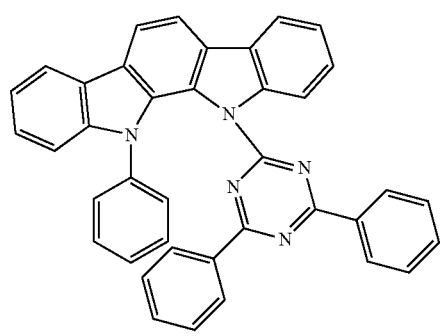

H2-77
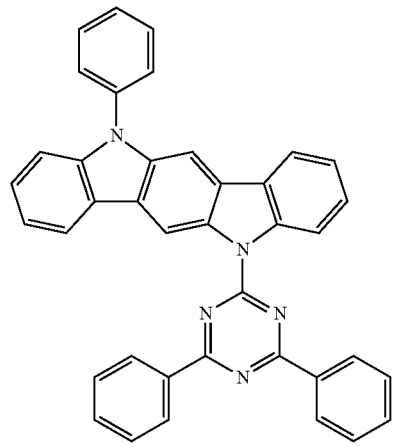
H2-78
H2-79
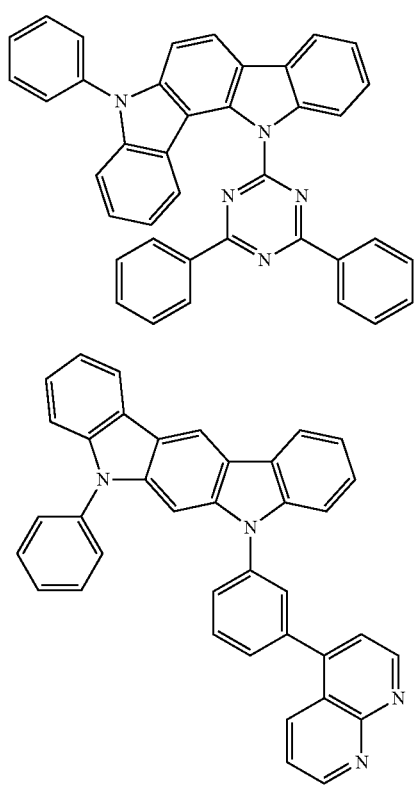
H2-80
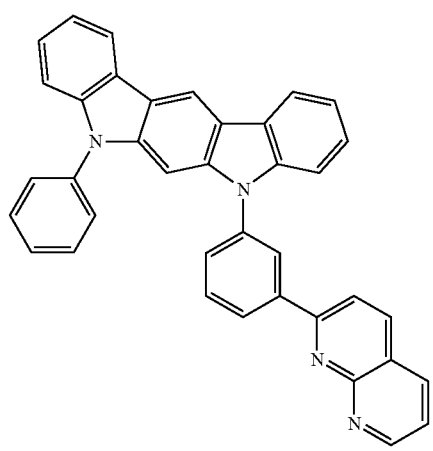
H2-81
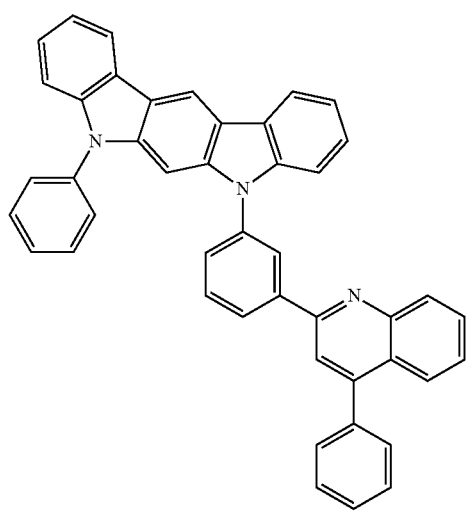
H2-82
H2-83
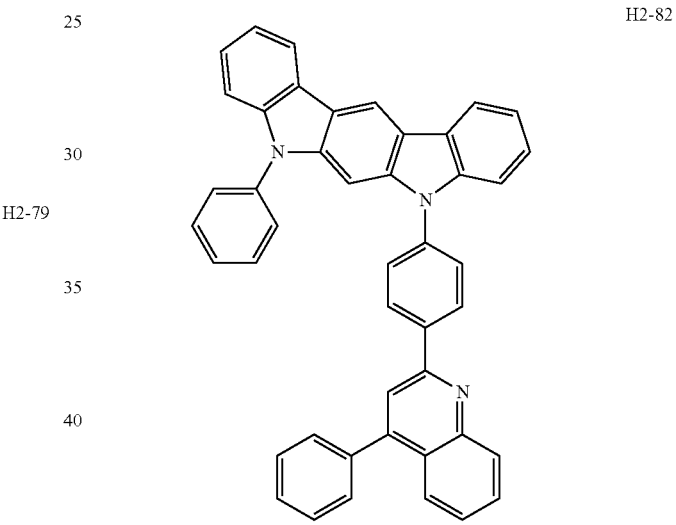
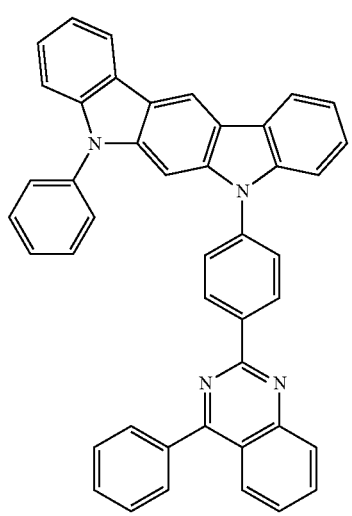

-continued
H2-84
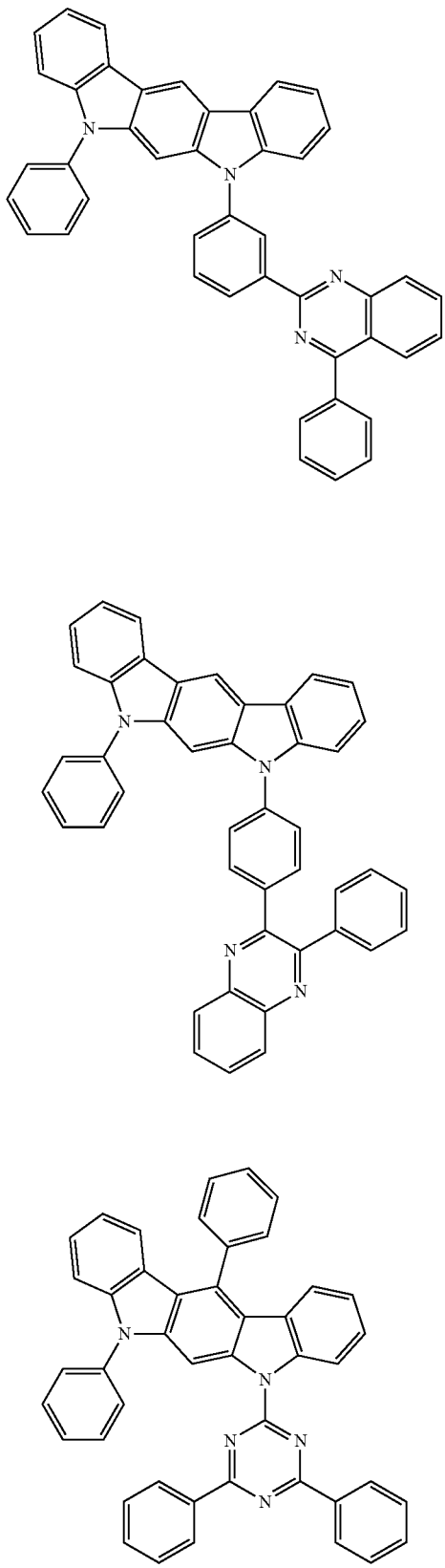
H2-85
H2-86
H2-87
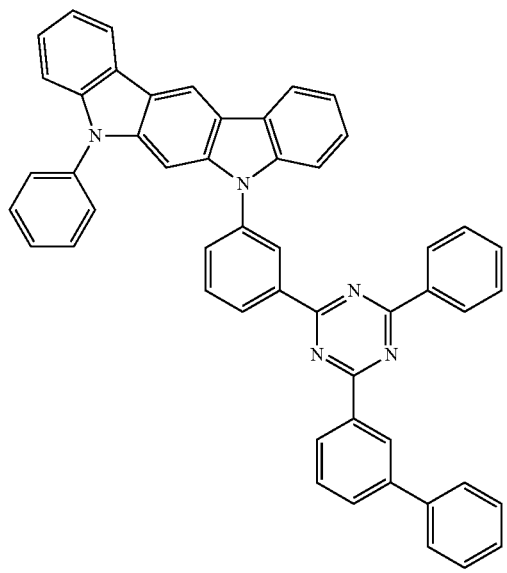
H2-88
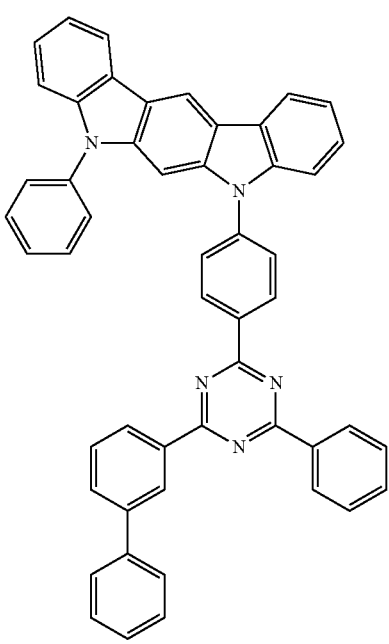

H2-89
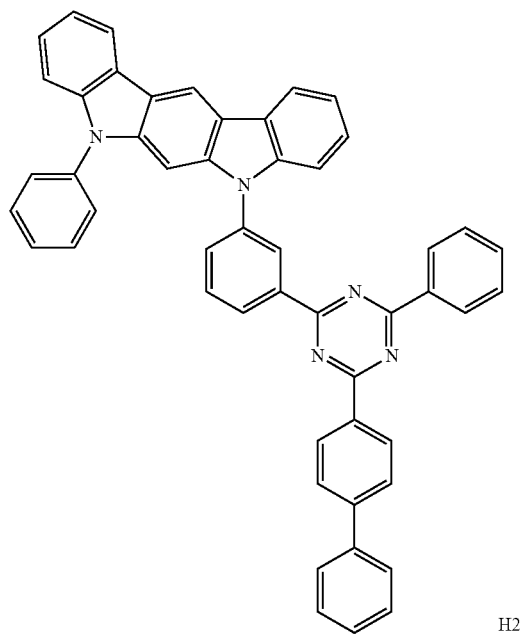
H2-90
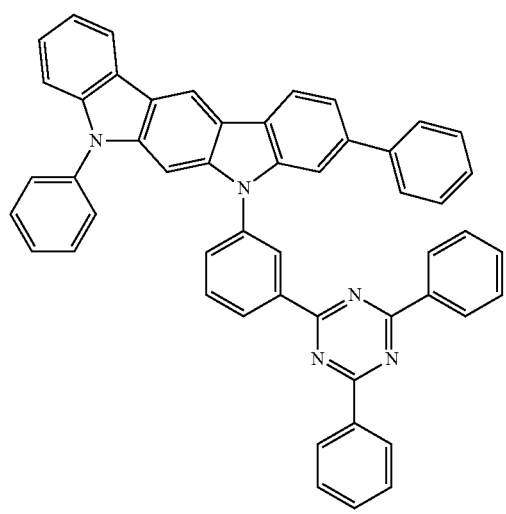
H2-91
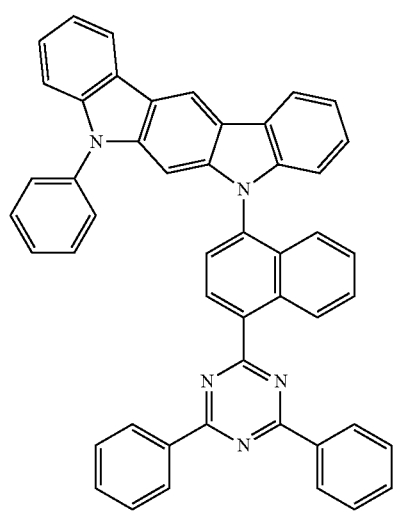
H2-92
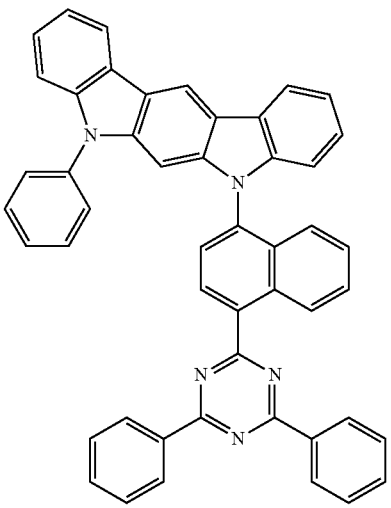
H2-93
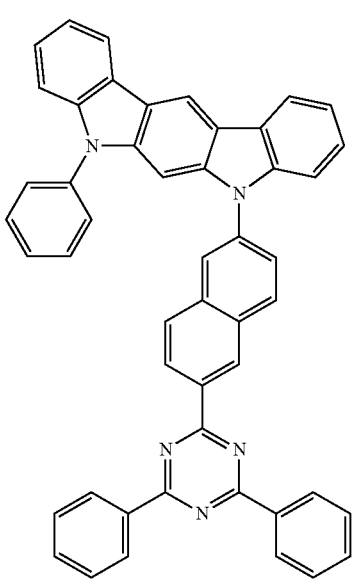
H2-94
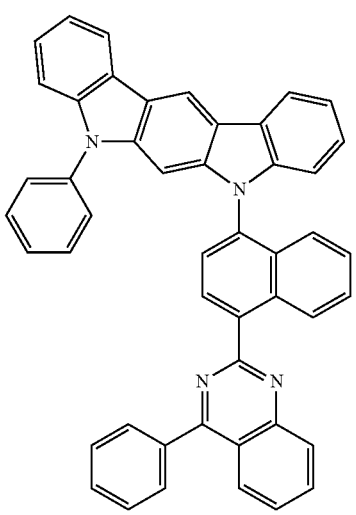

H2-95
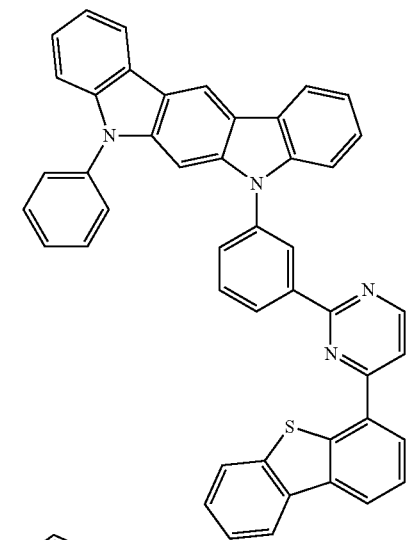
H2-96
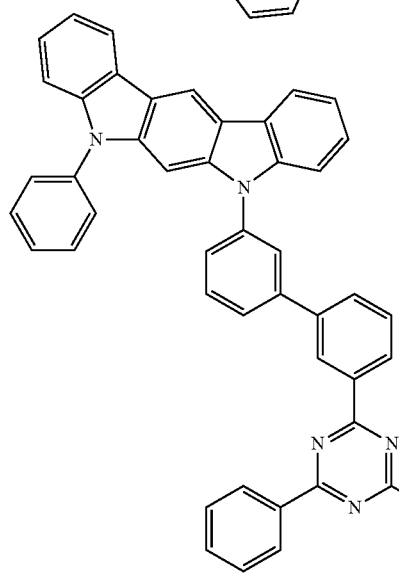
H2-97
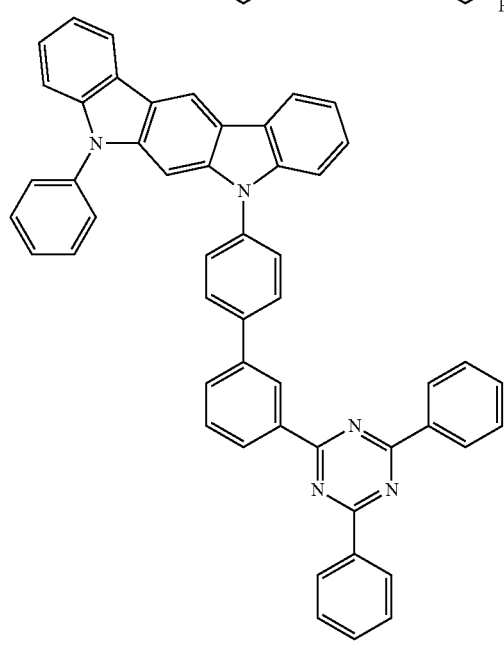
H2-98
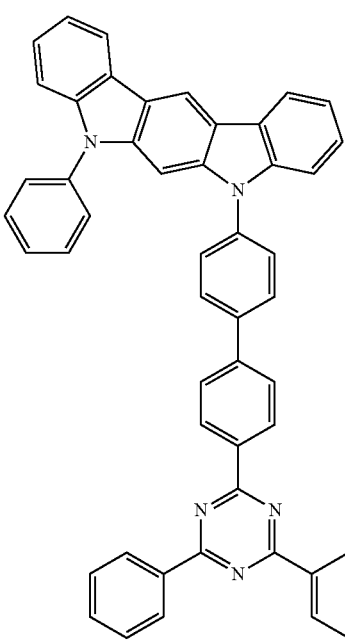
H2-99
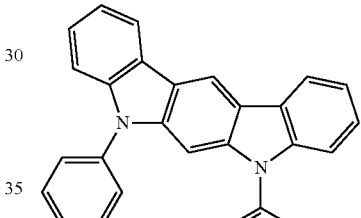
H2-100
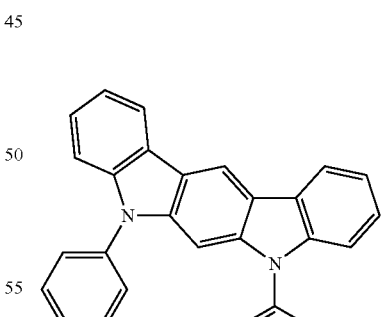
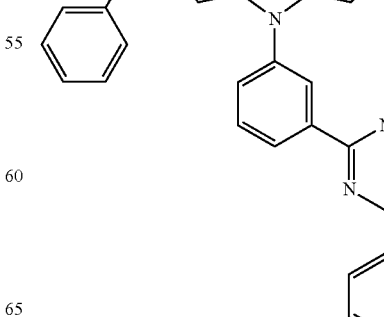

H2-101
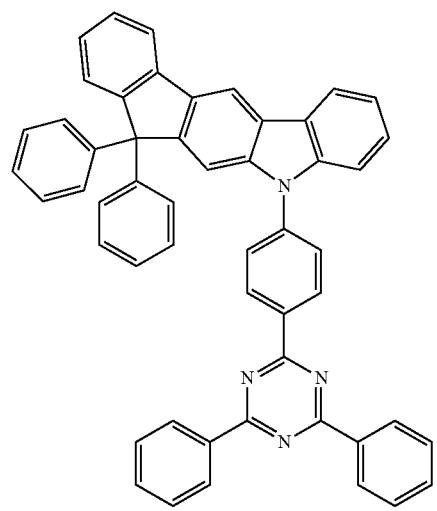
H2-102
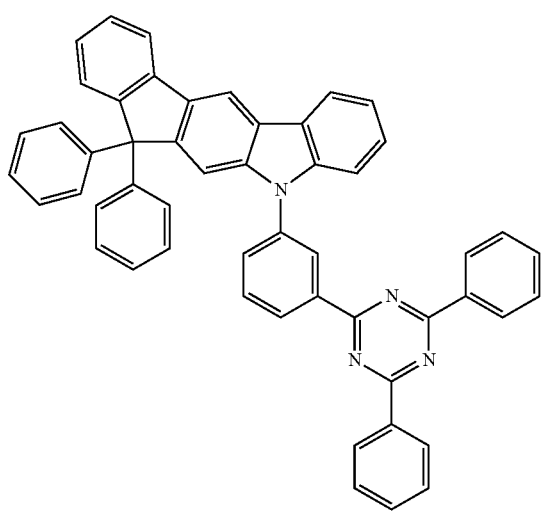
H2-103
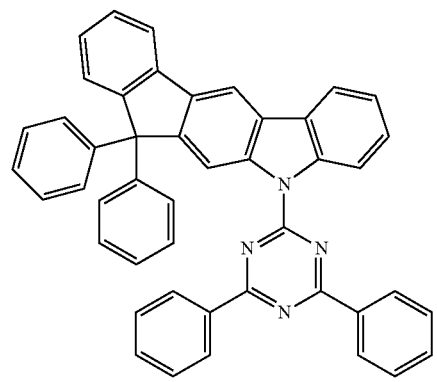
H2-104
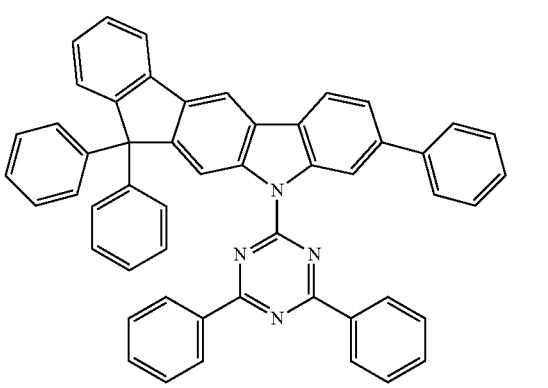
H2-105
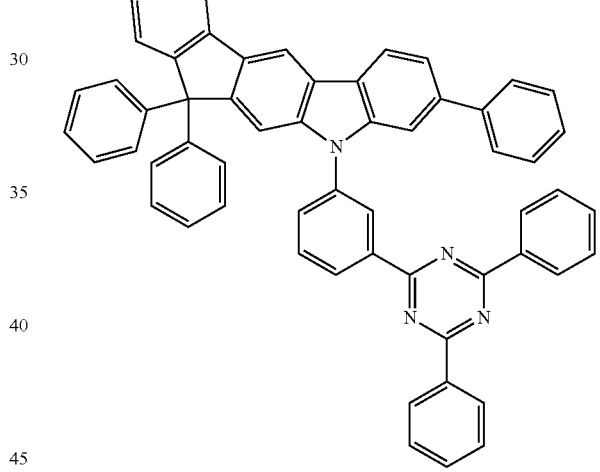
H2-106
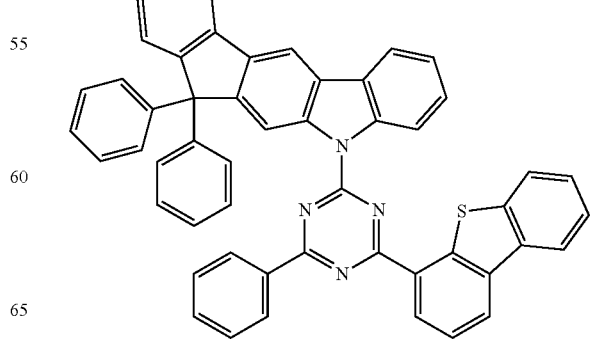

H2-107
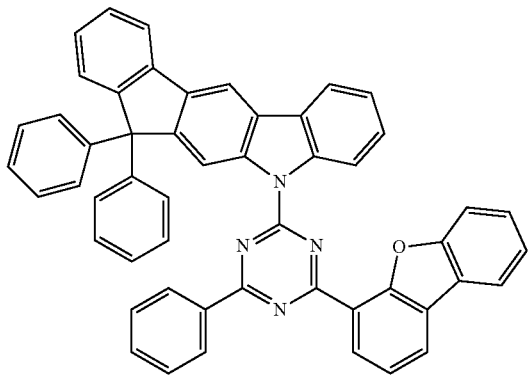
H2-108
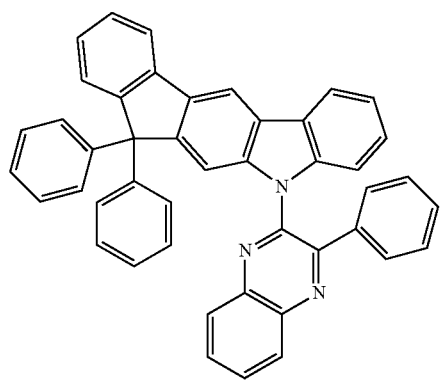
H2-109
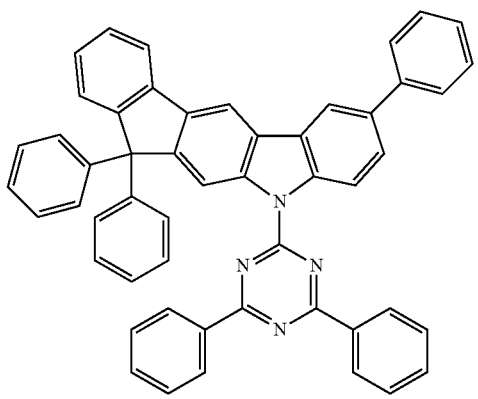
H2-111
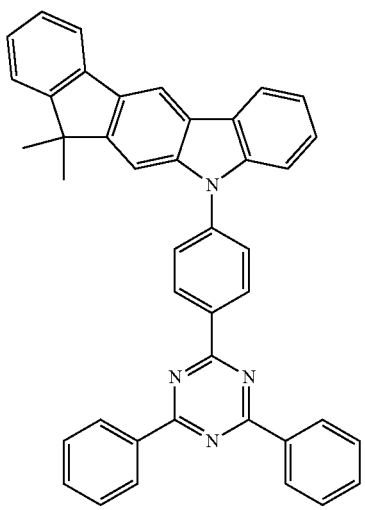
H2-112
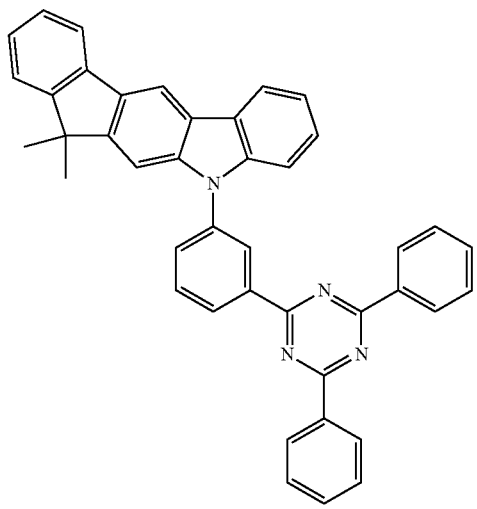
H2-113
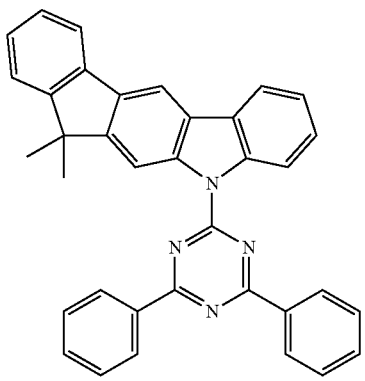
H2-110

H2-114
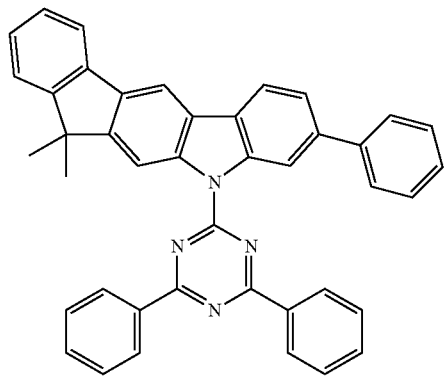
H2-115
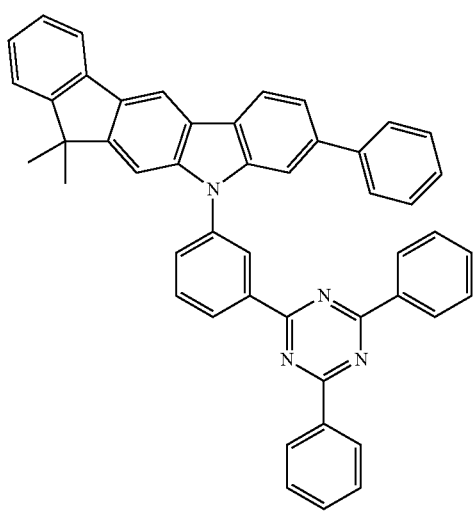
H2-116
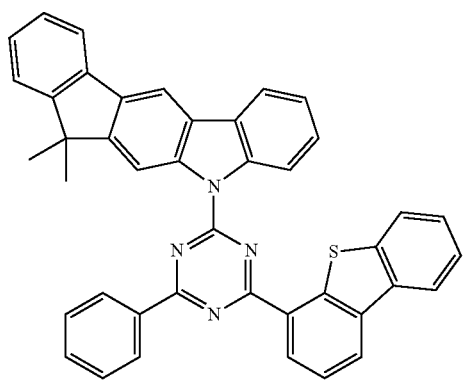
H2-117
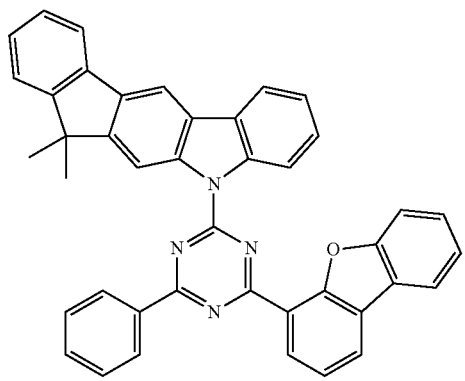
H2-118
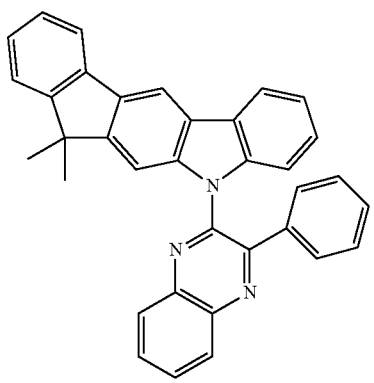
H2-119
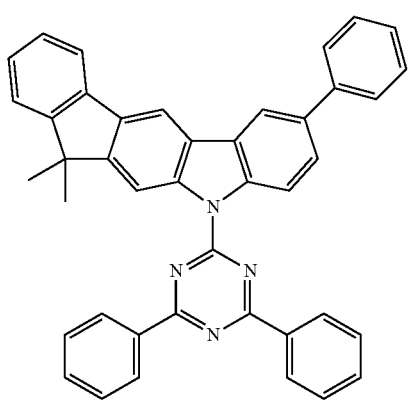
H2-120
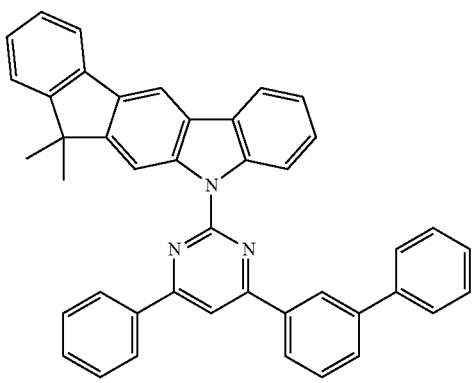
H2-121
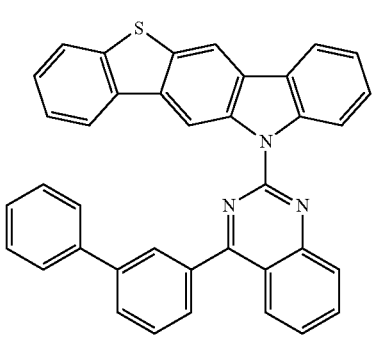

H2-122
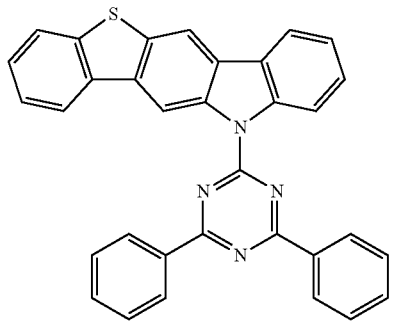
H2-123
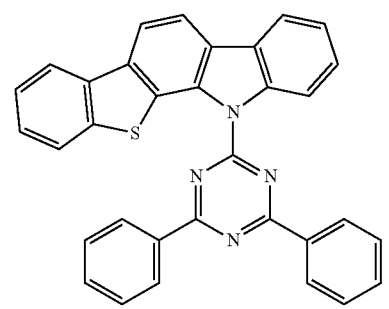
H2-124
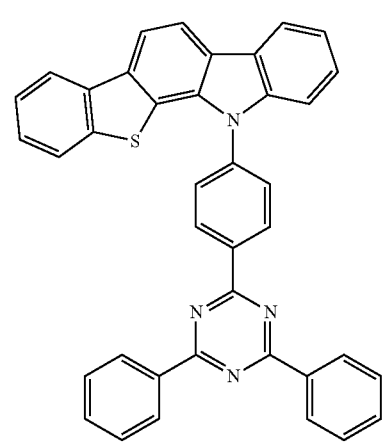
H2-125
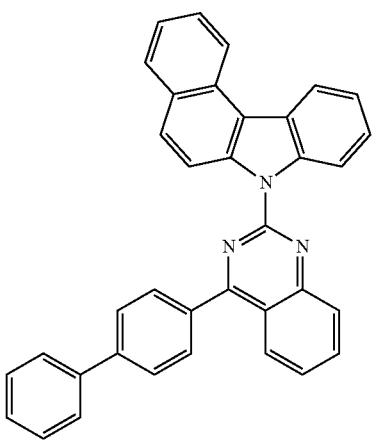
H2-126
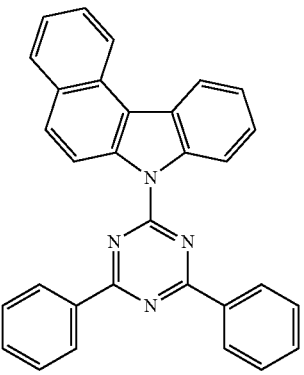
H2-127
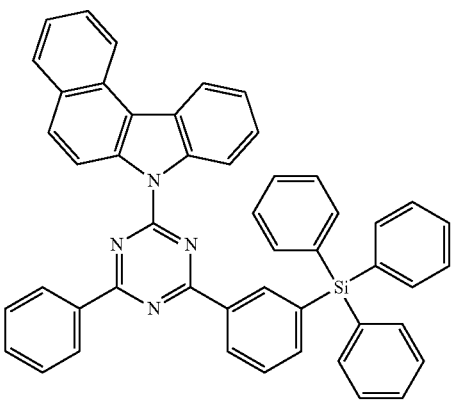
H2-128

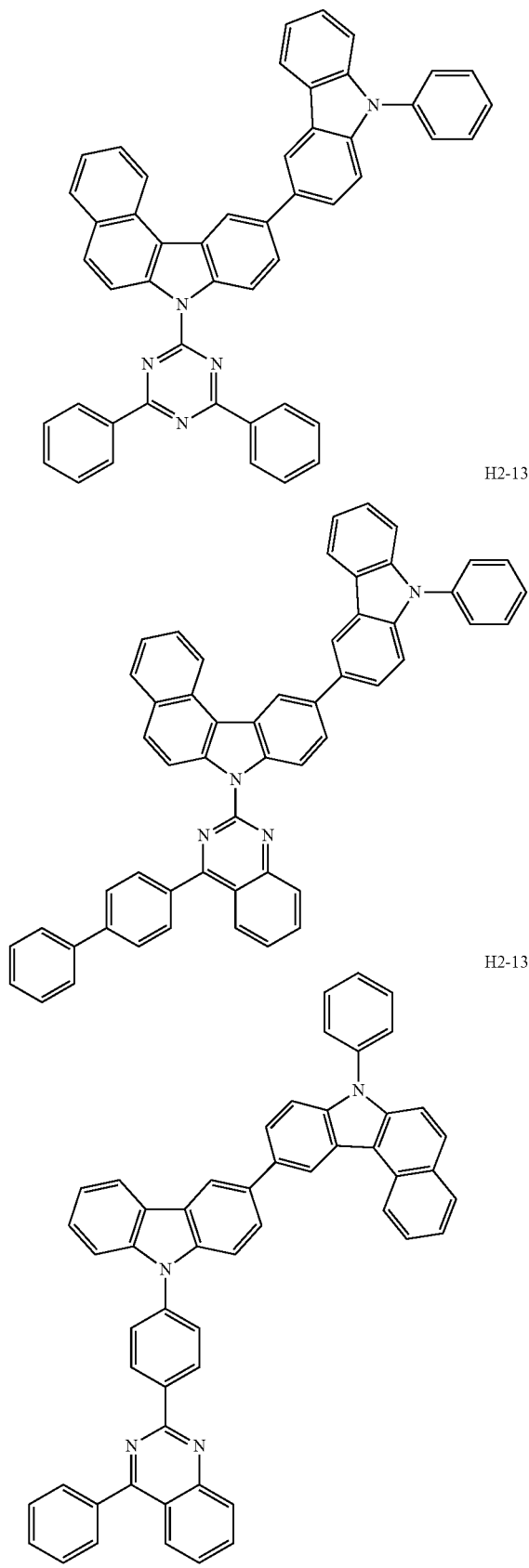
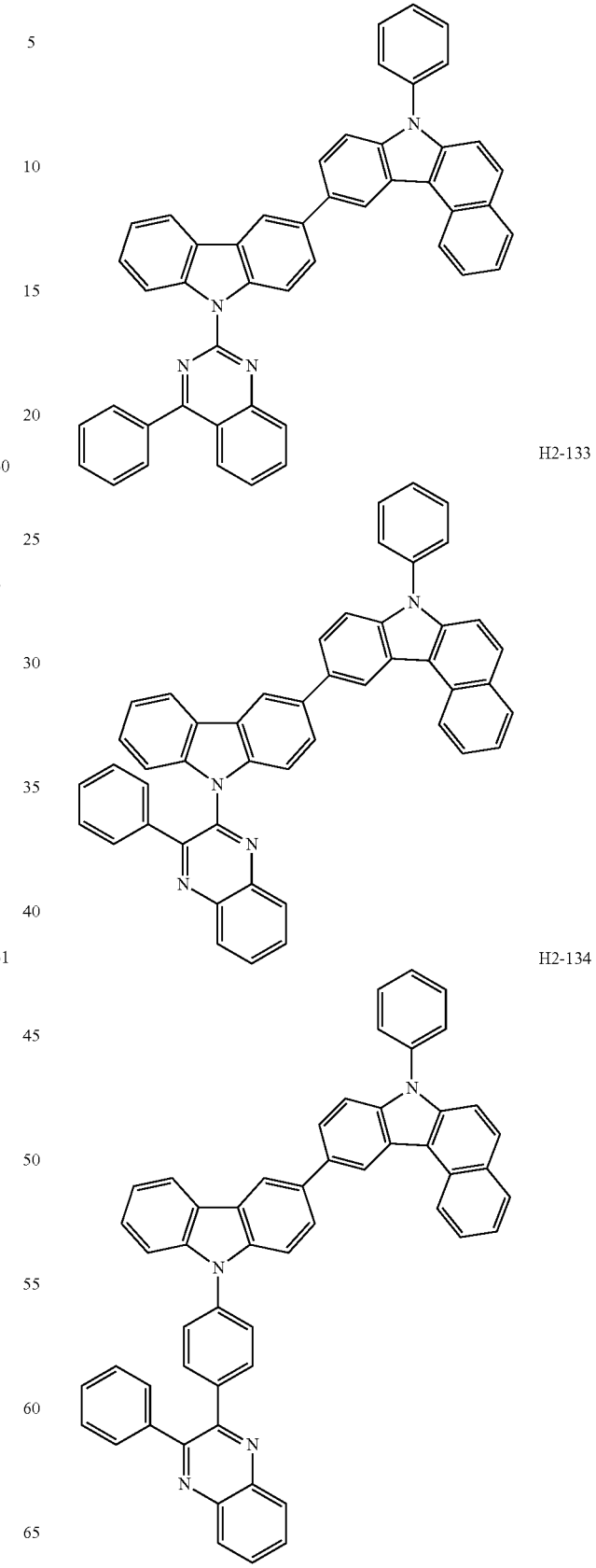

-continued
H2-135
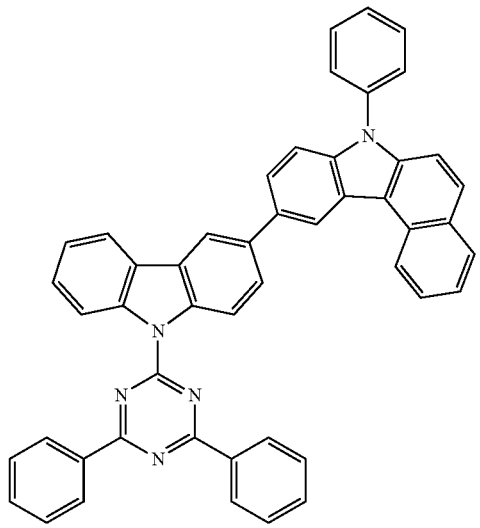
H2-136
H2-137
-continued
H2-138
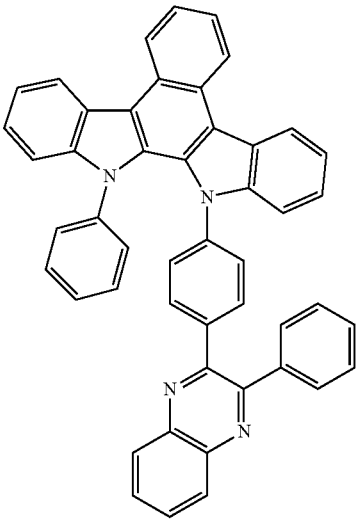
H2-139
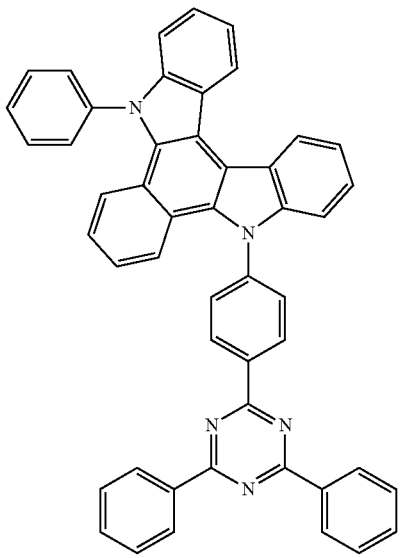
H2-140
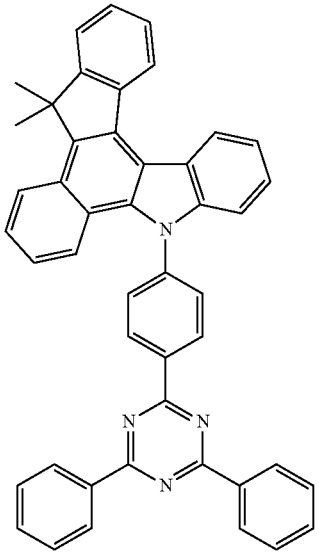

H2-141
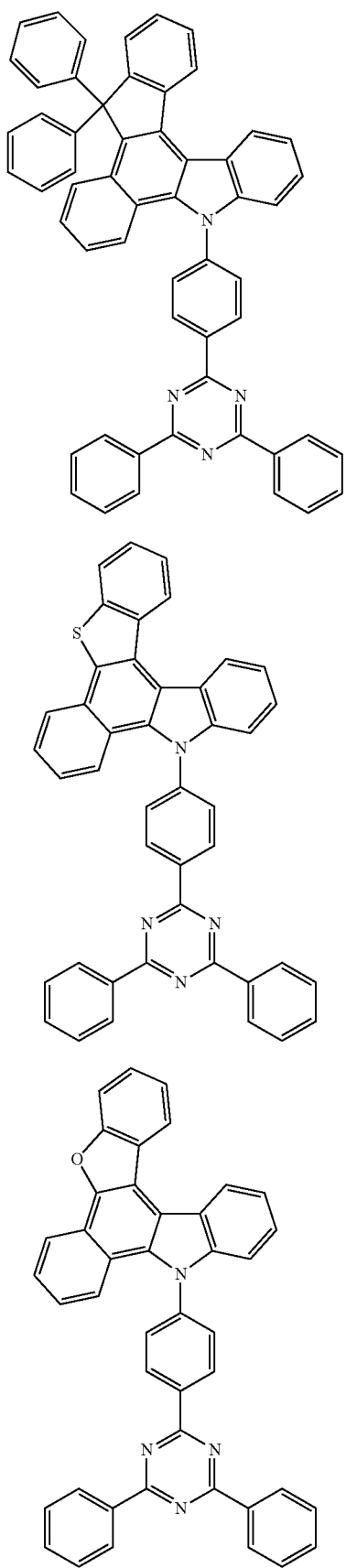
H2-142
H2-143
H2-144
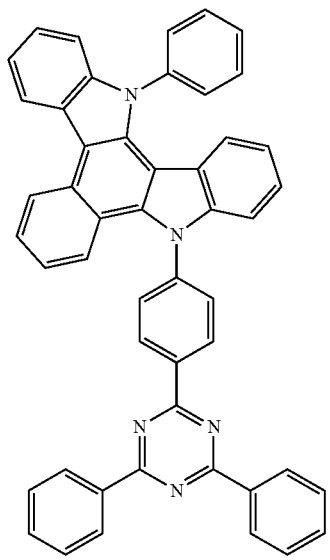
H2-145
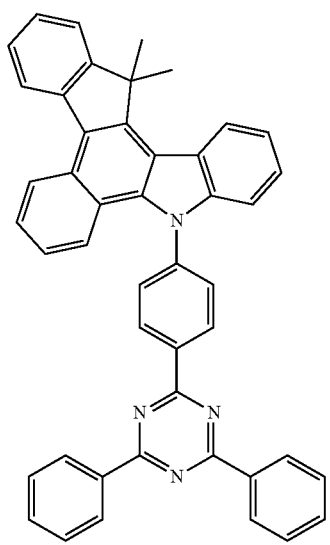

H2-146
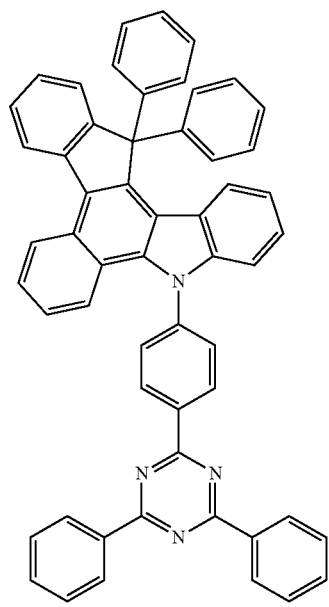
H2-147
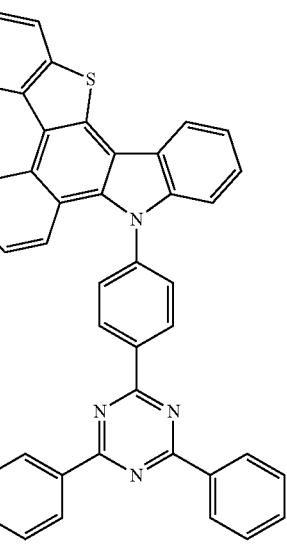
H2-148
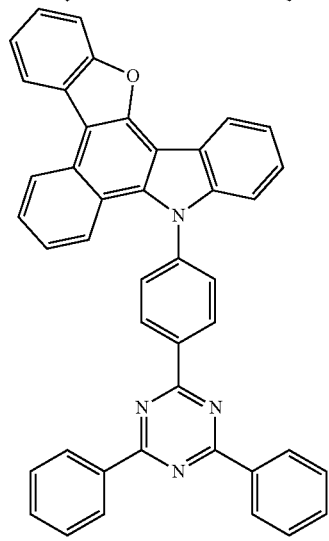
H2-149
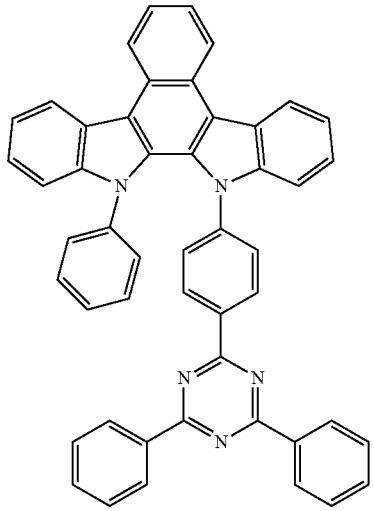
H2-150
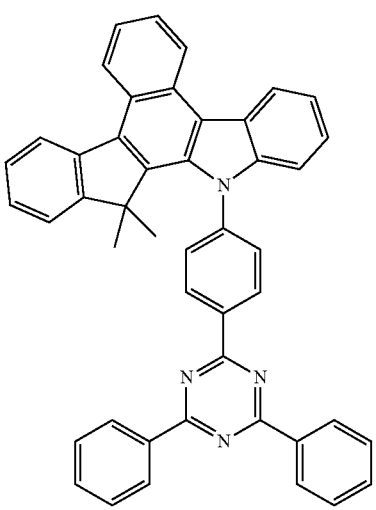
H2-151
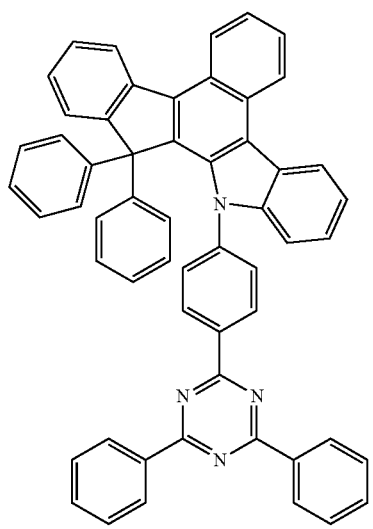

-continued
H2-152
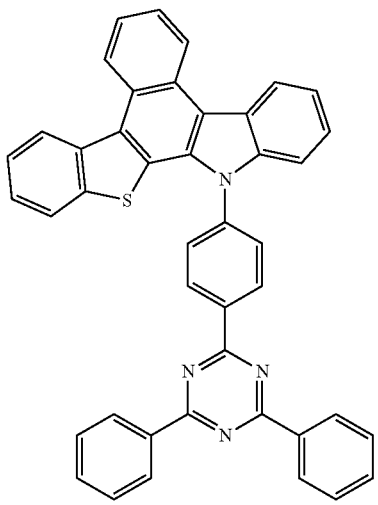
H2-153
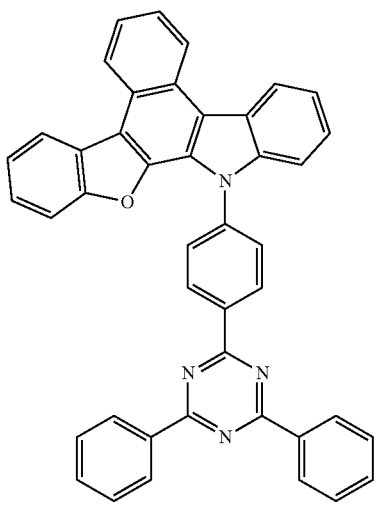
H2-154
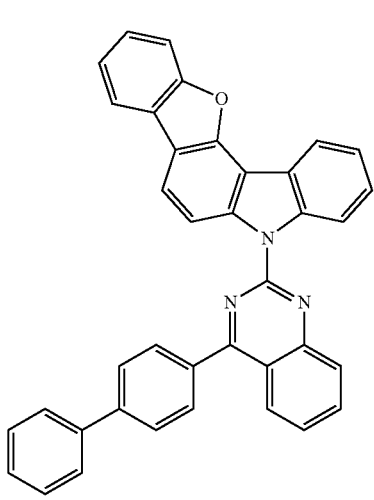
-continued
H2-155
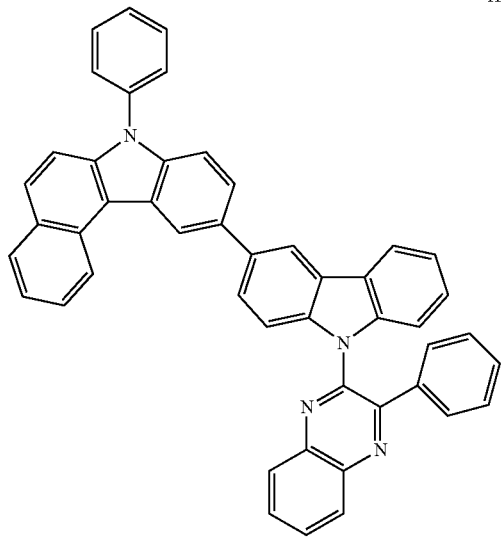
H2-156
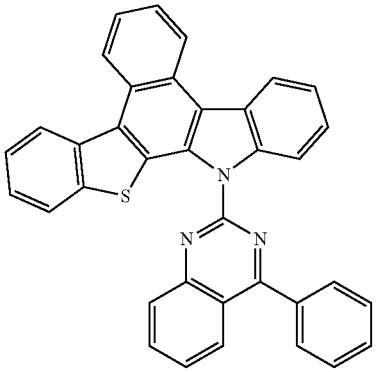
H2-157
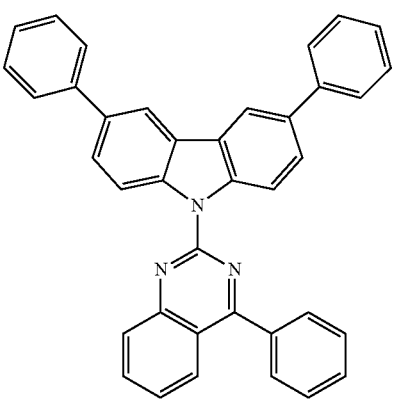

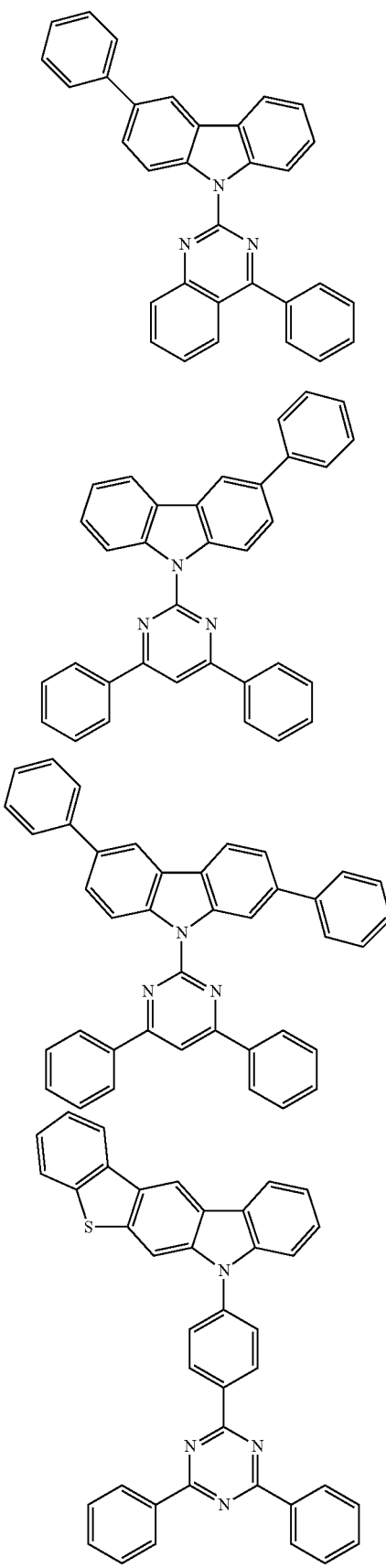
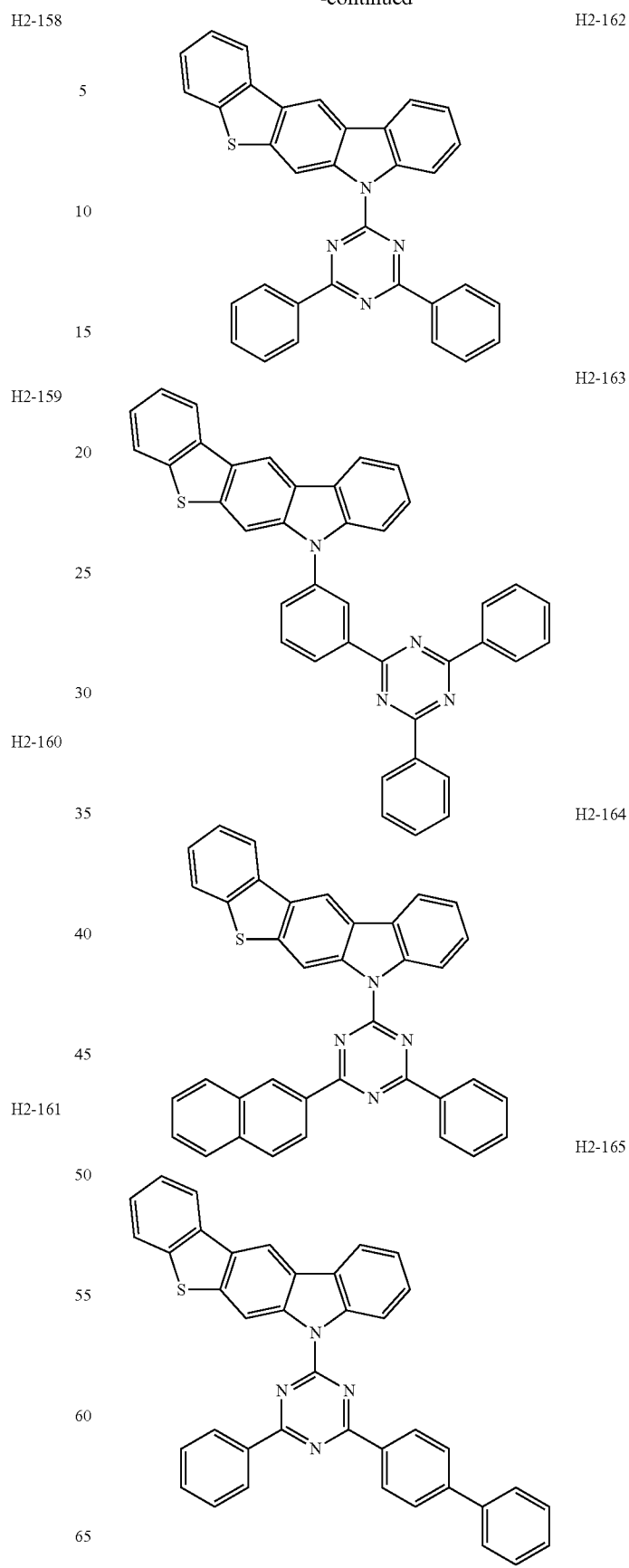

H2-166
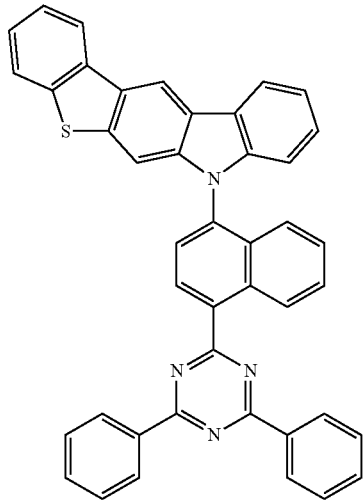
H2-167
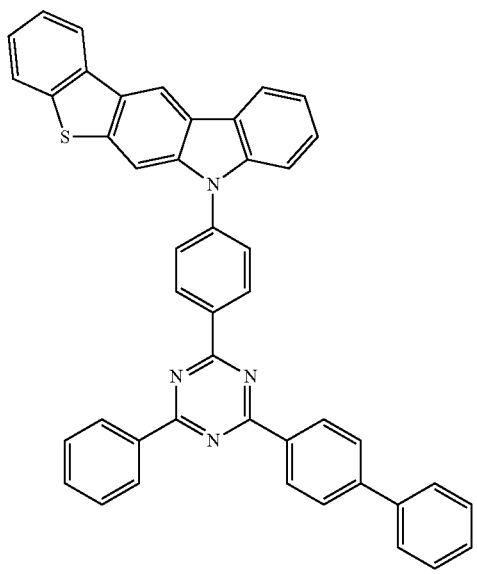
H2-168
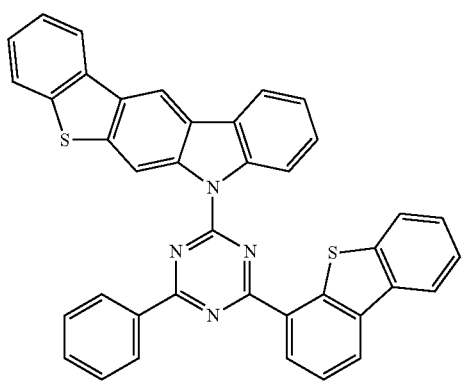
H2-169
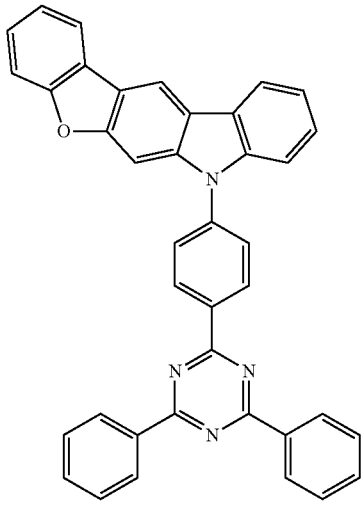
H2-170
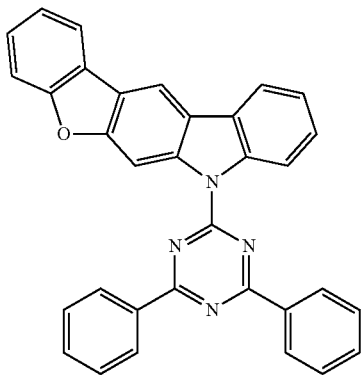
H2-171
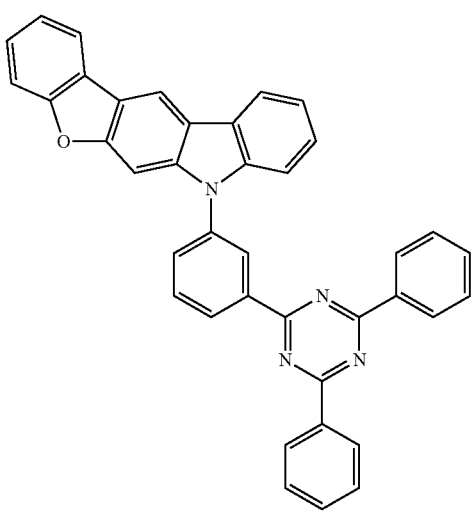

-continued
H2-172
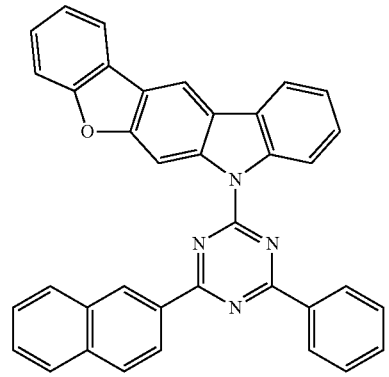
H2-173
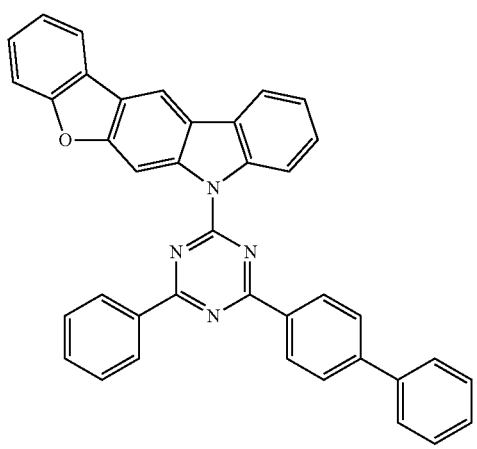
H2-174
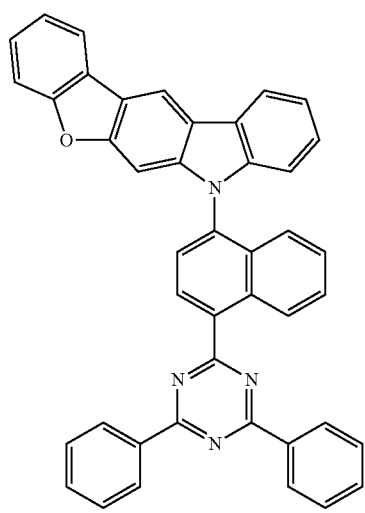
-continued
H2-175
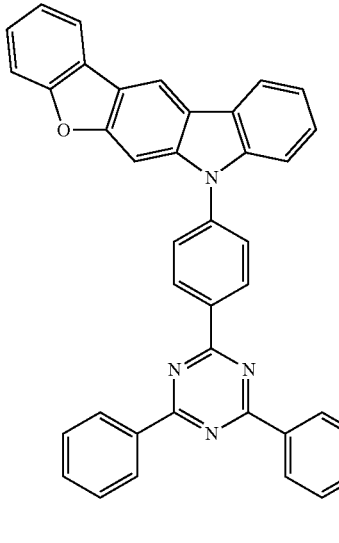
H2-176
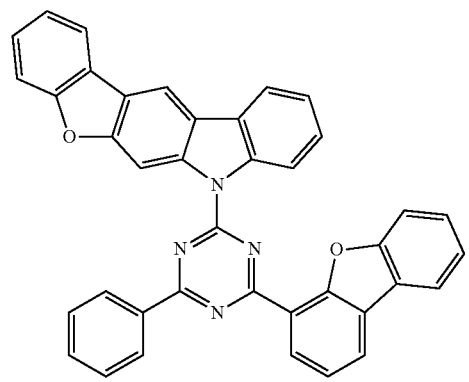
H2-177
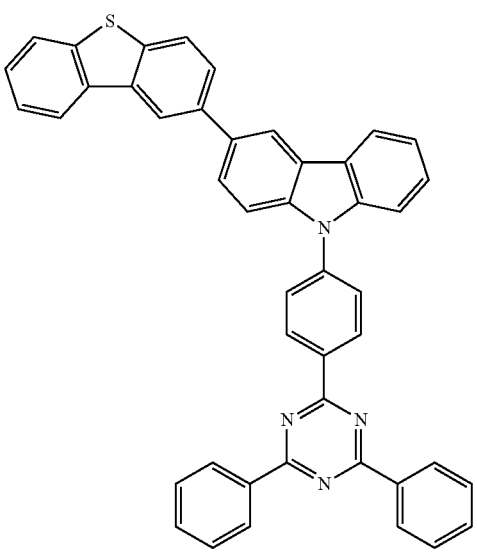

H2-178
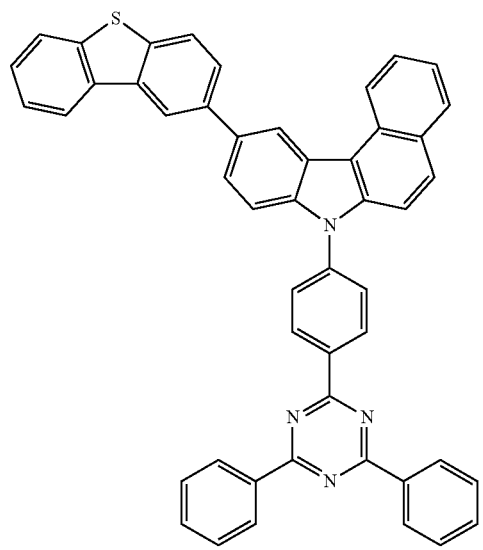
H2-179
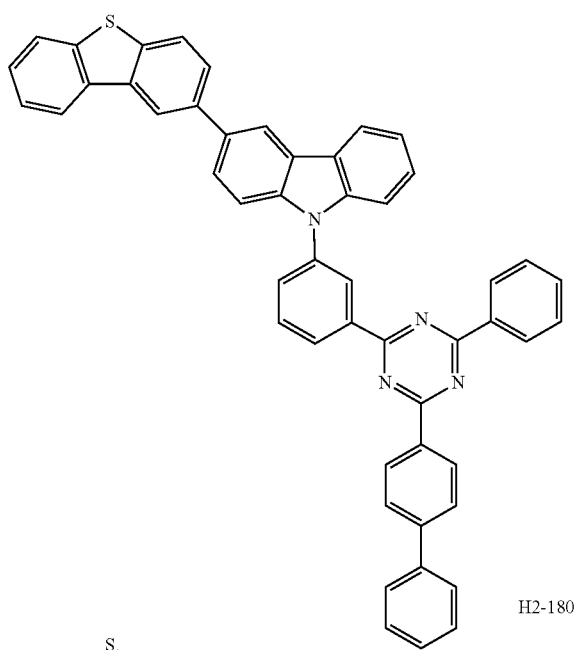
H2-180
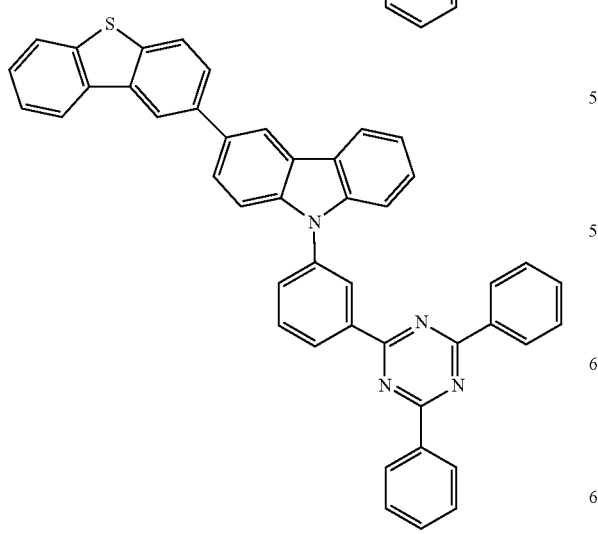
H2-181
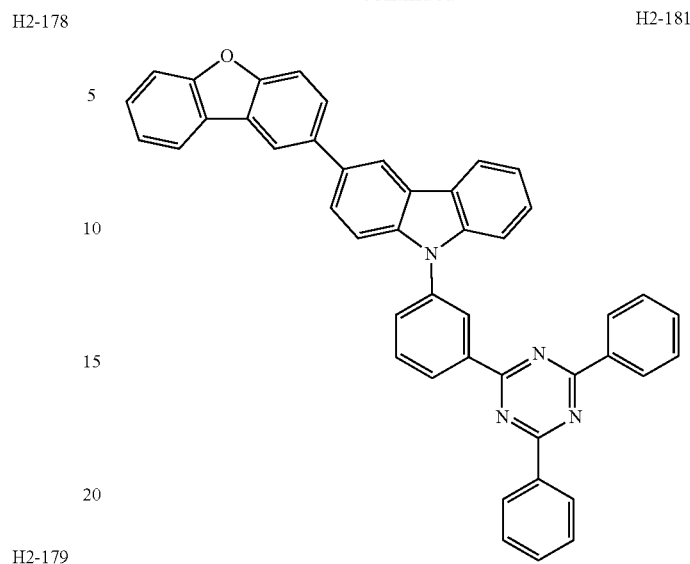
H2-182
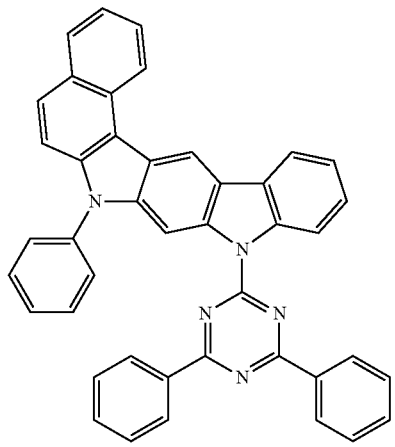
H2-183
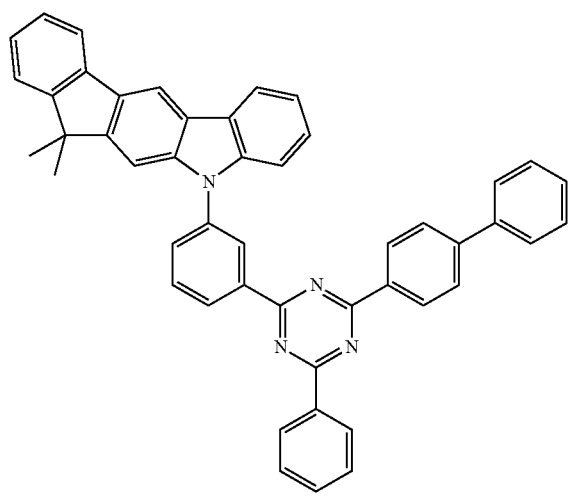

H2-184
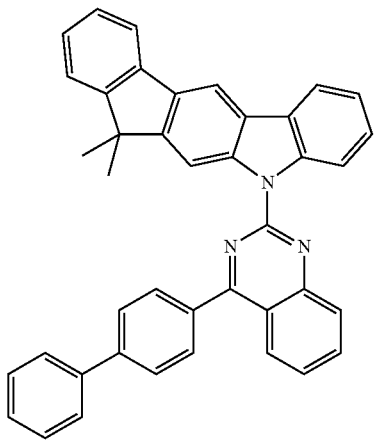
H2-185
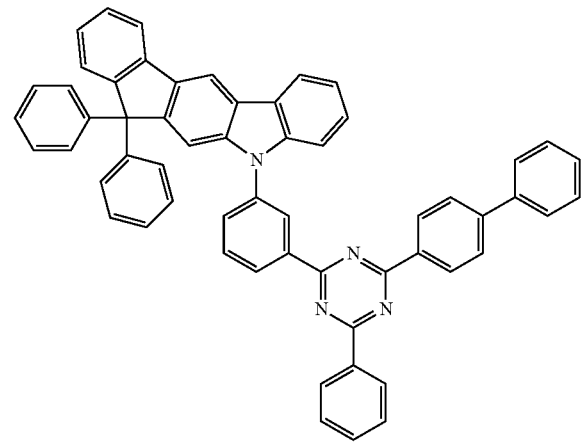
H2-186
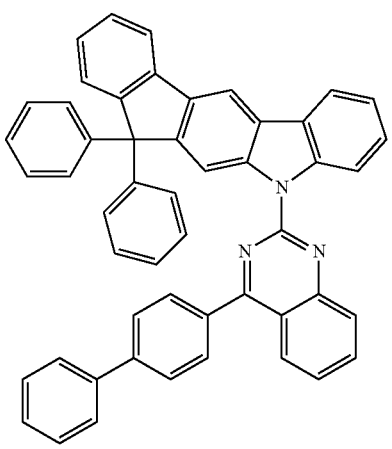
H2-187
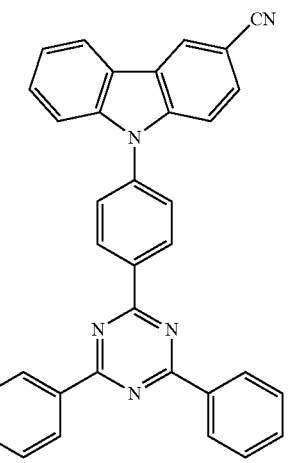
H2-188
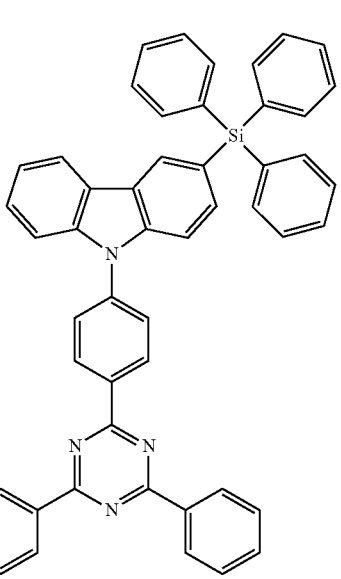
H2-189
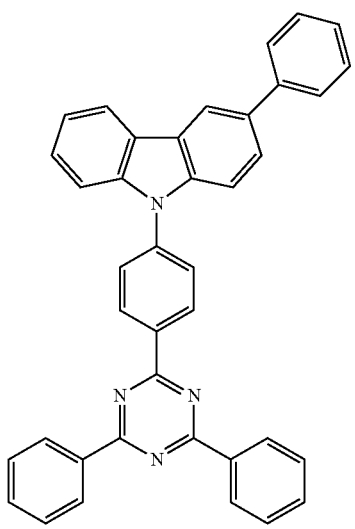

H2-190
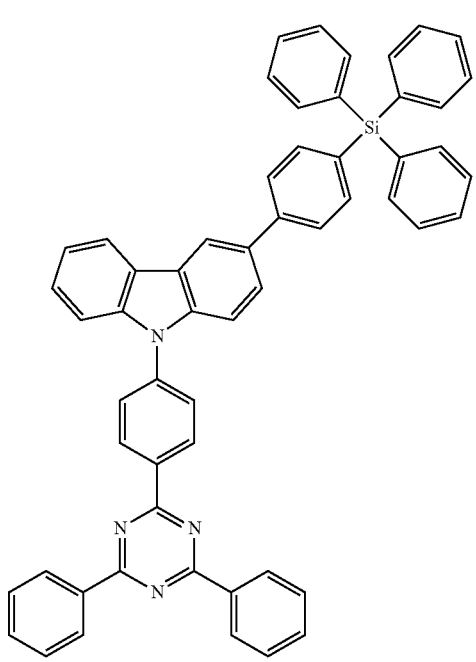
H2-191
H2-192
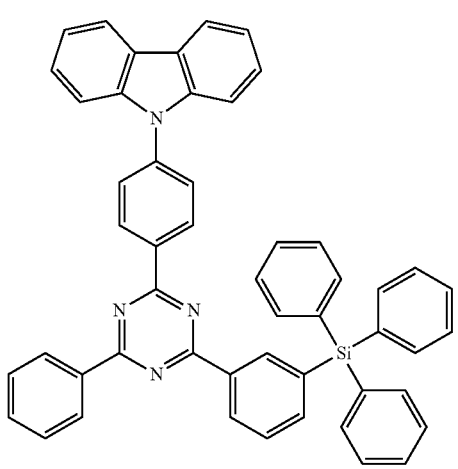
H2-193
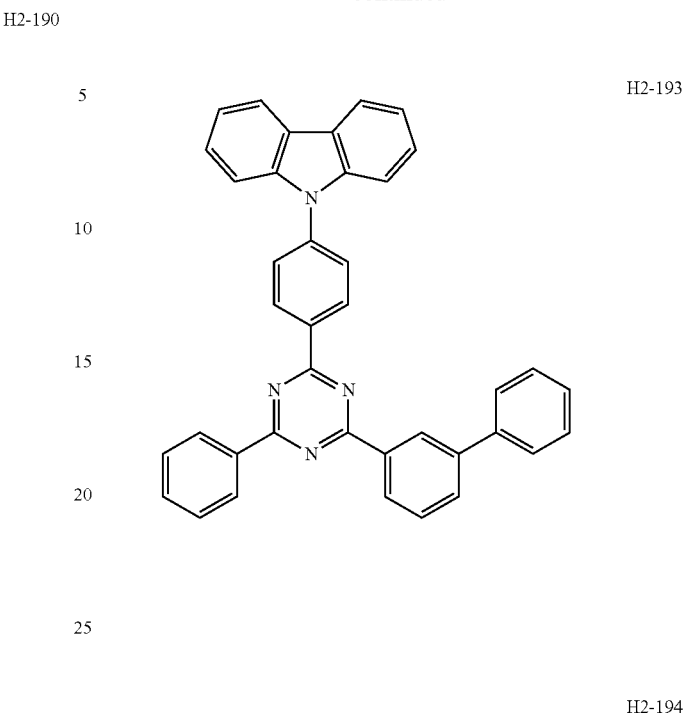
H2-194
H2-195
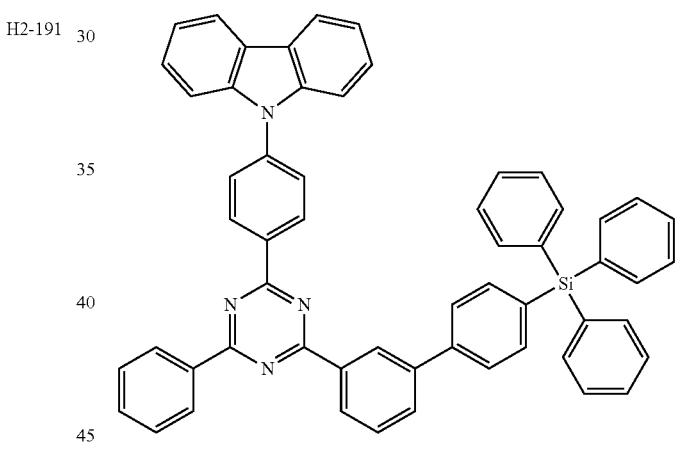
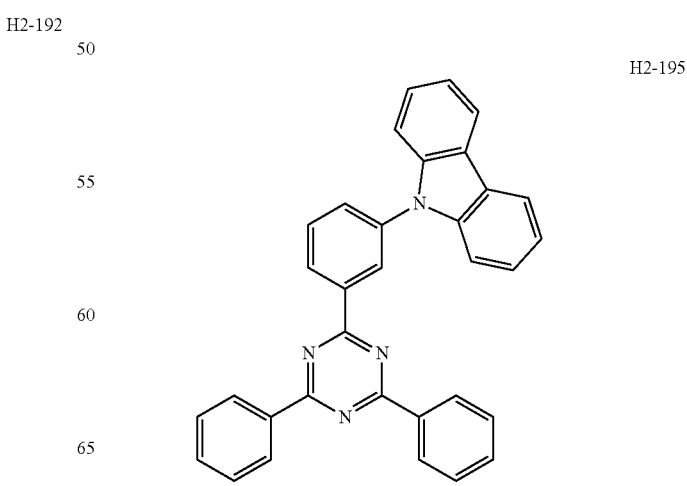

H2-196
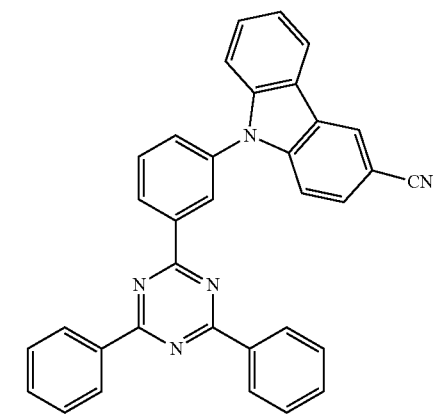
H2-197
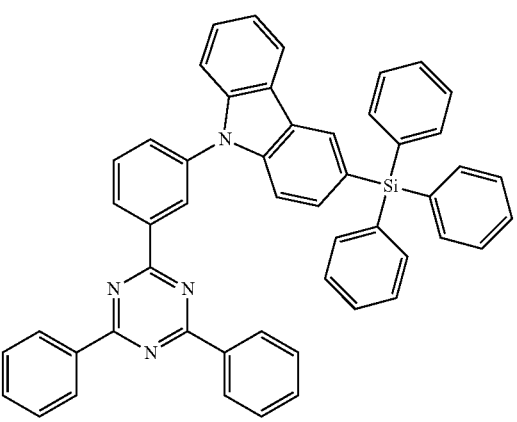
H2-198
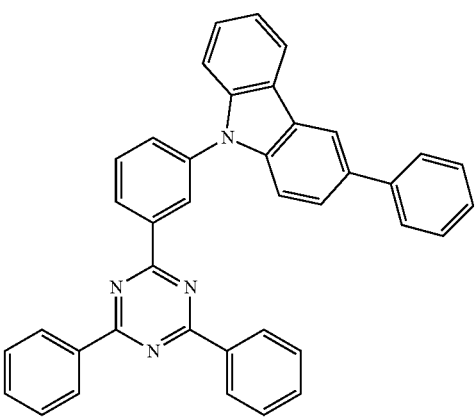
H2-199
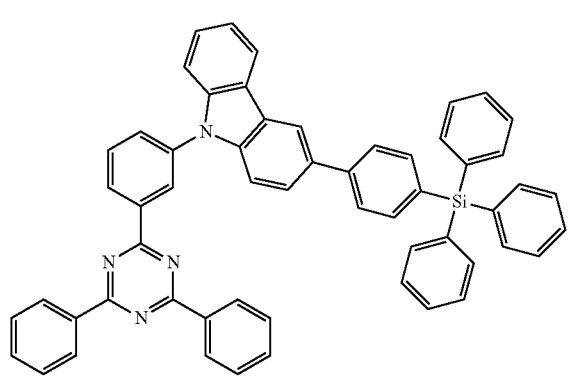
H2-200
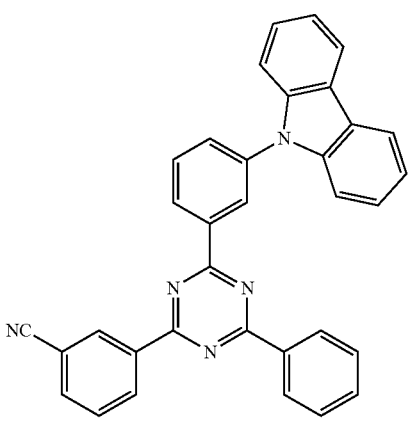
H2-201
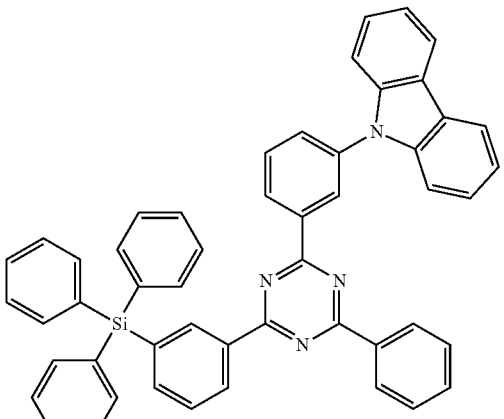
H2-202
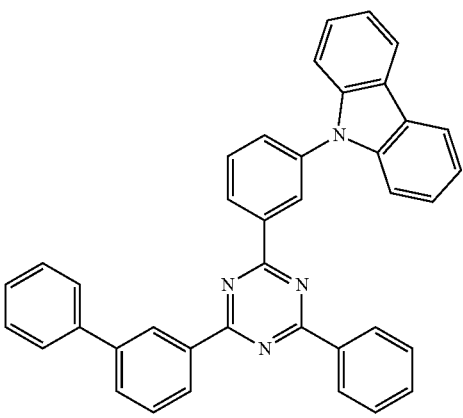

-continued
H2-203
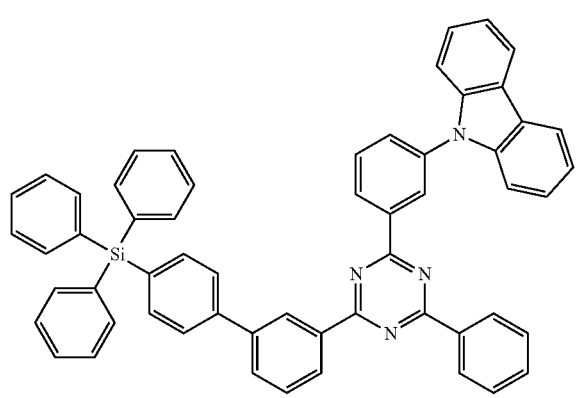
H2-204
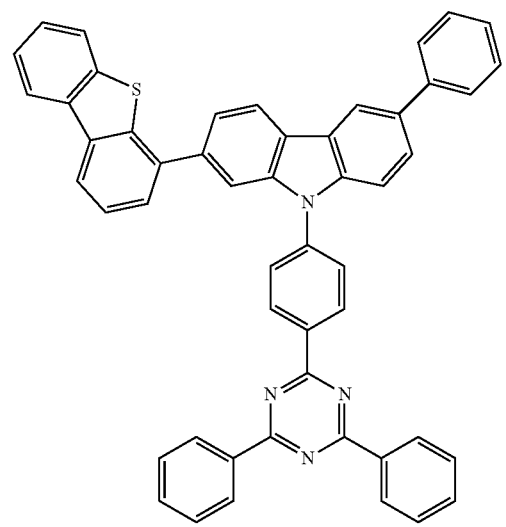
H2-205
-continued
H2-206
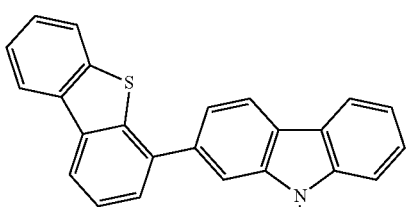
H2-207
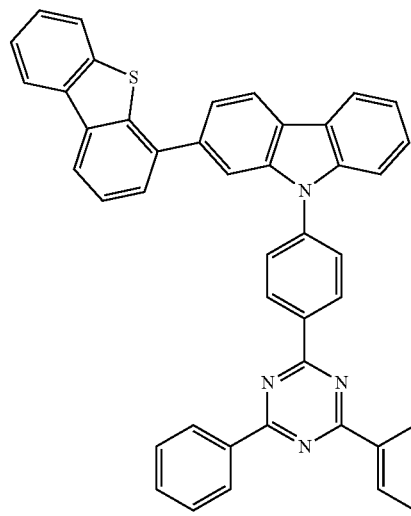
H2-208
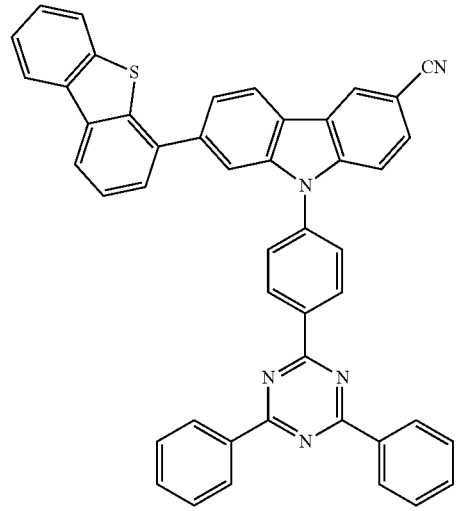

H2-209
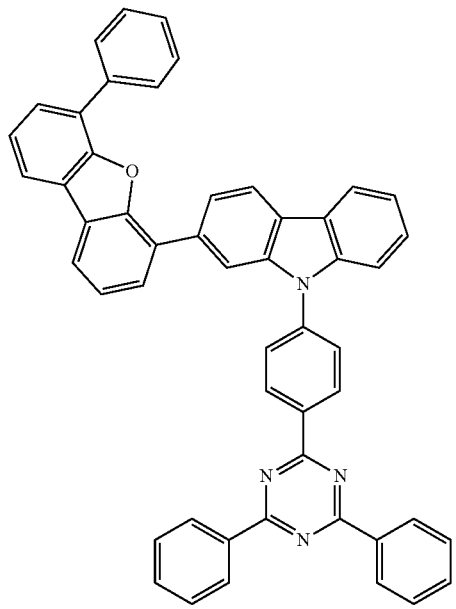
H2-210
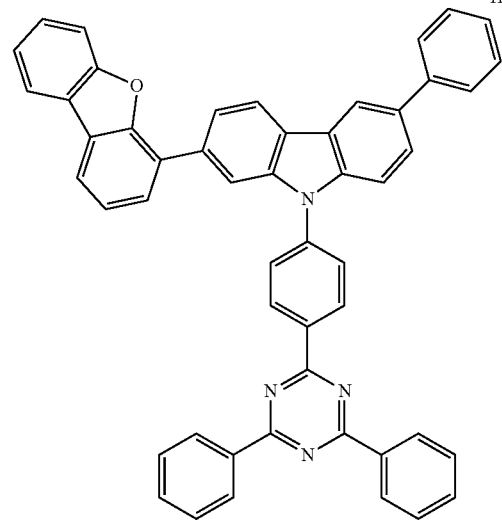
H2-211
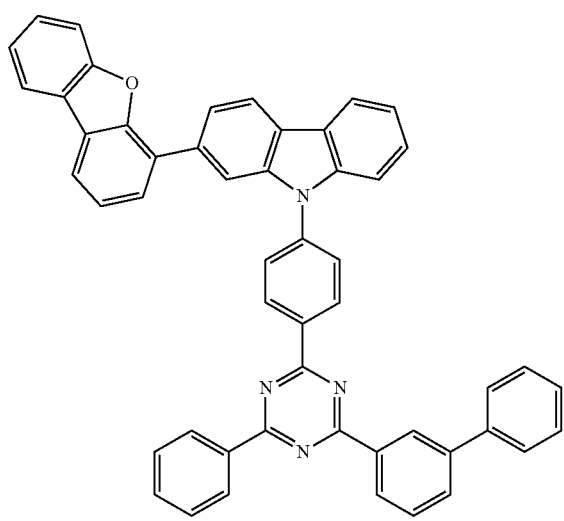
H2-212
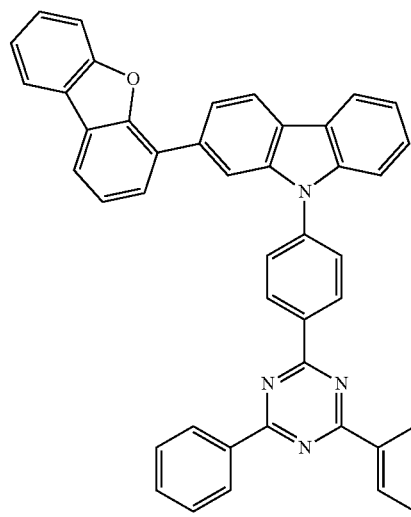
H2-213
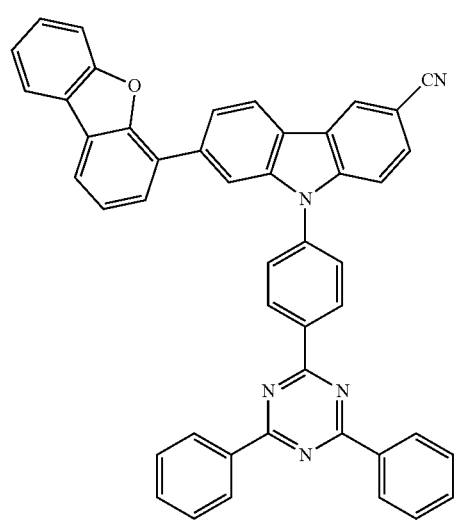
H2-214
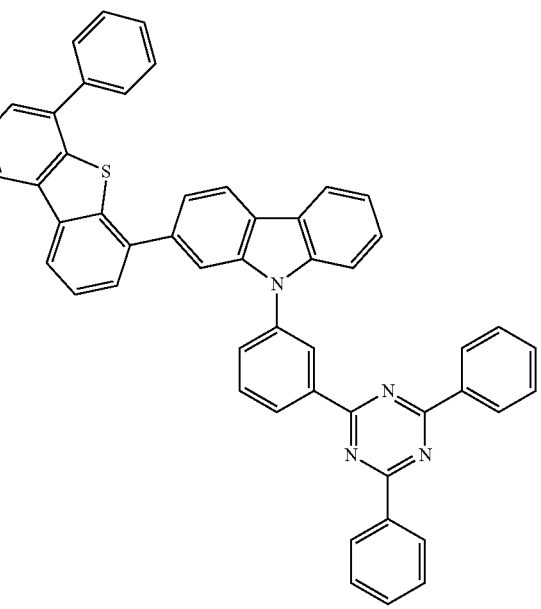

H2-215
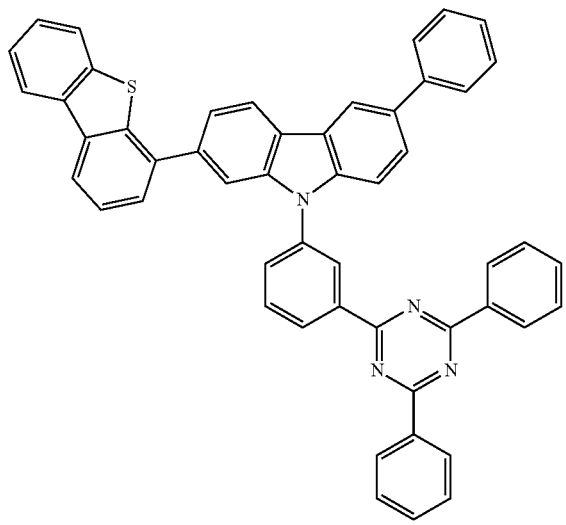
H2-216
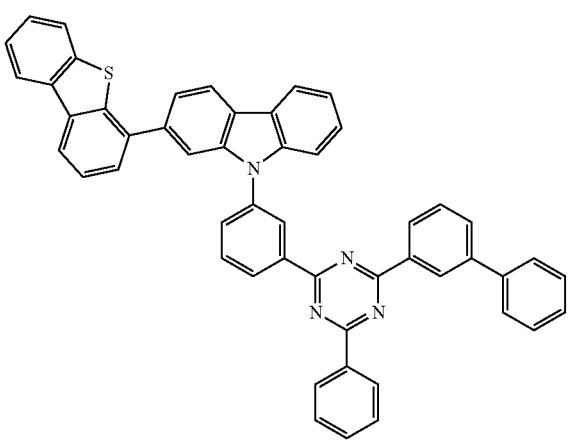
H2-217
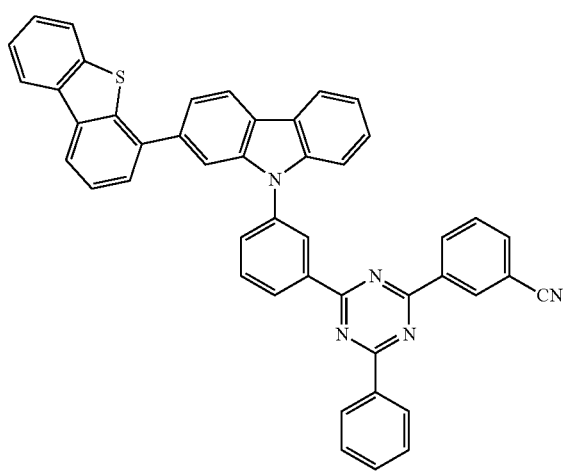
H2-218
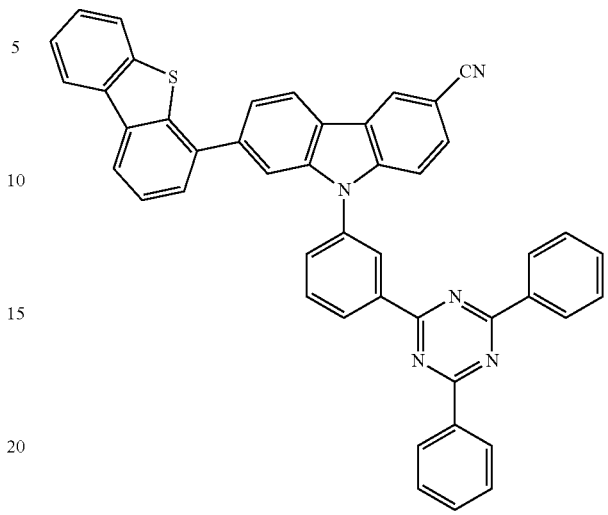
H2-219
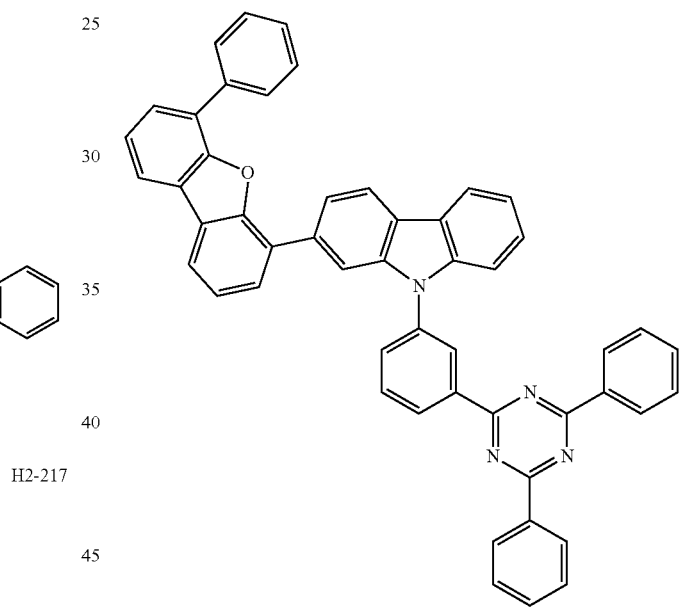

H2-220
H2-221
H2-222
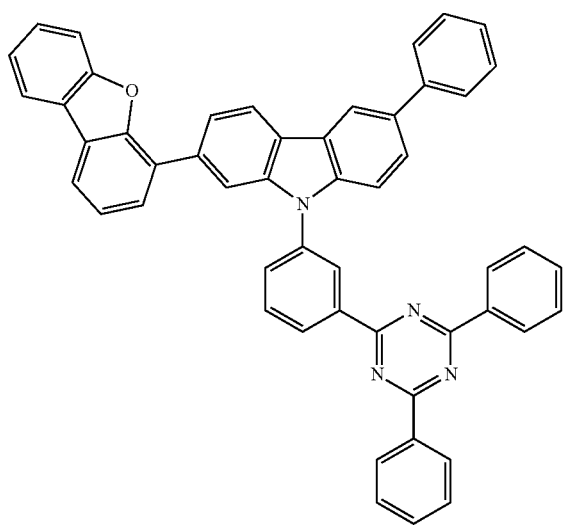
H2-223
H2-224
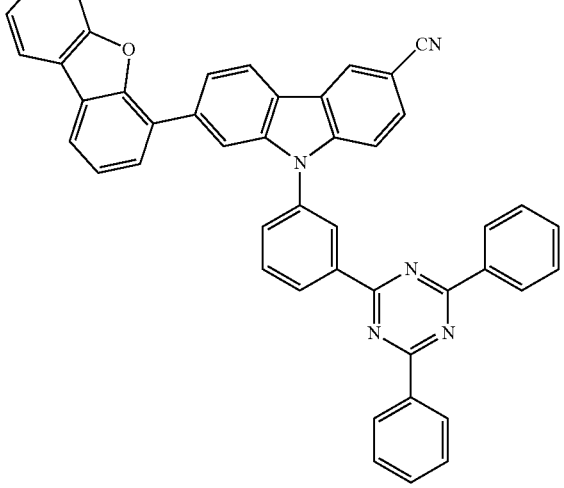
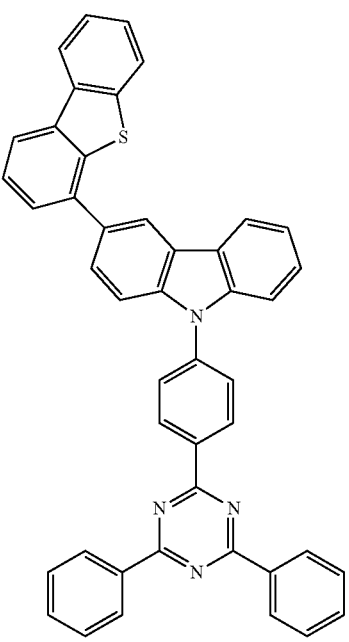

H2-225
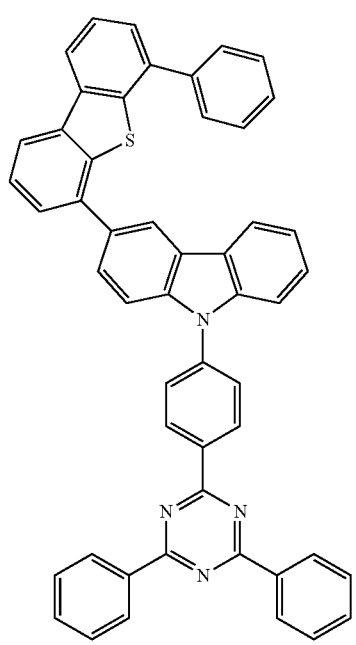
H2-227
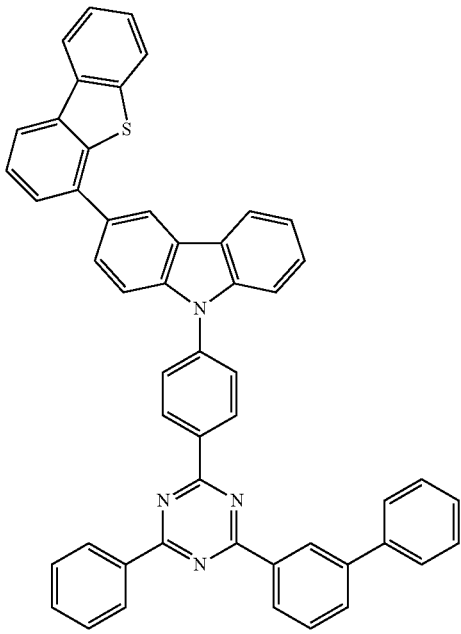
H2-226
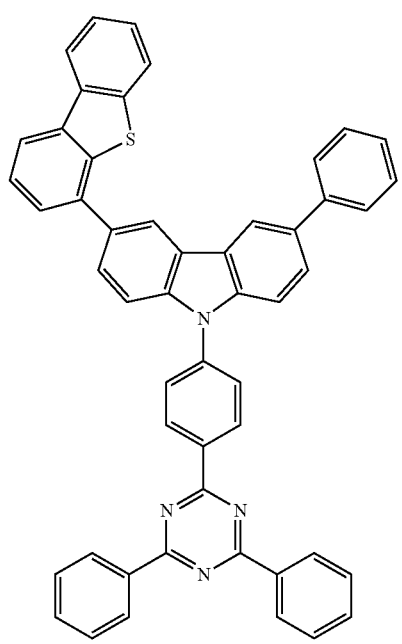
H2-228
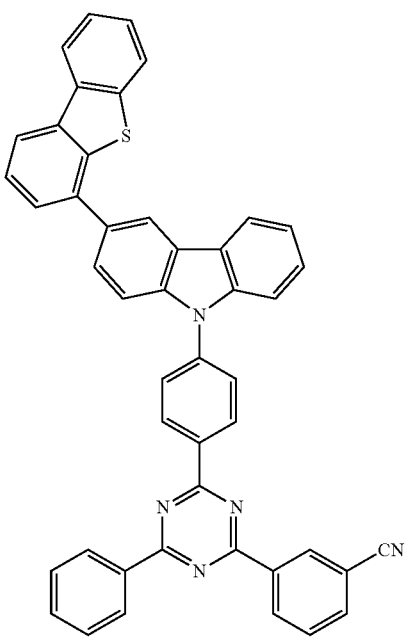

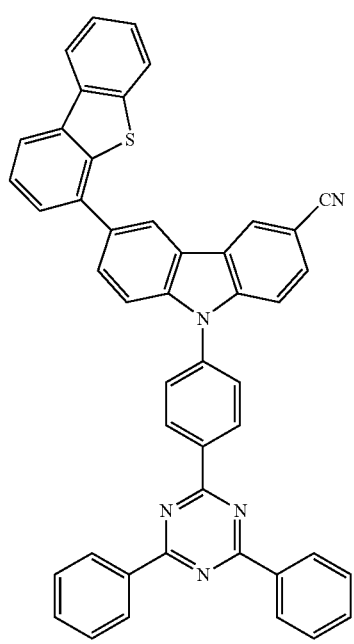 H2-229
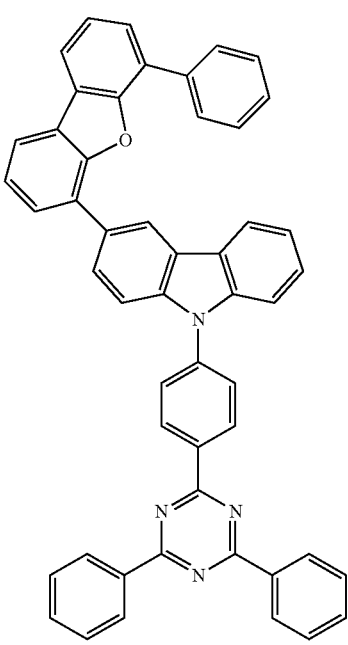 H2-231
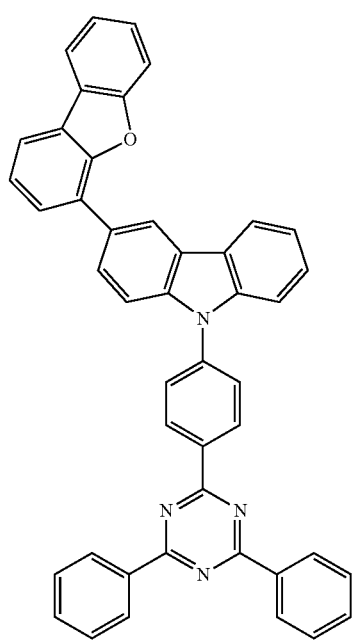 H2-230
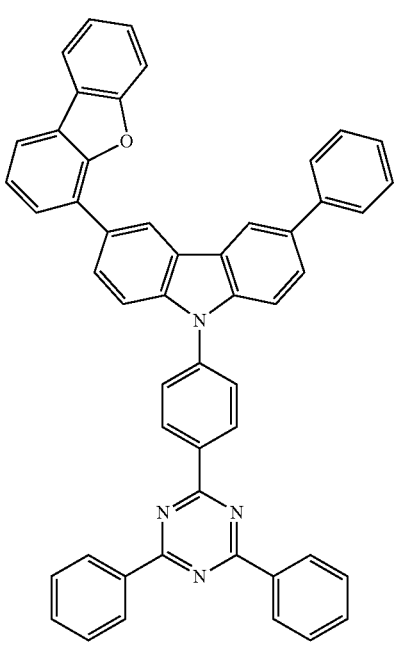 H2-232

H2-233
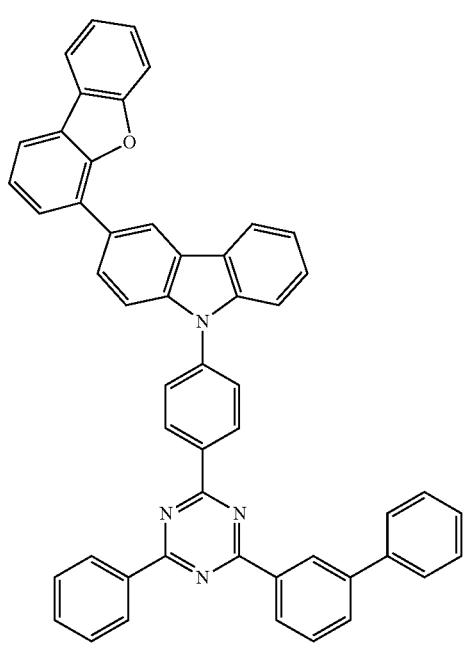
H2-234
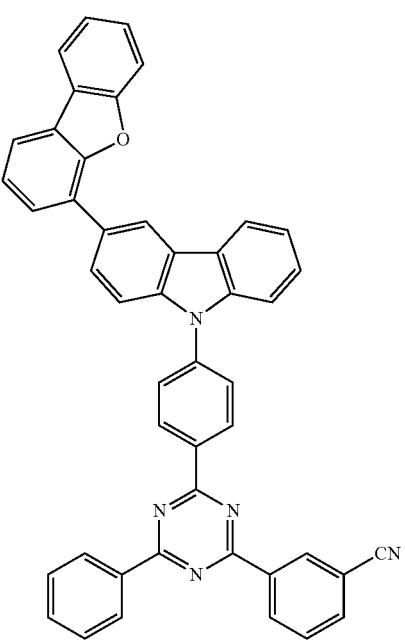
H2-235
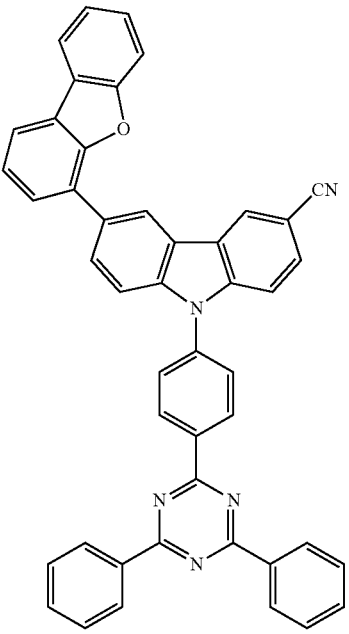
H2-236
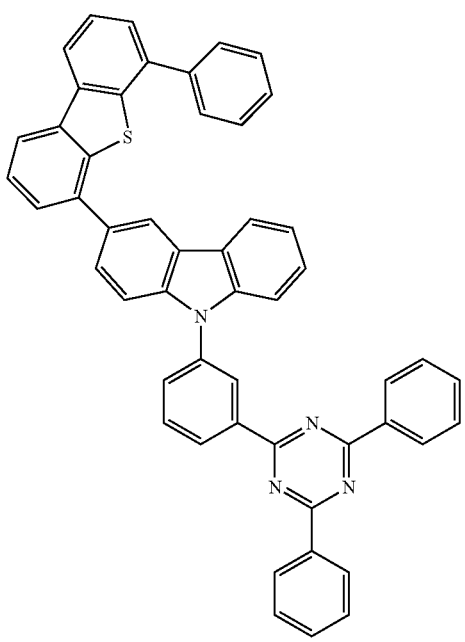

-continued
H2-237
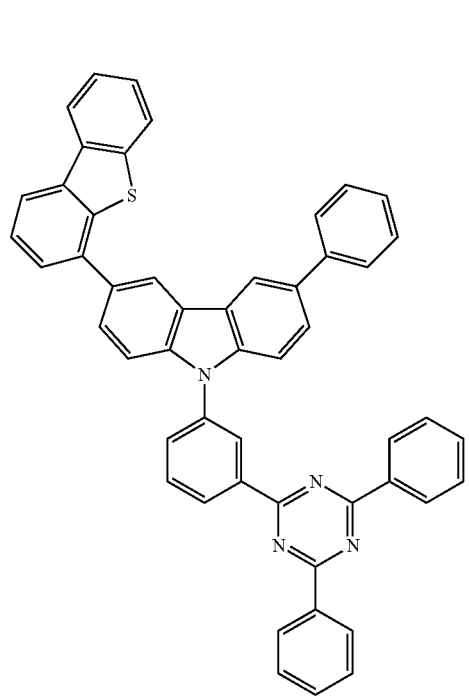
H2-239
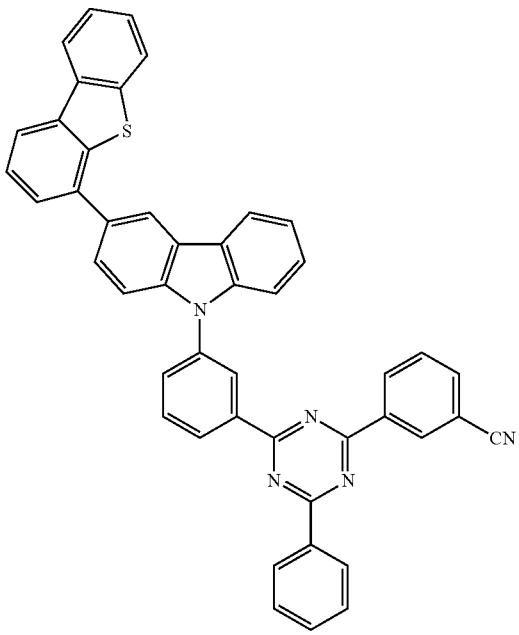
H2-238
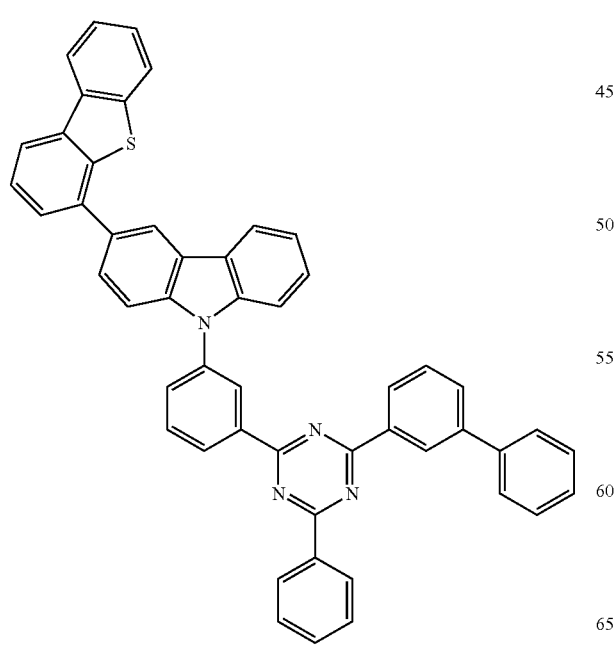
H2-240
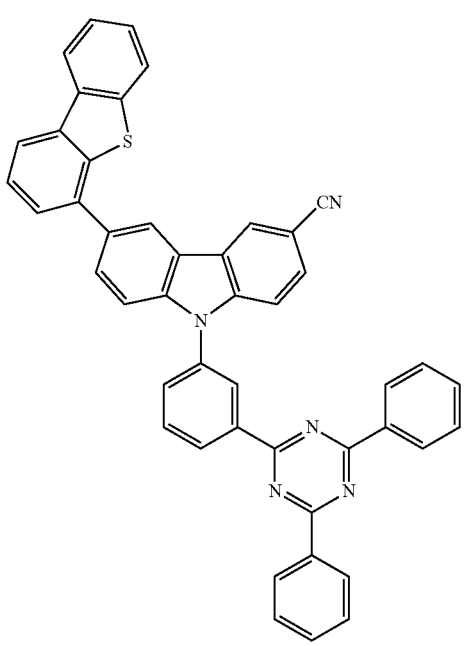

H2-241
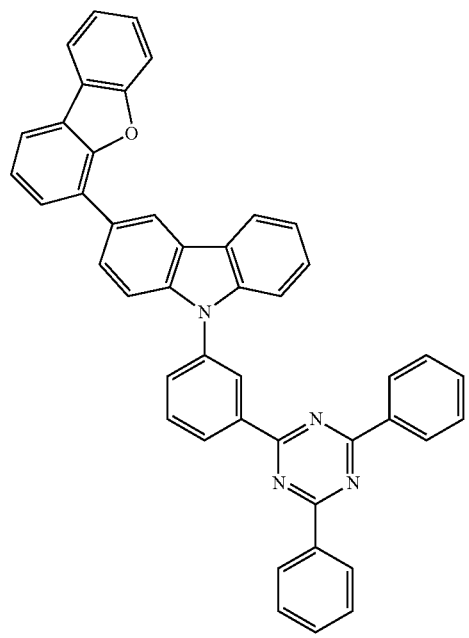
H2-243
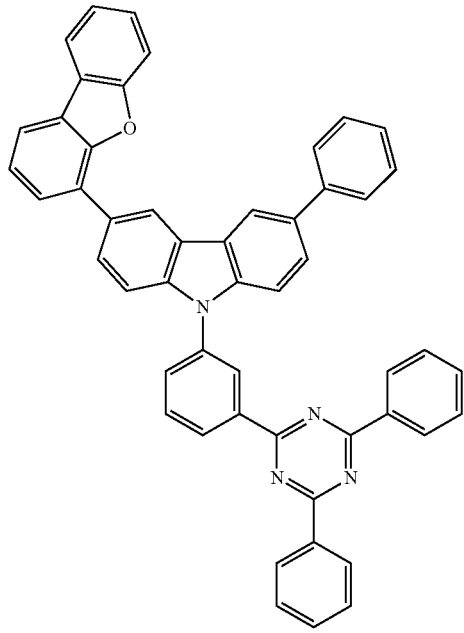
H2-242
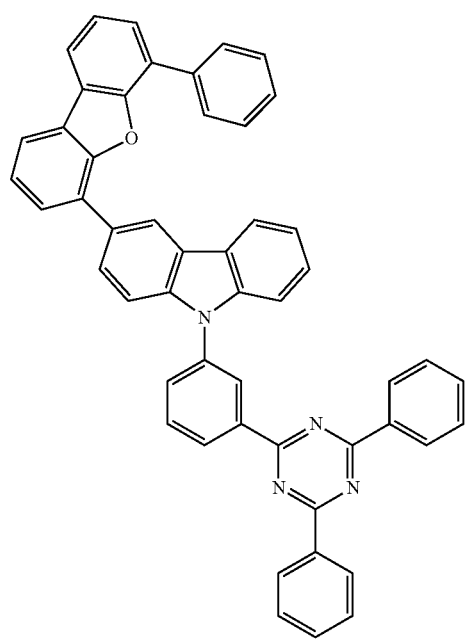
H2-244
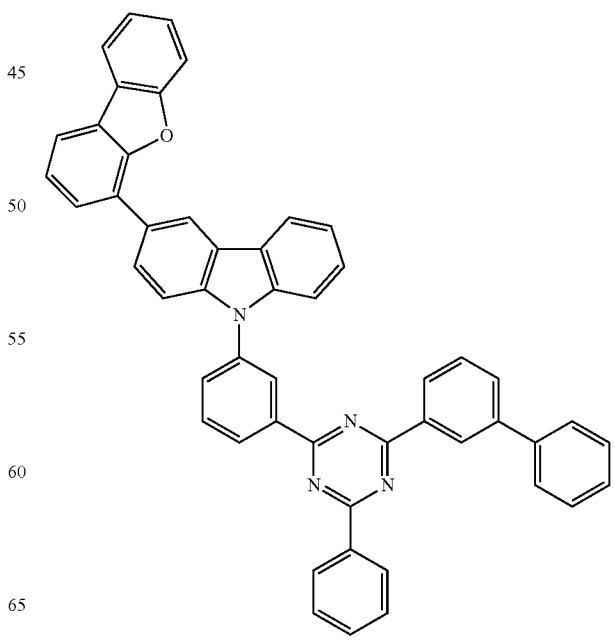

H2-245
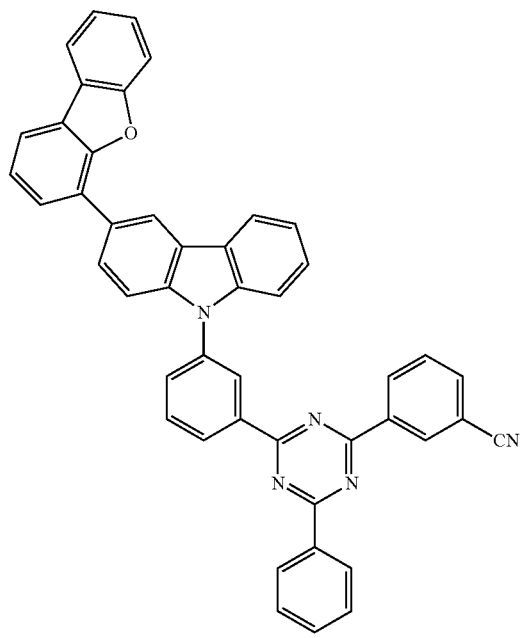
H2-246
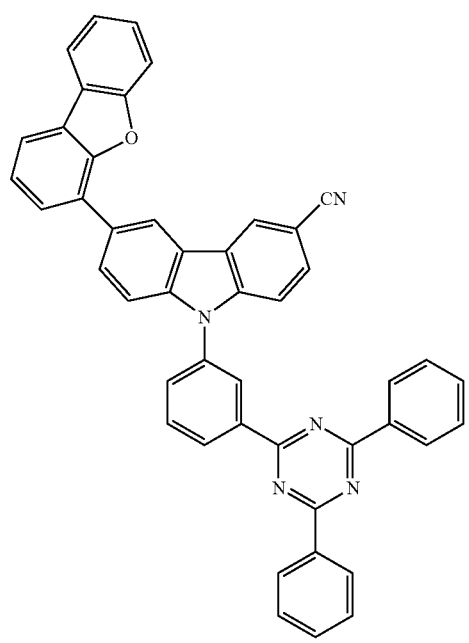
H2-247
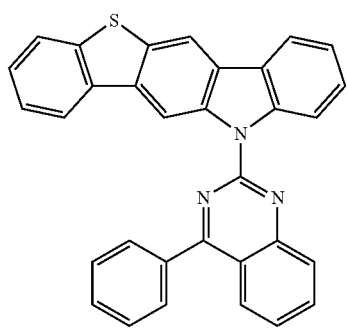
H2-248
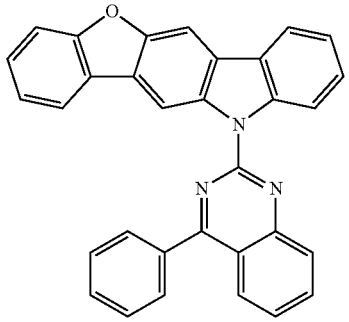
H2-249
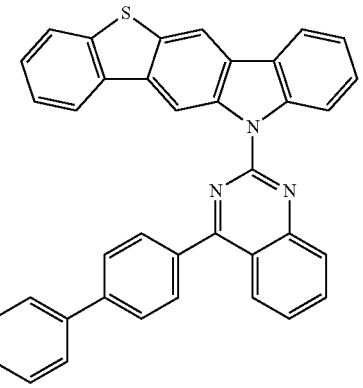
H2-250
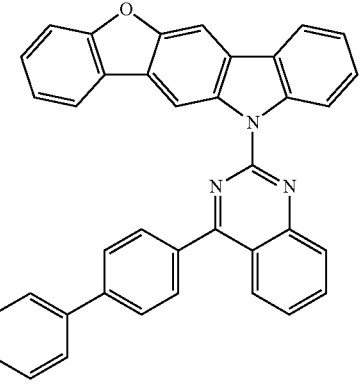
H2-251
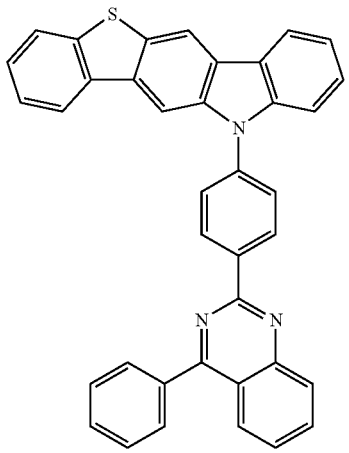

H2-252
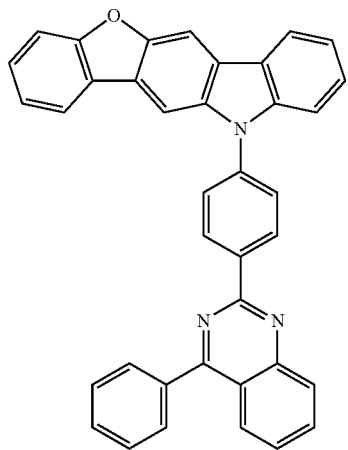
H2-255
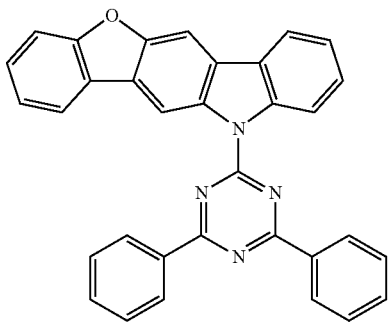
H2-256
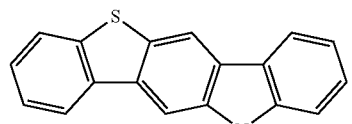
H2-253
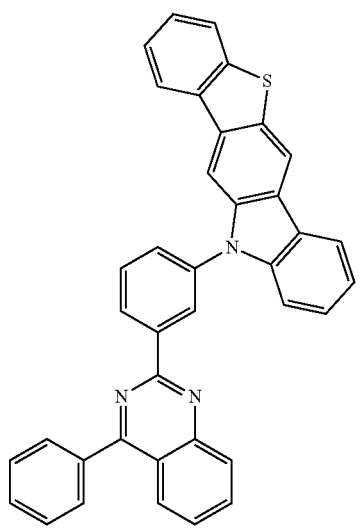
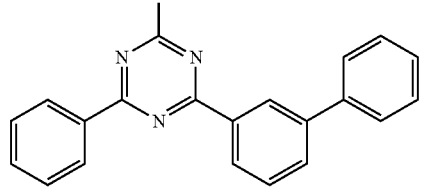
H2-257
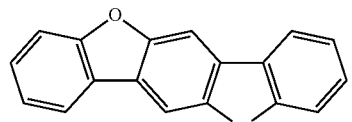
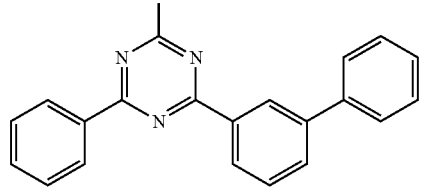
H2-254
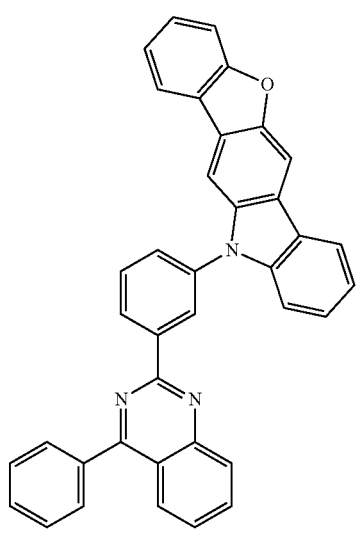
H2-258
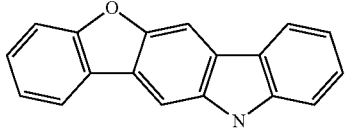
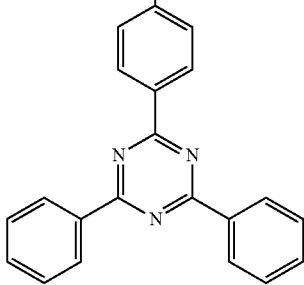

-continued
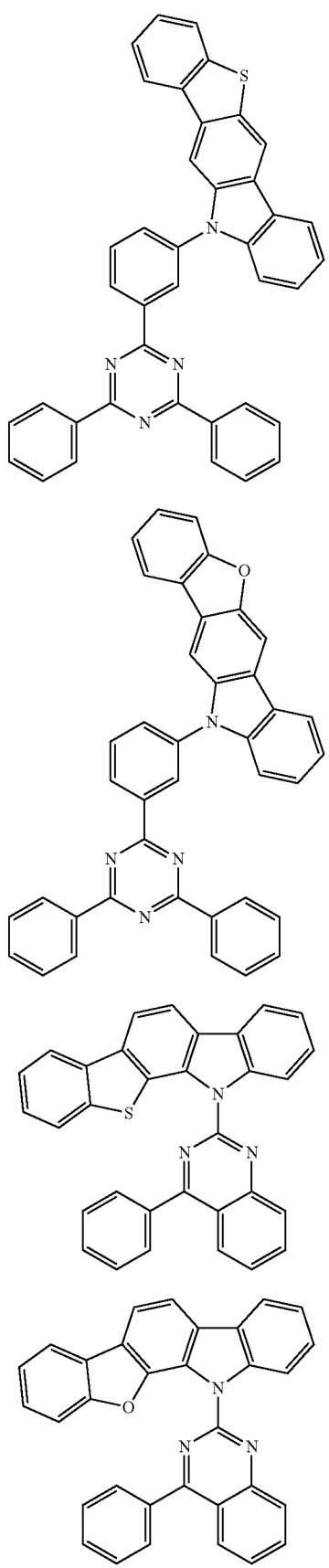
H2-259
H2-260
H2-261
H2-262
-continued
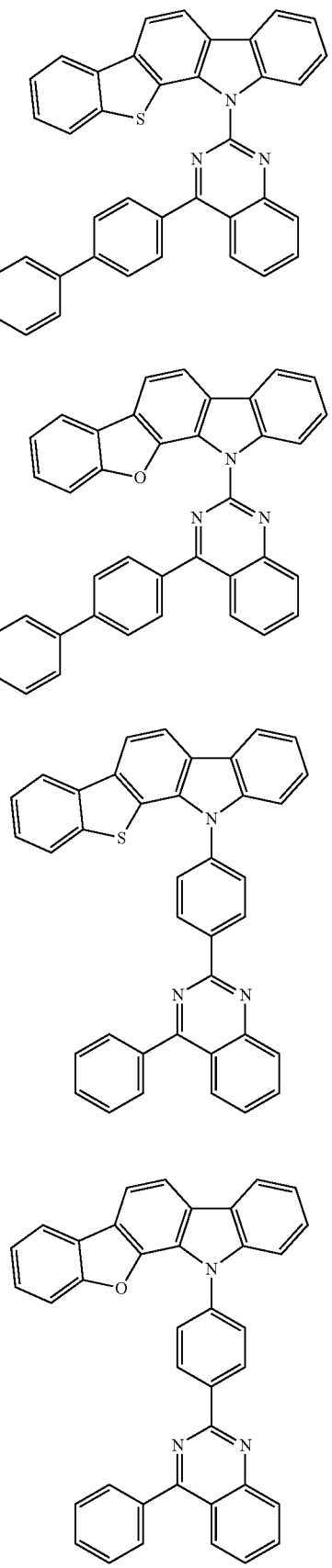
H2-263
H2-264
H2-265
H2-266

H2-267
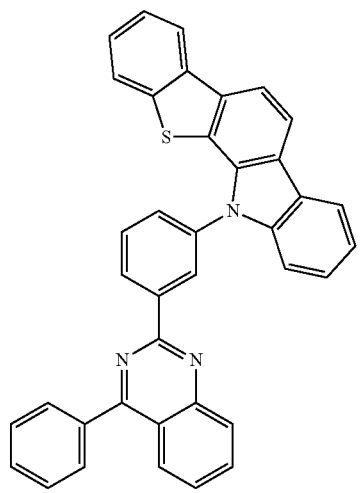
H2-268
H2-269
H2-270
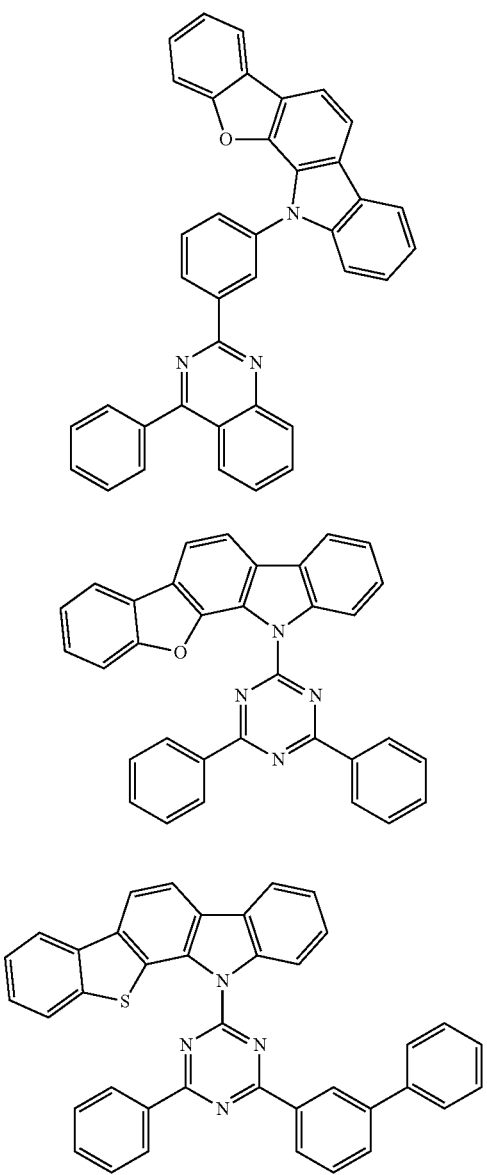
H2-271
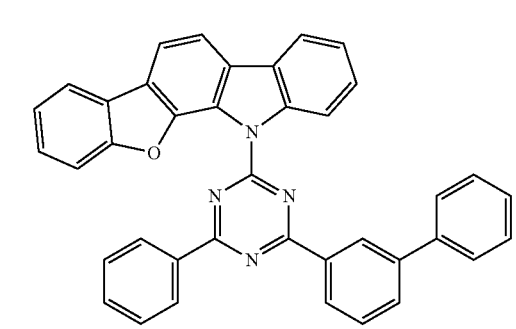
H2-272
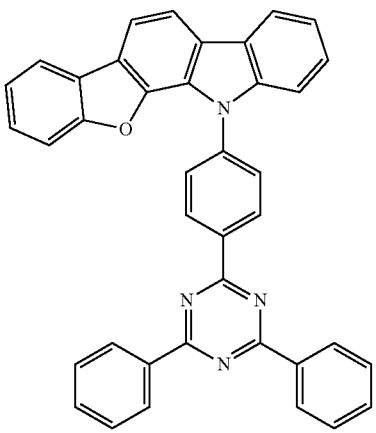
H2-273
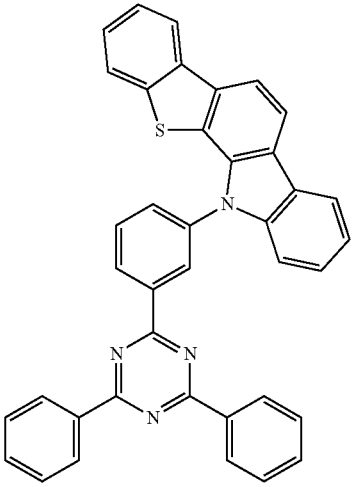

H2-274
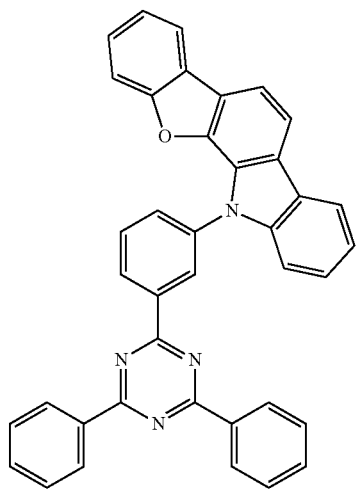
H2-275
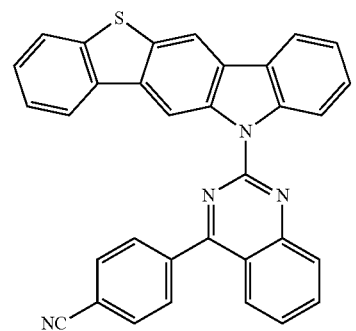
H2-276
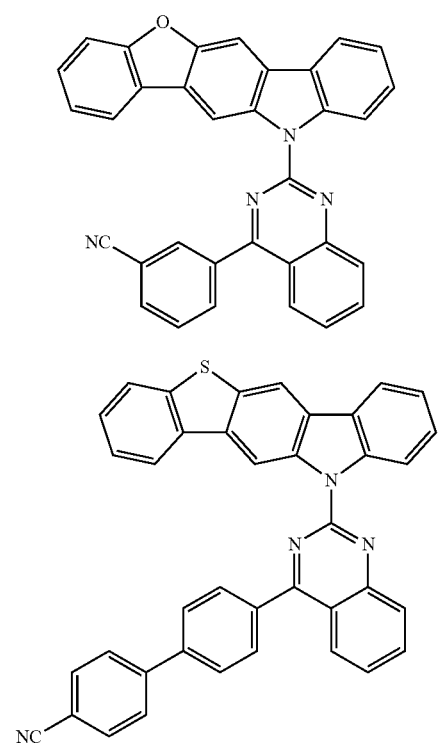
H2-277
H2-278
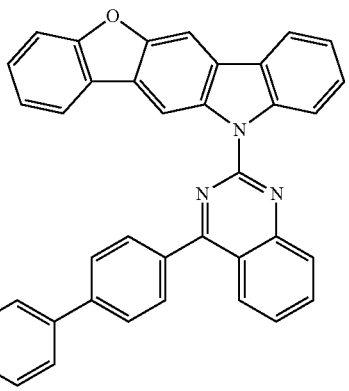
H2-279
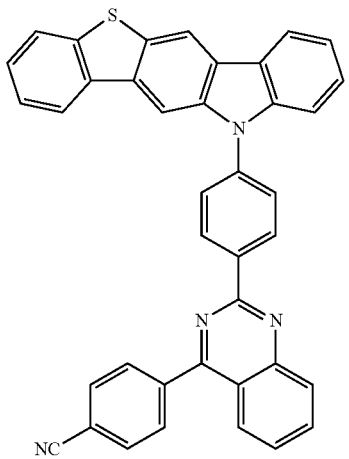
H2-280
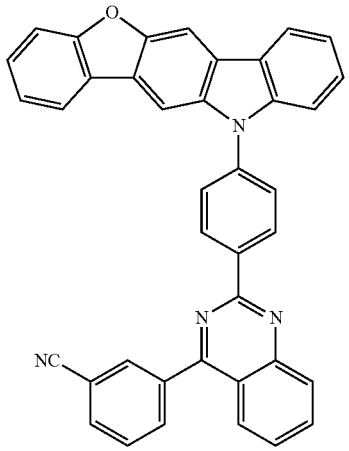

-continued
H2-281
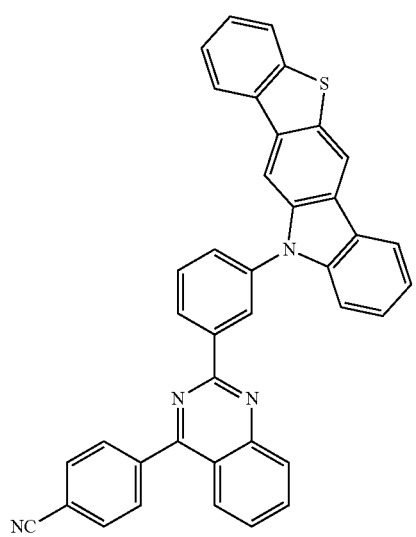
H2-282
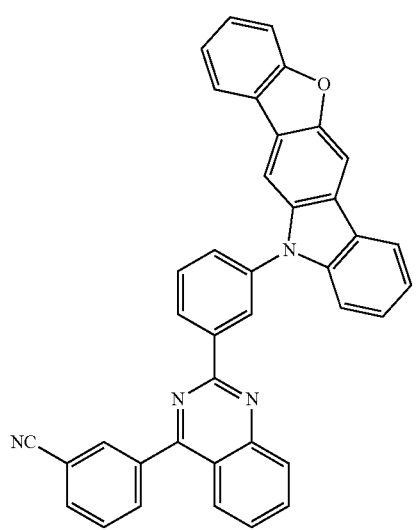
H2-283
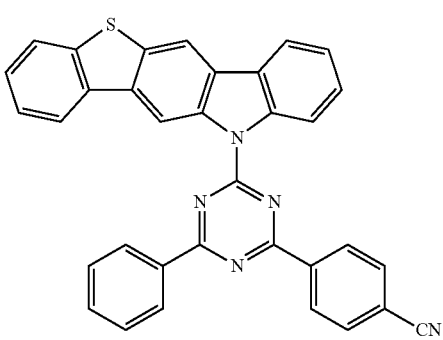
-continued
H2-284
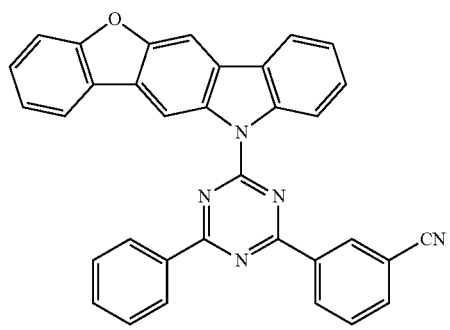
H2-285
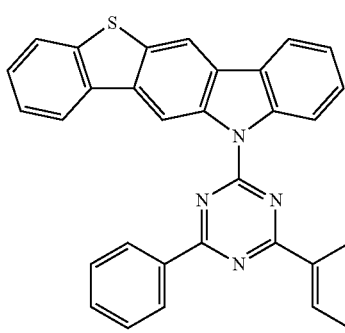
H2-286
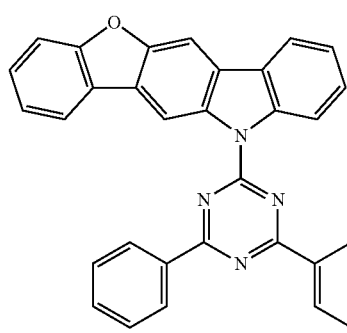
H2-287
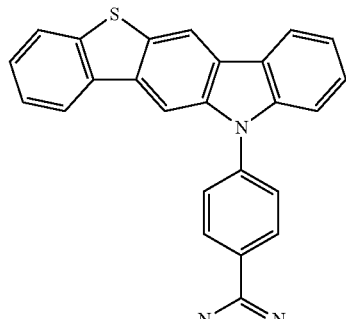
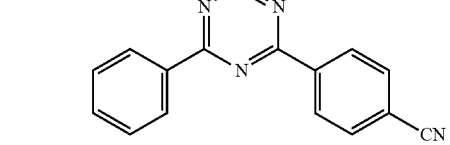

H2-288
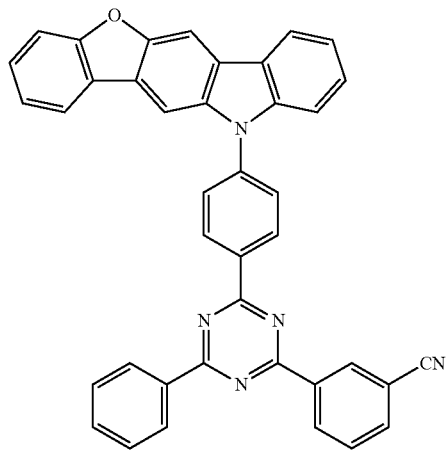
H2-289
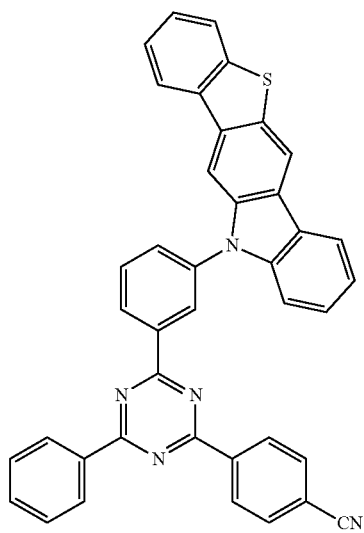
H2-290
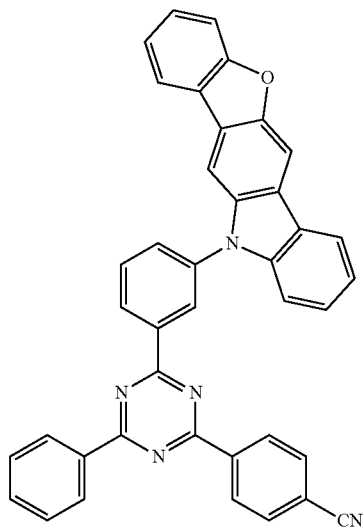
H2-291
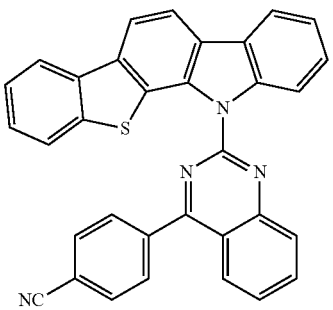
H2-292
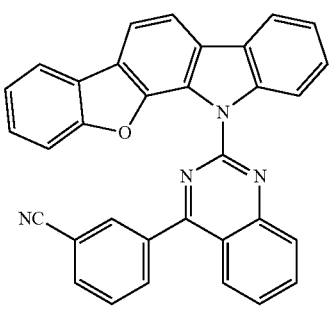
H2-293
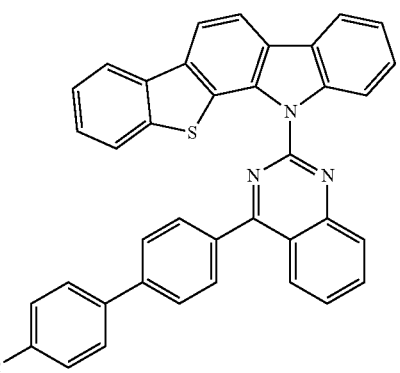
H2-294
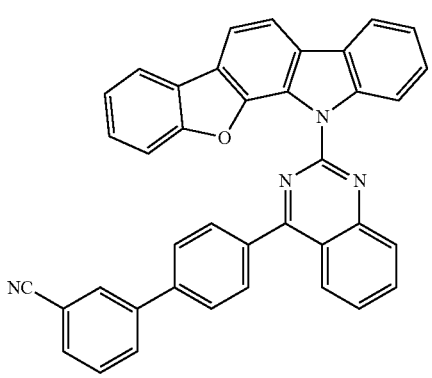

H2-295
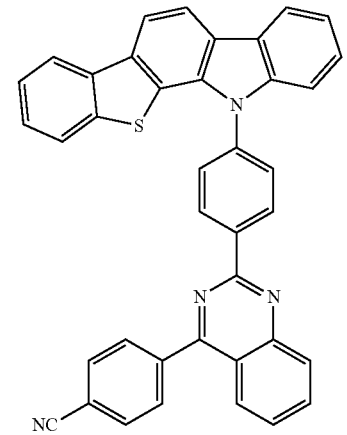
H2-296
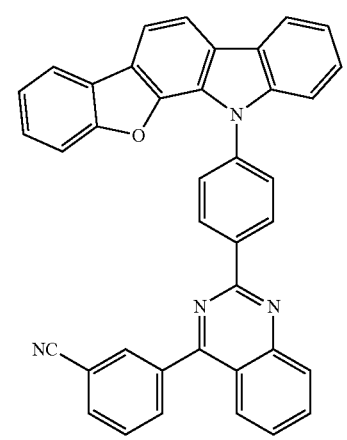
H2-297
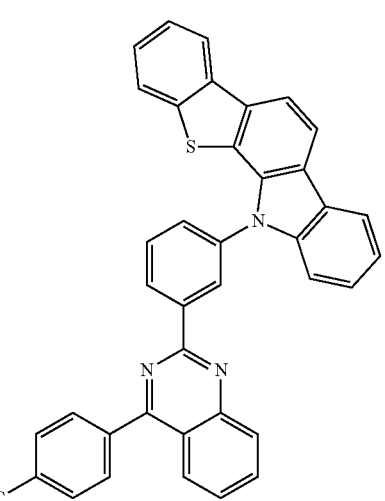
H2-298
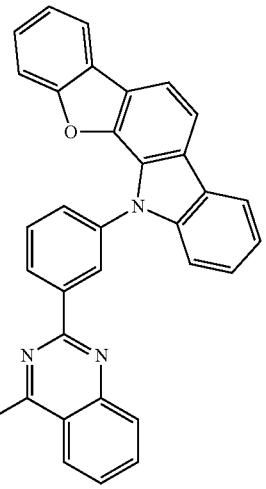
H2-299
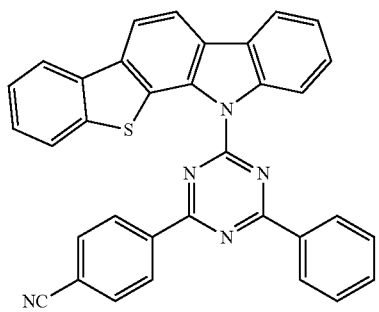
H2-300
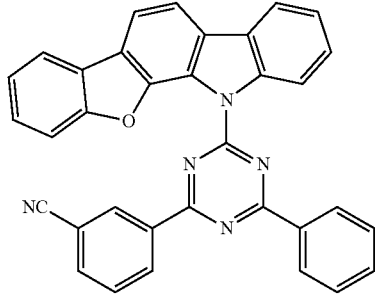
H2-301
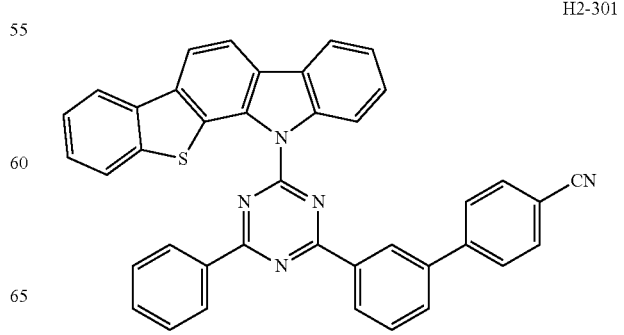

H2-302
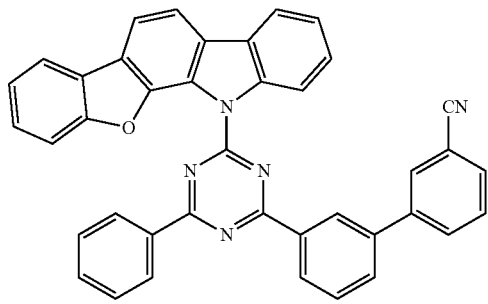
H2-303
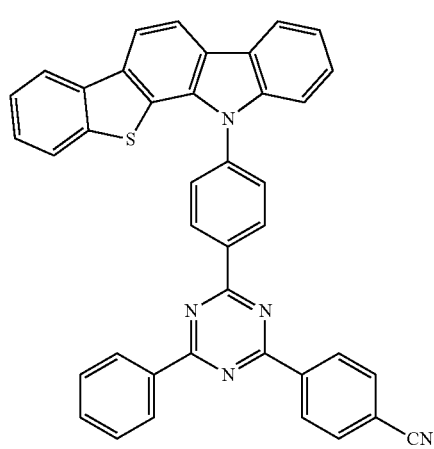
H2-304
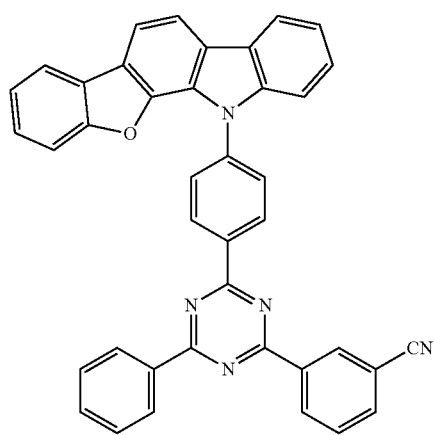
H2-305
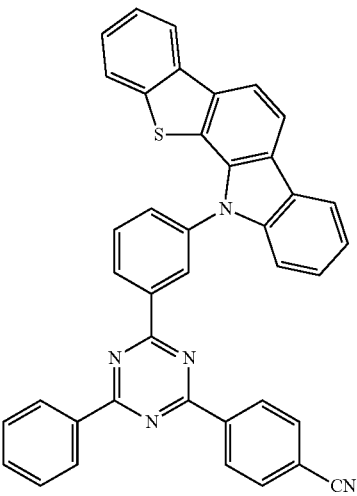
H2-306
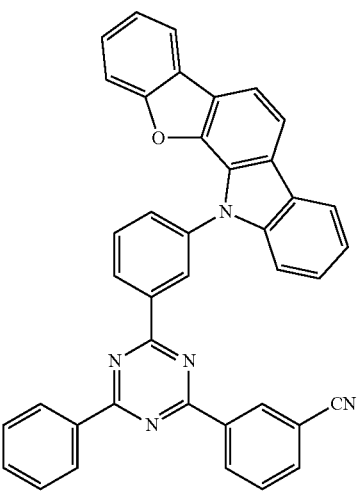
H2-307
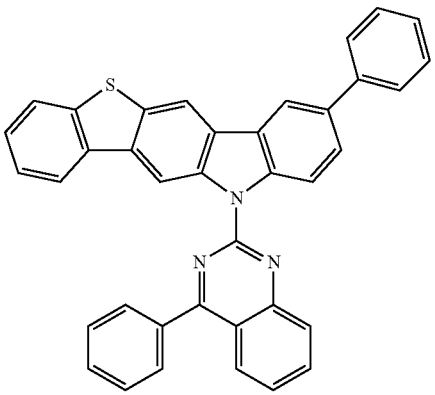

H2-308
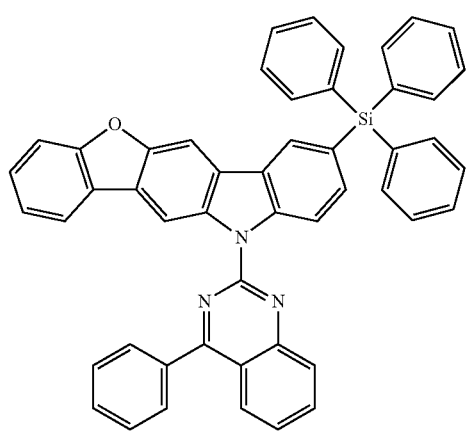
H2-309
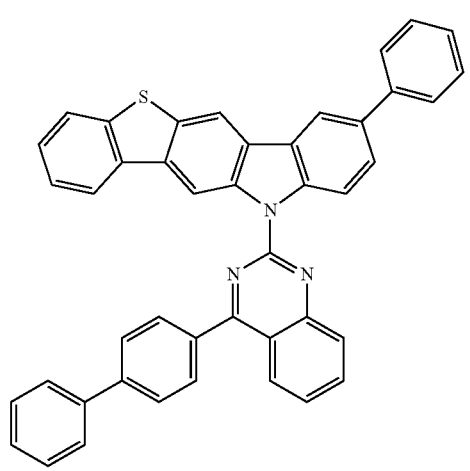
H2-310
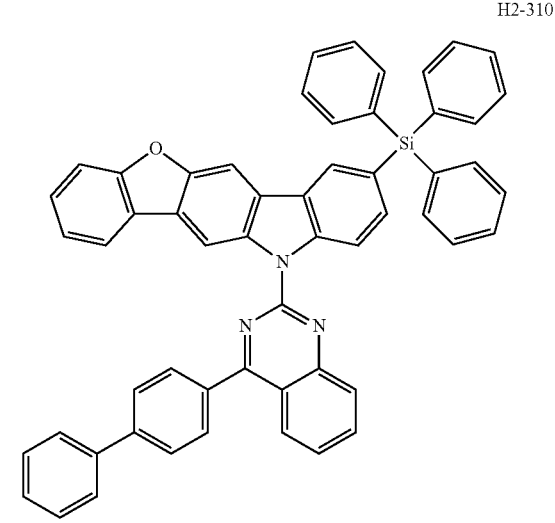
H2-311
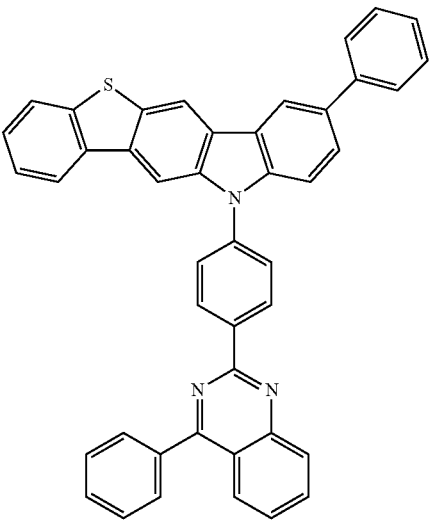
H2-312
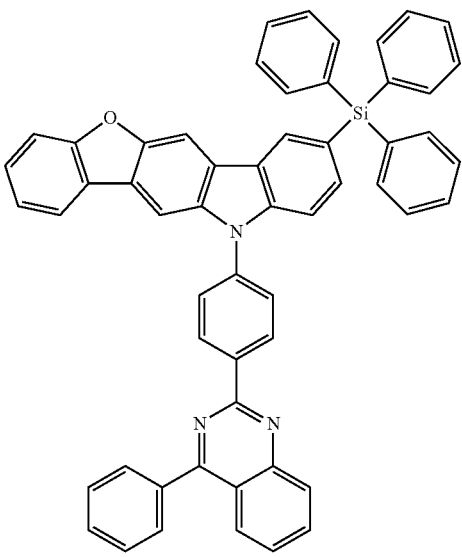
H2-313
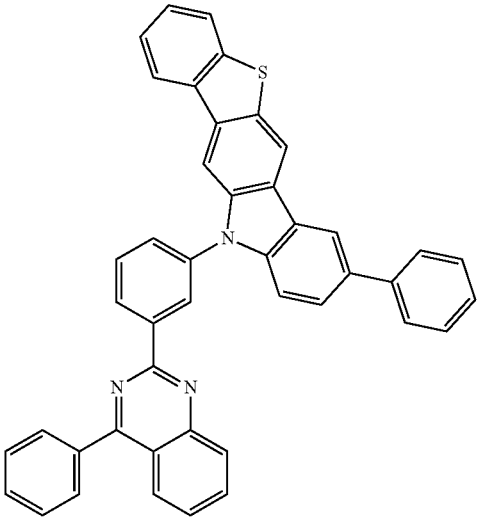

H2-314
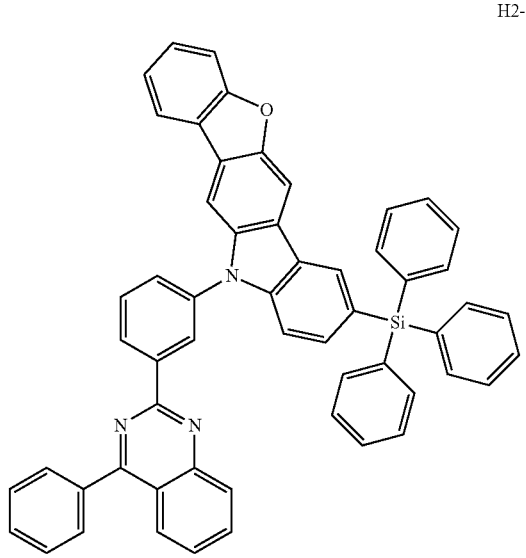
H2-315
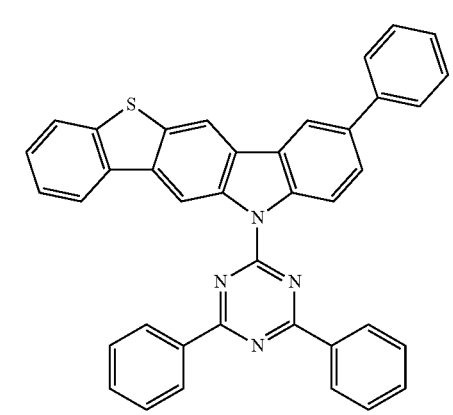
H2-316
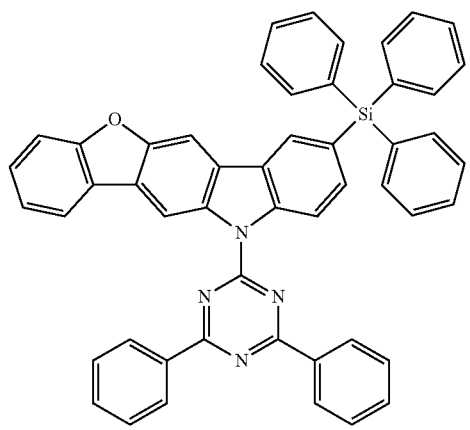
H2-317
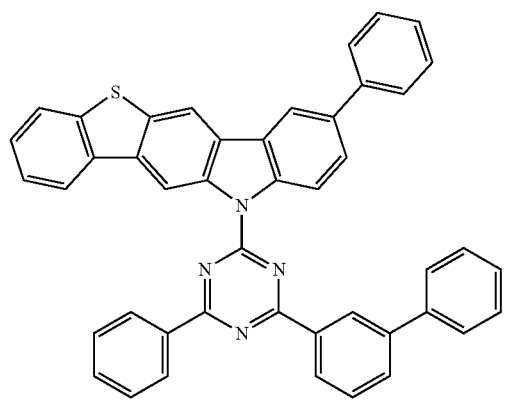
H2-318
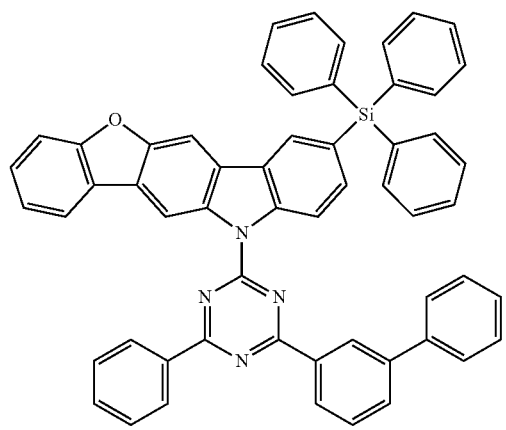
H2-319
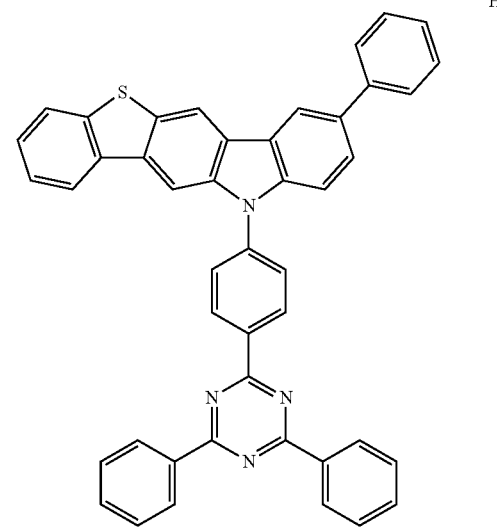

-continued
H2-320
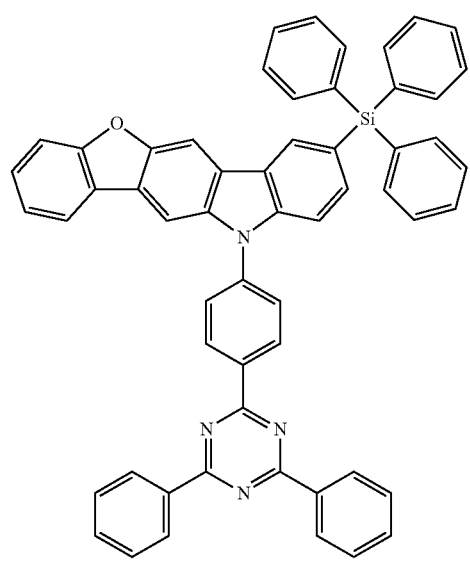
H2-321
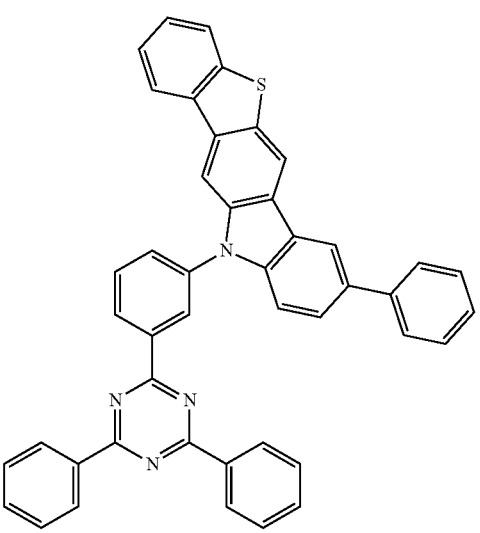
H2-322
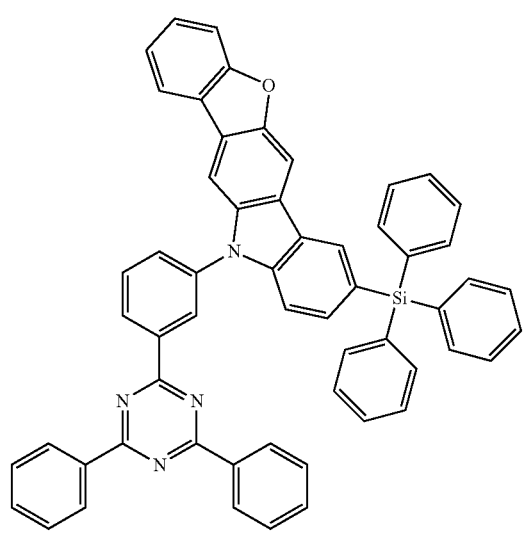
-continued
H2-323
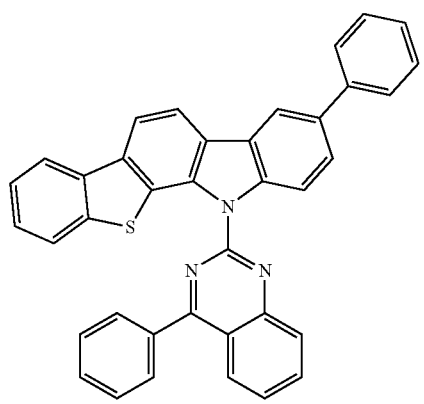
H2-324
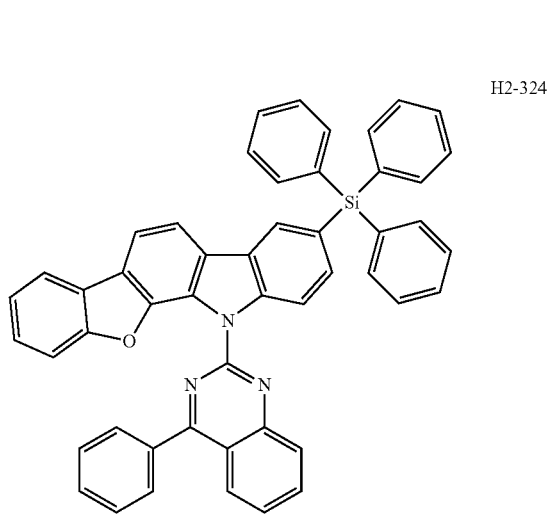
H2-325
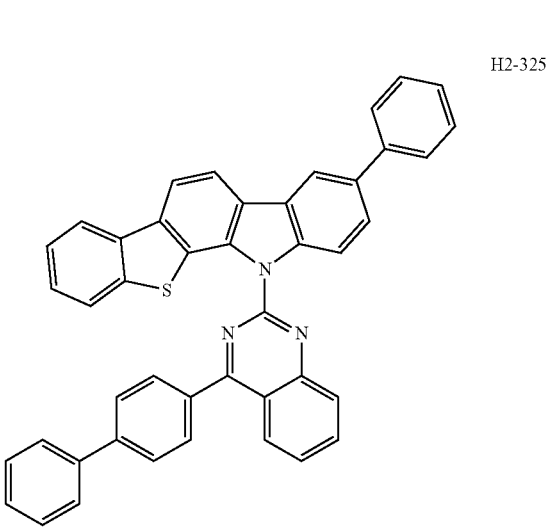

H2-326
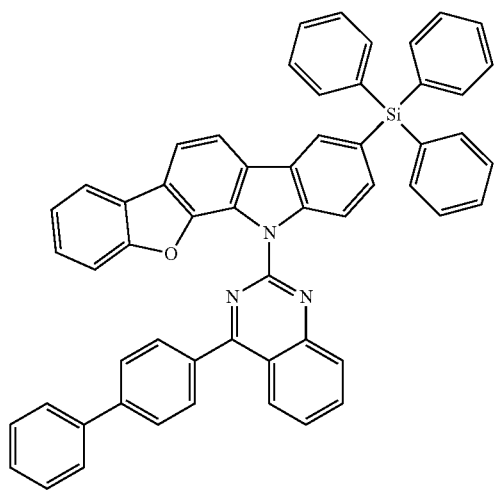
H2-327
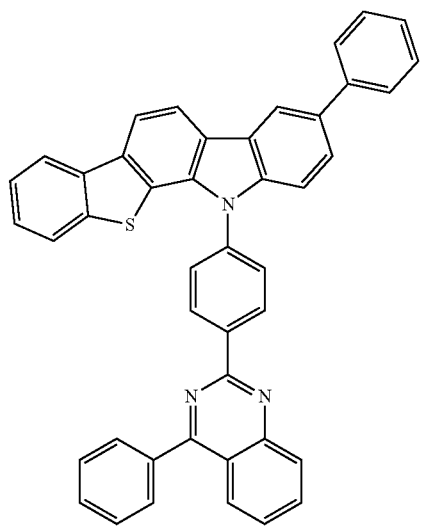
H2-328
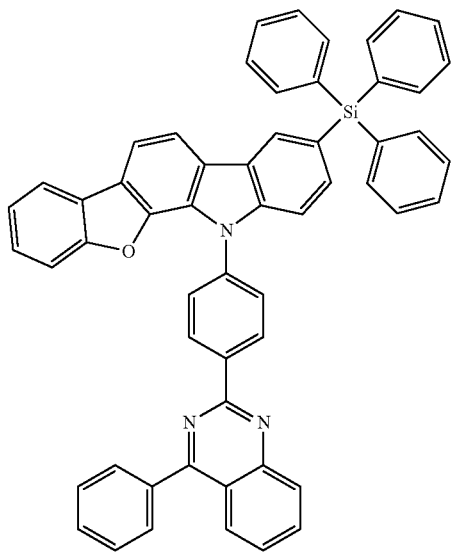
H2-329
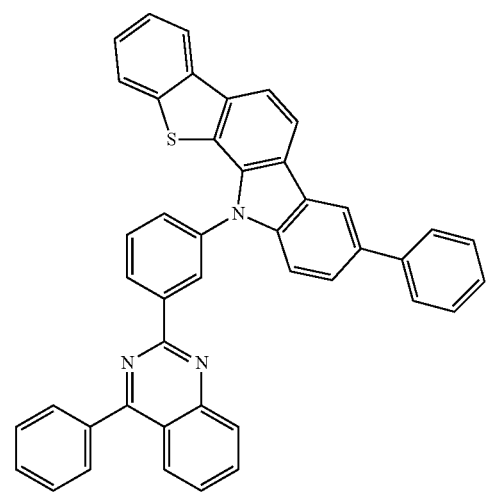
H2-330
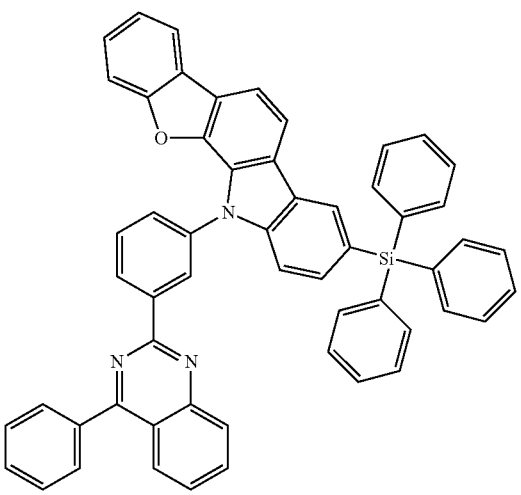
H2-331
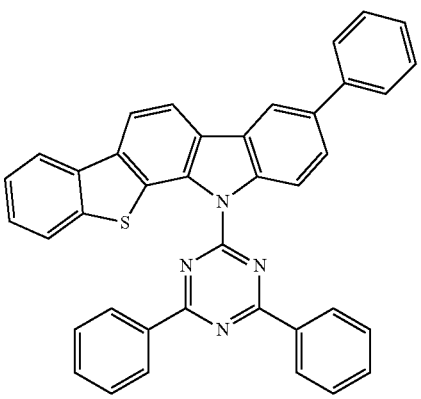

H2-332
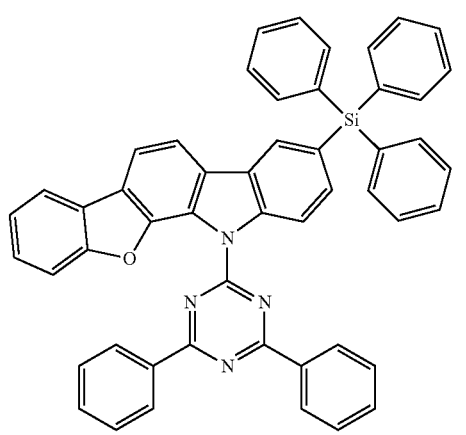
H2-333
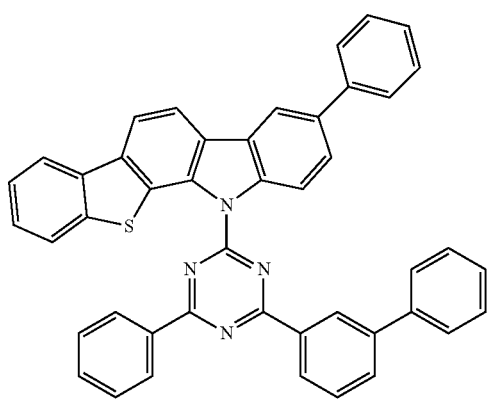
H2-334
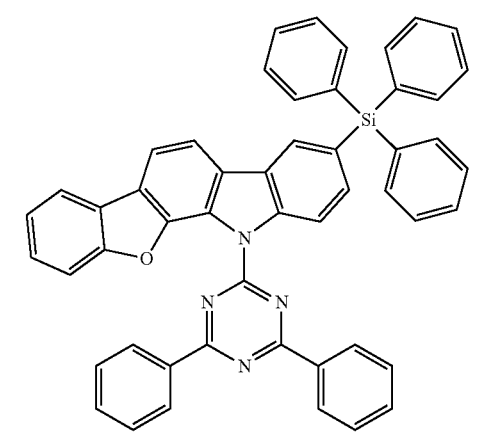
H2-335
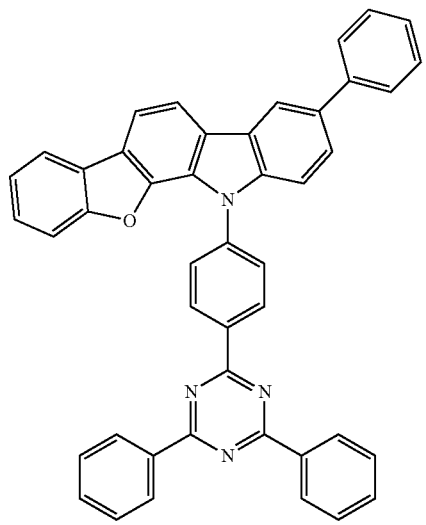
H2-336
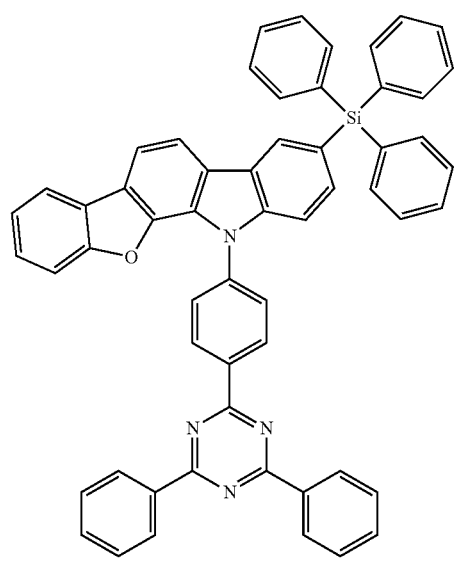
H2-337
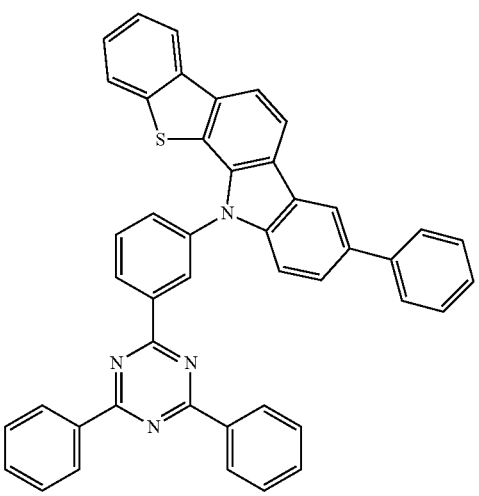

H2-338
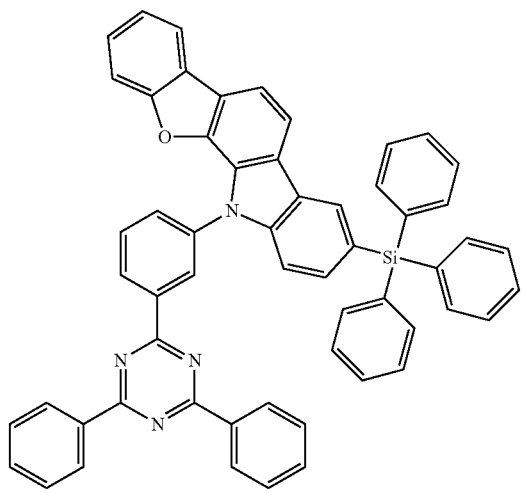
H2-341
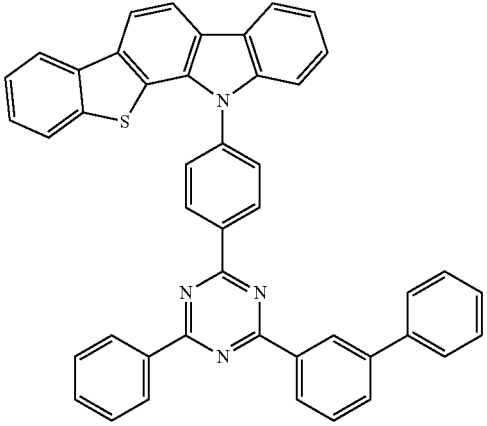
H2-339
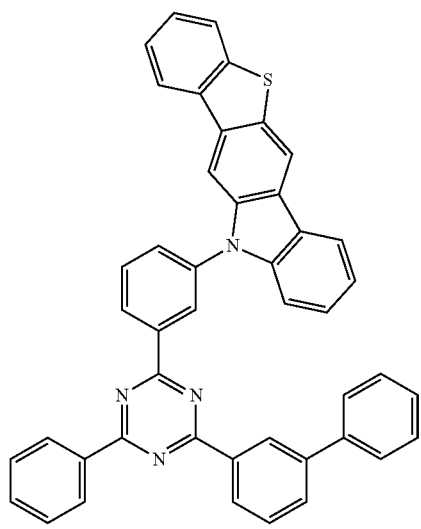
H2-342
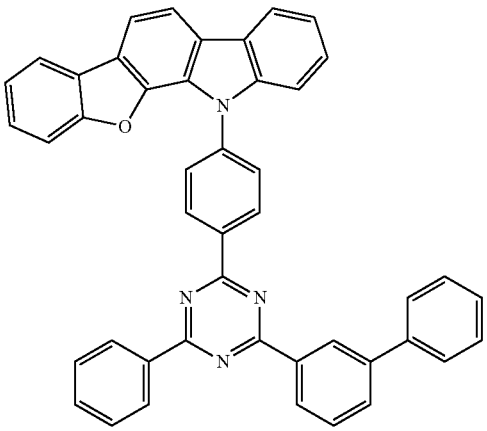
H2-340
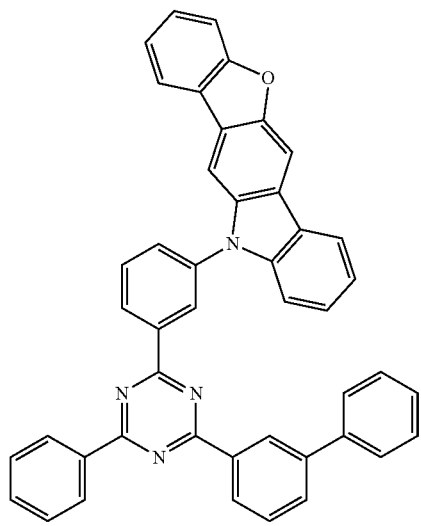
H2-343
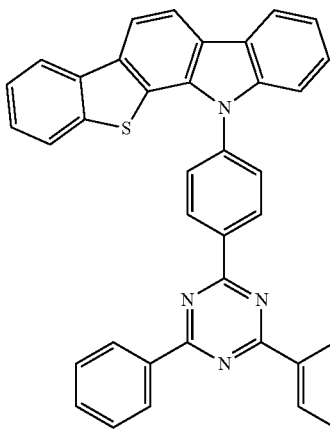

H2-344 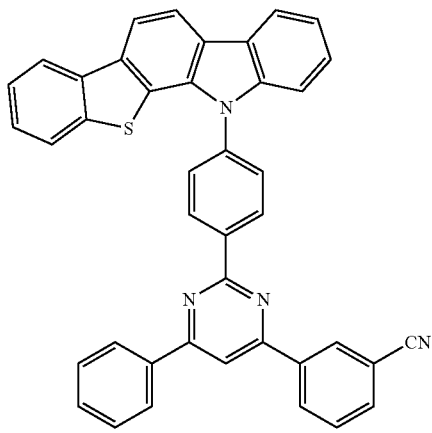
H2-345 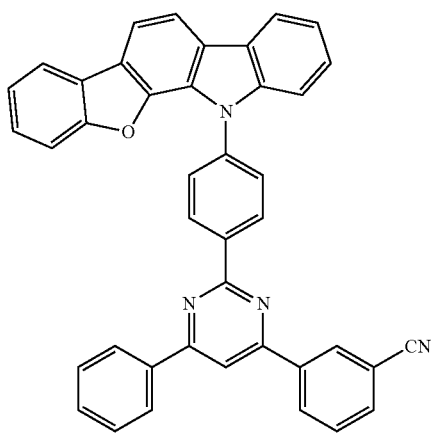
H2-346 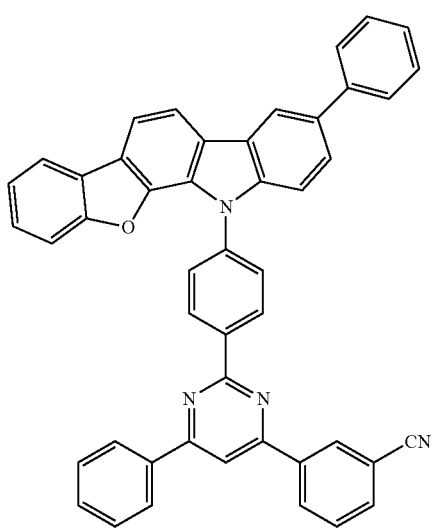
H2-347 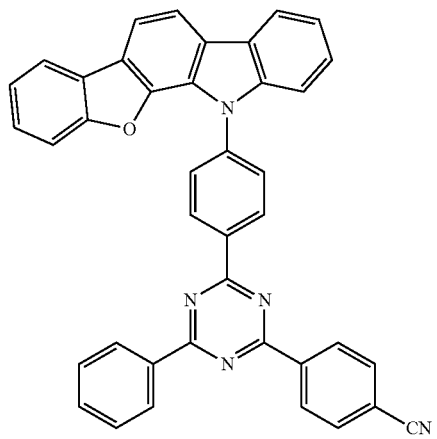
H2-348 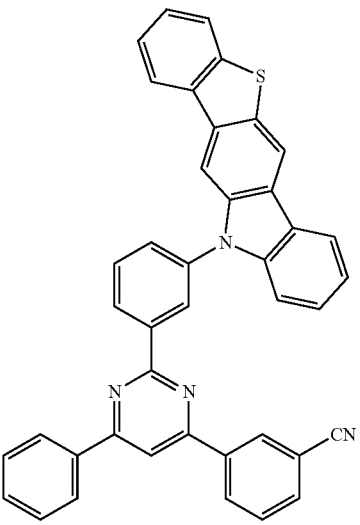
H2-349 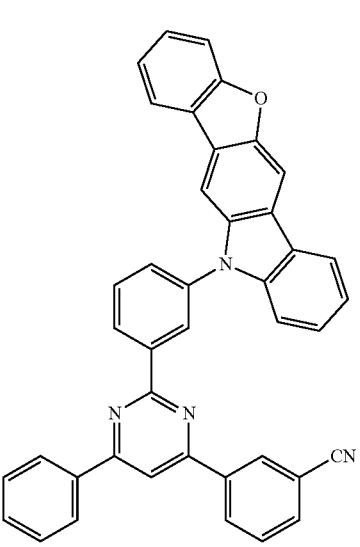

H2-350
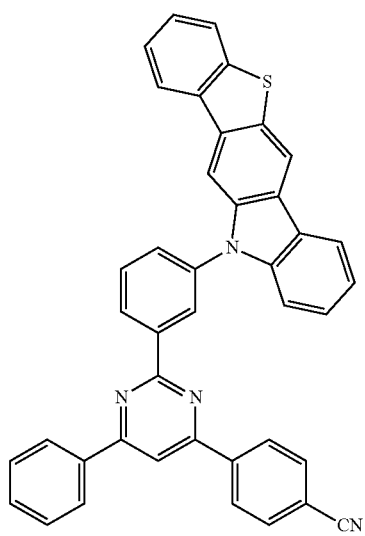
H2-351
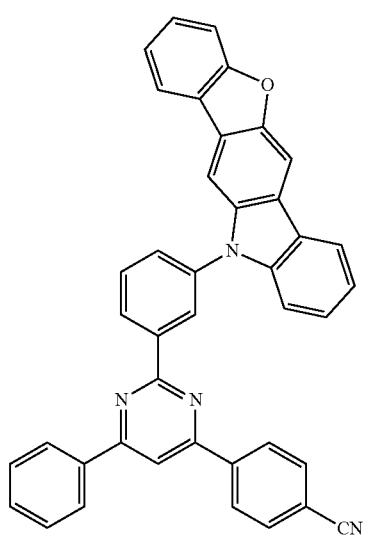
H2-352
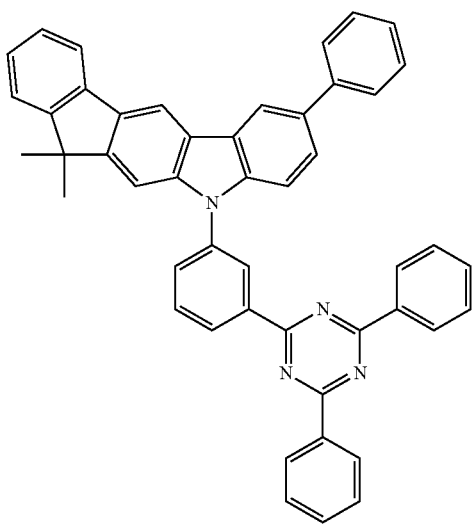
H2-353
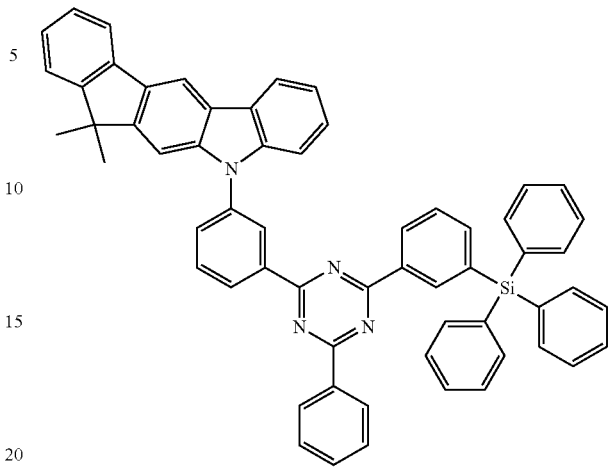
H2-354
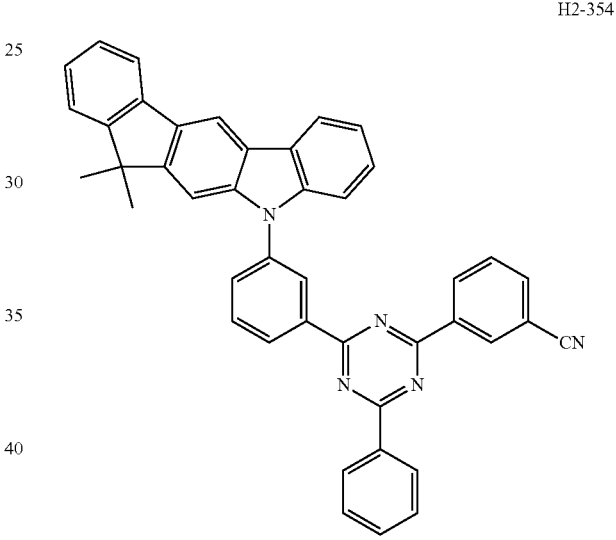
H2-355
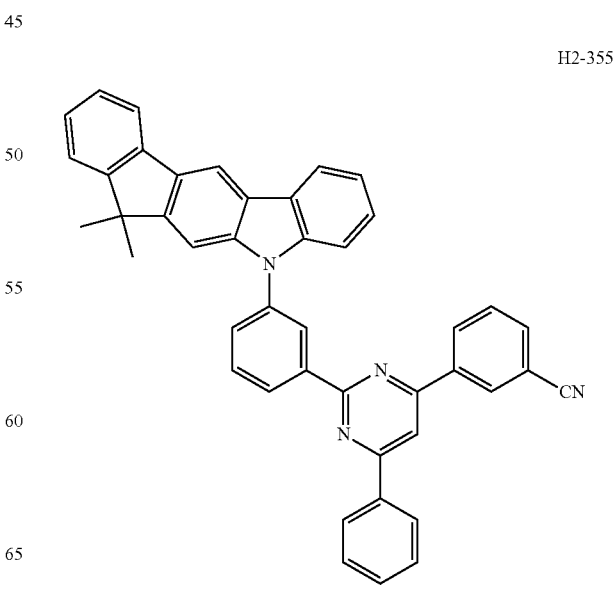

H2-356
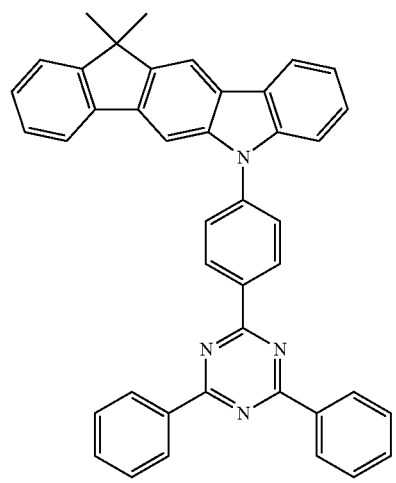
H2-357
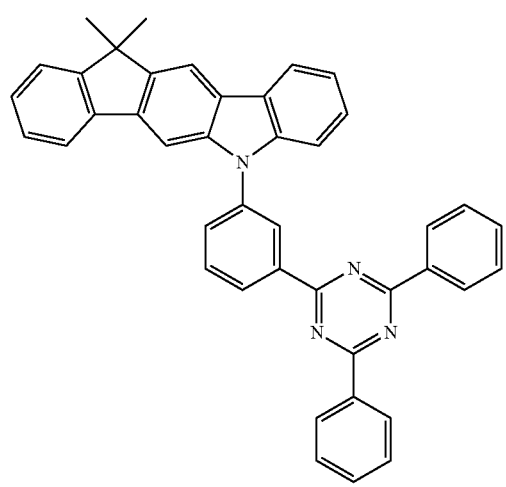
H2-358
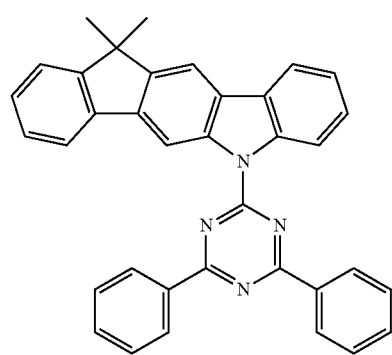
H2-359
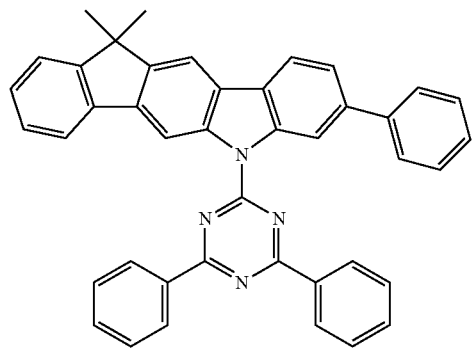
H2-360
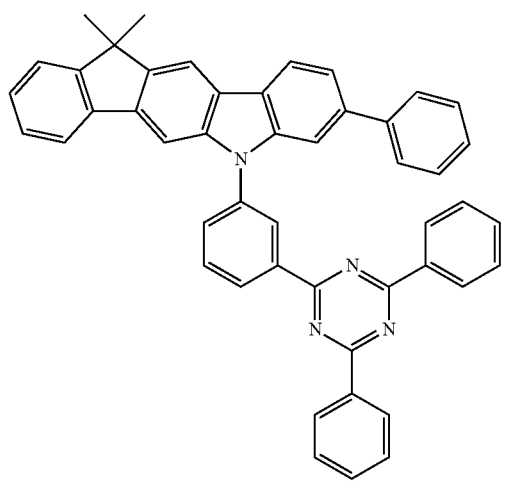
H2-361
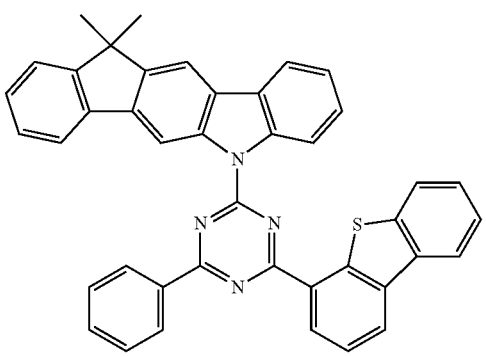
H2-362
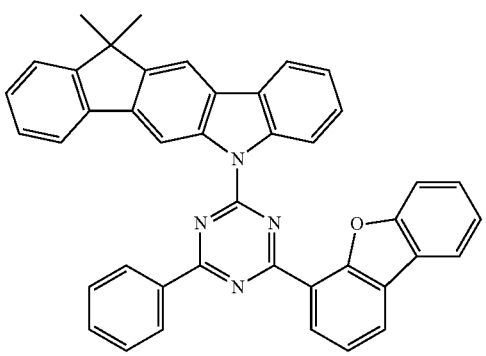

H2-363
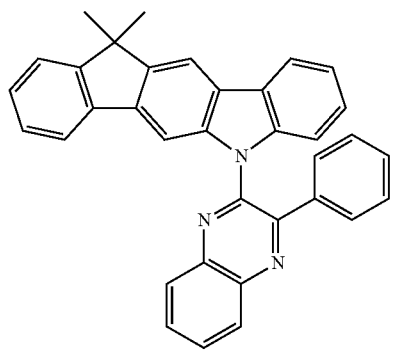
H2-364
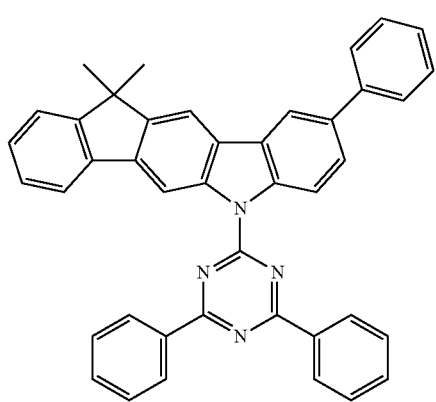
H2-365
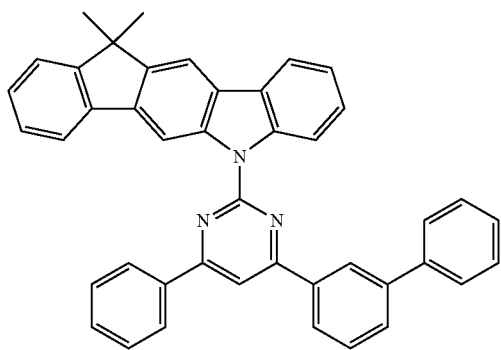
H2-366
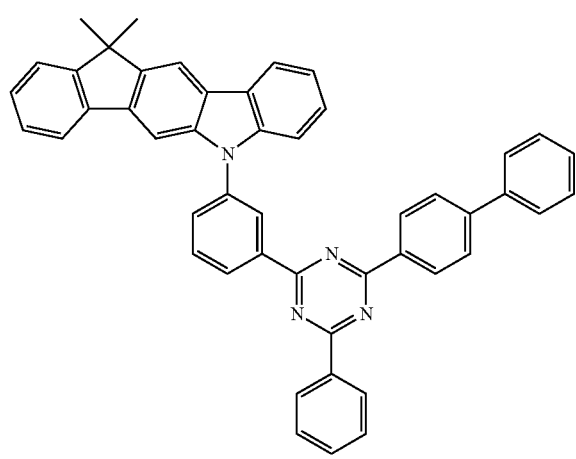
H2-367
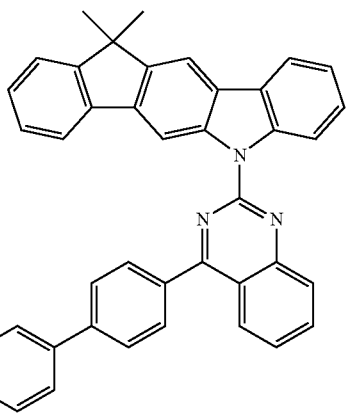
H2-368
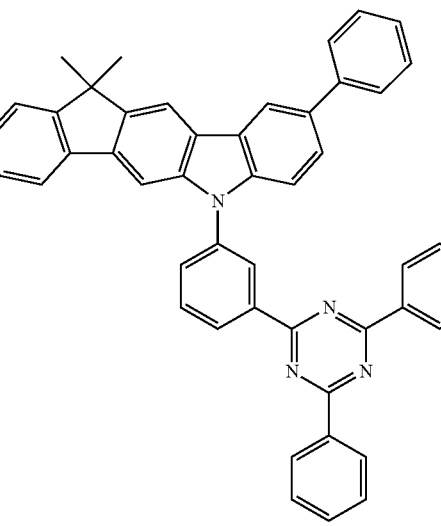
H2-369
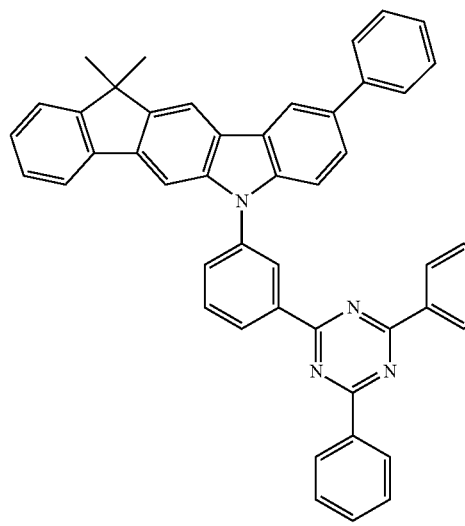

H2-370
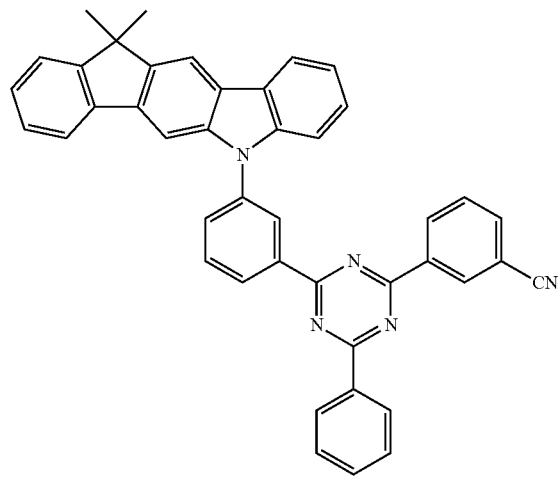
H2-371
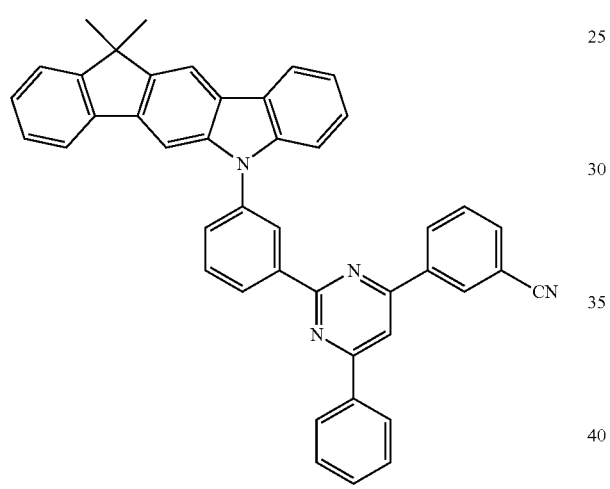
H2-372
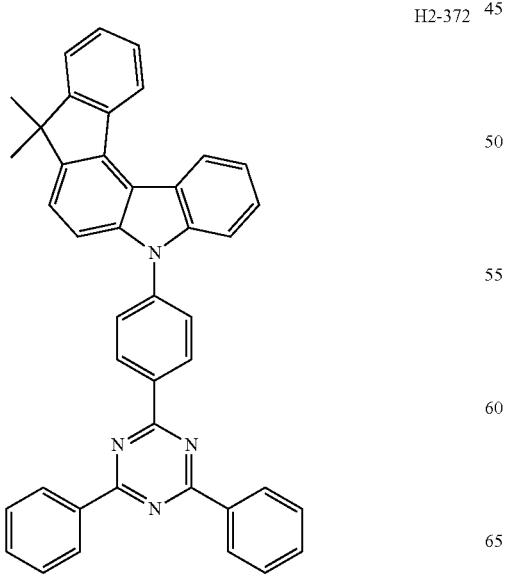
H2-373
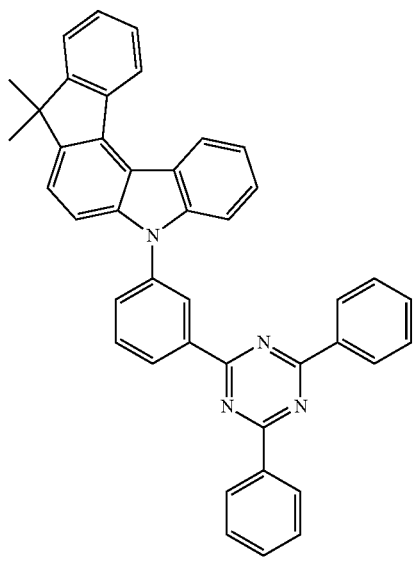
H2-374
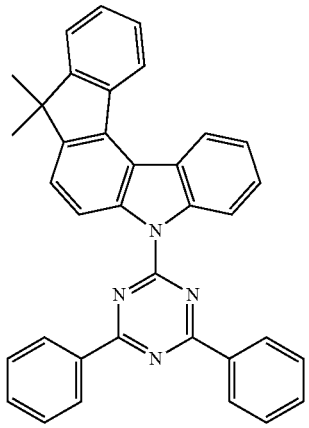
H2-375
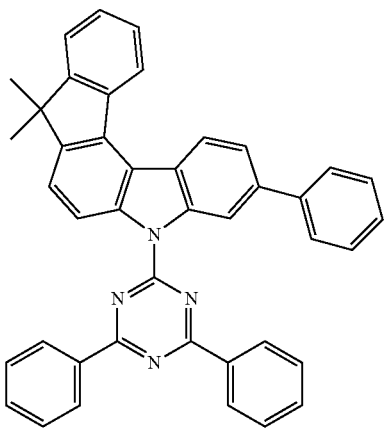

-continued
H2-376
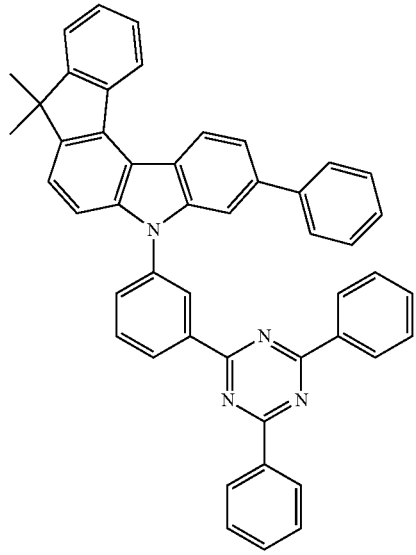
HS-377
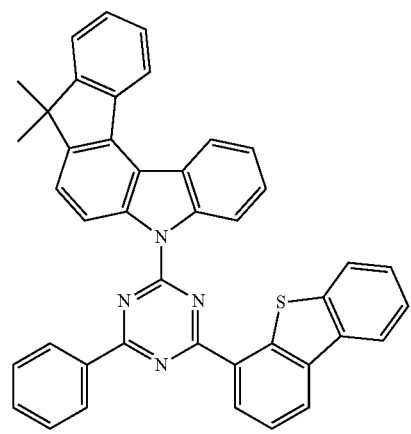
HS-378
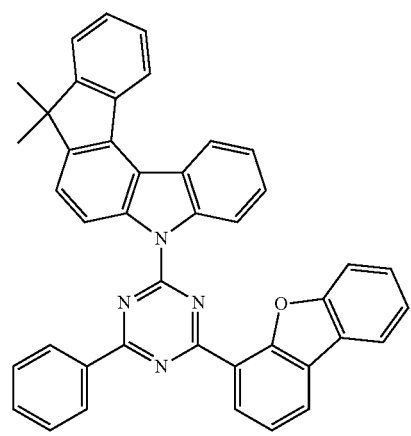
-continued
HS-379
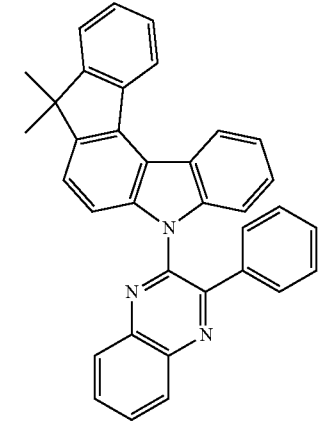
HS-380
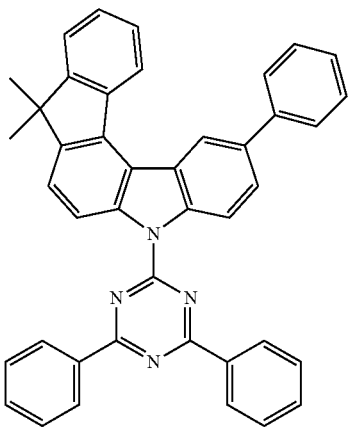
H2-381
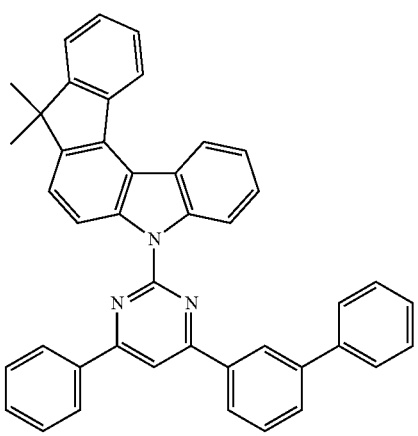

H2-382
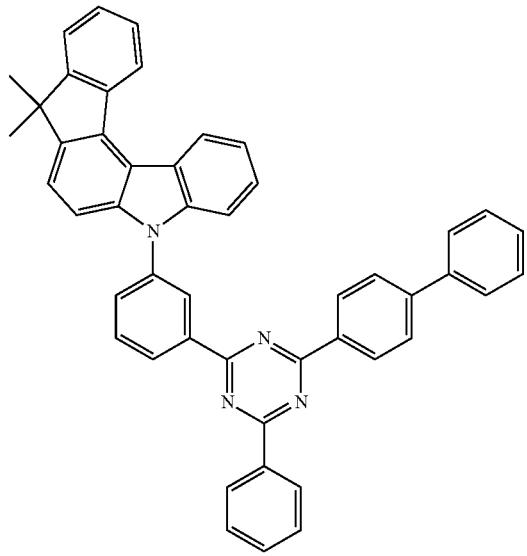
H2-383
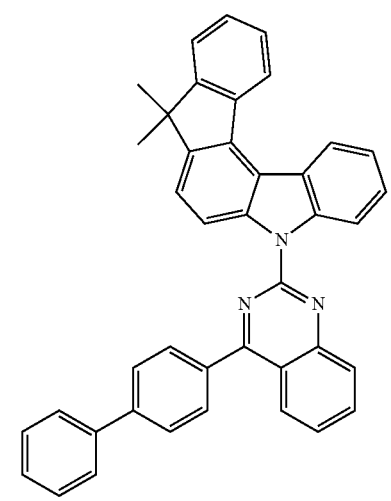
H2-384
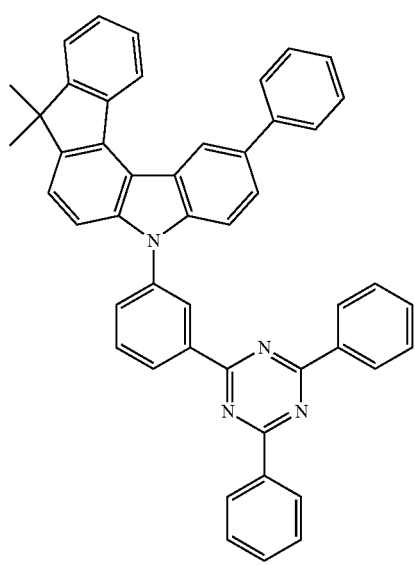
H2-385
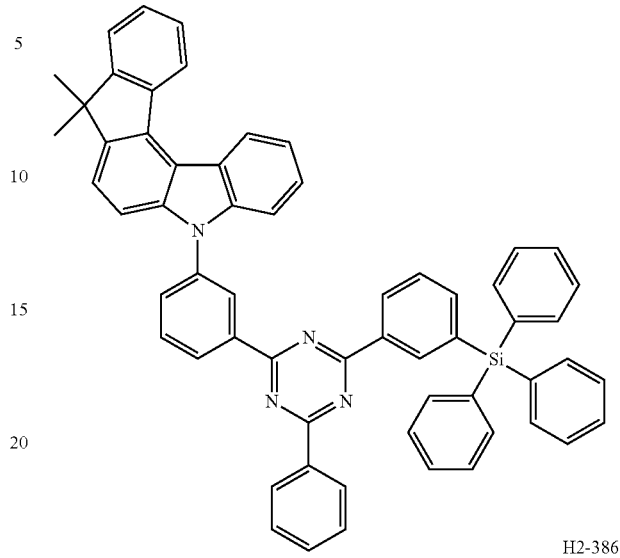
H2-386
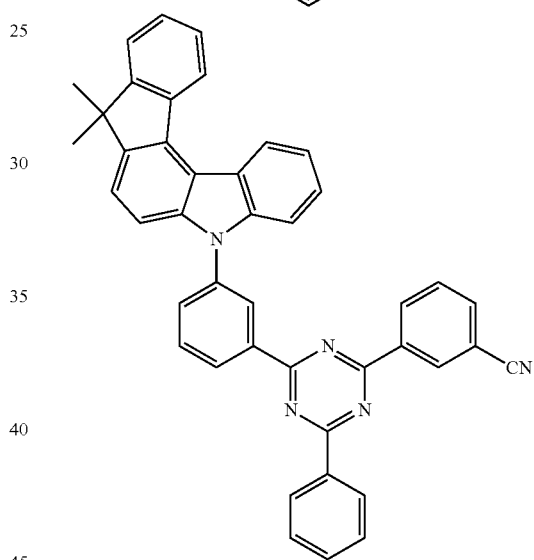
H2-387
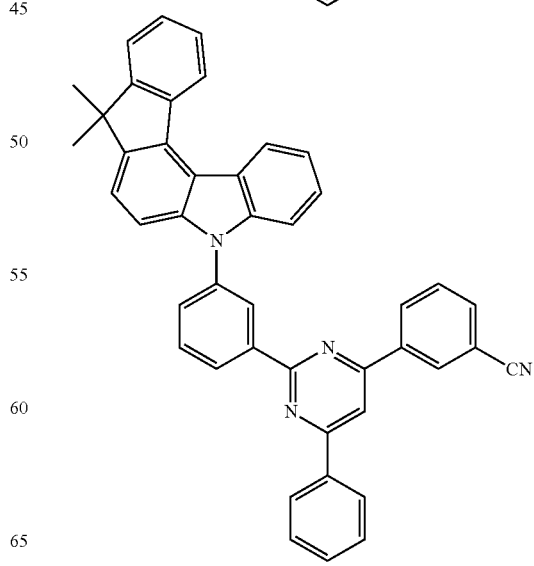

H2-388 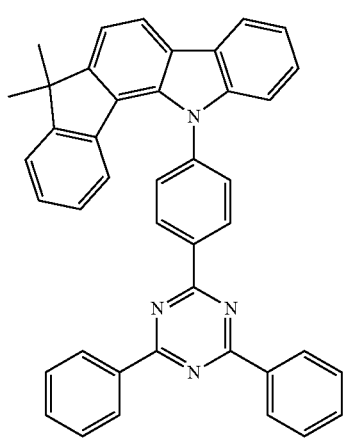
H2-389 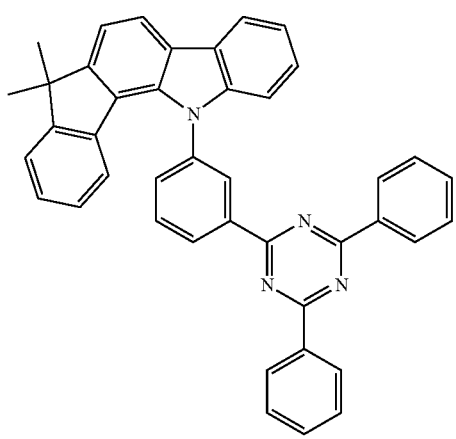
H2-390 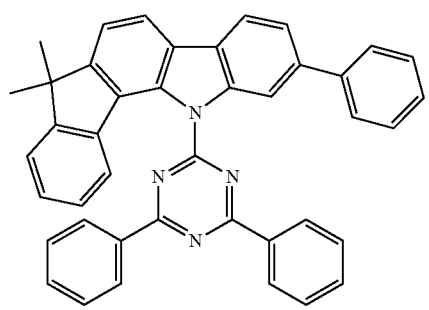
H2-391
H2-392 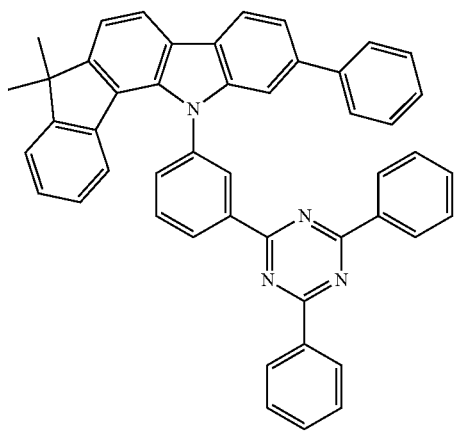
H2-393 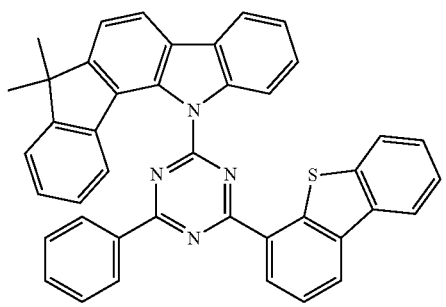
H2-394 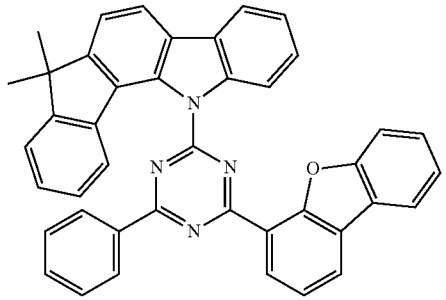
H2-395 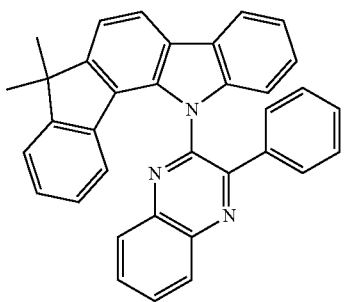

H2-396
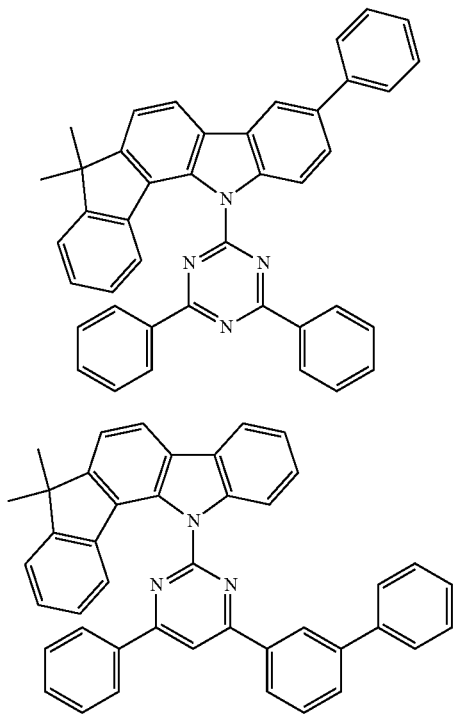
H2-397
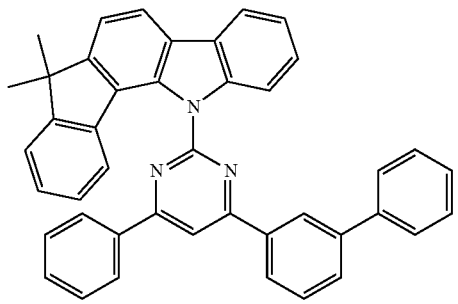
H2-398
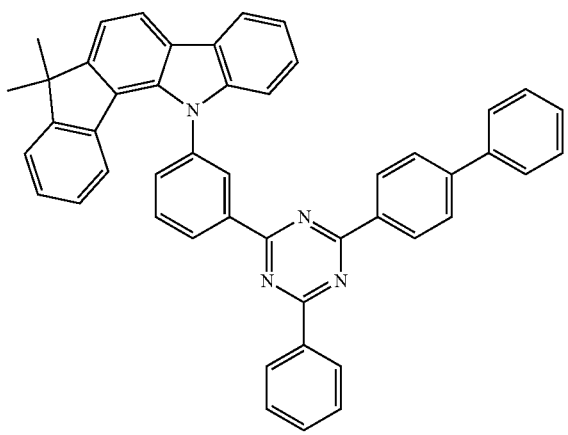
H2-399
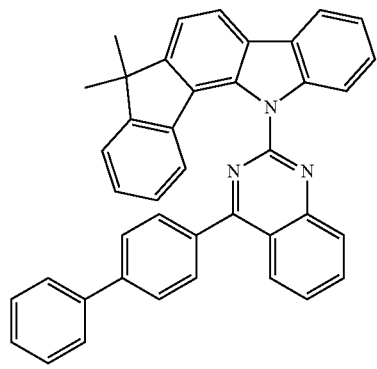
H2-400
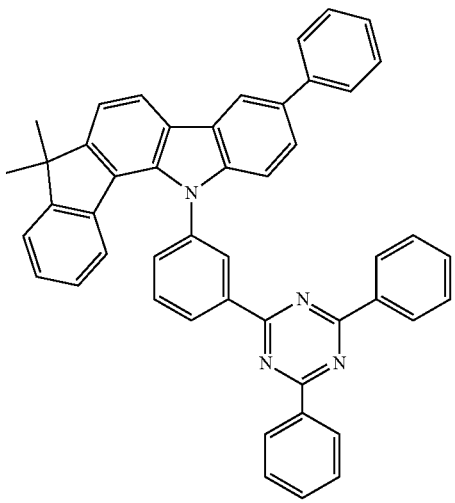
H2-401
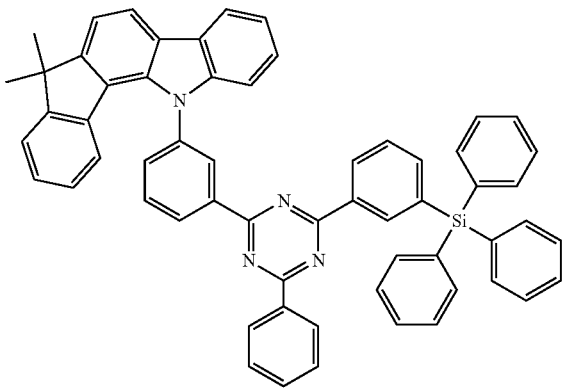
H2-402
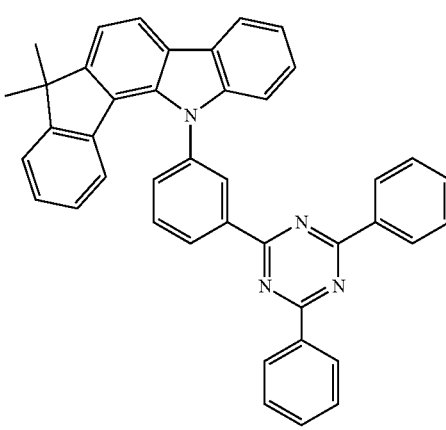

169
-continued
H2-403
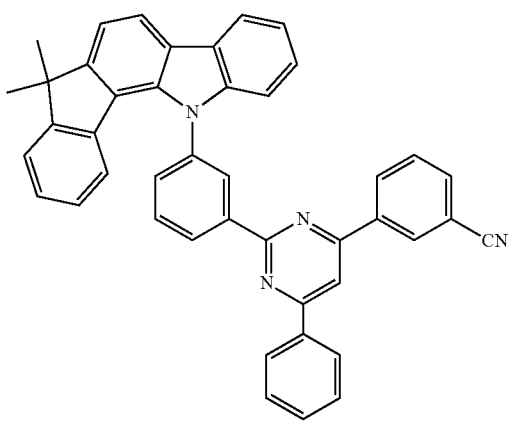
H2-404
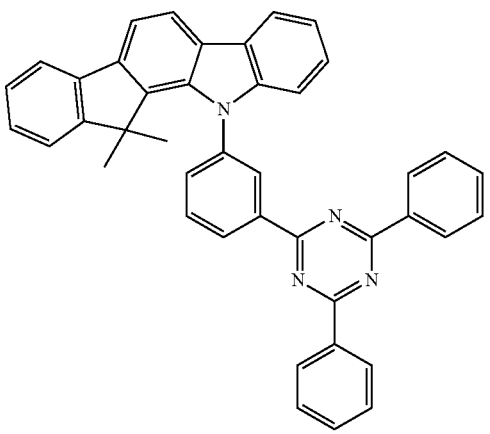
H2-405
H2-406
170
-continued
H2-407
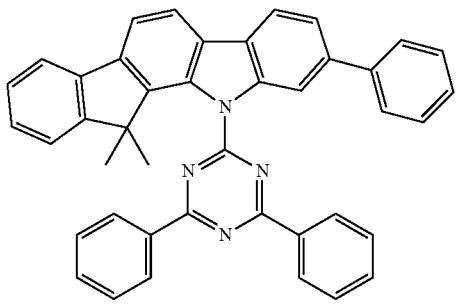
H2-408
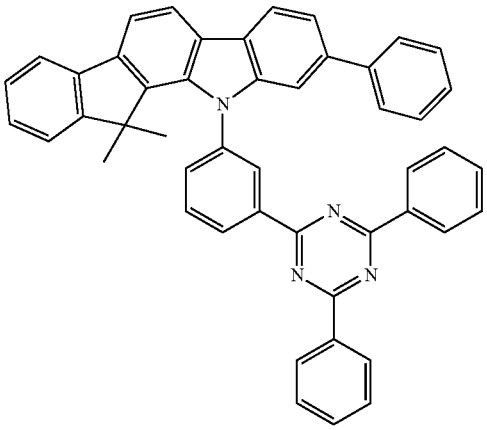
H2-409
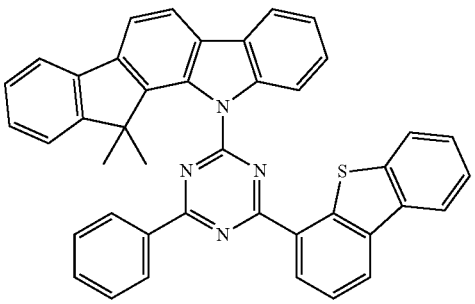
H2-410
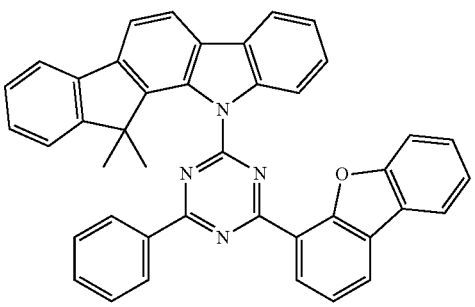
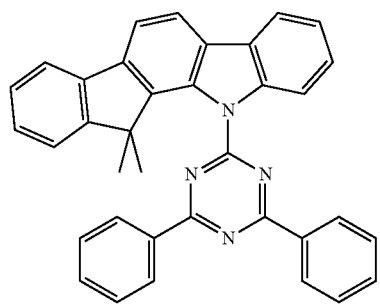

-continued
H2-411
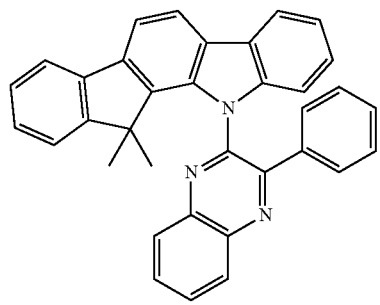
H2-412
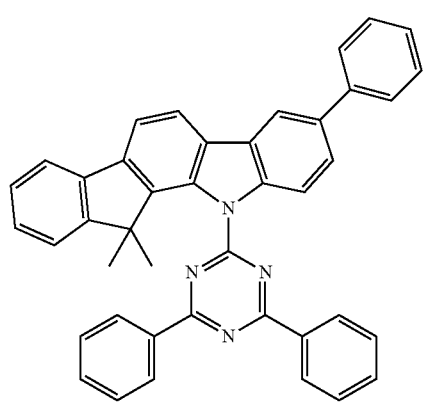
H2-413
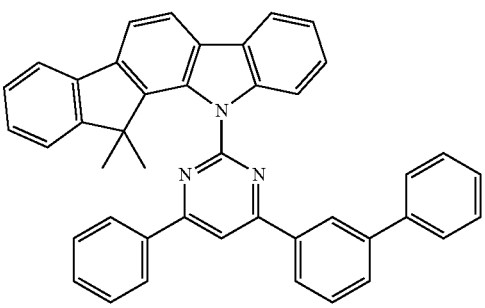
H2-414
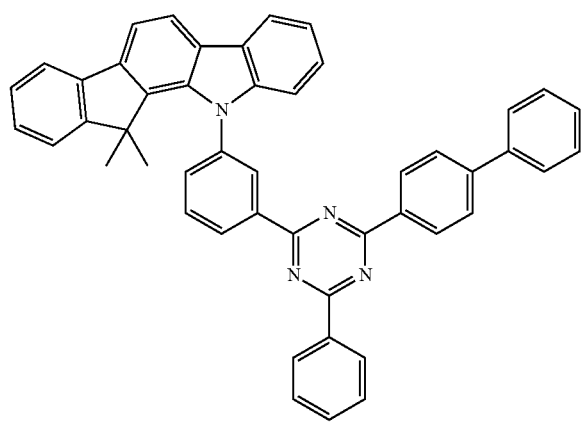
-continued
H2-415
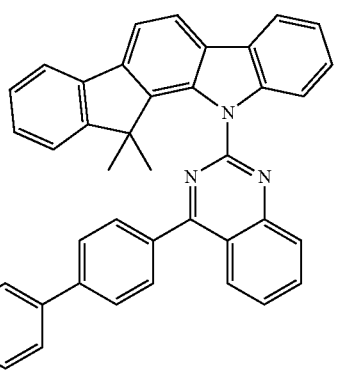
H2-416
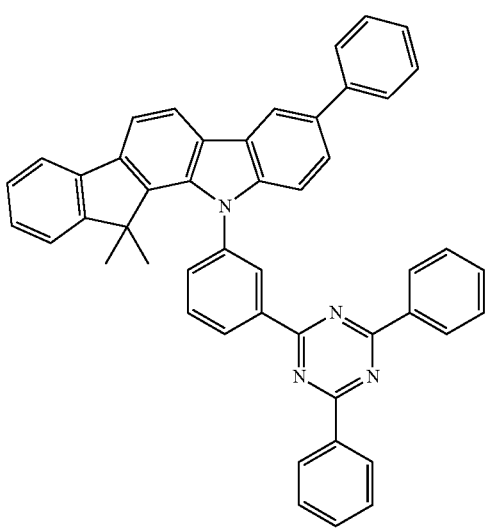
H2-417
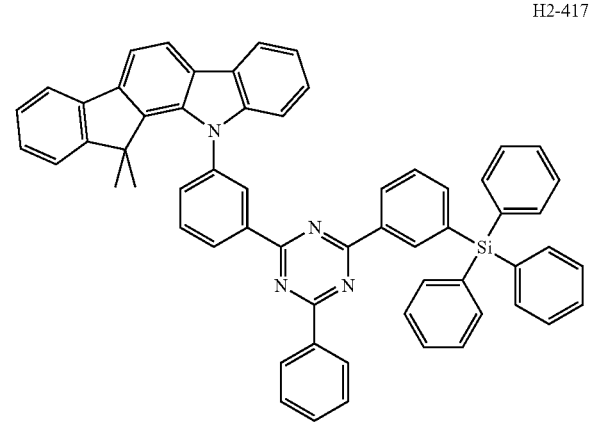

H2-418
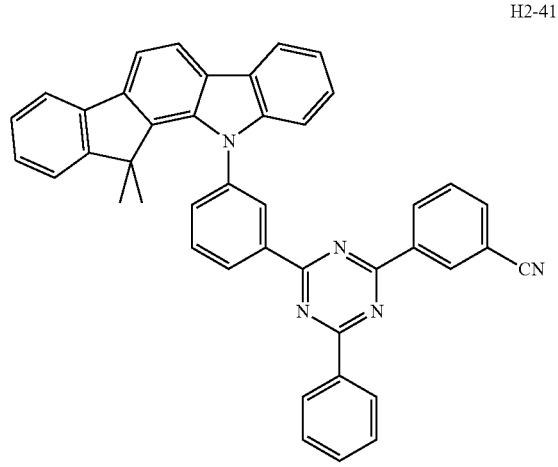
H2-421
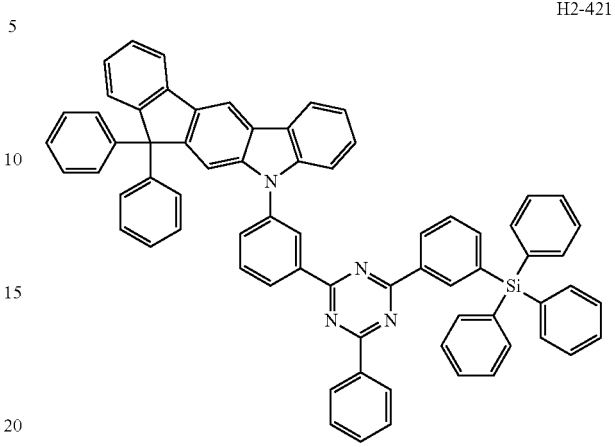
H2-419
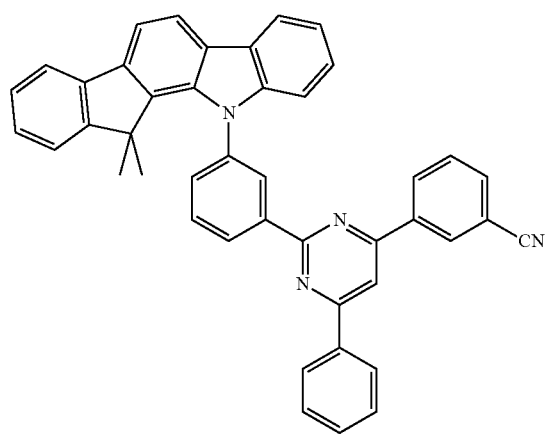
H2-422
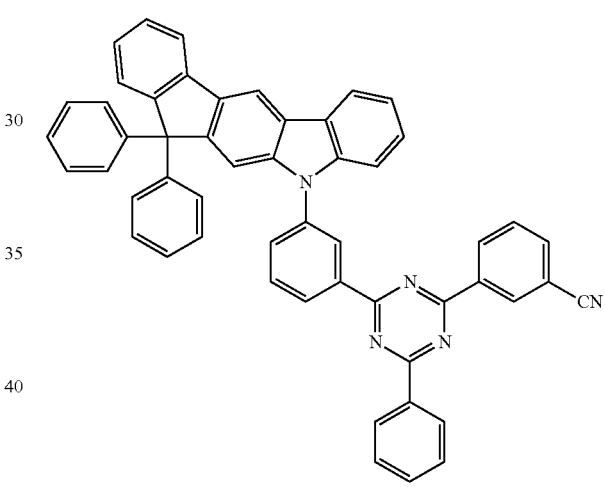
H2-420
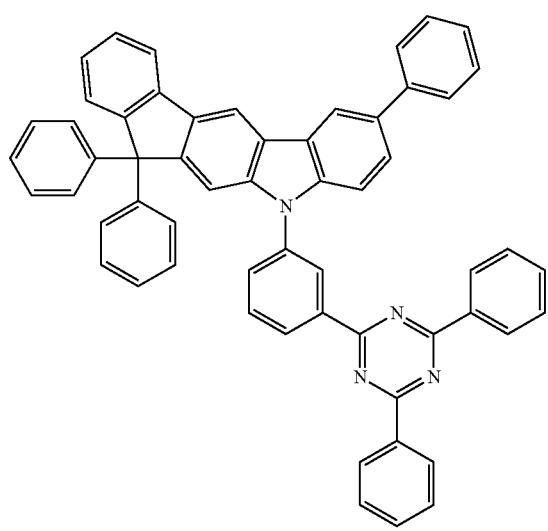
H2-423
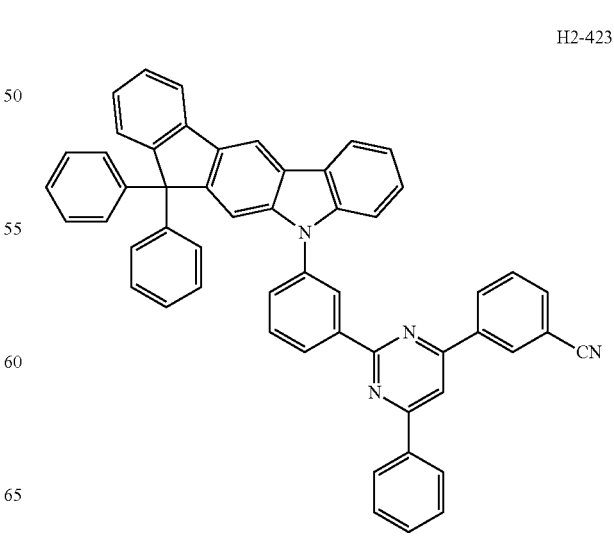

-continued
H2-424
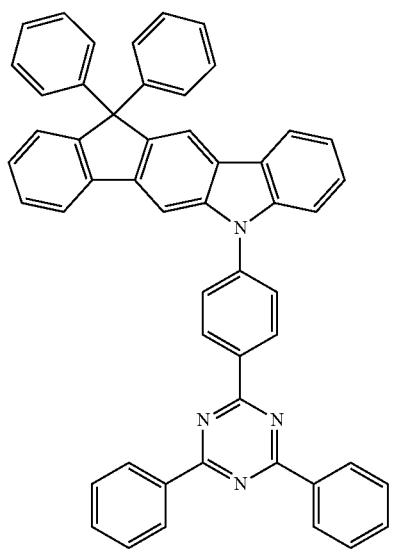
H2-425
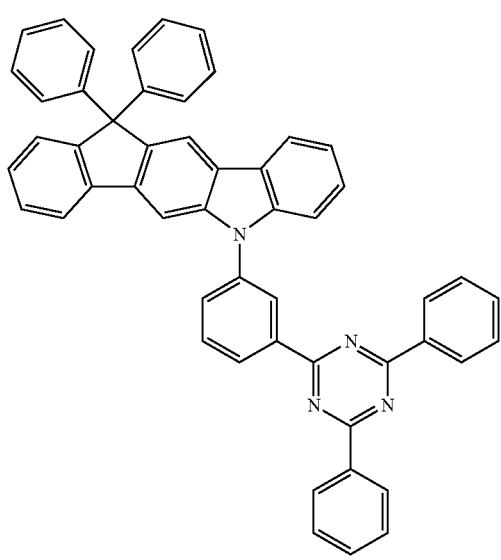
H2-426
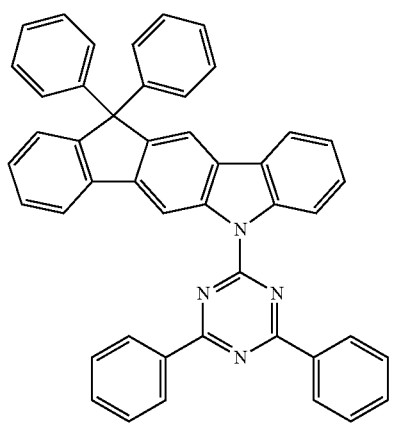
-continued
H2-427
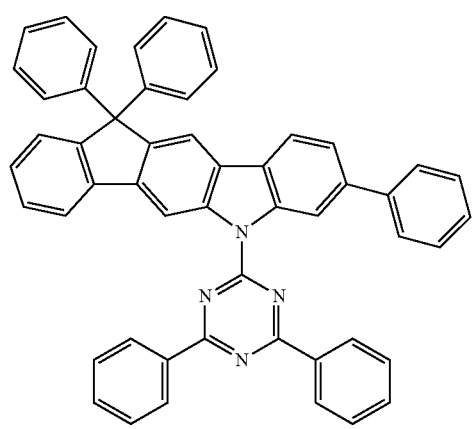
H2-428
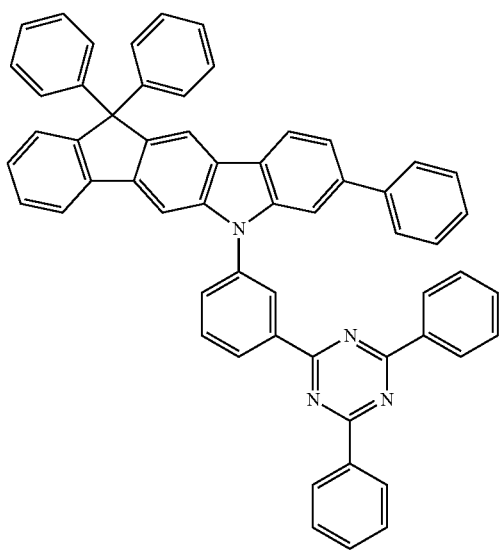
H2-429
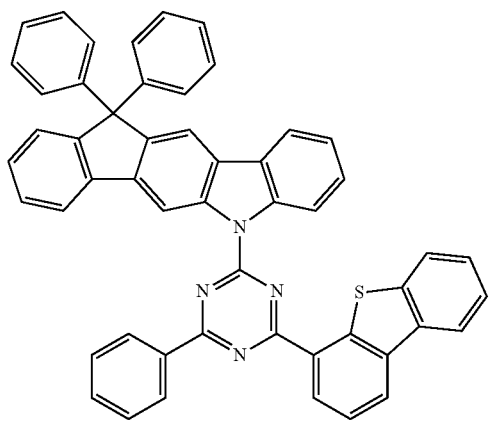

H2-430
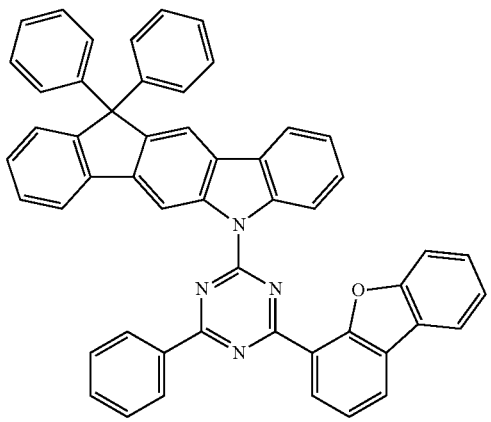
H2-431
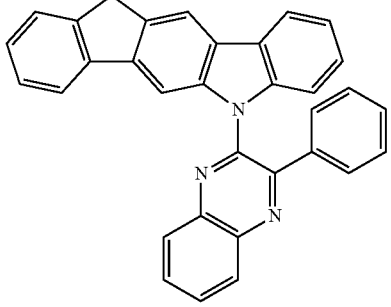
H2-432
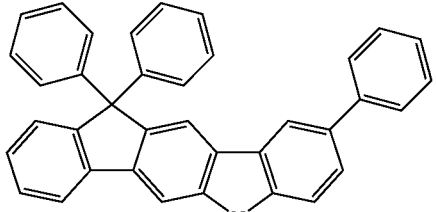
H2-433
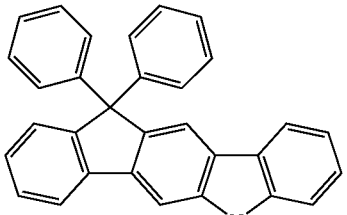
H2-434
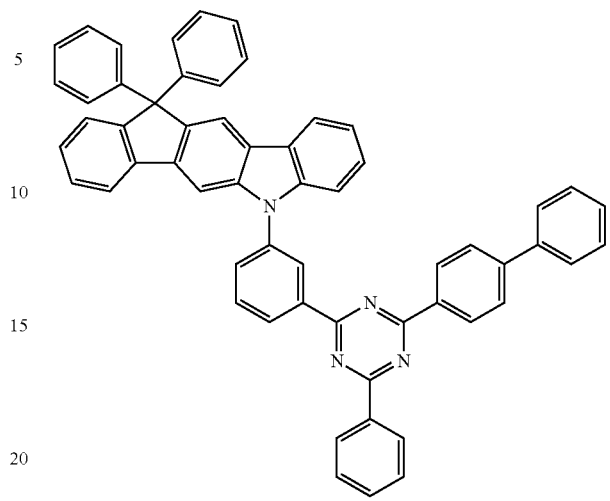
H2-435
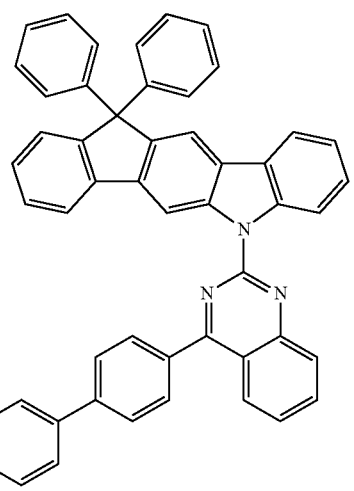
H2-436
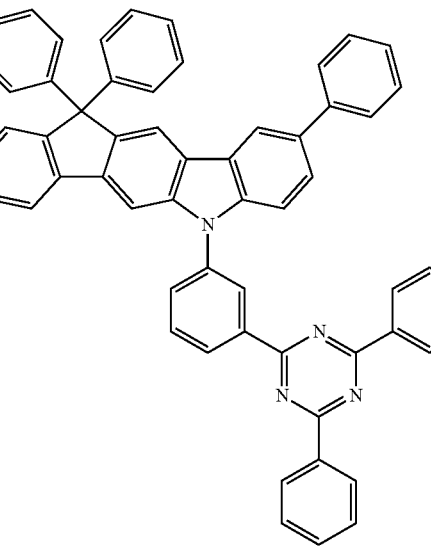

H2-437
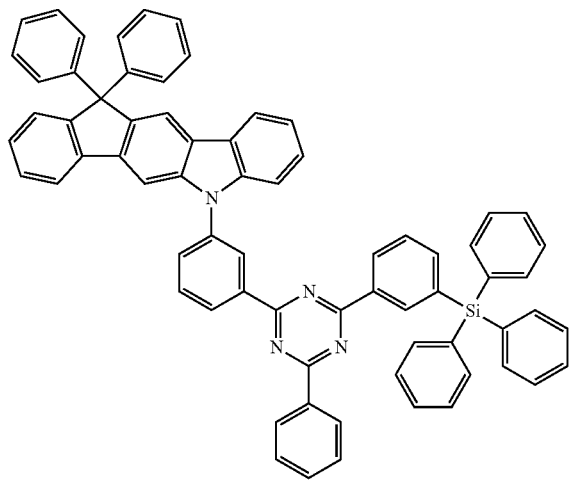
H2-438
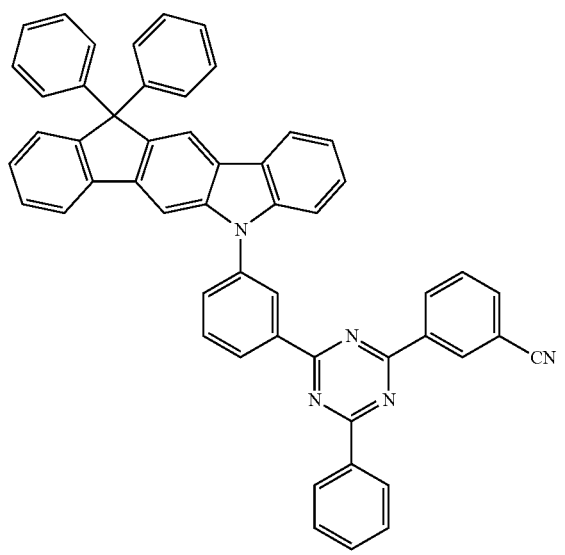
H2-439
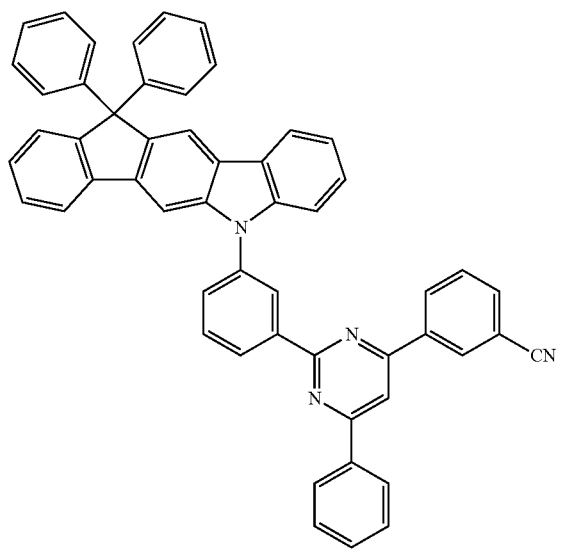
H2-440
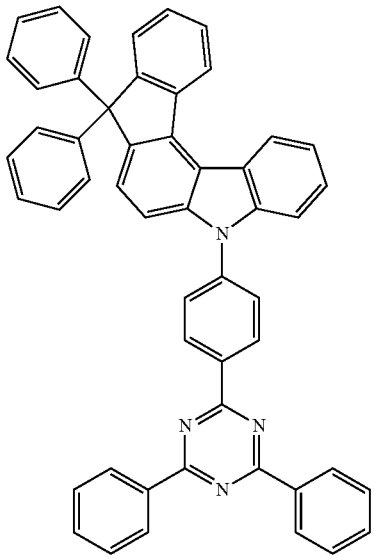
H2-441
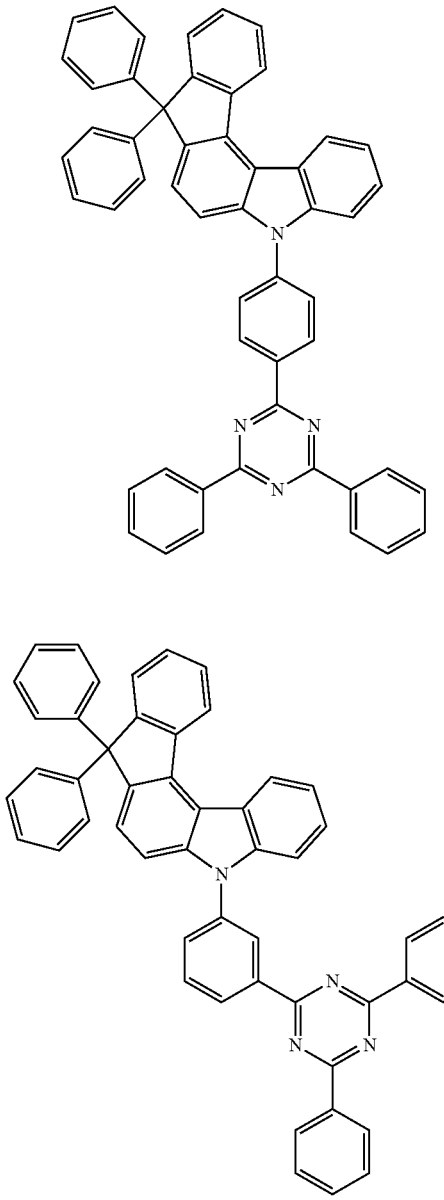
H2-442
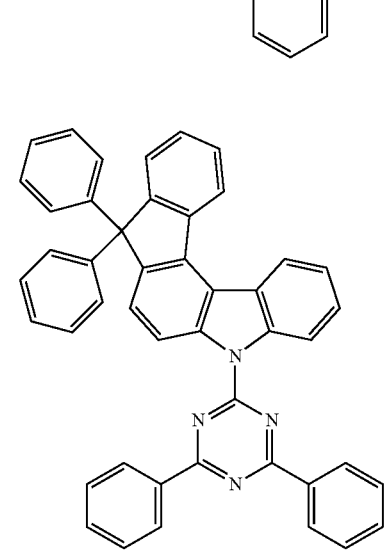

-continued
H2-443
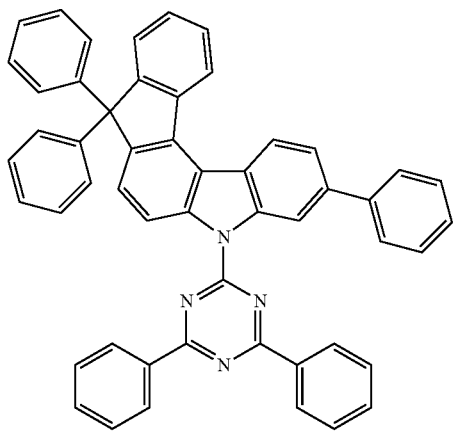
H2-444
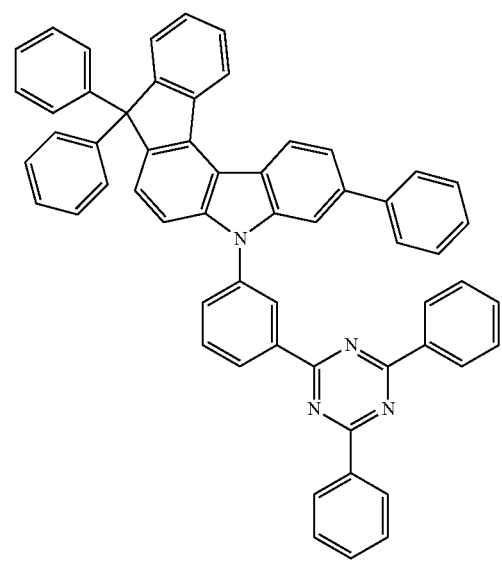
H2-445
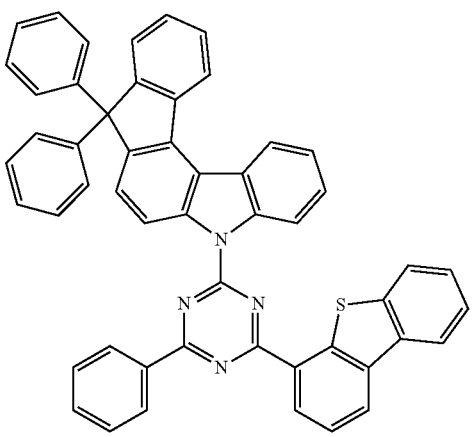
-continued
H2-446
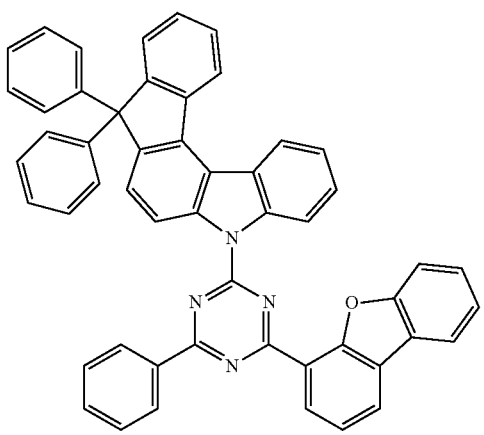
H2-447
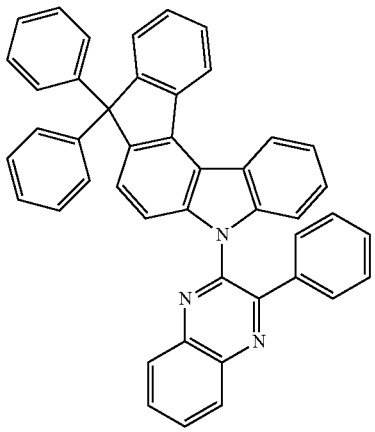
H2-448
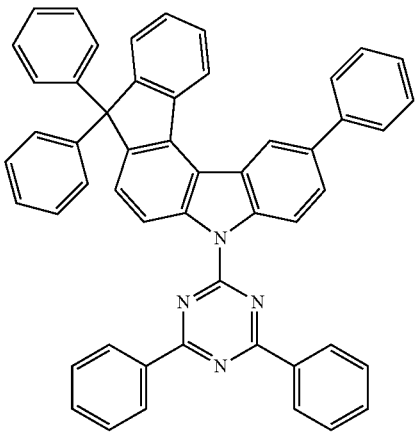

H2-449
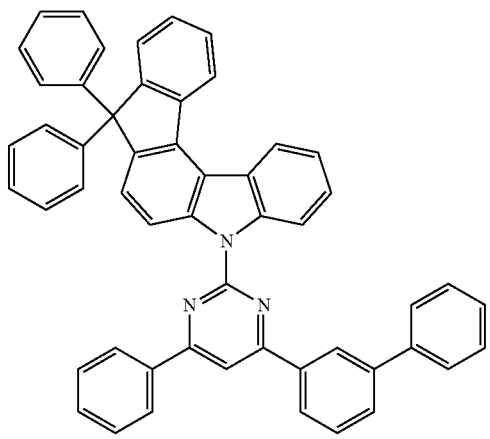
H2-450
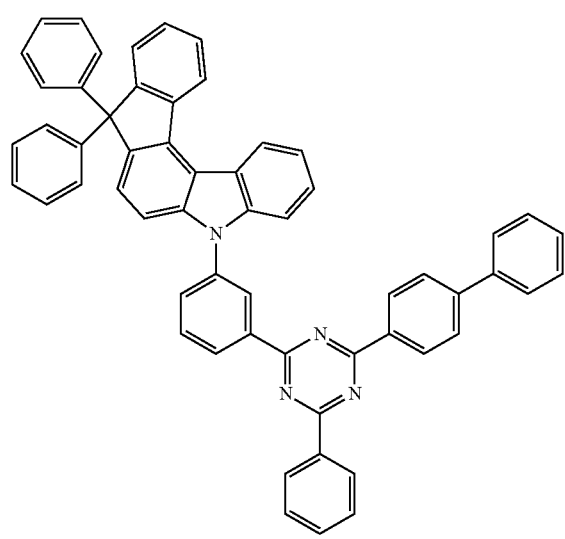
H2-451
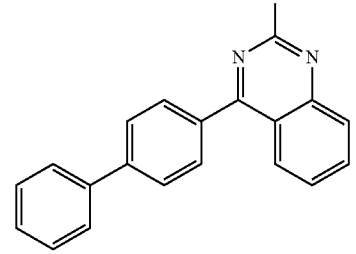
H2-452
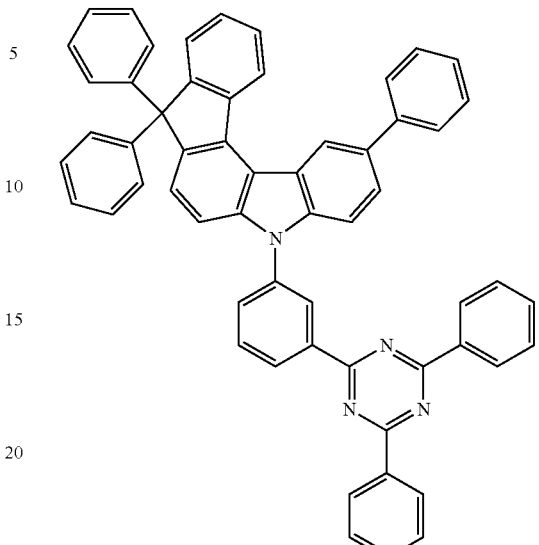
H2-453
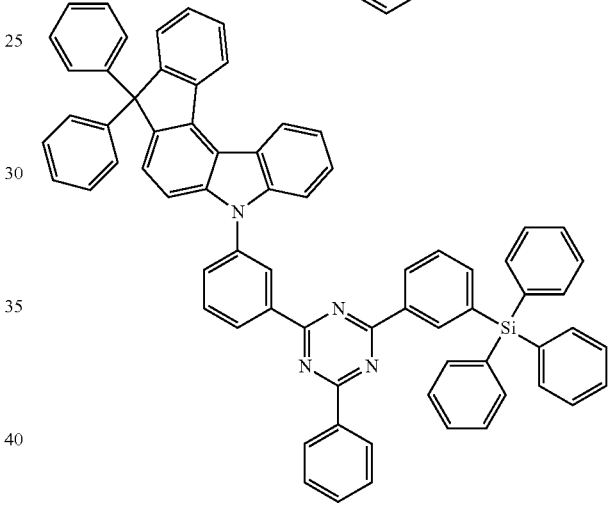
H2-454
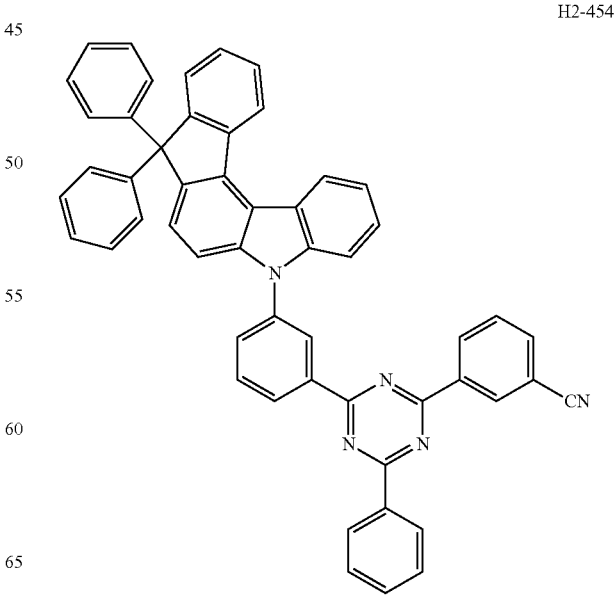

H2-455
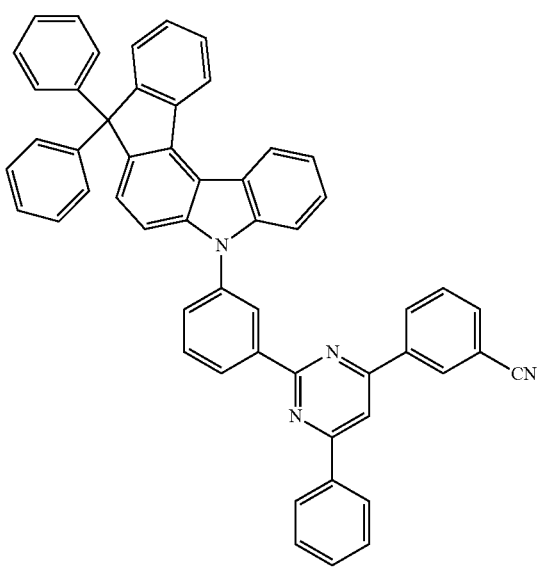
H2-456
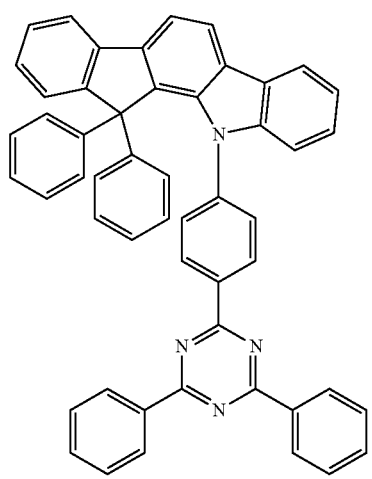
H2-457
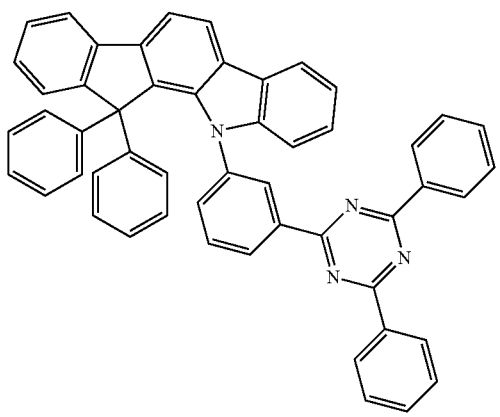
H2-458
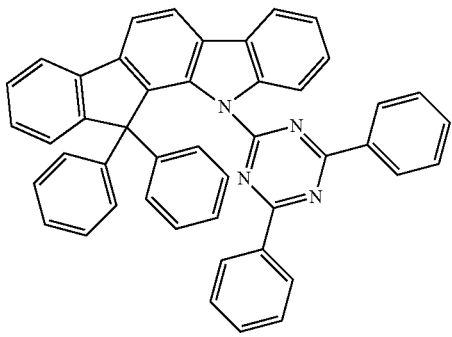
H2-459
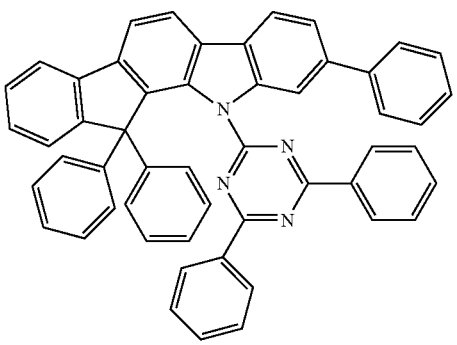
H2-460
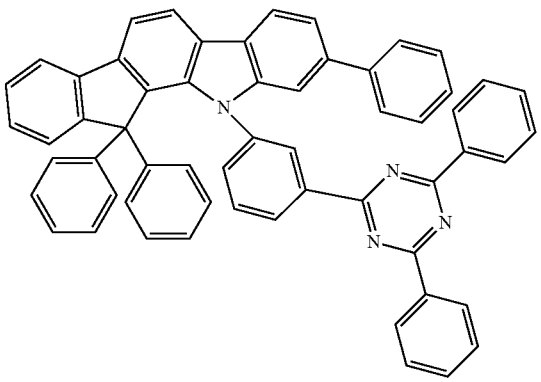
H2-461
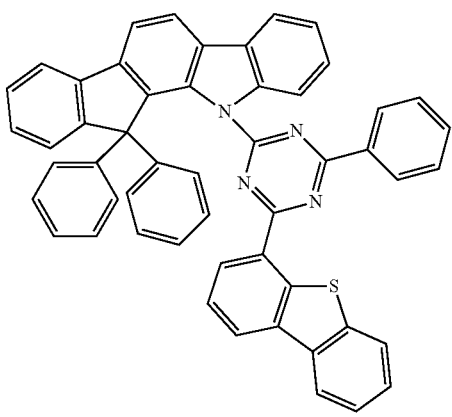

-continued
H2-462
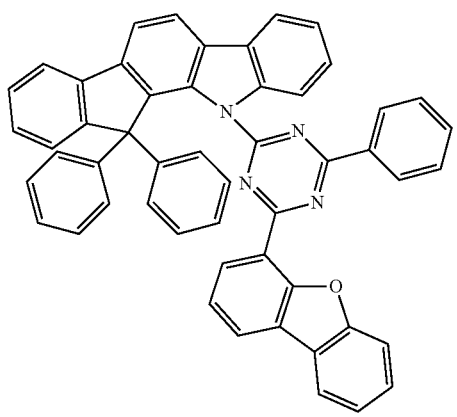
H2-463
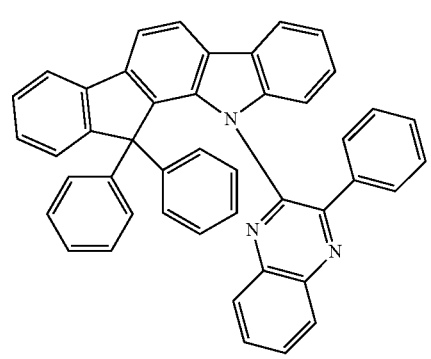
H2-464
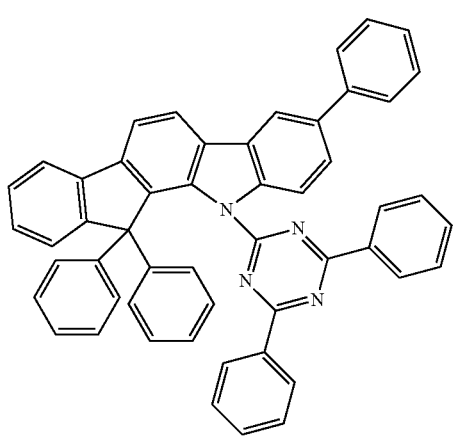
H2-465
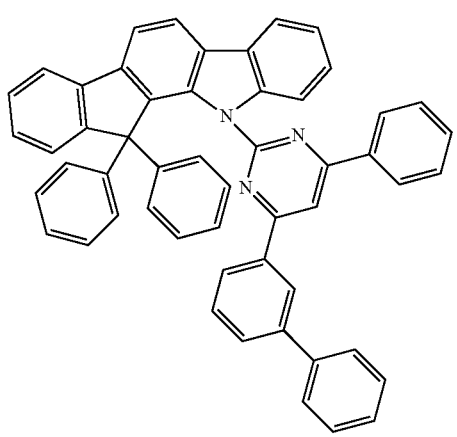
-continued
H2-466
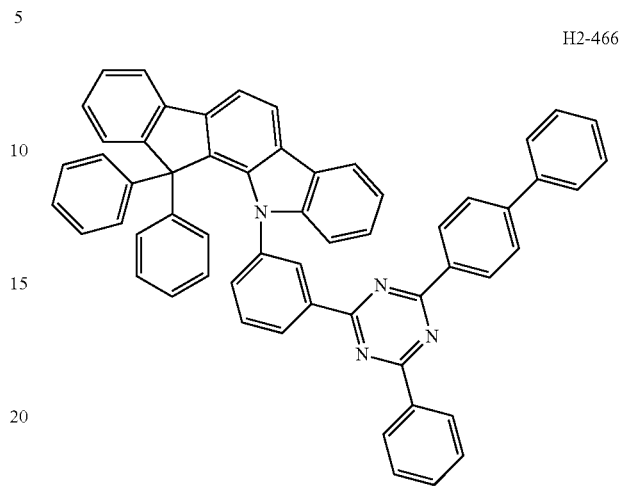
H2-467
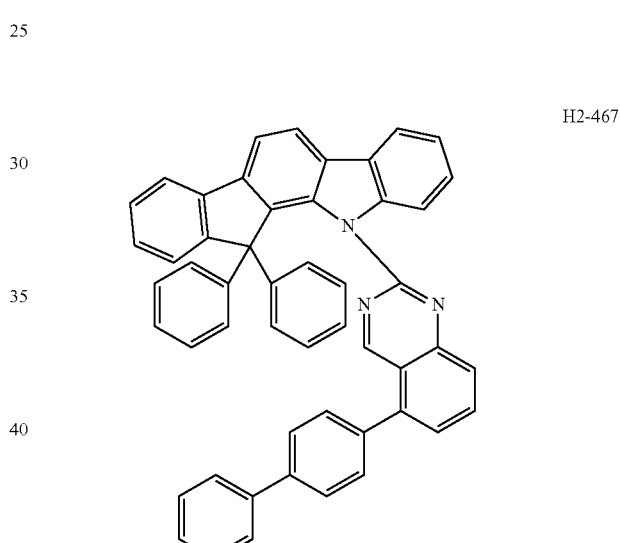
H2-468
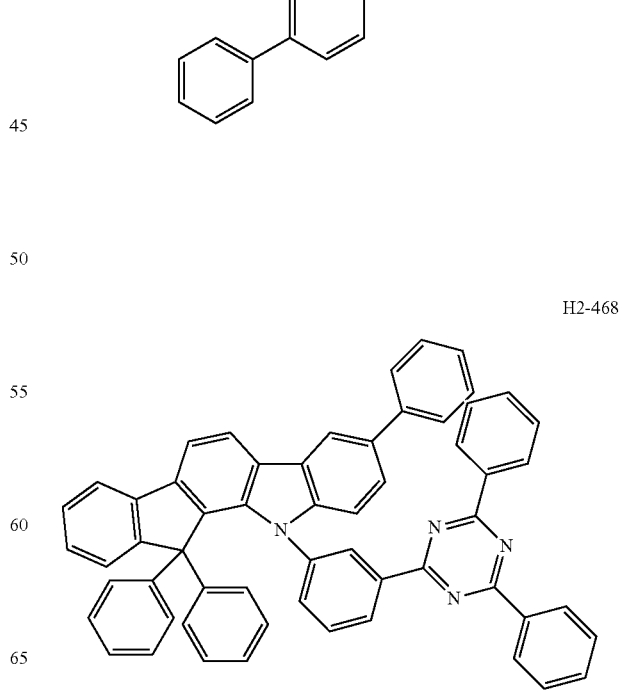

H2-469
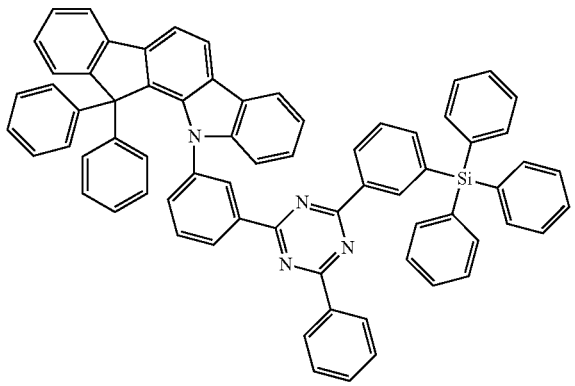
H2-473
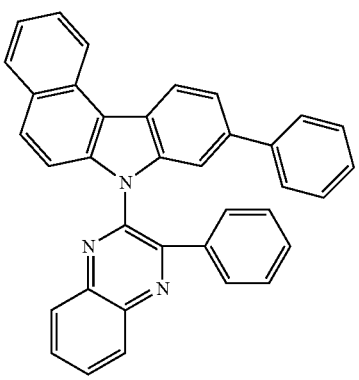
H2-470
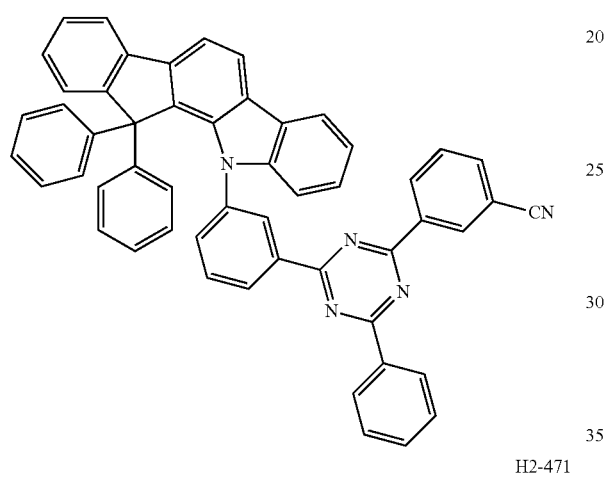
H2-474
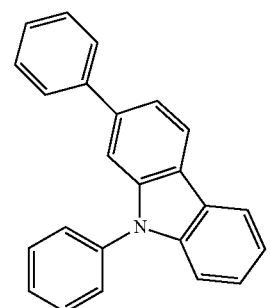
H2-471
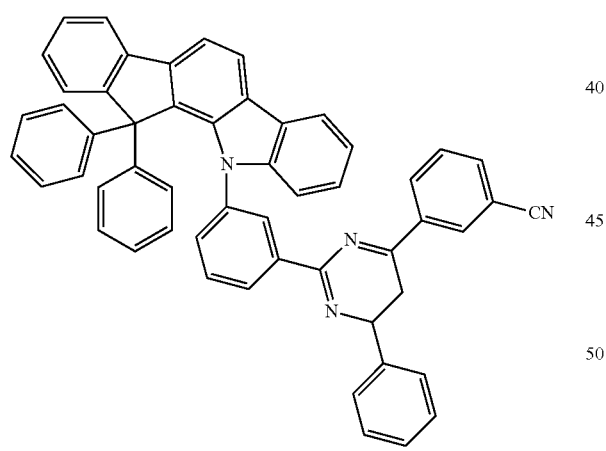
H2-475
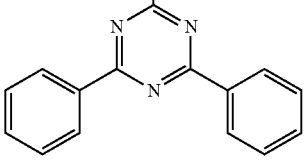
H2-472
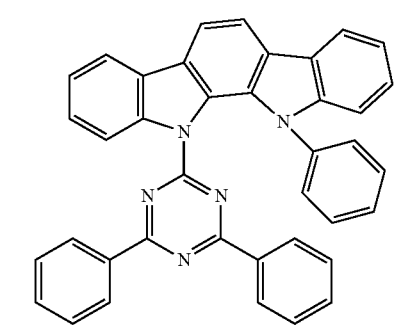
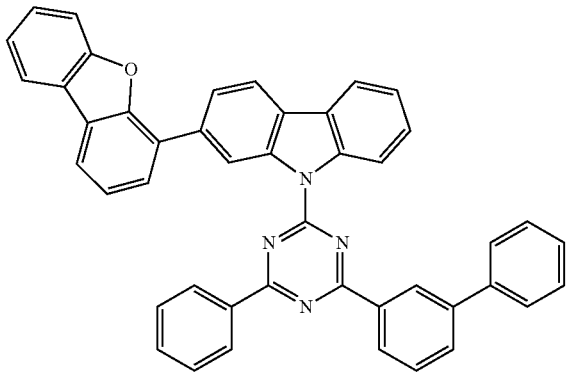

H2-476
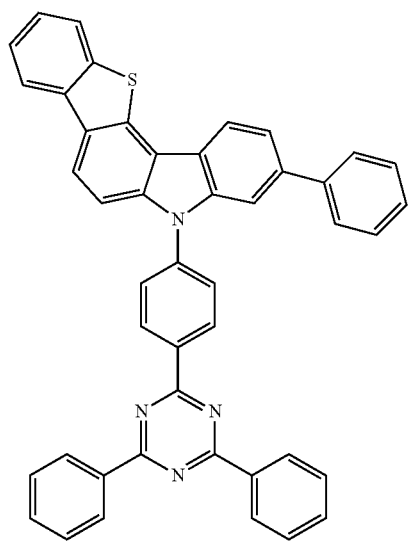
H2-477
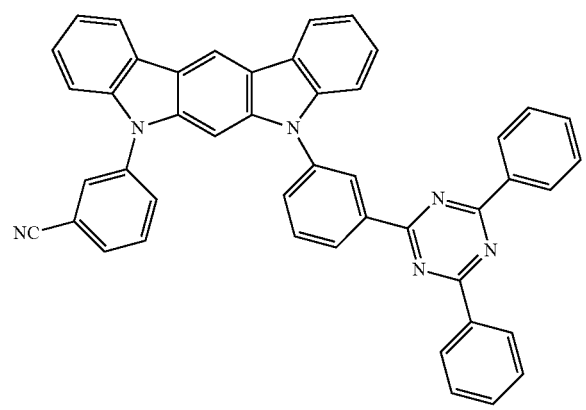
H2-478
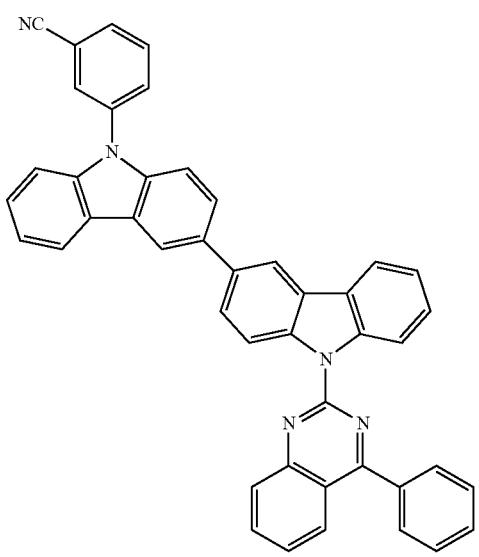
H2-479
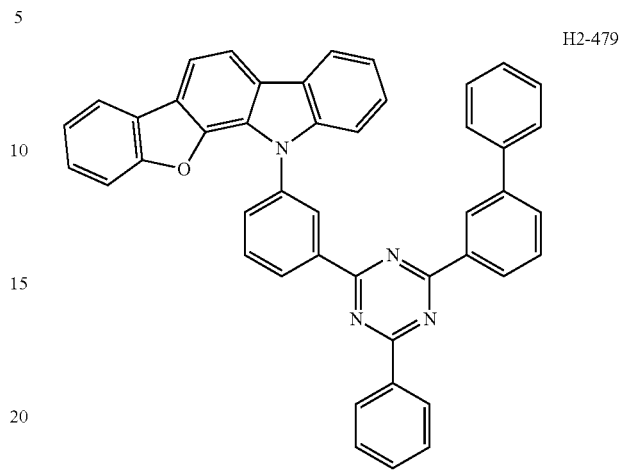
H2-480
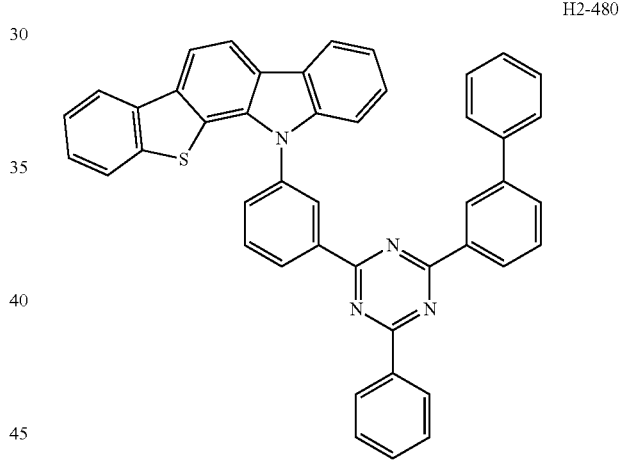
H2-481
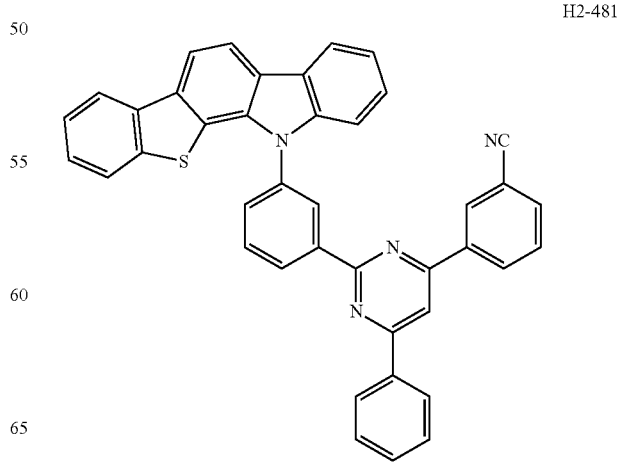

H2-482
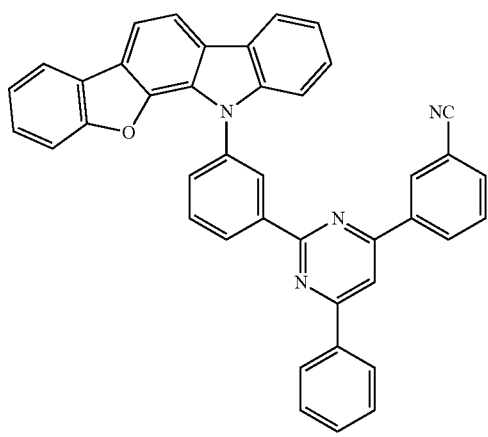
H2-485
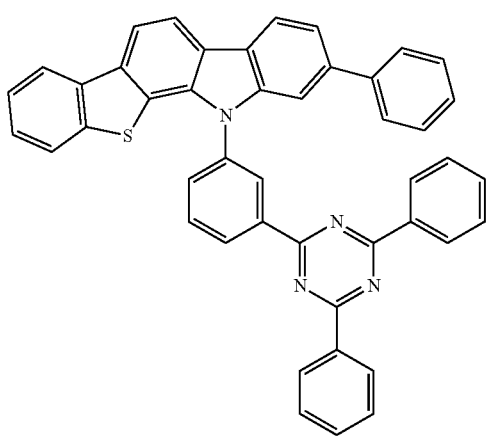
H2-483
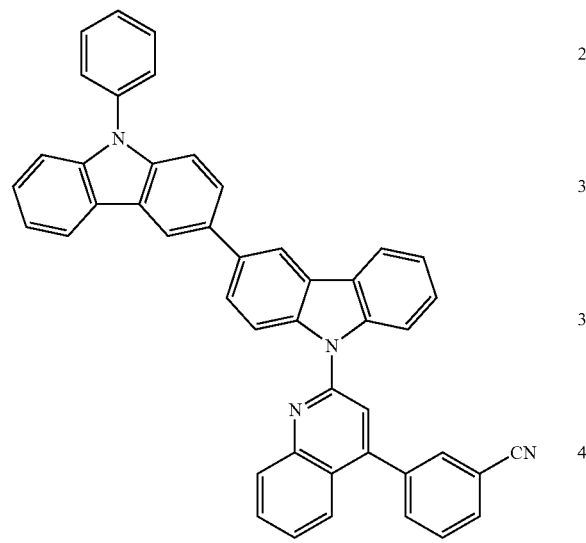
H2-486
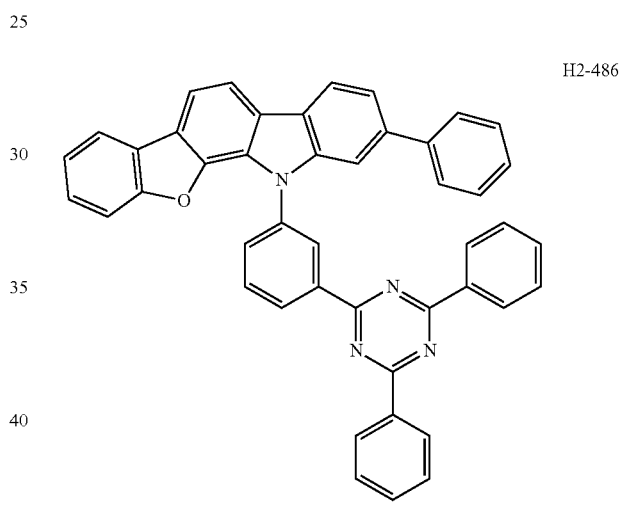
H2-484
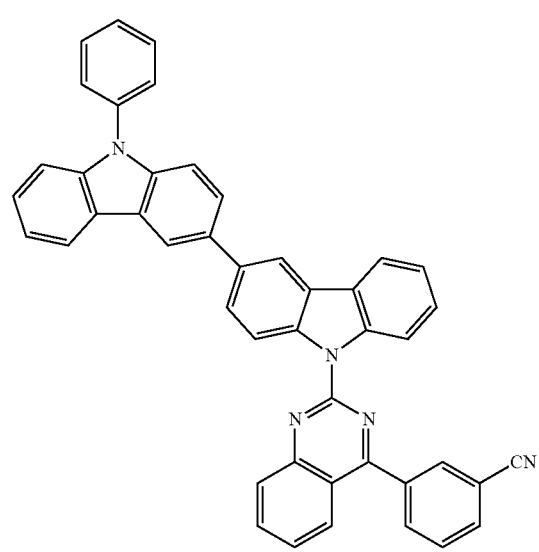
H2-487
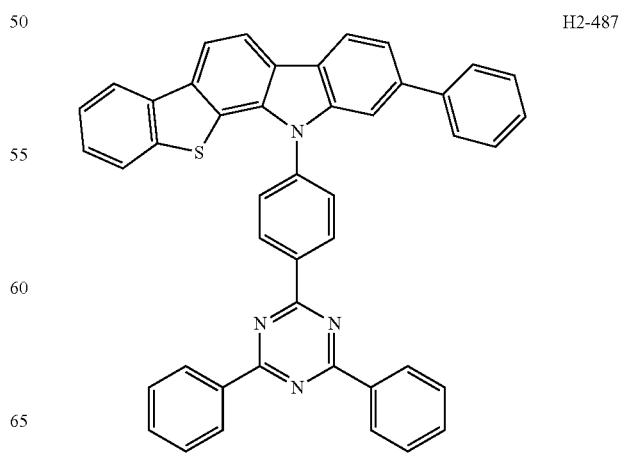

H2-488
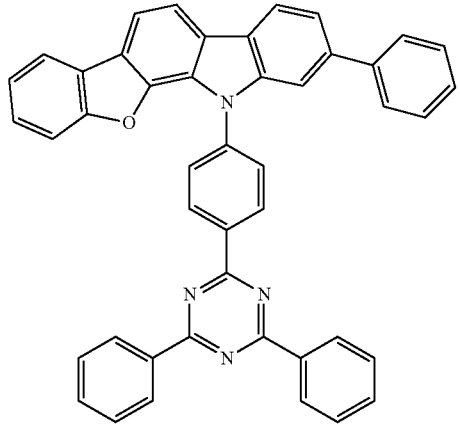
H2-489
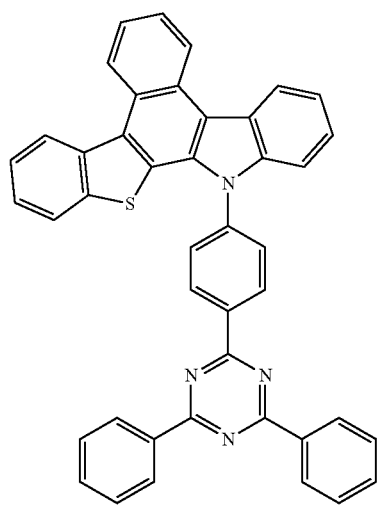
H2-490
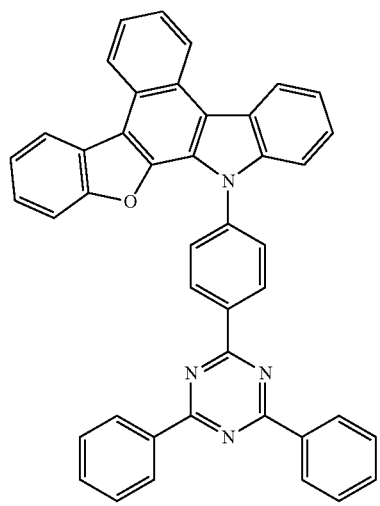
H2-491
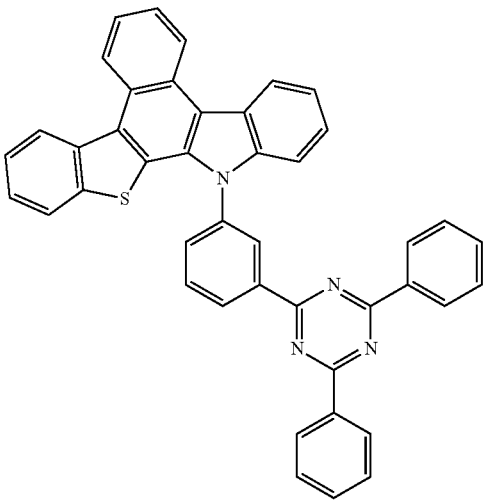
H2-492
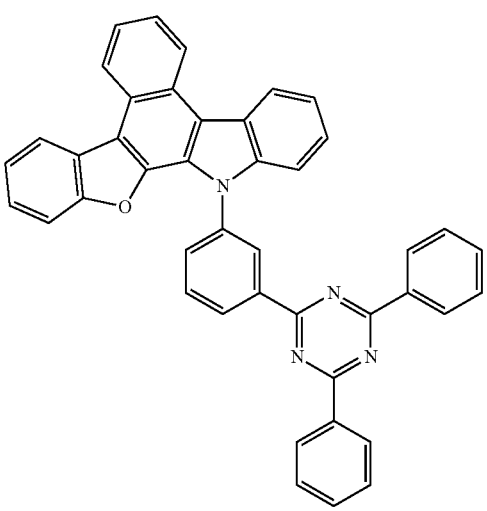
H2-493
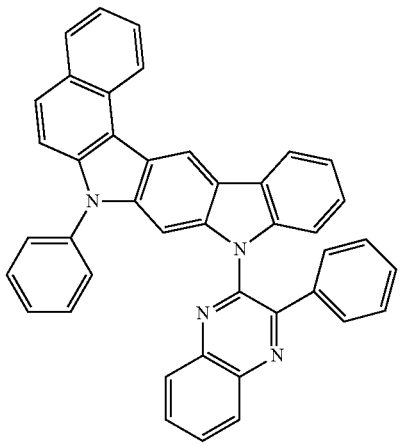

197
-continued

H2-494

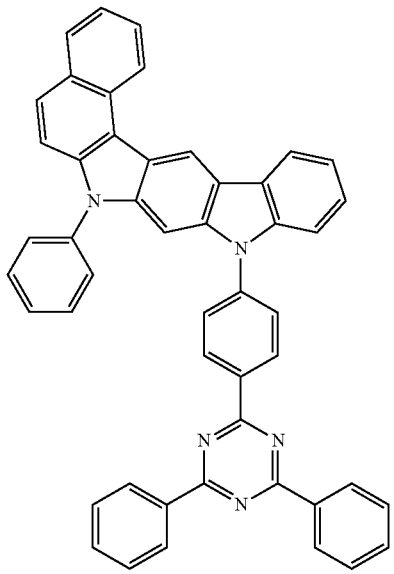

The dopant is preferably at least one phosphorescent dopant. The dopant materials applied to the organic electroluminescent device according to the present disclosure are not limited, but may be preferably selected from metallated complex compounds of iridium (Ir), osmium (Os), copper (Cu), and platinum (Pt), more preferably selected from ortho-metallated complex compounds of iridium (Ir), osmium (Os), copper (Cu), and platinum (Pt), and even more preferably ortho-metallated iridium complex compounds.

The phosphorescent dopant is preferably selected from compounds represented by the following formulas 101 to 103.

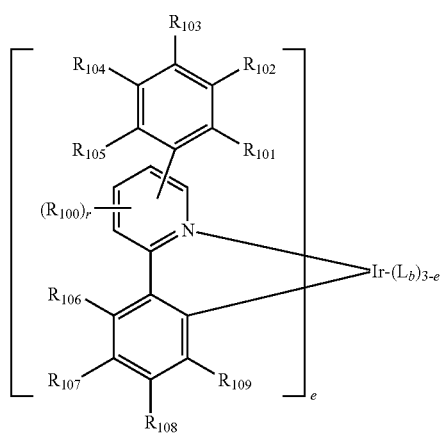
(101)

198
-continued

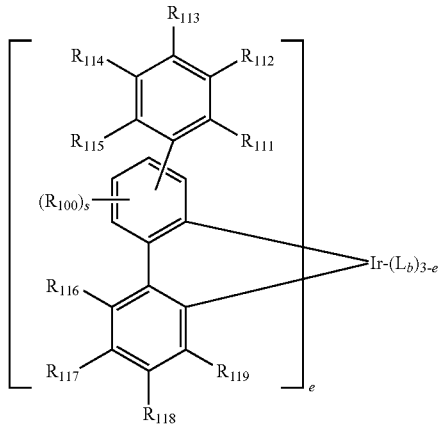
(102)

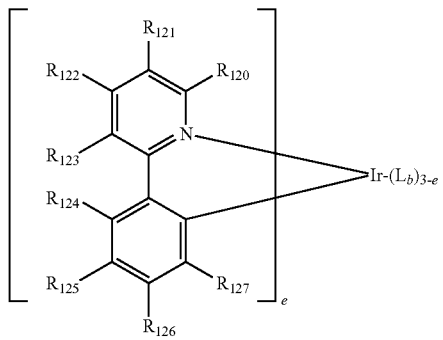
(103)

wherein $L_b$ is selected from the following structures:

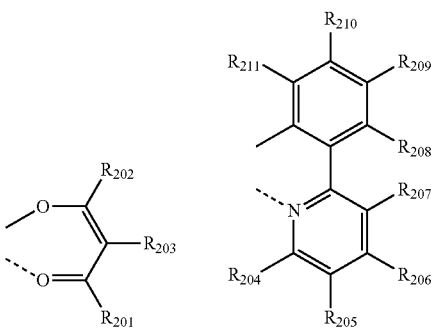

$R_{100}$ represents hydrogen, a substituted or unsubstituted (C1-C30)alkyl, or a substituted or unsubstituted (C3-C30)cycloalkyl;

$R_{101}$ to $R_{109}$, and $R_{111}$ to $R_{123}$ each independently represent hydrogen, deuterium, a halogen, a (C1-C30)alkyl unsubstituted or substituted with a halogen(s), a cyano, a substituted or unsubstituted (C1-C30)alkoxy, a substituted or unsubstituted (C6-C30)aryl, or a substituted or unsubstituted (C3-C30)cycloalkyl; adjacent substituents of $R_{106}$ to $R_{109}$ may be linked to each other to form a substituted or unsubstituted fused ring, e.g., fluorene unsubstituted or substituted with alkyl, dibenzothiophene unsubstituted or substituted with alkyl, or dibenzofuran unsubstituted or substituted with alkyl; and adjacent substituents of $R_{120}$ to $R_{123}$ may be linked to each other to form a substituted or unsubstituted fused ring, e.g., quinoline unsubstituted or substituted with alkyl or aryl;

$R_{124}$ to $R_{127}$ each independently represent hydrogen, deuterium, a halogen, a substituted or unsubstituted (C1-C30) alkyl, or a substituted or unsubstituted (C6-C30)aryl; and adjacent substituents of $R_{124}$ to $R_{127}$ may be linked to each other to form a substituted or unsubstituted fused ring, e.g., fluorene unsubstituted or substituted with alkyl, dibenzothiophene unsubstituted or substituted with alkyl, or dibenzofuran unsubstituted or substituted with alkyl;

$R_{201}$ to $R_{211}$ each independently represent hydrogen, deuterium, a halogen, a (C1-C30)alkyl unsubstituted or substituted with a halogen(s), a substituted or unsubstituted (C3-C30)cycloalkyl, or a substituted or unsubstituted (C6-C30) aryl; and adjacent substituents of $R_{208}$ to $R_{211}$ may be linked to each other to form a substituted or unsubstituted fused ring, e.g., fluorene unsubstituted or substituted with alkyl, dibenzothiophene unsubstituted or substituted with alkyl, or dibenzofuran unsubstituted or substituted with alkyl;

r and s each independently represent an integer of 1 to 3; where r or s is an integer of 2 or more, each of $R_{100}$ may be the same or different; and e represents an integer of 1 to 3.

Specifically, the phosphorescent dopant materials include the following:

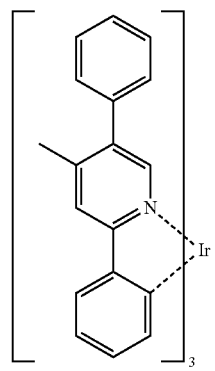

D-1

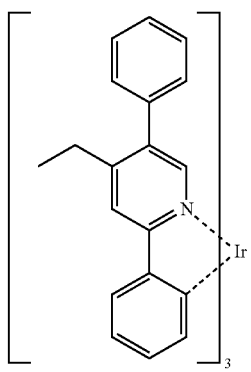

D-2

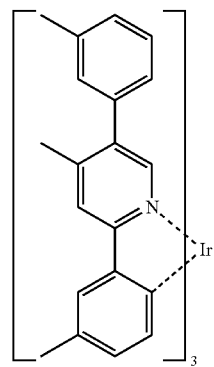

D-3

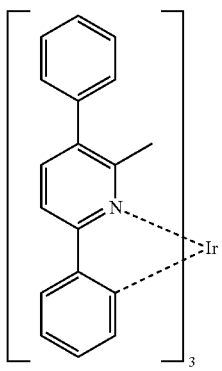

D-4

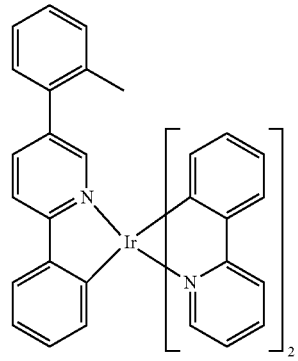

D-5

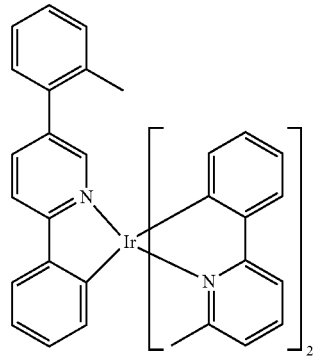

D-6

-continued
D-7
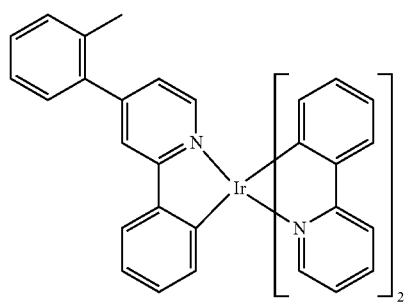
D-8
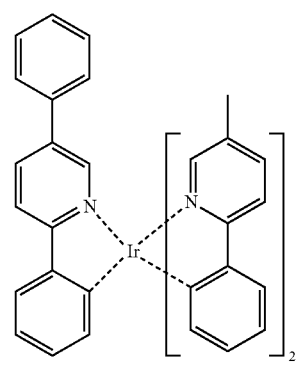
D-9
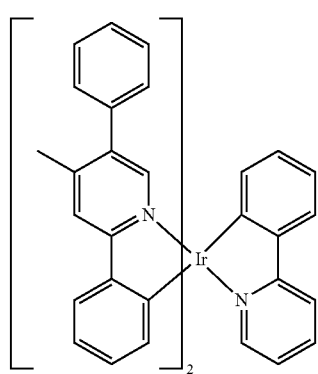
D-10
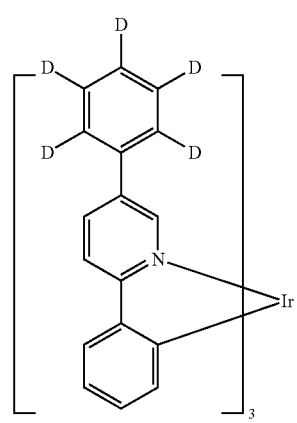
-continued
D-11
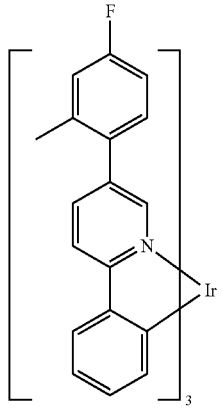
D-12
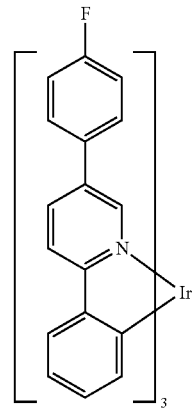
D-13
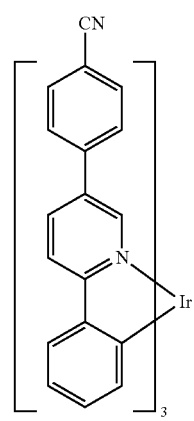
D-14
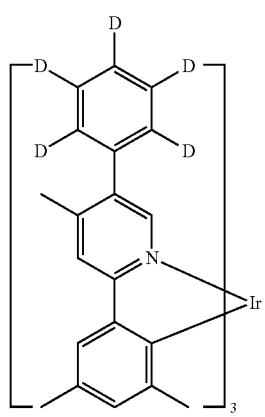

D-15
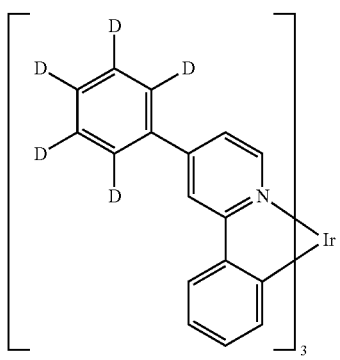
D-16
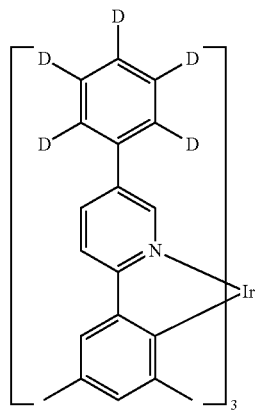
D-17
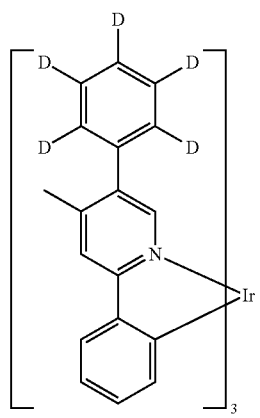
D-18
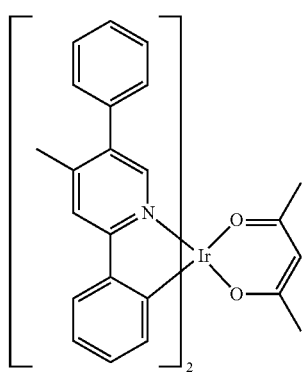
D-19
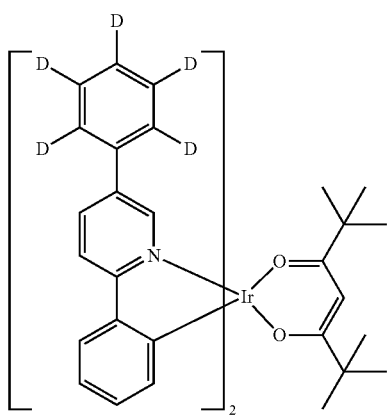
D-20
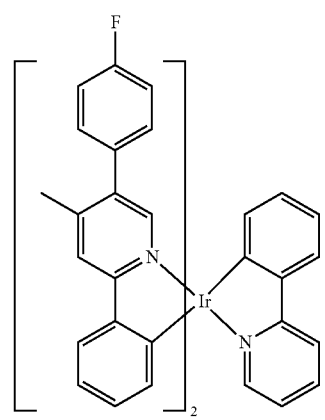
D-21
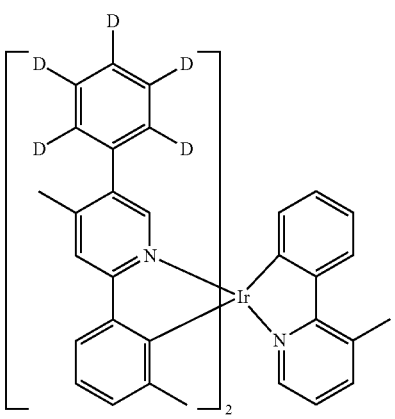
D-22
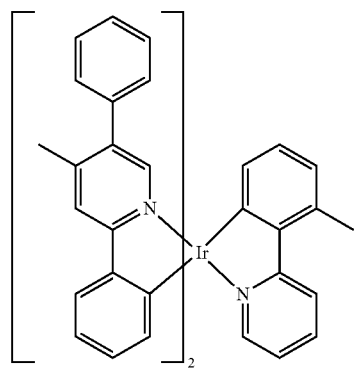

D-23 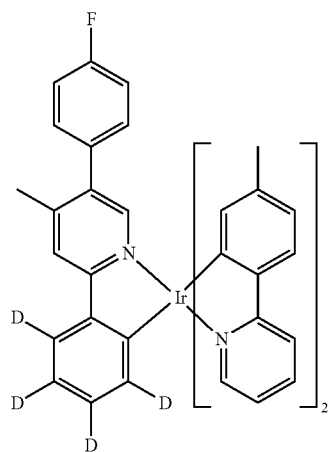
D-24 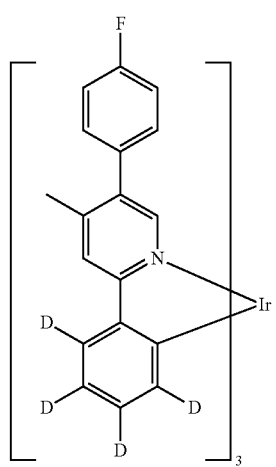
D-25
D-26
D-27 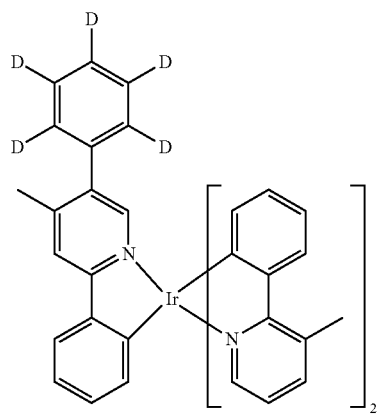
D-28 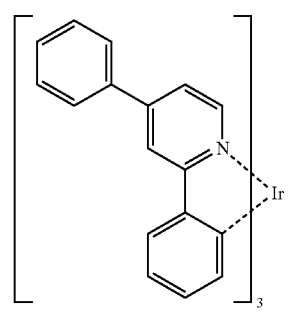
D-29 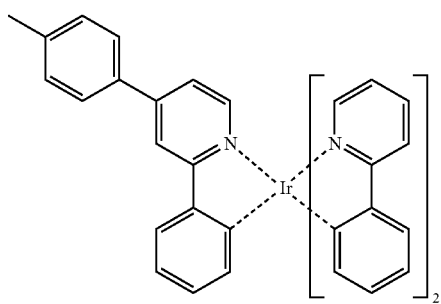
D-30 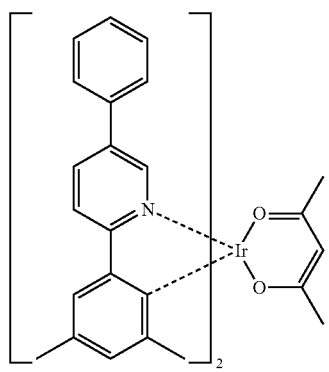

D-31 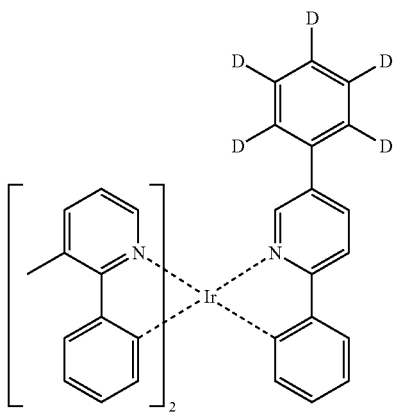
D-32 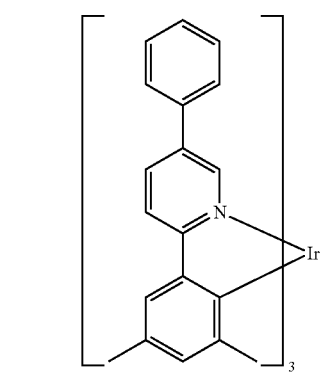
D-33 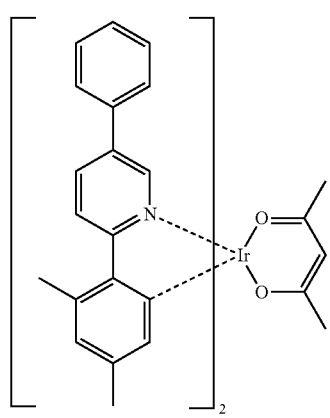
D-34 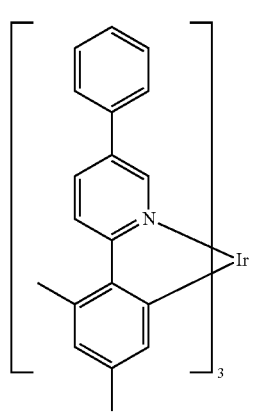
D-35 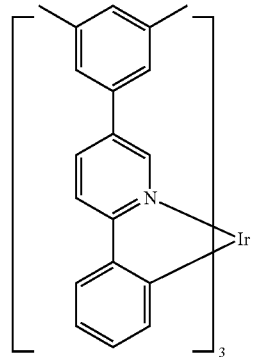
D-36 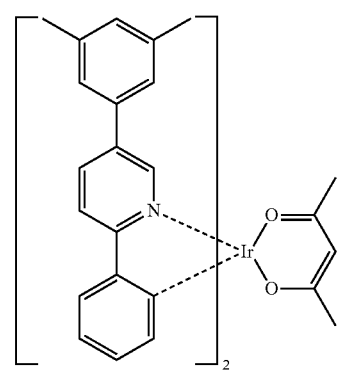
D-37 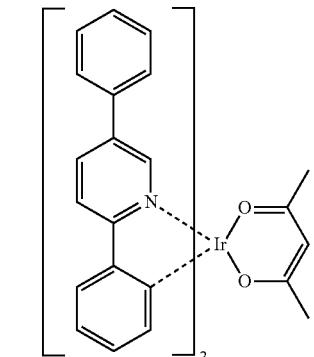
D-38 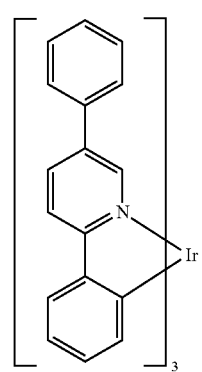

-continued
D-39
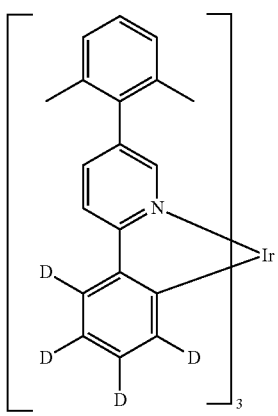
D-40
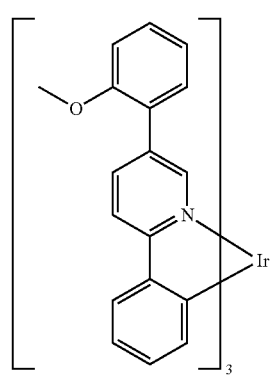
D-41
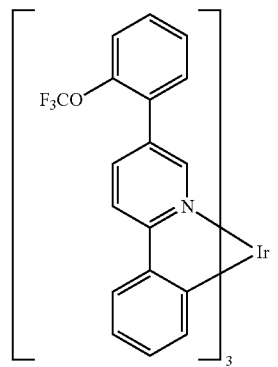
D-42
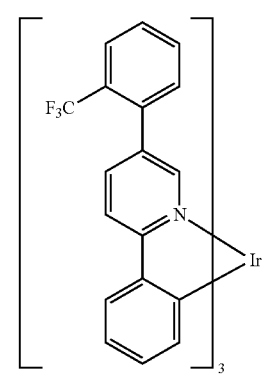
-continued
D-43
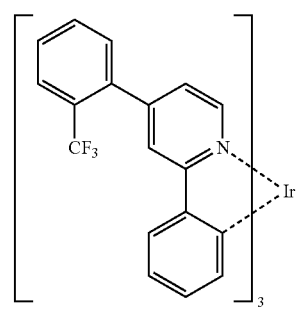
D-44
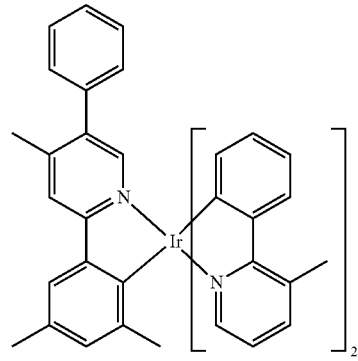
D-45
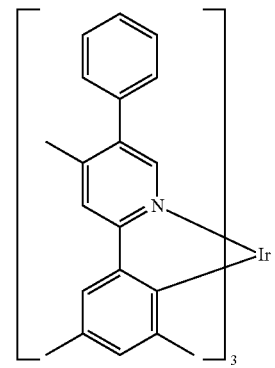
D-46
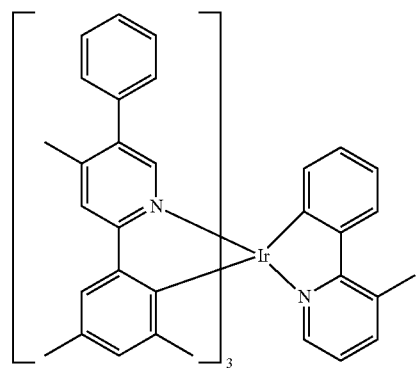

-continued
D-47
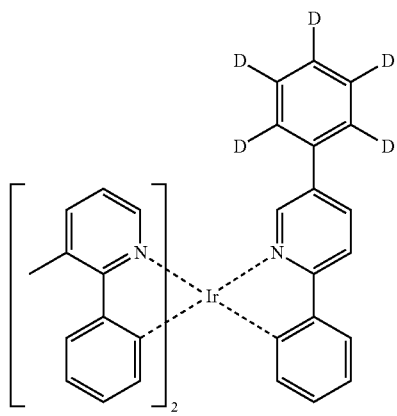
D-48
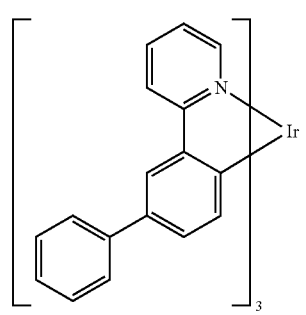
D-49
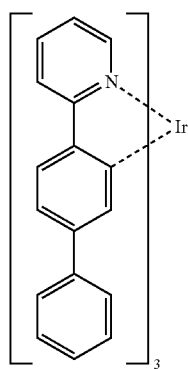
D-50
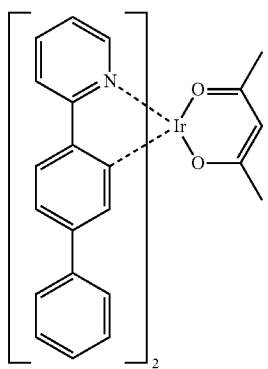
-continued
D-51
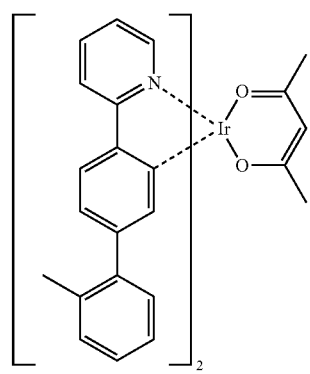
D-52
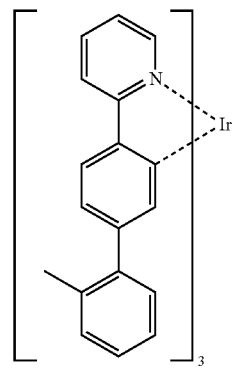
D-53
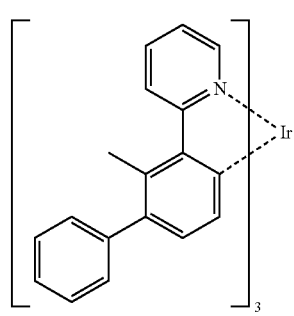
D-54
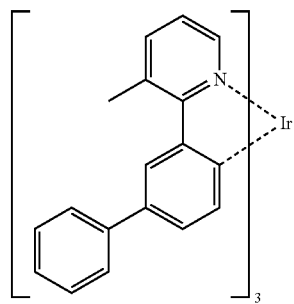

D-55 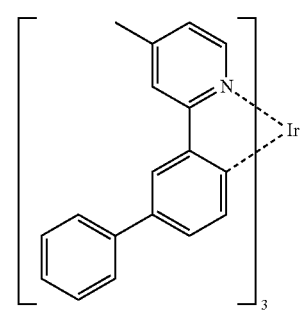
D-56 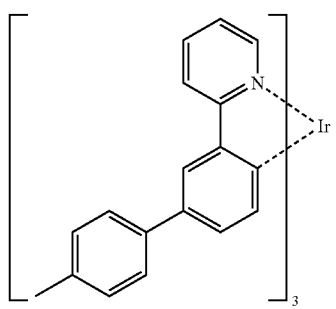
D-57 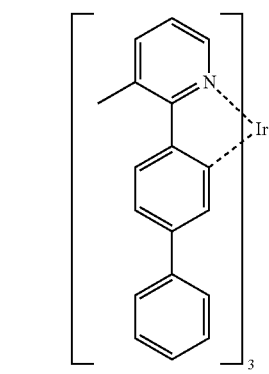
D-58 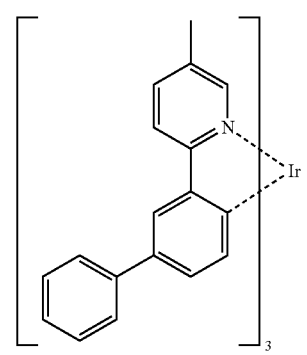
D-59 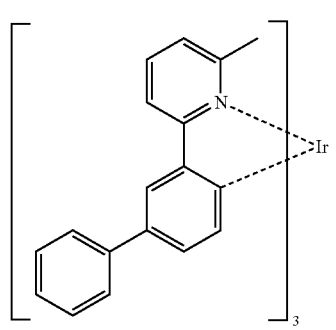
D-60 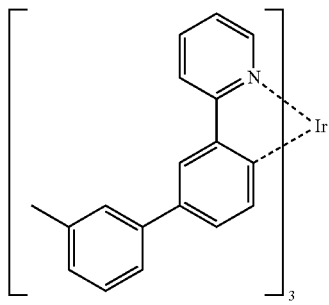
D-61 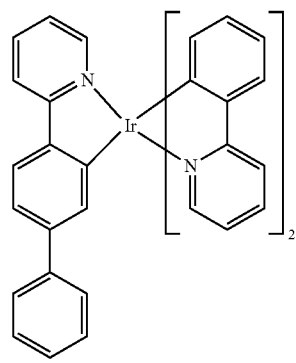
D-62 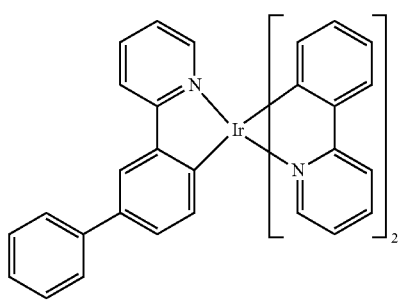
D-63 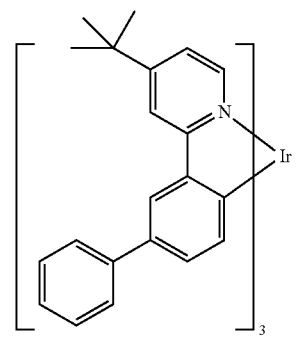
D-64 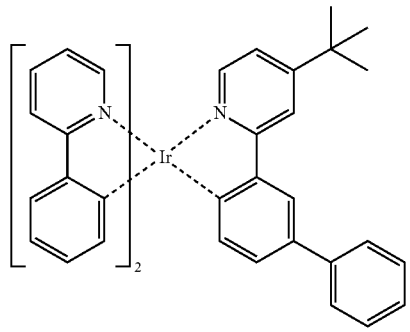

D-65
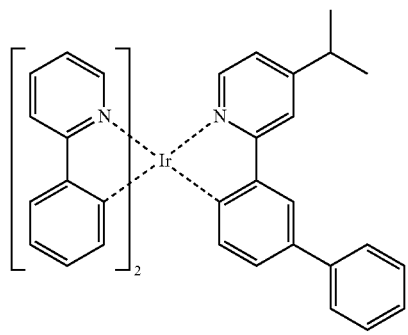
D-66
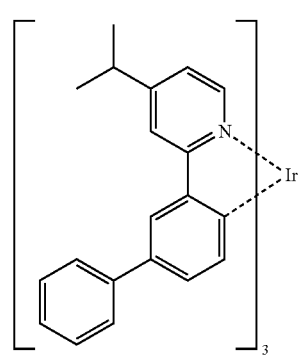
D-67
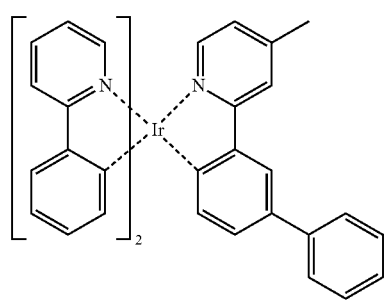
D-68
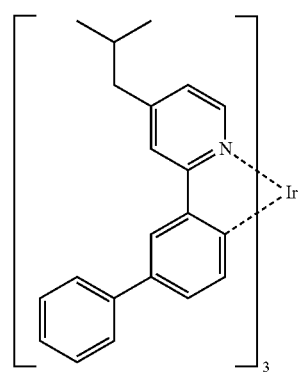
D-69
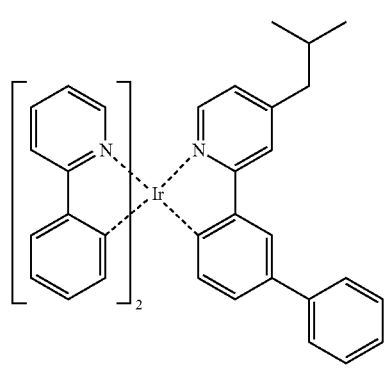
D-70
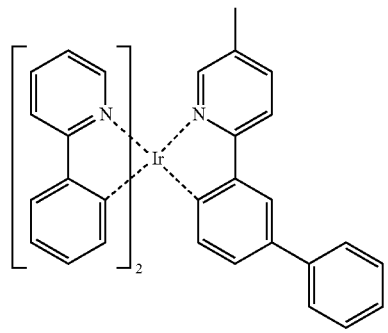
D-71
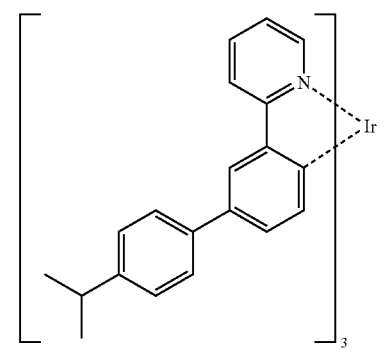
D-72
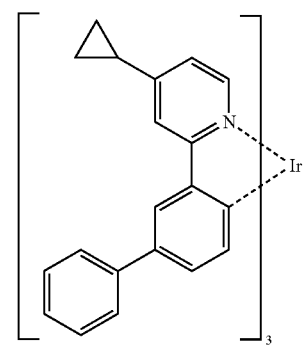

-continued
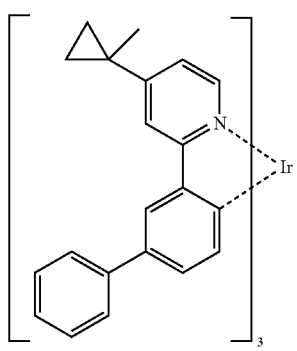
D-73
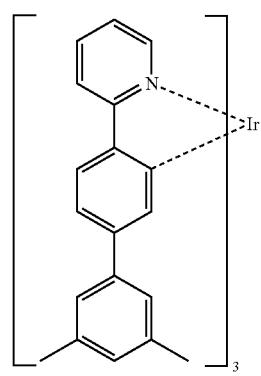
D-77
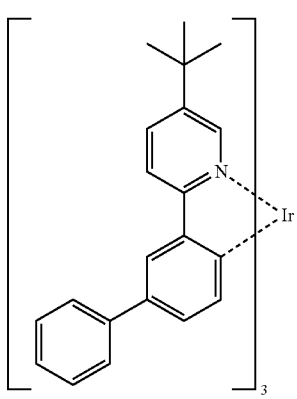
D-74
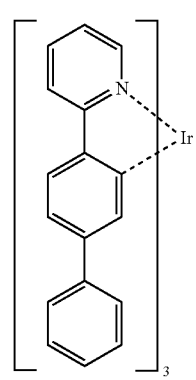
D-78
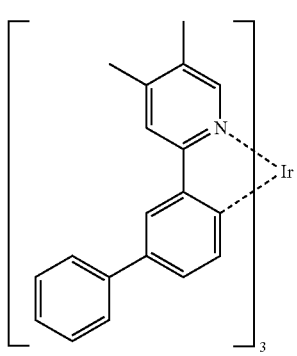
D-75
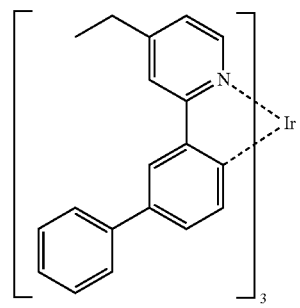
D-79
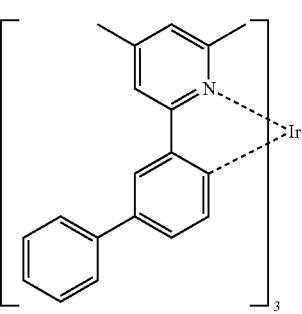
D-76
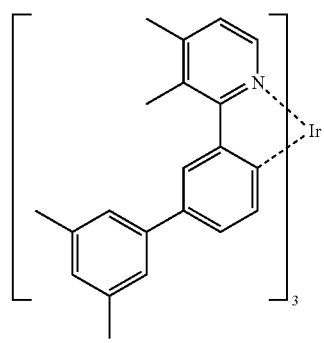
D-80

D-81 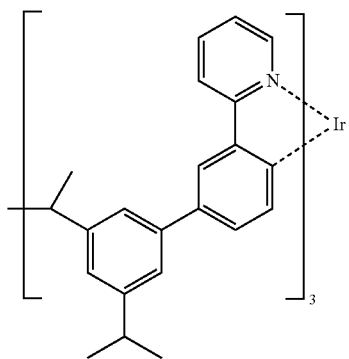
D-82 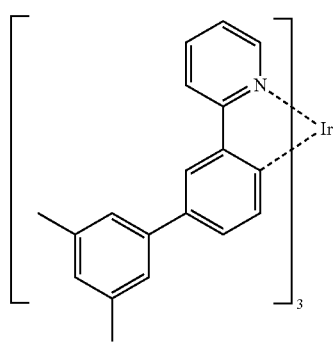
D-83 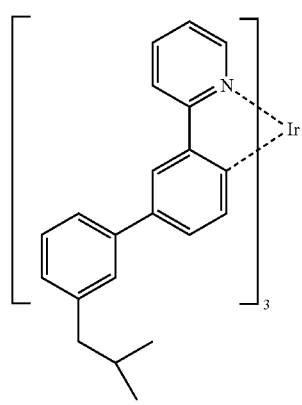
D-84 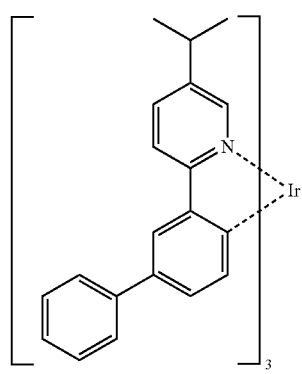
D-85 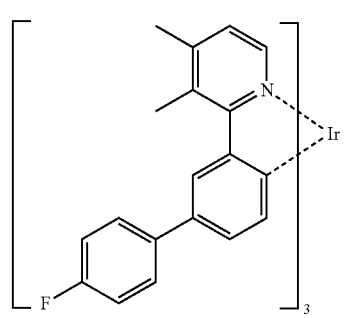
D-86 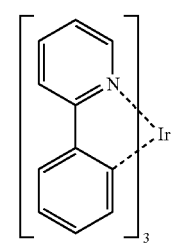
D-87 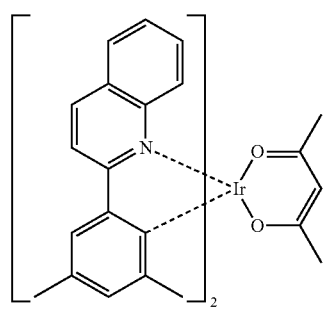
D-88 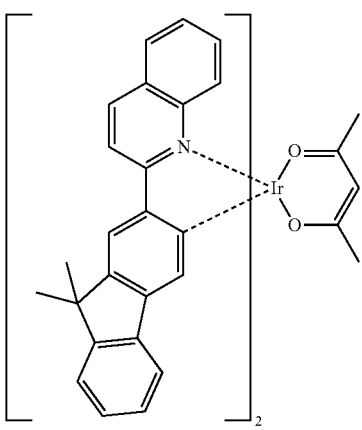
D-89 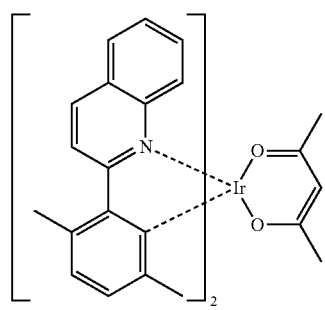

-continued
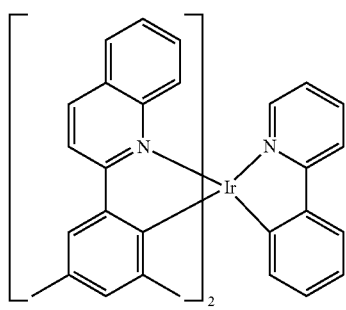
D-90
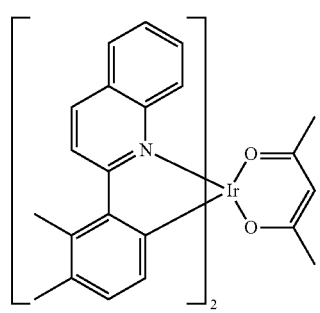
D-91
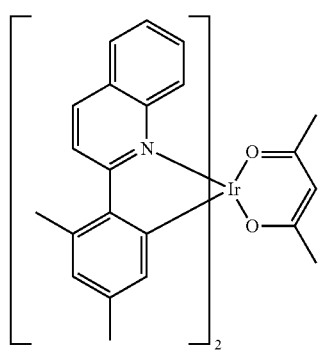
D-92
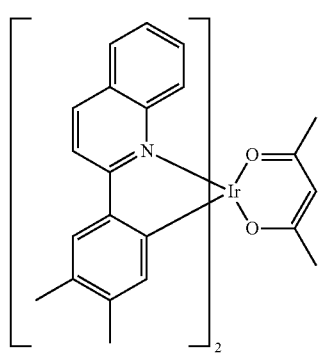
D-93
-continued
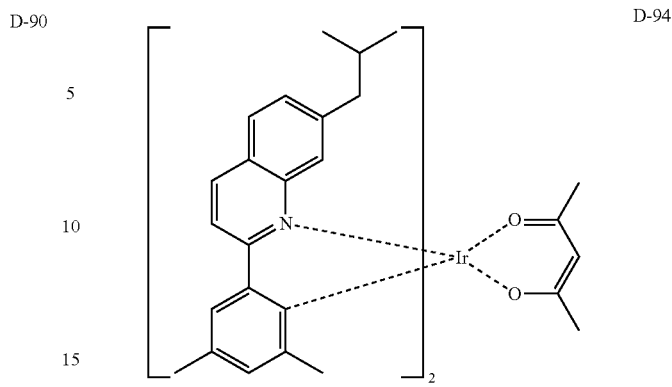
D-94
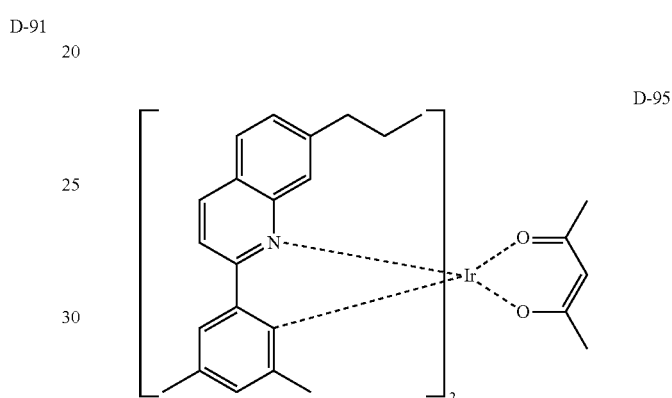
D-95
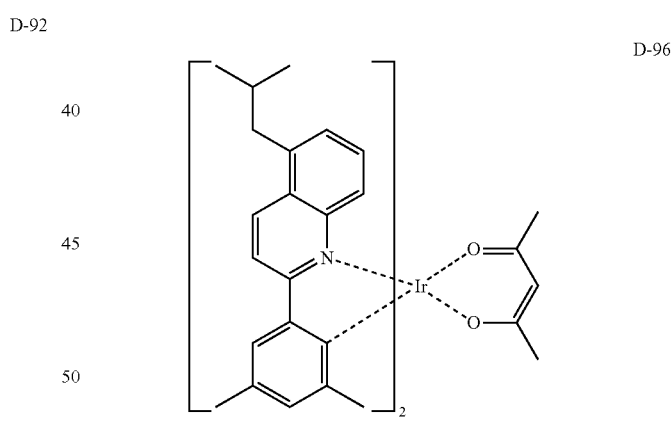
D-96
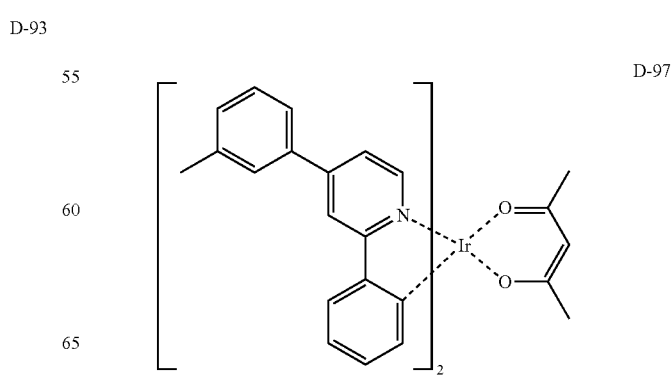
D-97

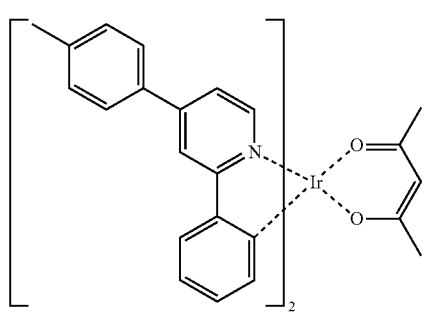
D-98
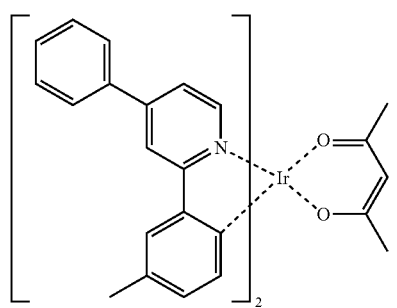
D-99
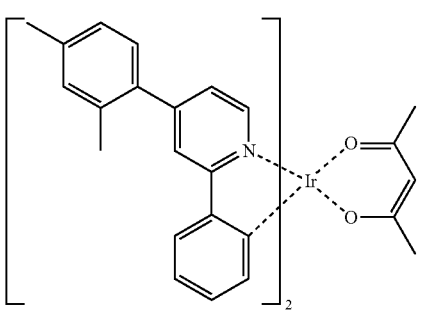
D-100
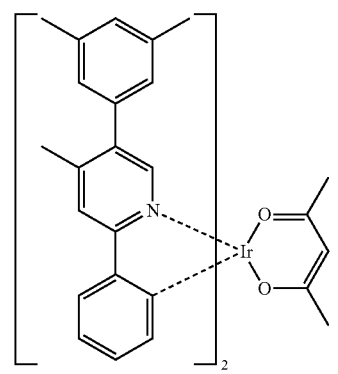
D-101
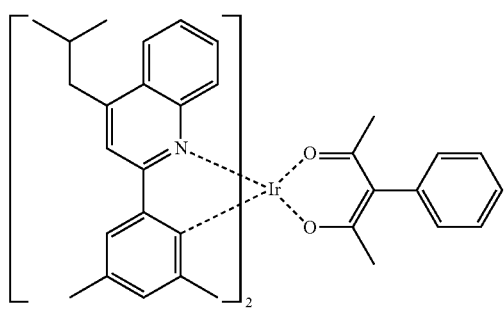
D-102
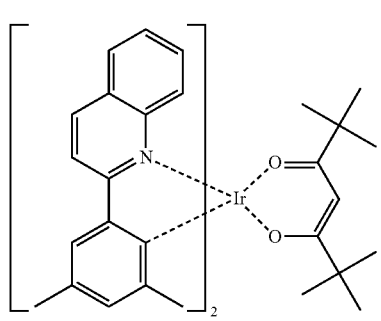
D-103
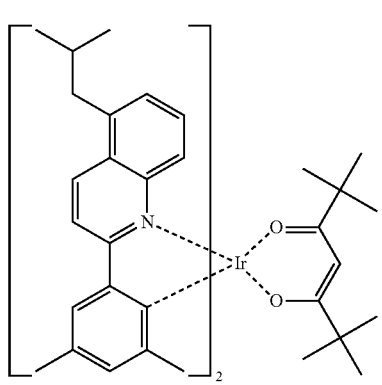
D-104
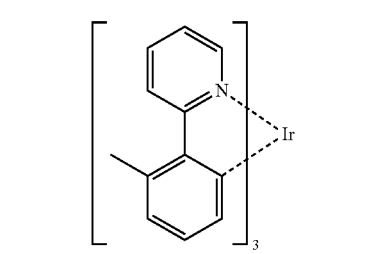
D-105
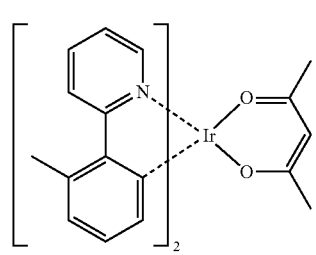
D-106
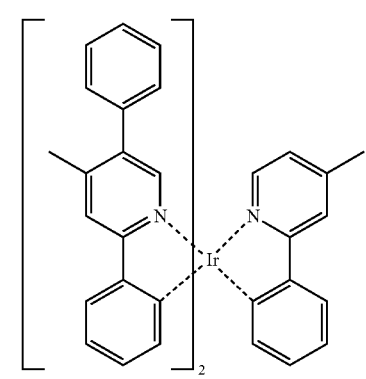
D-107

D-108
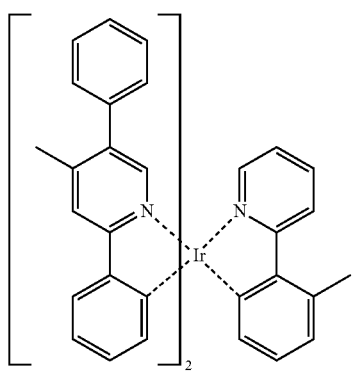
D-109
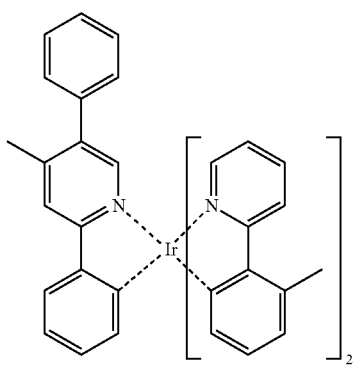
D-110
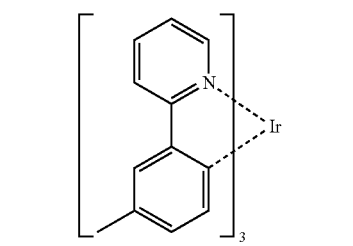
D-111
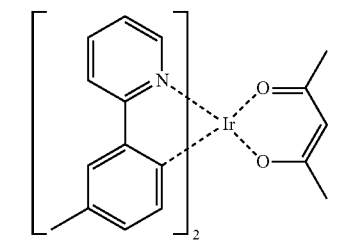
D-112
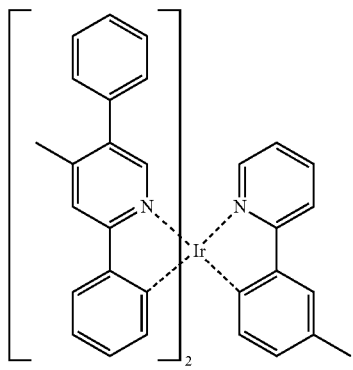
D-113
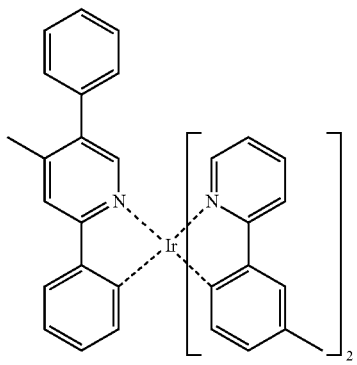
D-114
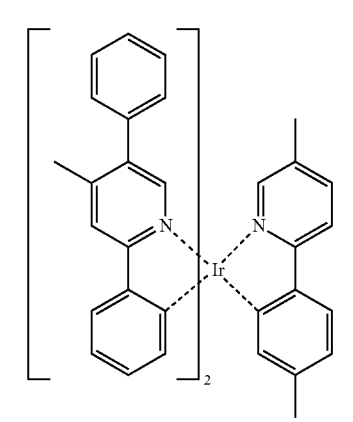
D-115
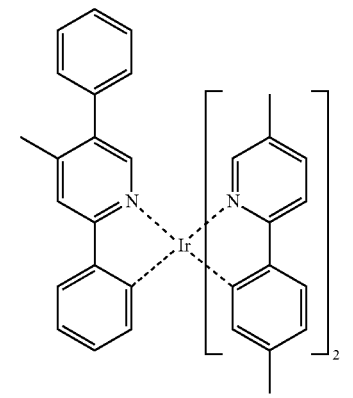
D-116
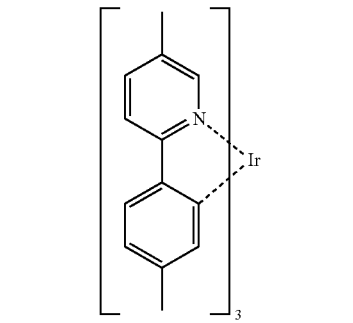

D-117
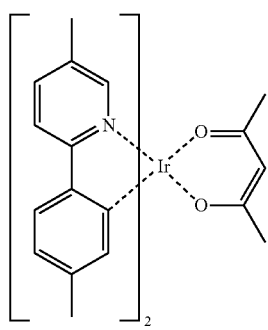
D-118
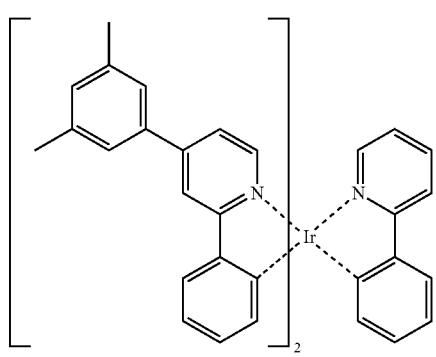
D-119
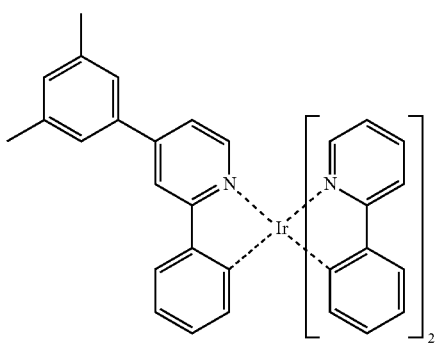
D-120
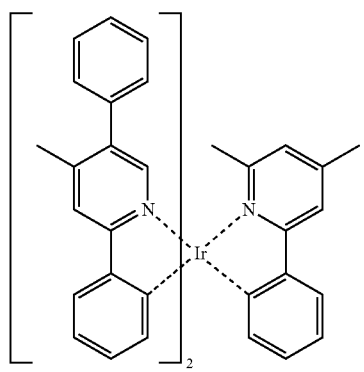
D-121
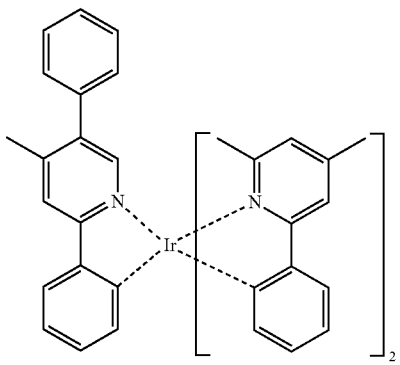
D-122
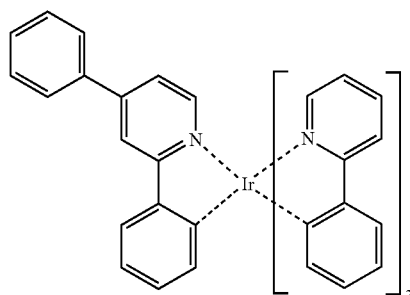
D-123
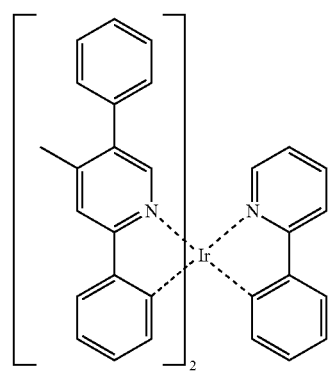
D-124
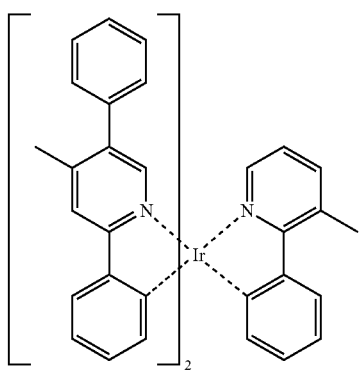

D-125
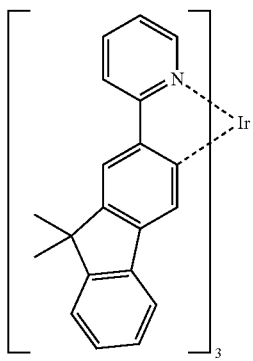
D-126
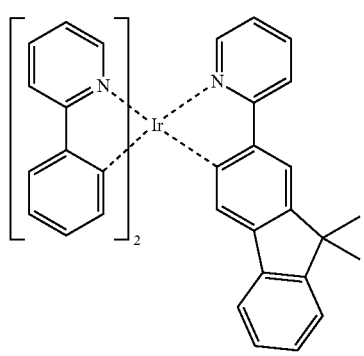
D-127
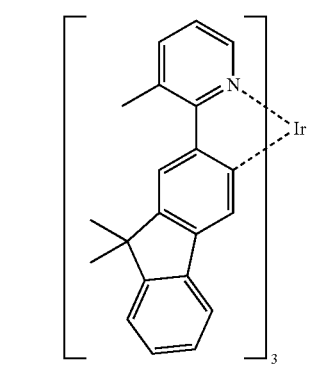
D-128
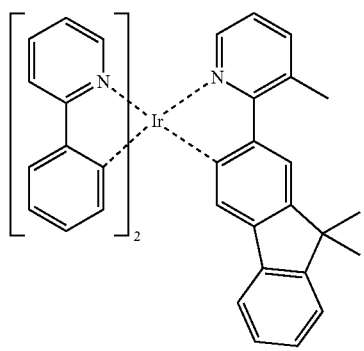
D-129
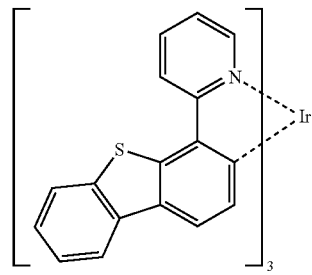
D-130
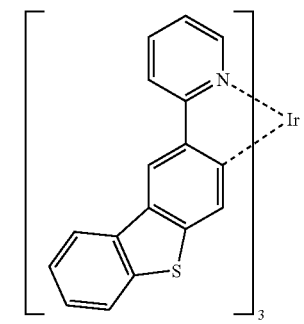
D-131
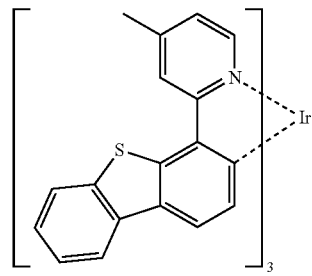
D-132
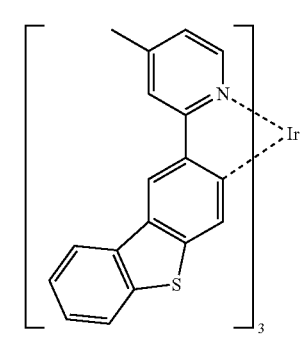
D-133
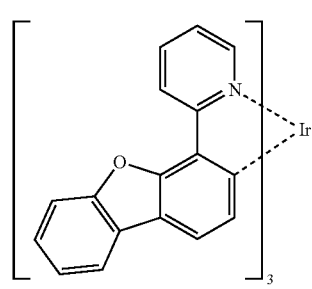

D-134
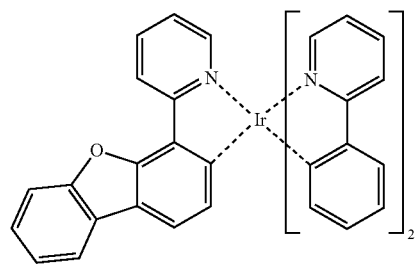
D-135
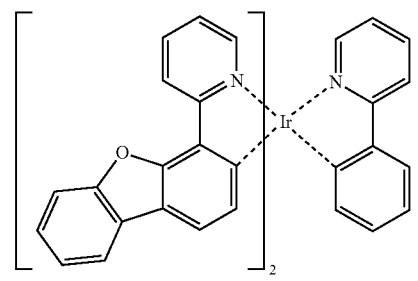
D-136
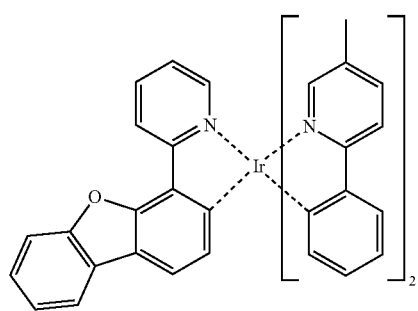
D-137
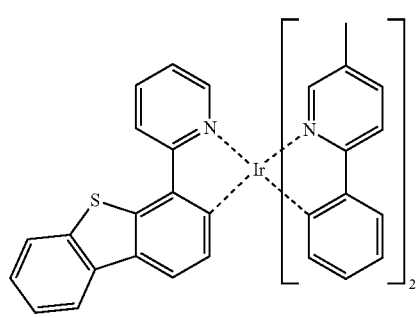
D-138
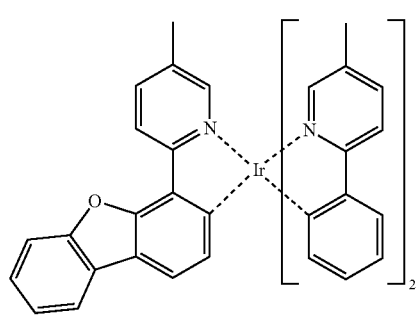
D-139
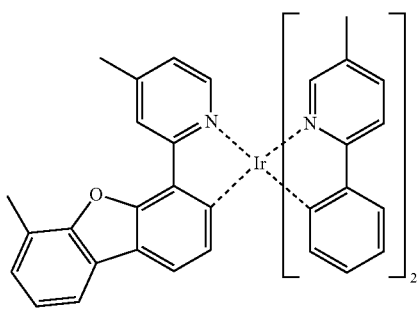
D-140
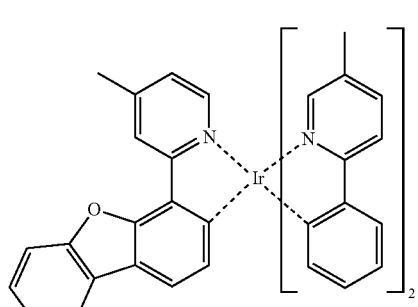
D-141
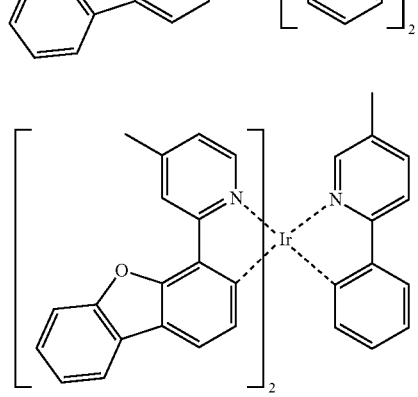
D-142
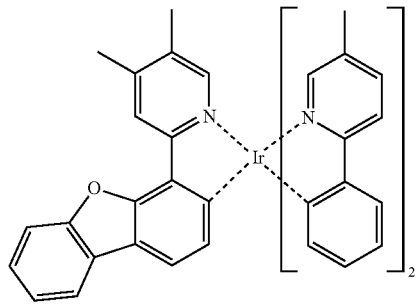
D-143
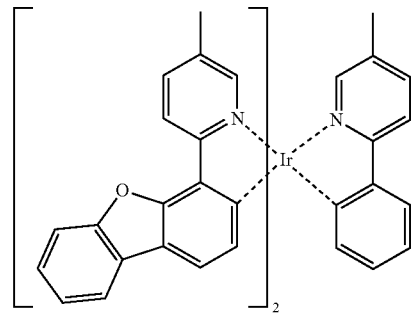

-continued
D-144
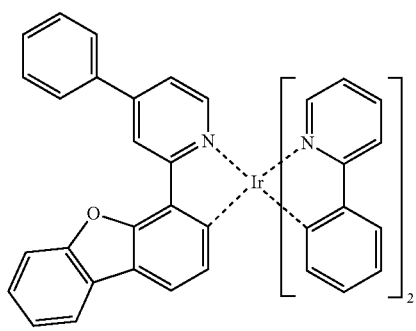
D-145
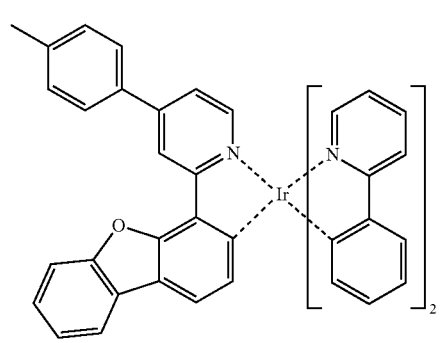
D-146
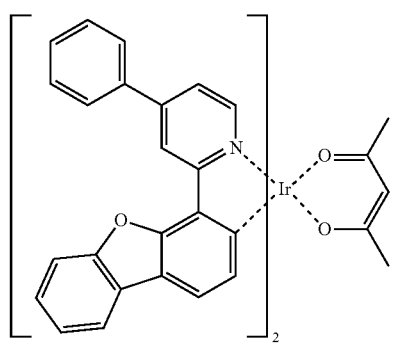
D-147
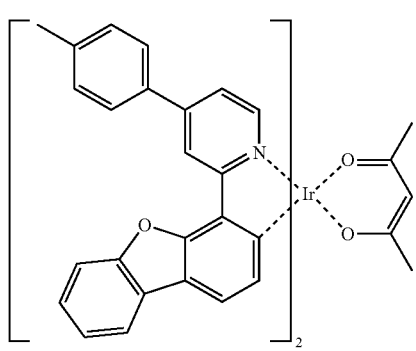
-continued
D-148
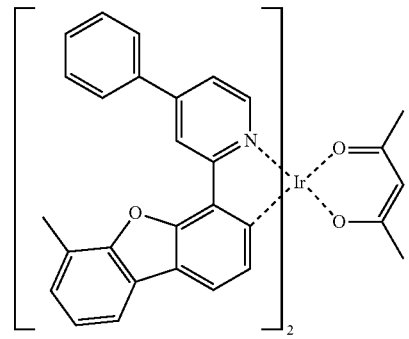
D-149
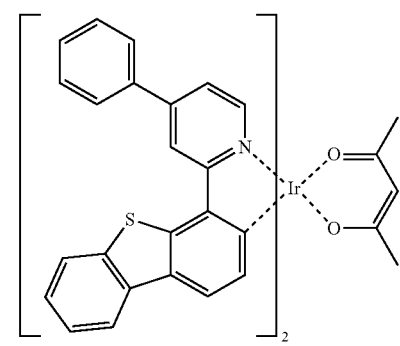
D-150
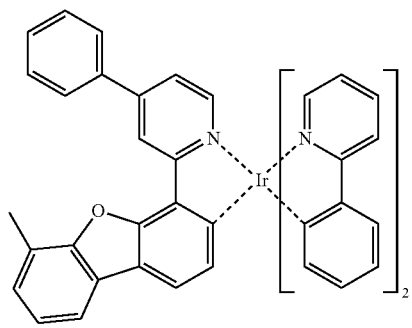
D-151
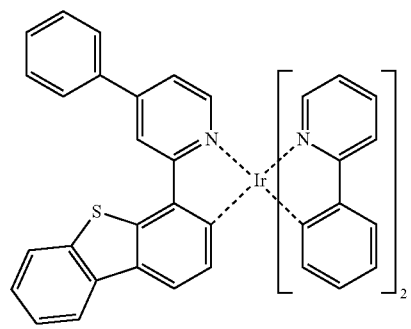
D-152
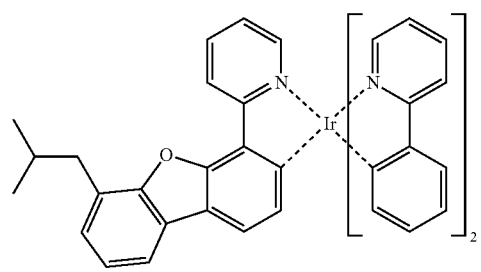

-continued
D-153
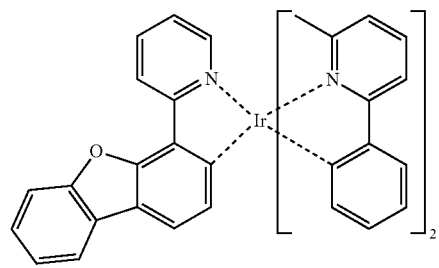
D-154
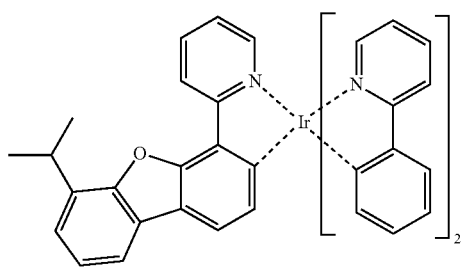
D-155
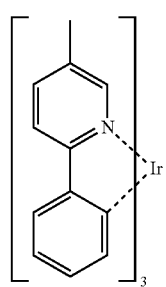
D-156
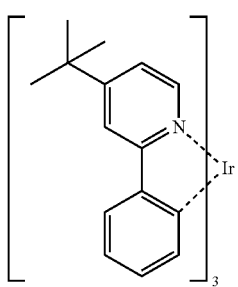
D-157
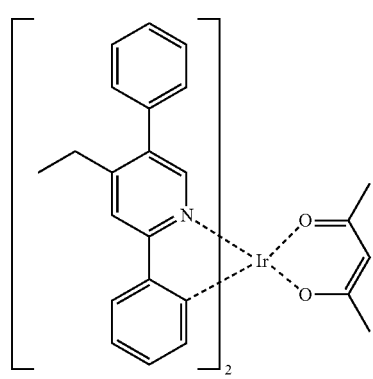
-continued
D-158
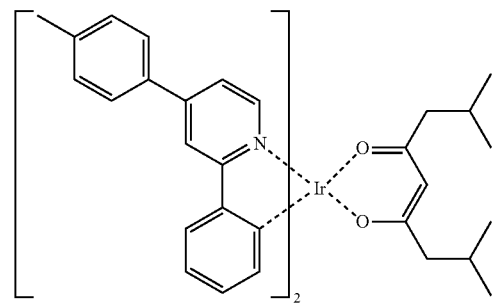
D-159
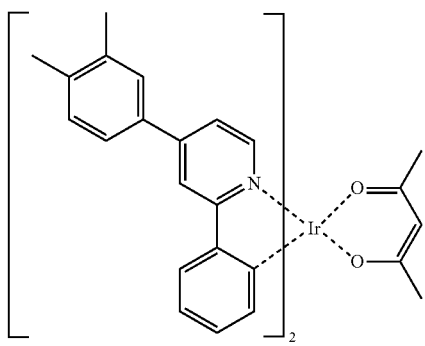
D-160
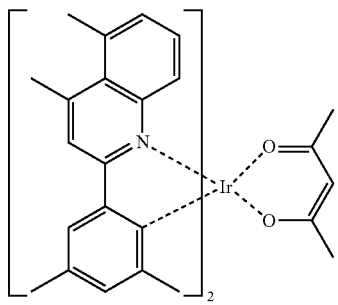
D-161
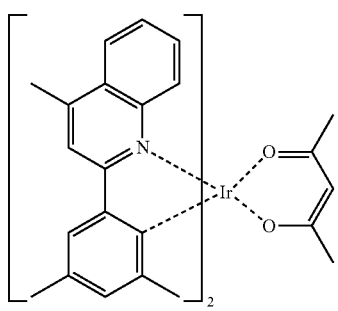
D-162
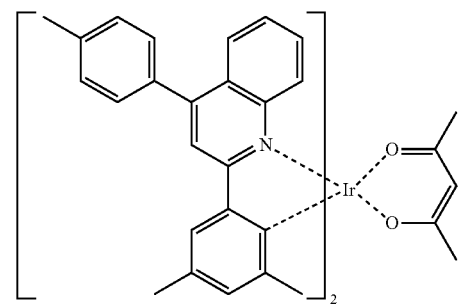

-continued
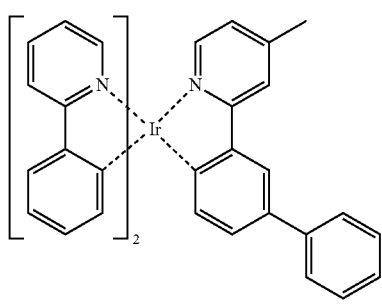
D-163
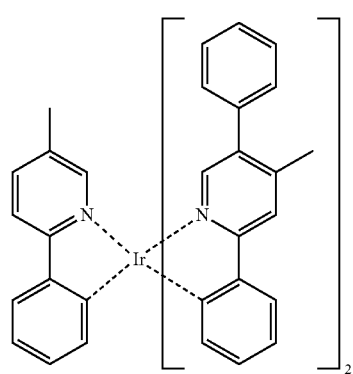
D-164
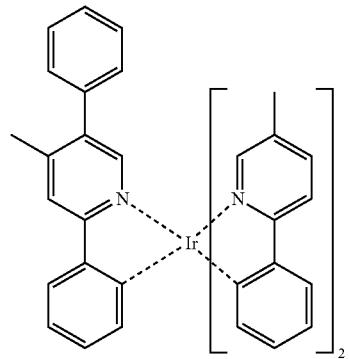
D-165
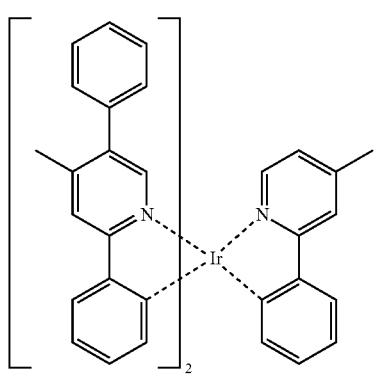
D-166
-continued
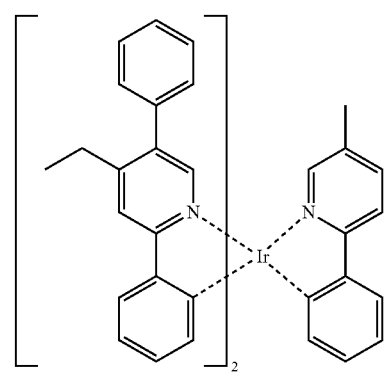
D-167
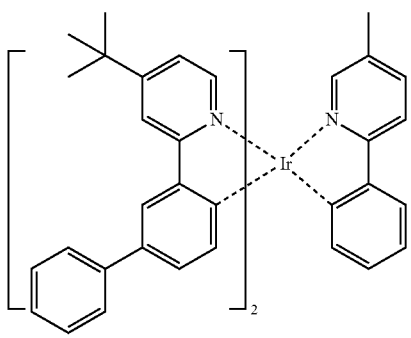
D-168
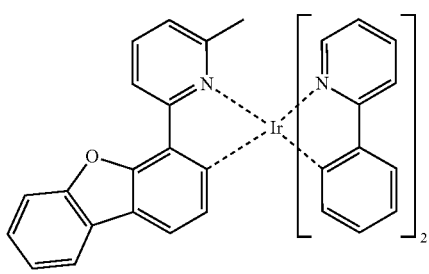
D-169
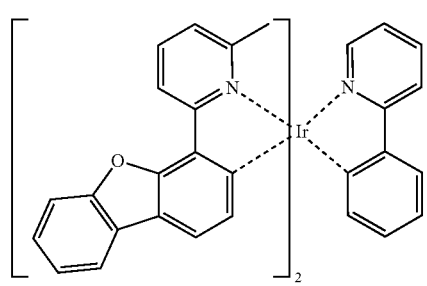
D-170
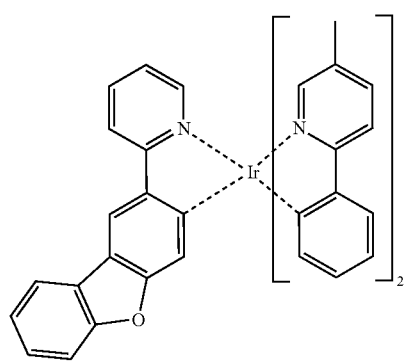
D-171

D-172
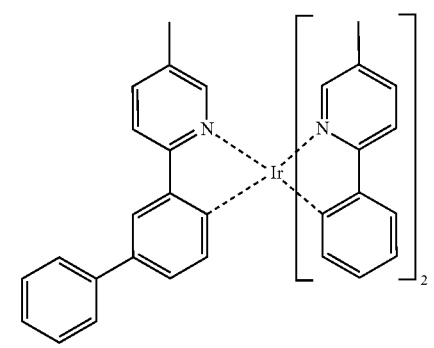
D-173
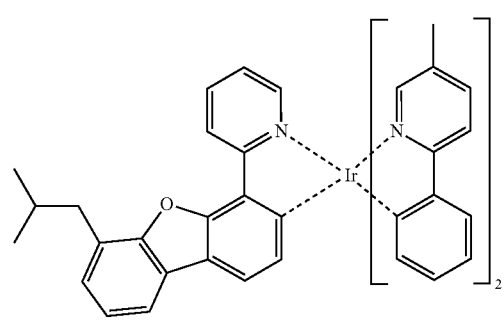
D-174
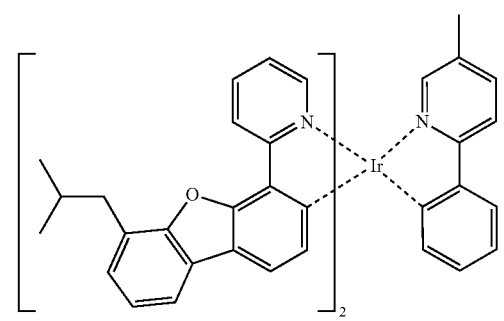
D-175
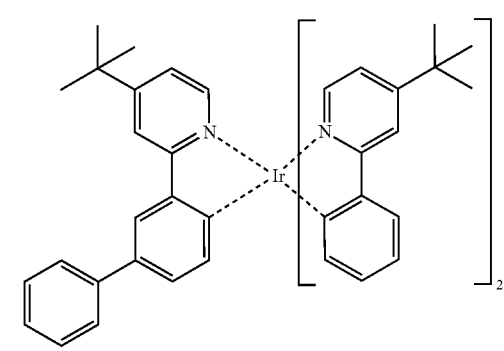
D-176
D-177
D-178
D-179
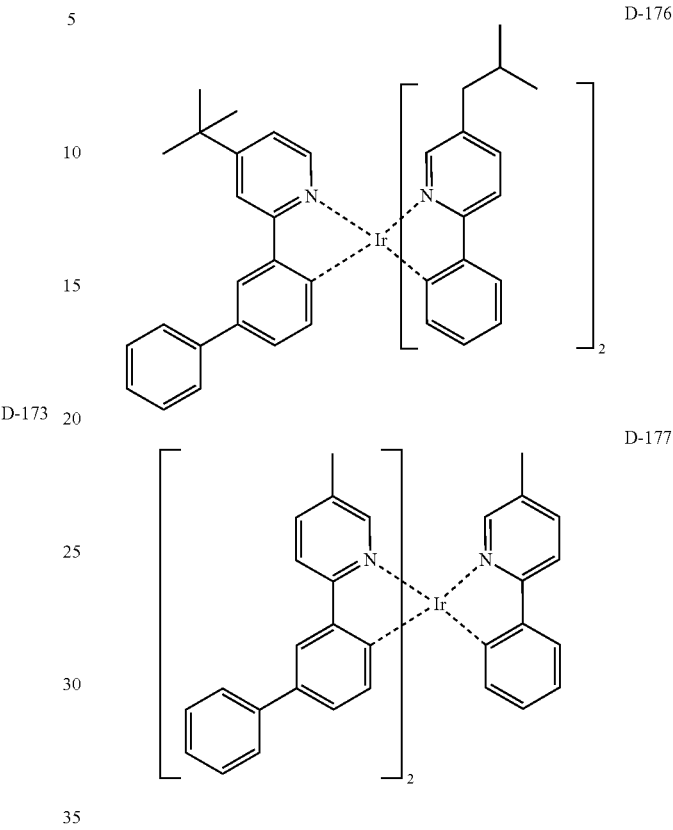
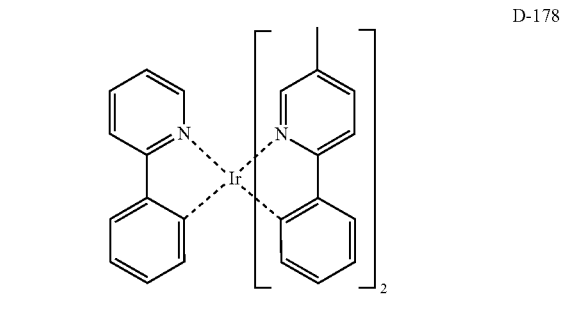
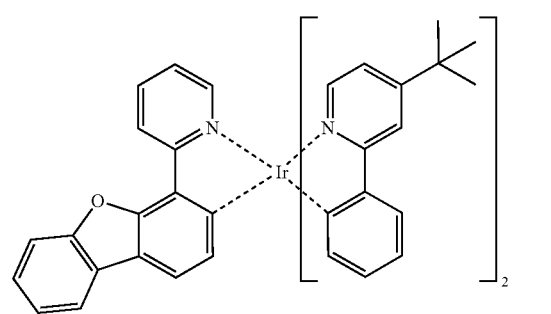

D-180
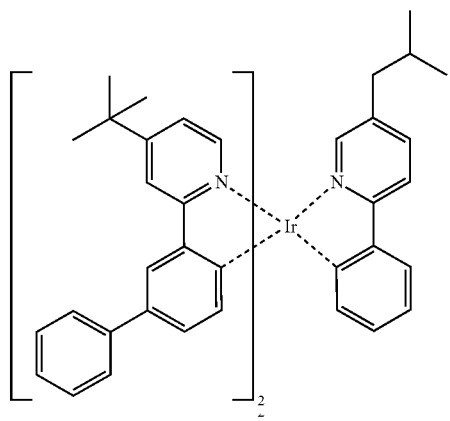
D-181
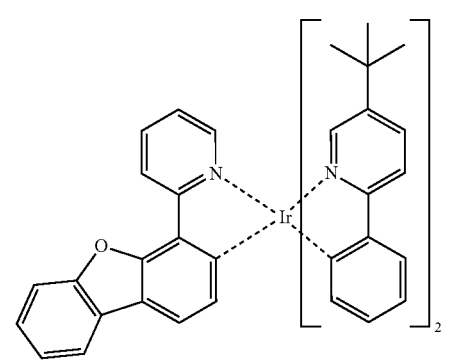
D-182
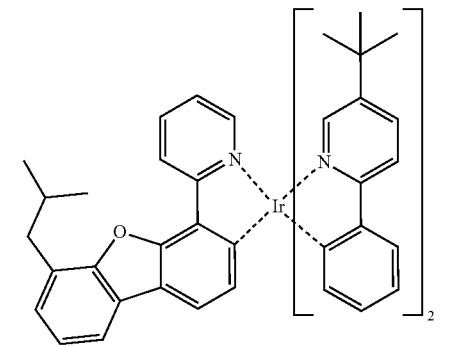
D-183
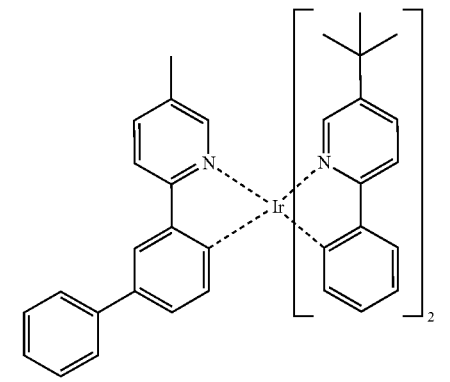
D-184
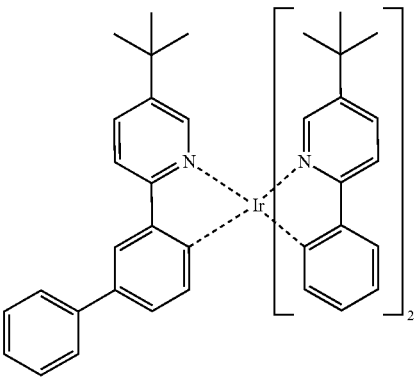
D-185
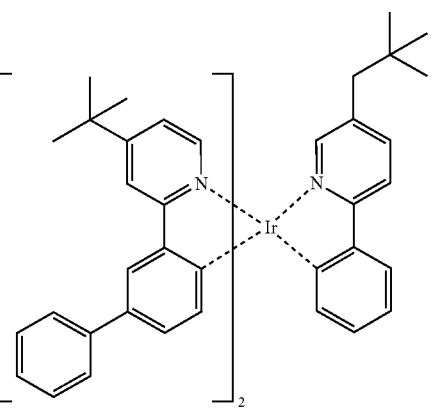
D-186
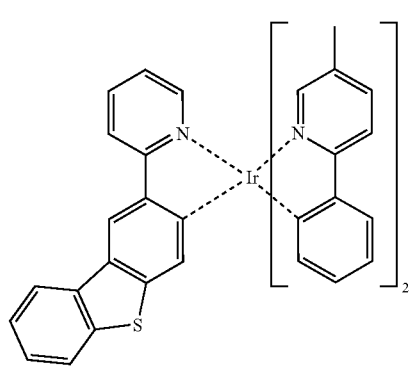
D-187
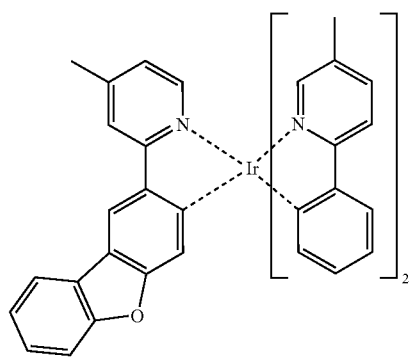

D-188 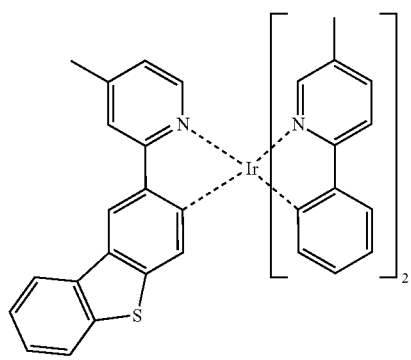
D-189 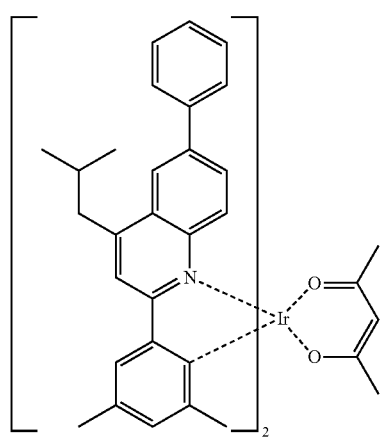
D-190 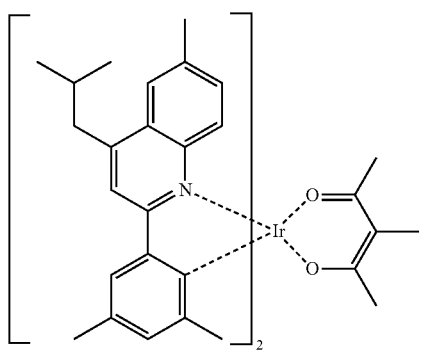
D-191 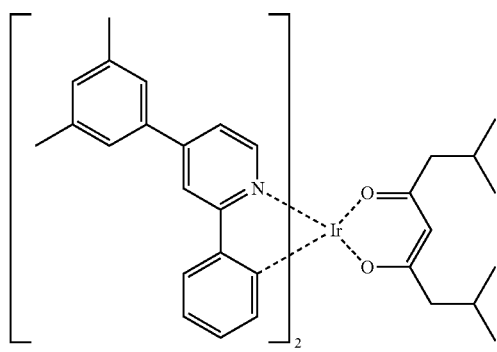
D-192 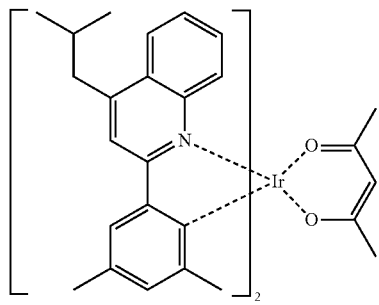
D-193 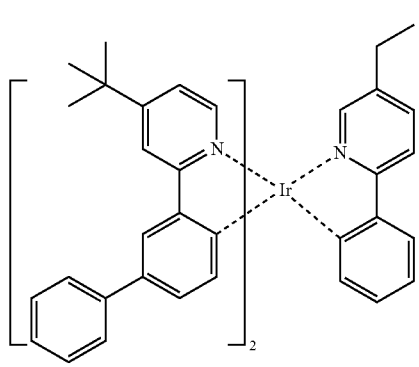
D-194 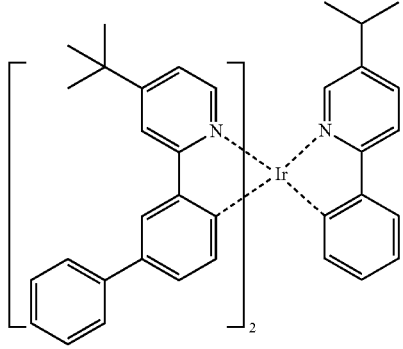
D-195 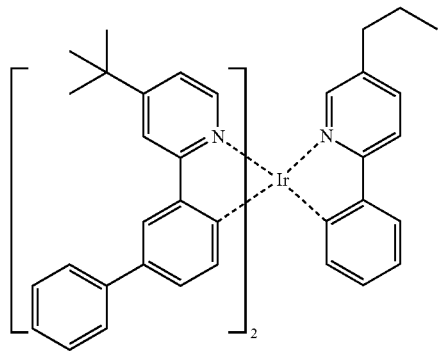

-continued

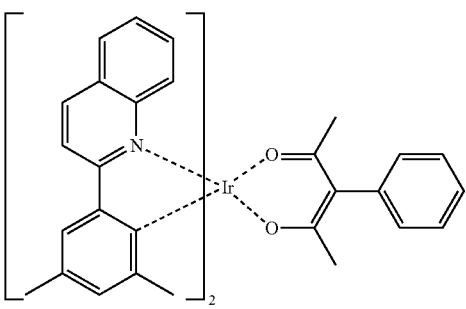

D-196

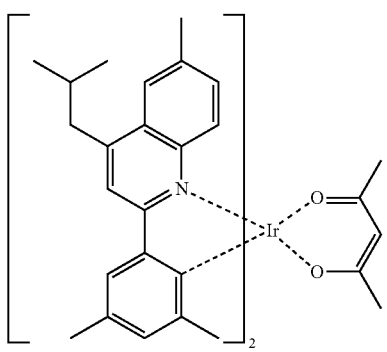

D-197

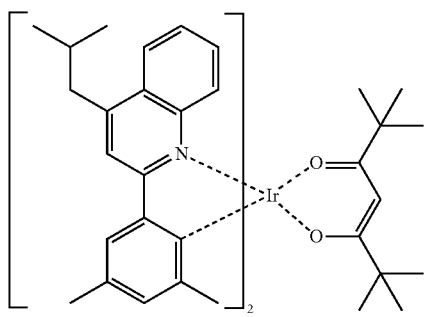

D-198

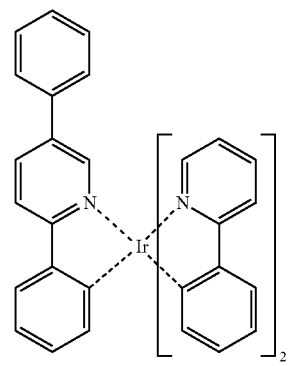

D-199

According to an additional aspect of the present disclosure, a material for preparing an organic electroluminescent device is provided. The material comprises the compound of the present disclosure.

The organic electroluminescent device of the present disclosure may comprise a first electrode, a second electrode, and at least one organic layer disposed between the first and second electrodes, wherein the organic layer comprises a light-emitting layer, and wherein the light-emitting layer may comprise the material for the organic electroluminescent device of the present disclosure.

The organic electroluminescent device of the present disclosure may further comprise, in addition to the compound of formula 1, at least one compound selected from the group consisting of arylamine-based compounds and styrylarylamine-based compounds.

In the organic electroluminescent device of the present disclosure, the organic layer may further comprise, in addition to the compound of formula 1, at least one metal selected from the group consisting of metals of Group 1, metals of Group 2, transition metals of the $4^{th}$ period, transition metals of the $5^{th}$ period, lanthanides and organic metals of the d-transition elements of the Periodic Table, or at least one complex compound comprising the metal. The organic layer may further comprise one or more additional light-emitting layers and a charge generating layer.

In addition, the organic electroluminescent device of the present disclosure may emit white light by further comprising at least one light-emitting layer, which comprises a blue electroluminescent compound, a red electroluminescent compound or a green electroluminescent compound known in the field, besides the compound of the present disclosure. If necessary, it may further comprise a yellow light-emitting layer or an orange light-emitting layer.

In the organic electroluminescent device of the present disclosure, preferably, at least one layer (hereinafter, "a surface layer") may be placed on an inner surface(s) of one or both electrode(s), selected from a chalcogenide layer, a metal halide layer and a metal oxide layer. Specifically, a chalcogenide (includes oxides) layer of silicon or aluminum is preferably placed on an anode surface of an electroluminescent medium layer, and a metal halide layer or a metal oxide layer is preferably placed on a cathode surface of an electroluminescent medium layer. Such a surface layer provides operation stability for the organic electroluminescent device. Preferably, the chalcogenide includes $SiO_x(1 \leq X \leq 2)$, $AlO_x(1 \leq X \leq 1.5)$, SiON, SiAlON, etc.; the metal halide includes LiF, $MgF_2$, $CaF_2$, a rare earth metal fluoride, etc.; and the metal oxide includes $Cs_2O$, $Li_2O$, MgO, SrO, BaO, CaO, etc.

In the organic electroluminescent device of the present disclosure, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to an electroluminescent medium. Furthermore, the hole transport compound is oxidized to a cation, and thus it becomes easier to inject and transport holes from the mixed region to the electroluminescent medium. Preferably, the oxidative dopant includes various Lewis acids and acceptor compounds, and the reductive dopant includes alkali metals, alkali metal compounds, alkaline earth metals, rare-earth metals, and mixtures thereof. A reductive dopant layer may be employed as a charge generating layer to prepare an electroluminescent device having two or more light-emitting layers and emitting white light.

In order to form each layer of the organic electroluminescent device of the present disclosure, dry film-forming methods such as vacuum evaporation, sputtering, plasma and ion plating methods, or wet film-forming methods such as ink jet printing, nozzle printing, slot coating, spin coating, dip coating, and flow coating methods can be used.

When using a wet film-forming method, a thin film can be formed by dissolving or diffusing materials forming each layer into any suitable solvent such as ethanol, chloroform, tetrahydrofuran, dioxane, etc. The solvent can be any solvent where the materials forming each layer can be dissolved or diffused, and where there are no problems in film-formation capability.

Hereinafter, the compound of the present disclosure, the preparation method of the compound, and the luminescent properties of the device will be explained in detail with reference to the following examples.

EXAMPLE 1

Preparation of Compound H-1

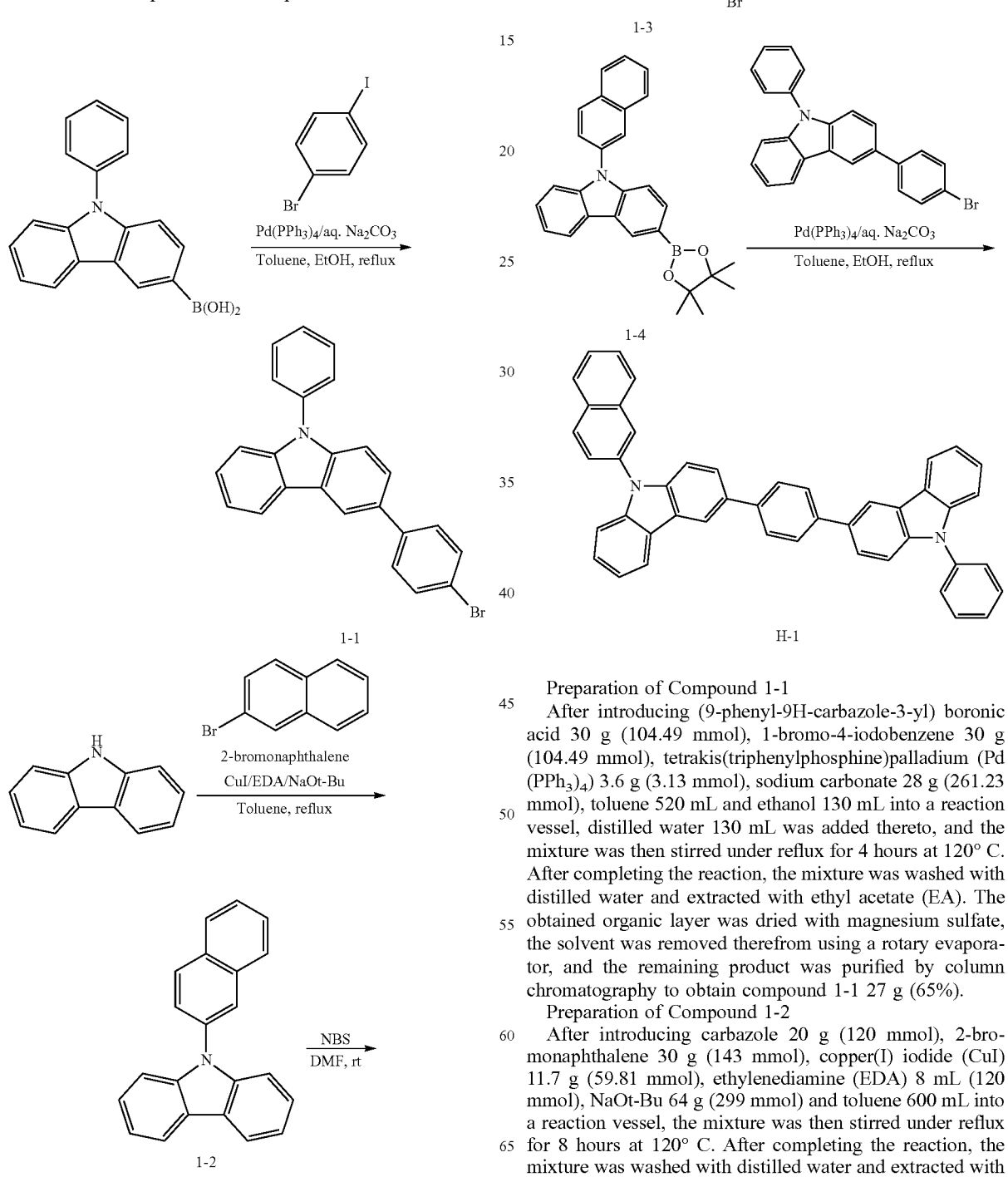

Preparation of Compound 1-1

After introducing (9-phenyl-9H-carbazole-3-yl) boronic acid 30 g (104.49 mmol), 1-bromo-4-iodobenzene 30 g (104.49 mmol), tetrakis(triphenylphosphine)palladium (Pd(PPh$_3$)$_4$) 3.6 g (3.13 mmol), sodium carbonate 28 g (261.23 mmol), toluene 520 mL and ethanol 130 mL into a reaction vessel, distilled water 130 mL was added thereto, and the mixture was then stirred under reflux for 4 hours at 120° C. After completing the reaction, the mixture was washed with distilled water and extracted with ethyl acetate (EA). The obtained organic layer was dried with magnesium sulfate, the solvent was removed therefrom using a rotary evaporator, and the remaining product was purified by column chromatography to obtain compound 1-1 27 g (65%).

Preparation of Compound 1-2

After introducing carbazole 20 g (120 mmol), 2-bromonaphthalene 30 g (143 mmol), copper(I) iodide (CuI) 11.7 g (59.81 mmol), ethylenediamine (EDA) 8 mL (120 mmol), NaOt-Bu 64 g (299 mmol) and toluene 600 mL into a reaction vessel, the mixture was then stirred under reflux for 8 hours at 120° C. After completing the reaction, the mixture was washed with distilled water and extracted with ethyl acetate (EA). The obtained organic layer was dried with magnesium sulfate, the solvent was removed therefrom using a rotary evaporator, and the remaining product was purified by column chromatography to obtain compound 1-2 13 g (37%).

Preparation of Compound 1-3

After dissolving compound 1-2 13 g (44 mmol) in dimethylformamide (DMF) into a reaction vessel, N-bromo succinamide (NBS) was dissolved in dimethylformamide and introduced into the reaction mixture. After stirring the mixture for 4 hours at room temperature, the mixture was washed with distilled water and extracted with ethyl acetate (EA). The obtained organic layer was dried with magnesium sulfate, the solvent was removed therefrom using a rotary evaporator, and the remaining product was purified by column chromatography to obtain compound 1-3 14 g (83%).

Preparation of Compound 1-4

After introducing compound 1-3 14 g (36 mmol), bis(pinacolato)diboran 11 g (44 mmol), bis(triphenylphosphine)palladium(II)dichloride (PdCl$_2$(PPh$_3$)$_2$) 1.3 g (2 mmol), potassium acetate (KOAc) 9 g (91 mmol) and 1,4-dioxane 180 mL into a reaction vessel, the mixture was then stirred under reflux for 2 hours at 140° C. After completing the reaction, the mixture was washed with distilled water and extracted with ethyl acetate (EA). The obtained organic layer was dried with magnesium sulfate, the solvent was removed therefrom using a rotary evaporator, and the remaining product was purified by column chromatography to obtain compound 1-4 8 g (52%).

Preparation of Compound H-1

After introducing compound 1-1 7 g (17 mmol), compound 1-4 8 g (19 mmol), tetrakis(triphenylphosphine)palladium (Pd(PPh$_3$)$_4$) 0.6 g (0.5 mmol), sodium carbonate 4.5 g (43 mmol), toluene 100 mL and ethanol 25 mL into a reaction vessel, distilled water 25 mL was added thereto, and the mixture was then stirred under reflux for 4 hours at 120° C. After completing the reaction, the mixture was washed with distilled water and extracted with ethyl acetate (EA). The obtained organic layer was dried with magnesium sulfate, the solvent was removed therefrom using a rotary evaporator, and the remaining product was purified by column chromatography to obtain compound H-1 4 g (37%).

| MW | UV | PL | M.P. |
|---|---|---|---|
| 610.74 | 354 nm | 397 nm | 198° C. |

EXAMPLE 2

Preparation of Compound H-2

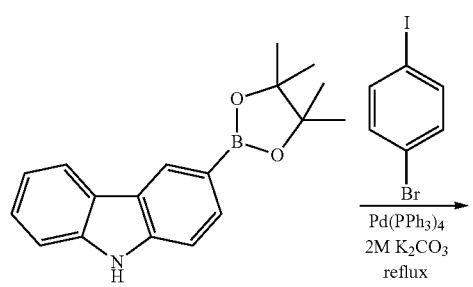

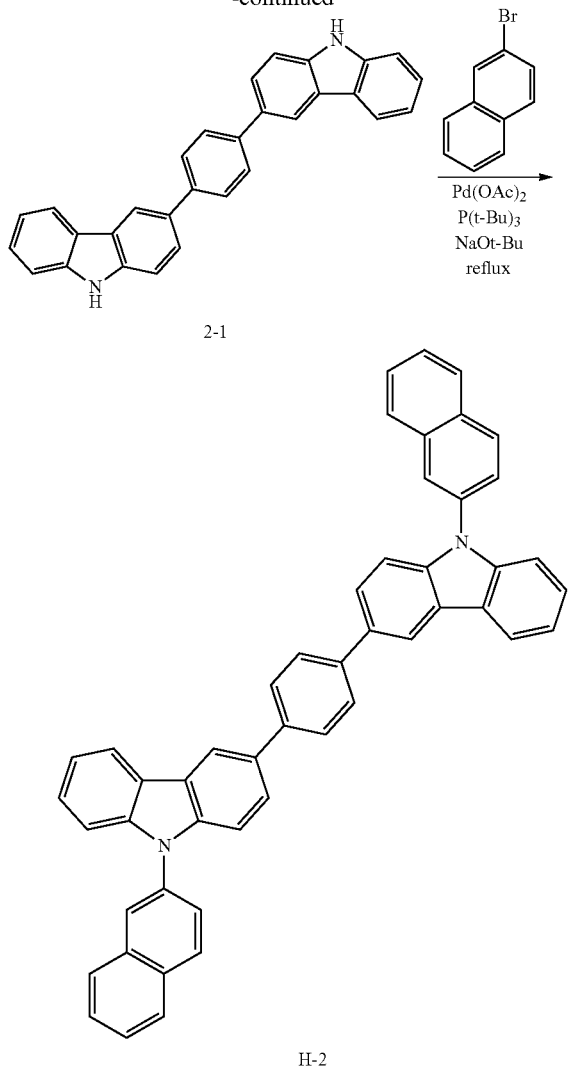

H-2

Preparation of Compound 2-1

After introducing 3-(4,4,5,5-tetramethyl-1,3,2-dioxaborolan-2-yl)-9H-carbazole 30 g (102.3 mmol), 1-bromo-4-iodobenzene 13.2 g (46.5 mmol), tetrakis(triphenylphosphine)palladium (Pd(PPh$_3$)$_4$) 2.7 g (2.3 mmol), K$_2$CO$_3$ 32.1 g (232 mmol), toluene 300 mL, EtOH 100 mL and H$_2$O 100 mL into a flask, the mixture was then stirred. After stirring under reflux for 6 hours, the mixture was cooled to room temperature and extracted with EA and distilled water. The obtained organic layer was distilled under reduced pressure, and the remaining product was purified by column chromatography to obtain compound 2-1 18 g (91%).

Preparation of Compound H-2

After introducing compound 2-1 18 g (44.1 mmol), 2-bromonaphthalene 27.4 g (132.2 mmol), palladium (II) acetate (Pd(OAc)$_2$) 1.0 g (4.4 mmol), 50% tri-tert-butylphosphine (P(t-Bu)$_3$) 4.3 mL (8.8 mmol), NaOt-Bu 21 g (220.3 mmol) and toluene 600 mL into a flask, the mixture was then stirred under reflux for 3 hours. The mixture was cooled to room temperature and extracted with EA and distilled water. The obtained organic layer was distilled under reduced pressure, and the remaining product was purified by column chromatography to obtain compound H-2 5.8 g (20%).

| MW | UV | PL | M.P. |
|---|---|---|---|
| 660.8 | 360 nm | 397 nm | 290.7° C. |

EXAMPLE 3

Preparation of Compound H-16

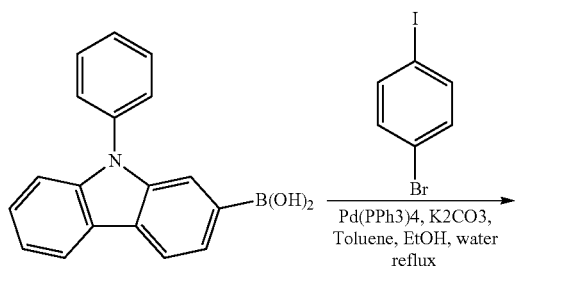

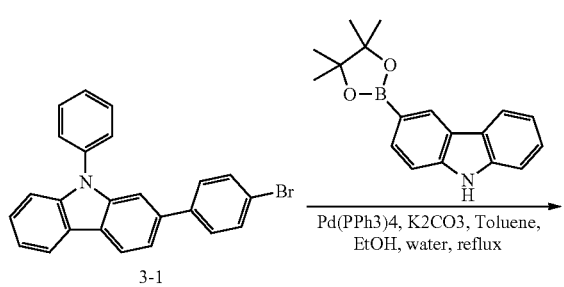

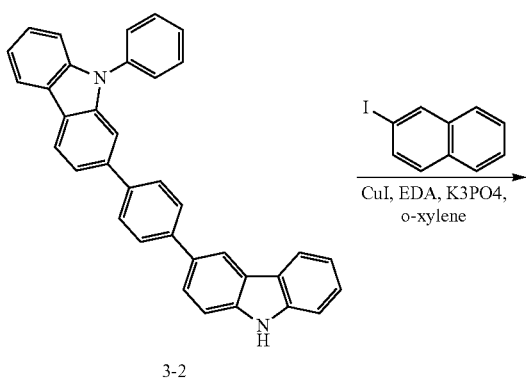

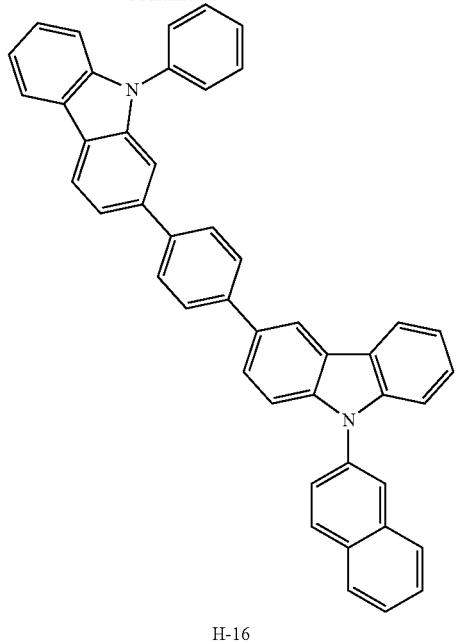

H-16

Preparation of Compound 3-1

After dissolving (9-phenyl-9H-carbazole-2-yl) boronic acid 13.5 g (46.9 mmol), 1-bromo-4-iodobenzene 26.5 g (93.8 mmol), tetrakis(triphenylphosphine)palladium (Pd(PPh$_3$)$_4$) 2.7 g (2.35 mmol), potassium carbonate (K$_2$CO$_3$) 16.2 g (117.3 mmol), toluene 180 mL, EtOH 30 mL and H$_2$O 60 mL into a flask, the mixture was then under reflux for 5 hours at 120° C. After completing the reaction, the mixture was filtered under reduced pressure with methylene chloride (MC) and was purified by column chromatography. The solid produced by introducing a methanol was filtered under reduced pressure to obtain compound 3-1 14.0 g (75%).

Preparation of Compound 3-2

After dissolving compound 3-1 14.0 g (35.2 mmol), 3-(4,4,5,5-tetramethyl-1,3,2-dioxaborolan-2-yl)-9H-carbazole 9.4 g (31.9 mmol), tetrakis(triphenylphosphine)palladium (Pd(PPh$_3$)$_4$) 1.84 g (1.6 mmol), potassium carbonate (K$_2$CO$_3$) 11 g (79.8 mmol), toluene 120 mL, EtOH 20 mL and H$_2$O 40 mL into a flask, the mixture was then under reflux for 4 hours at 120° C. After completing the reaction, the mixture was filtered under reduced pressure with methylene chloride (MC) and was purified by column chromatography. The solid produced by introducing a methanol was filtered under reduced pressure to obtain compound 3-2 9.2 g (60%).

Preparation of Compound H-16

After dissolving compound 3-2 9.14 g (18.9 mmol), 2-iodonaphthalene 5.9 g (28.3 mmol), CuI 1.8 g (9.43 mmol), ethylenediamine (EDA) 1.27 mL (18.86 mmol), K$_3$PO$_4$ 10.0 g (47.2 mmol) and o-xylene 95 mL into a flask, the mixture was then under reflux for 5 hours at 150° C. After completing the reaction, the mixture was filtered under reduced pressure with methylene chloride (MC) and was purified by column chromatography. The solid produced by introducing a methanol was filtered under reduced pressure to obtain compound H-16 10.5 g (91%).

| MW | UV | PL | M.P. |
|---|---|---|---|
| 610.74 | 368 nm | 407 nm | 212° C. |

EXAMPLE 4

Preparation of Compound H-61

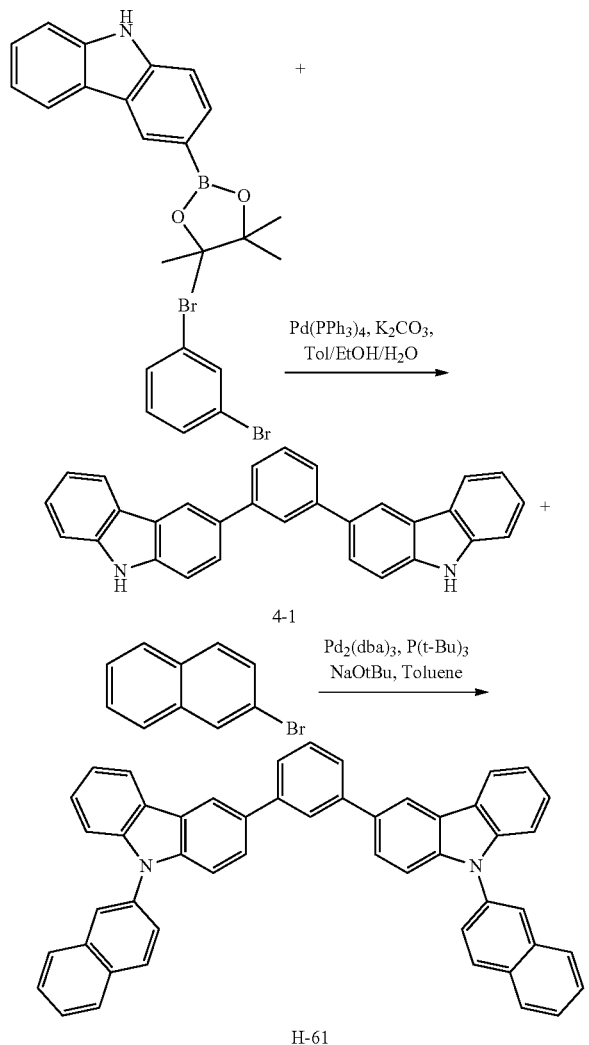

Preparation of Compound 4-1

After dissolving 3-(4,4,5,5-tetramethyl-1,3,2-dioxaborolan-2-yl)-9H-carbazole 30 g (102.30 mmol), 1,3-dibromobenzene 6.4 mL (51.20 mmol), tetrakis(triphenylphosphine)palladium (Pd(PPh$_3$)$_4$) 7.10 g (6.14 mmol), potassium carbonate (K$_2$CO$_3$) 70.7 g (511.50 mmol), toluene 512 mL, EtOH 128 mL and H$_2$O 128 mL into a flask, the mixture was then under reflux for 2 days at 120° C. After completing the reaction, the obtained organic layer was extracted with ethyl acetate and concentrated, and the remaining product was washed with MeOH to obtain compound 4-1 15.2 g (73%).

Preparation of Compound H-61

After dissolving compound 4-1 21 g (51.20 mmol), 2-bromonaphthalene 27 g (127.9 mmol), tris(dibenzylideneacetone)dipalladium (Pd$_2$(dba)$_3$) 2.4 g (2.56 mmol), P(t-Bu)$_3$ 2.5 mL (5.12 mmol) and NaOt-Bu 15 g (153.6 mmol) in toluene 256 mL, the mixture was then under reflux for 5 hours. After completing the reaction, the remaining product was purified by column chromatography to obtain compound H-61 8.7 g (26%).

| MW | UV | PL | M.P. |
|---|---|---|---|
| 660.80 | 358 nm | 383 nm | 156.8° C. |

DEVICE EXAMPLE 1

Preparation of an OLED Device Using the Organic Electroluminescent Compounds of the Present Disclosure An OLED device was produced using the organic electroluminescent compound according to the present disclosure. A transparent electrode indium tin oxide (ITO) thin film (10Ω/sq) on a glass substrate for an organic light-emitting diode (OLED) device (Geomatec) was subjected to an ultrasonic washing with acetone, ethanol, and distilled water, sequentially, and then was stored in isopropanol. The ITO substrate was then mounted on a substrate holder of a vacuum vapor depositing apparatus. Compound HI-1 was introduced into a cell of said vacuum vapor depositing apparatus, and then the pressure in the chamber of said apparatus was controlled to $10^{-6}$ torr. Thereafter, an electric current was applied to the cell to evaporate the above introduced material, thereby forming a first hole injection layer having a thickness of 80 nm on the ITO substrate. Next, compound HI-2 was introduced into another cell of said vacuum vapor depositing apparatus, and was evaporated by applying an electric current to the cell, thereby forming a second hole injection layer having a thickness of 5 nm on the first hole injection layer. Compound HT-1 was then introduced into another cell of said vacuum vapor depositing apparatus, and was evaporated by applying an electric current to the cell, thereby forming a first hole transport layer having a thickness of 10 nm on the second hole injection layer. Compound HT-3 was then introduced into another cell of said vacuum vapor depositing apparatus, and was evaporated by applying an electric current to the cell, thereby forming a second hole transport layer having a thickness of 60 nm on the first hole transport layer. After forming the hole injection layer and the hole transport layer, a light-emitting layer was formed thereon as follows: Compound H-1 was introduced into one cell of said vacuum vapor depositing apparatus as a first host, compound H2-41 was introduced into another cell as a second host, and compound D-96 was introduced into another cell as a dopant. The two host materials were evaporated at the same rate in an amount of 50 wt %, respectively, while the dopant was evaporated at a different rate from the host materials, so that the dopant was deposited in a doping amount of 3 wt % based on the total amount of the host and dopant to coevaporate and form a light-emitting layer having a thickness of 40 nm on the second hole transport layer. Compounds ET-1 and EI-1 were then introduced into two cells of the vacuum vapor depositing apparatus, respectively, and evaporated at a 1:1 rate to form an electron transport layer having a thickness of 30 nm on the light-emitting layer. After depositing compound EI-1 as an electron injection layer having a thickness of 2 nm on the electron transport layer, an Al cathode having a thickness of 80 nm was deposited by another vacuum vapor deposition apparatus. Thus, an OLED device was produced.

HI-1

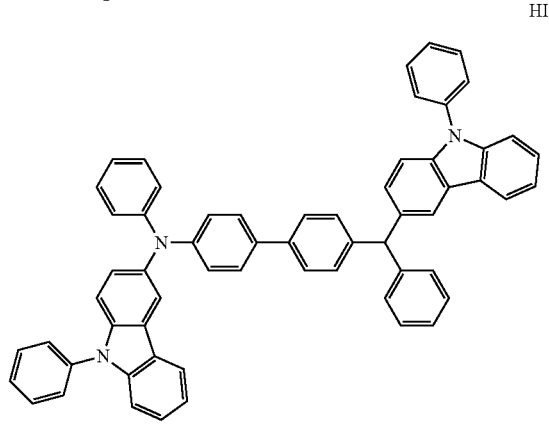

HI-2

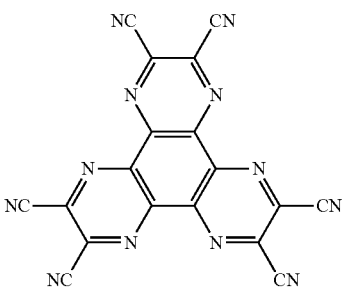

HT-1

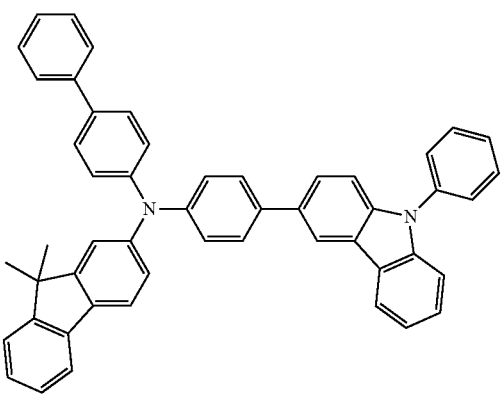

HT-2

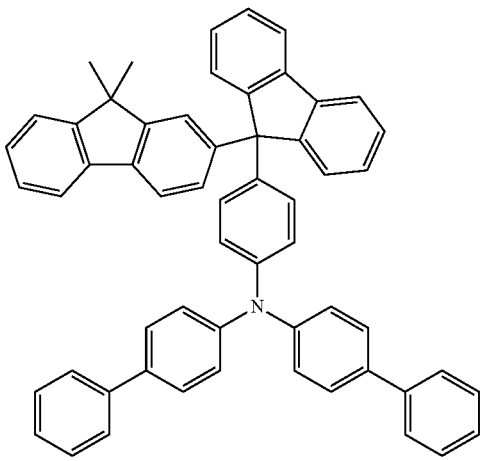

HT-3

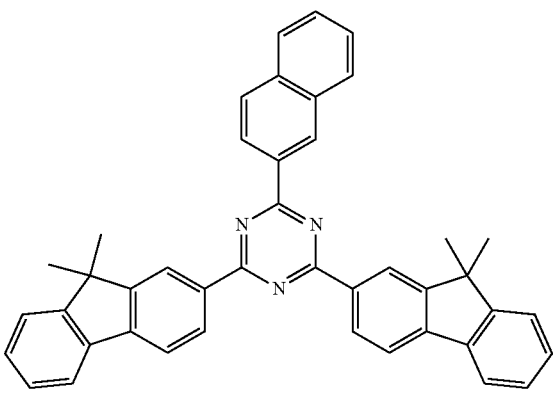

ET-1

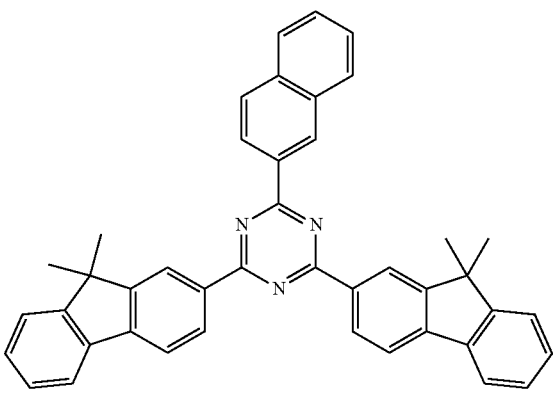

EI-1

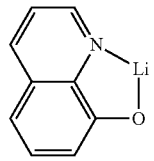

The produced OLED device showed a red emission having a luminance of 7,000 cd/m² and a luminous efficiency of 27.2 cd/A at 5.1 V. The minimum time for the luminance to decrease to 97% at 5,000 nit was 98 hours.

DEVICE EXAMPLE 2

Preparation of an OLED Device Using the Organic Electroluminescent Compounds of the Present Disclosure An OLED device was produced in the same manner as in Device Example 1, except for using compound HT-2 instead of compound HT-3 as the second hole transport layer, and depositing compound H-1 and compound H2-41 by mixing them in one cell before the deposition, not co-evaporation by introducing them into respective cells.

The produced OLED device showed a red emission having a luminance of 7,000 cd/m² and a luminous efficiency of 25.8 cd/A at 5.4 V. The minimum time for the luminance to decrease to 97% at 5,000 nit was 113 hours.

DEVICE EXAMPLE 3

Preparation of an OLED Device Using the Organic Electroluminescent Compounds of the Present Disclosure An OLED device was produced in the same manner as in Device Example 1, except for using compound H-2 as the first host of the light-emitting material.

The produced OLED device showed a red emission having a luminance of 7,000 cd/m$^2$ and a luminous efficiency of 27.4 cd/A at 5.0 V. The minimum time for the luminance to decrease to 97% at 5,000 nit was 76 hours.

DEVICE EXAMPLE 4

Preparation of an OLED Device Using the Organic Electroluminescent Compounds of the Present Disclosure An OLED device was produced in the same manner as in Device Example 1, except for using compound H-61 as the first host of the light-emitting material.

The produced OLED device showed a red emission having a luminance of 7,000 cd/m$^2$ and a luminous efficiency of 26.5 cd/A at 5.0 V. The minimum time for the luminance to decrease to 97% at 5,000 nit was 41 hours.

DEVICE EXAMPLE 5

Preparation of an OLED Device Using the Organic Electroluminescent Compounds of the Present Disclosure An OLED device was produced in the same manner as in Device Example 1, except for using compound H-16 as the first host of the light-emitting material.

The produced OLED device showed a red emission having a luminance of 7,000 cd/m$^2$ and a luminous efficiency of 24.7 cd/A at 5.1 V. The minimum time for the luminance to decrease to 97% at 5,000 nit was 101 hours.

COMPARATIVE EXAMPLE 1

Preparation of an OLED Device Using Conventional Organic Electroluminescent Compounds An OLED device was produced in the same manner as in Device Example 1, except for using compound X shown below as the first host of the light-emitting material.

The produced OLED device showed a red emission having a luminance of 7000 cd/m$^2$ and a luminous efficiency of 26.8 cd/A at 5.4 V. The minimum time for the luminance to decrease to 97% at 5,000 nit was 10 hours.

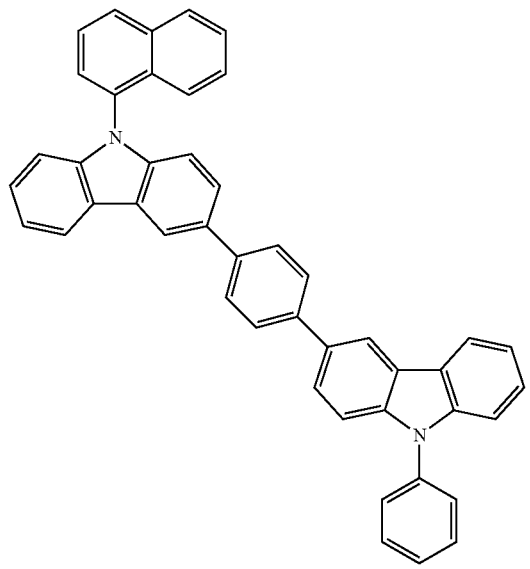

X

COMPARATIVE EXAMPLE 2

Preparation of an OLED Device Using Conventional Organic Electroluminescent Compounds An OLED was produced in the same manner as in Device Example 1, except for using compound HT-2 instead of compound HT-3 as the second hole transport layer, using compound Y shown below as the first host of the light-emitting material, and using compound H2-48 instead of compound H2-41 as the second host of the light-emitting material.

The produced OLED device showed a red emission having a luminance of 7,000 cd/m$^2$ and a luminous efficiency of 22.4 cd/A at 5.4 V. The minimum time for the luminance to decrease to 97% at 5,000 nit was 33 hours.

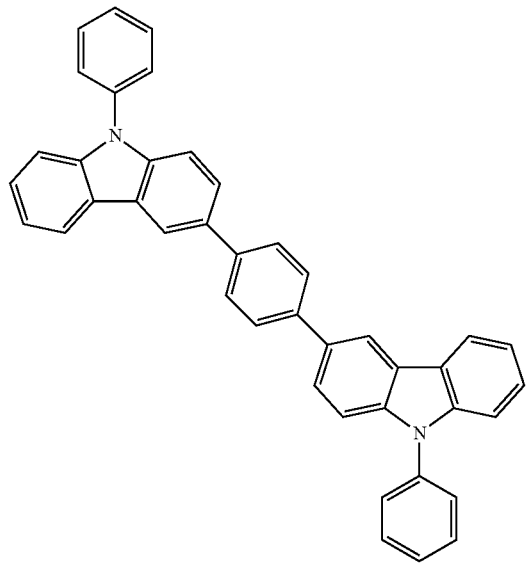

Y

The organic electroluminescent compound according to the present disclosure shows the advantages of improved driving lifespan while having equal or greater efficiency compared to conventional devices. Particularly, the organic electroluminescent compound according to the present disclosure is an advangageous characteristic in recent trends requiring ultra high resolution (UHD) by having long life span and maintaining high luminous efficiency.

The invention claimed is:

1. An organic electroluminescent compound represented by formula 1:

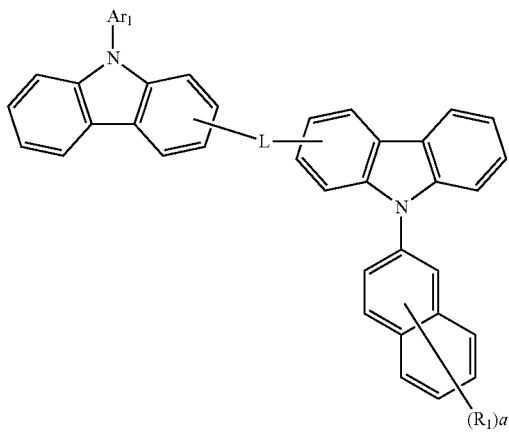

(1)

wherein
Ar1 represents a substituted phenyl, or a substituted or unsubstituted (C10-C30)aryl;
L represents a phenylene;
R1 represents hydrogen, deuterium, a halogen, a cyano, a substituted or unsubstituted (C1-C30)alkyl, or a substituted or unsubstituted (C6-C30)aryl;
a represents an integer of 0 to 4; where a represents an integer of 2 or more, each of R1 may be the same or different.

2. The organic electroluminescent compound according to claim 1,
wherein Ar1 represents a substituted phenyl, or a substituted or unsubstituted (C10-C15)aryl;
L represents a phenlylene;
R1 represents hydrogen, a substituted or unsubstituted (C1-C10)alkyl, or a substituted or unsubstituted (C6-C15)aryl.

3. The organic electroluminescent compound according to claim 1,
wherein Ar1 represents (C10-C15)aryl unsubstituted or substituted with a (C1-C10)alkyl, a halogen, a cyano or deuterium; L represents a phenlylene;
R1 represents hydrogen, or an unsubstituted (C6-C15)aryl.

4. The organic electroluminescent compound according to claim 1,
wherein the substituents of the substituted alkyl, the substituted phenyl or the substituted aryl, each independently, are at least one selected from the group consisting of deuterium, a halogen, a cyano, a carboxyl, a nitro, a hydroxyl, a (C1-C30)alkyl, a halo(C1-C30)alkyl, a (C2-C30)alkenyl, a (C2-C30)alkynyl, a (C1-C30)alkoxy, a (C1-C30)alkylthio, a (C3-C30)cycloalkyl, a (C3-C30)cycloalkenyl, a (3- to 7-membered)heterocycloalkyl, a (C6-C30)aryloxy, a (C6-C30)arylthio, a (3- to 30-membered)heteroaryl unsubstituted or substituted with a (C6-C30)aryl, a (C6-C30)aryl unsubstituted or substituted with a (3- to 30-membered)heteroaryl, a tri(C1-C30)alkylsilyl, a tri(C6-C30)arylsilyl, a di(C1-C30)alkyl(C6-C30)arylsilyl, a (C1-C30)alkyldi(C6-C30)arylsilyl, an amino, a mono- or di-(C1-C30)alkylamino, a mono- or di-(C6-C30)arylamino, a (C1-C30)alkyl(C6-C30)arylamino, a (C1-C30)alkylcarbonyl, a (C1-C30)alkoxycarbonyl, a (C6-C30)arylcarbonyl, a di(C6-C30)arylboronyl, a di(C1-C30)alkylboronyl, a (C1-C30)alkyl(C6-C30)arylboronyl, a (C6-C30)aryl(C1-C30)alkyl and a (C1-C30)alkyl(C6-C30)aryl.

5. The organic electroluminescent compound according to claim 1,
wherein the compound represented by formula 1 is selected from the group consisting of:

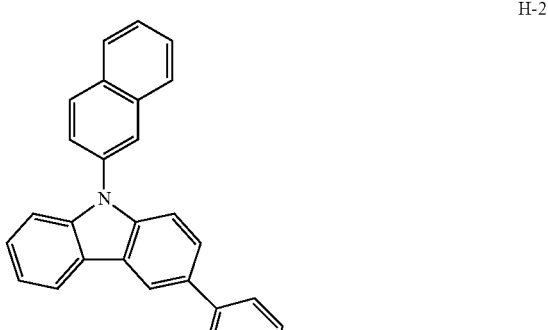

H-2

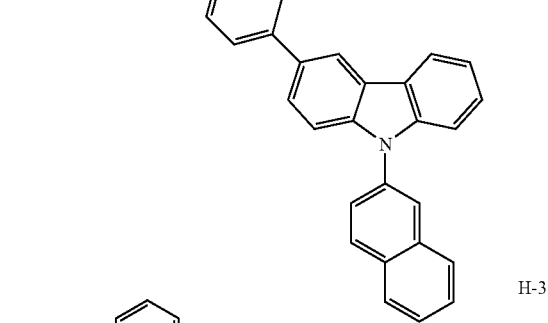

H-3

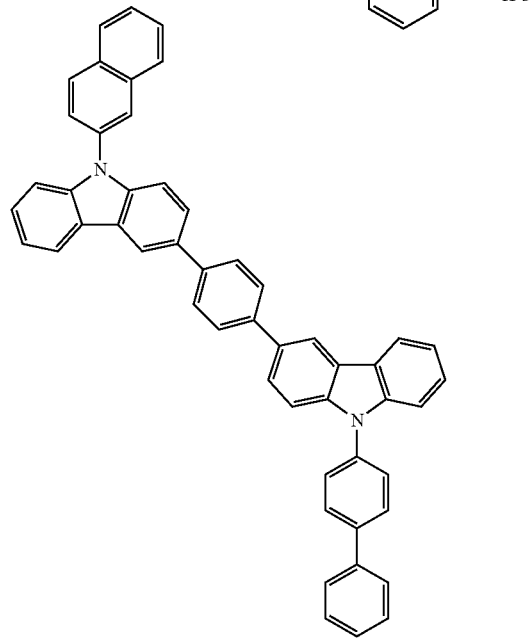

-continued
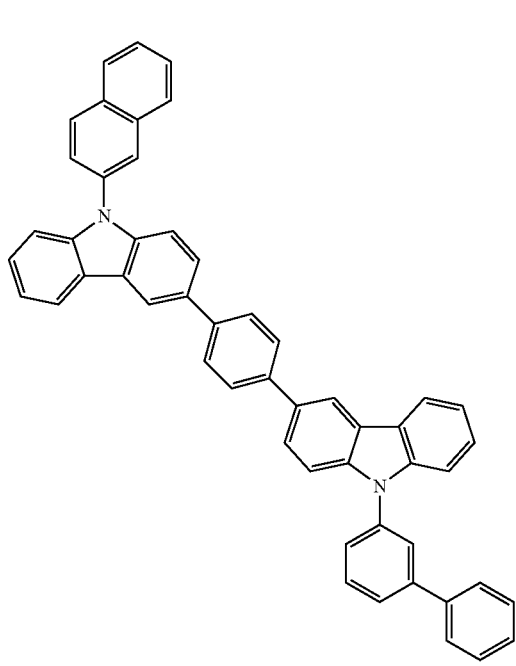
H-4
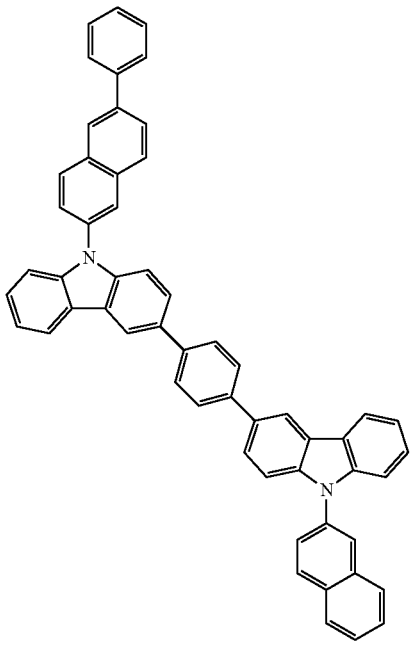
H-7
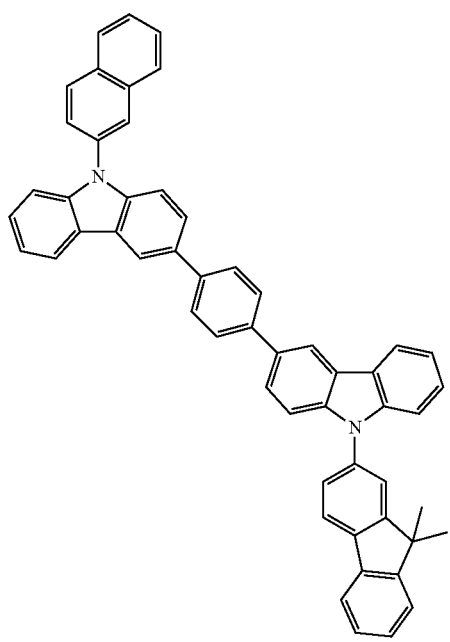
H-5
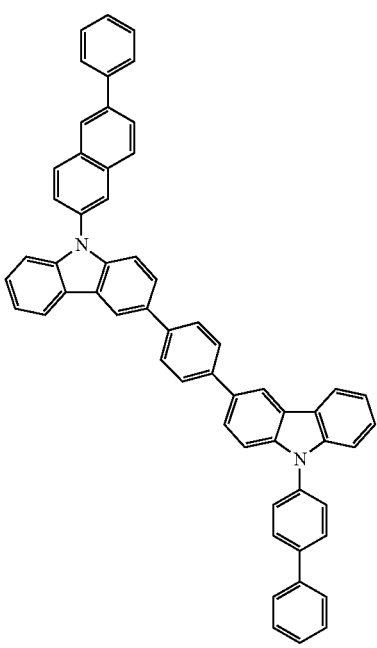
H-8

H-9
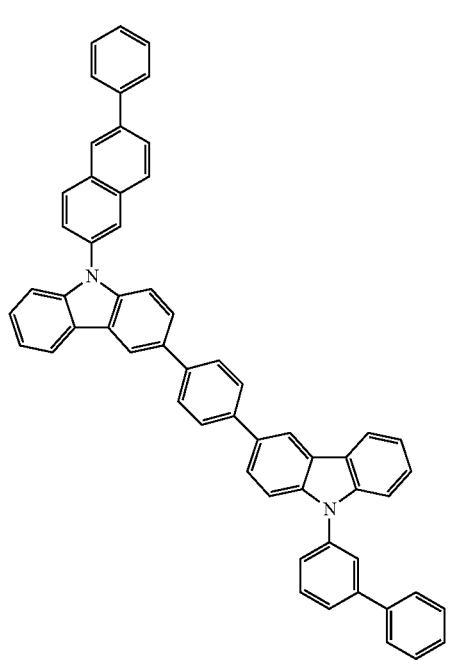
H-10
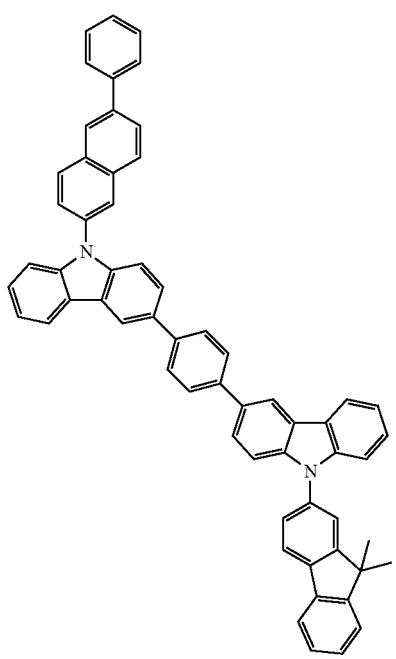
H-11
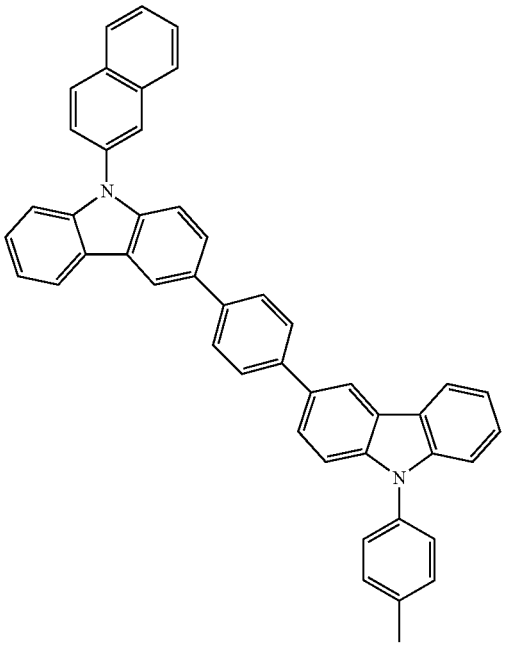
H-12
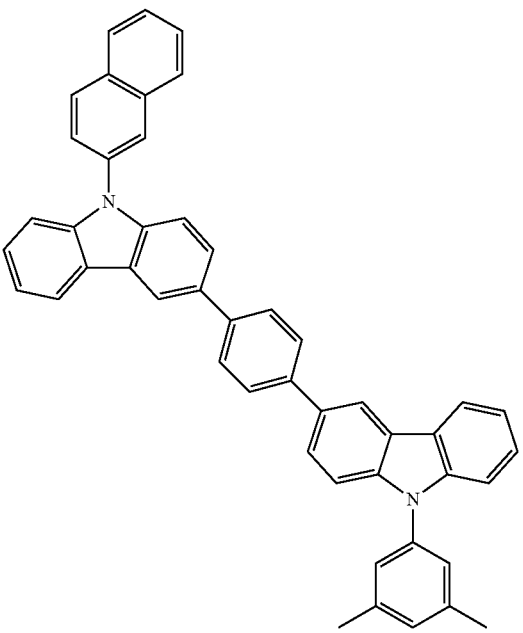

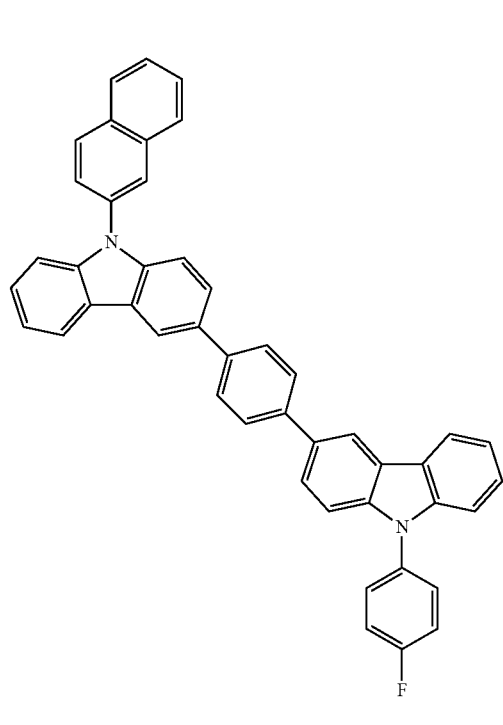
H-13
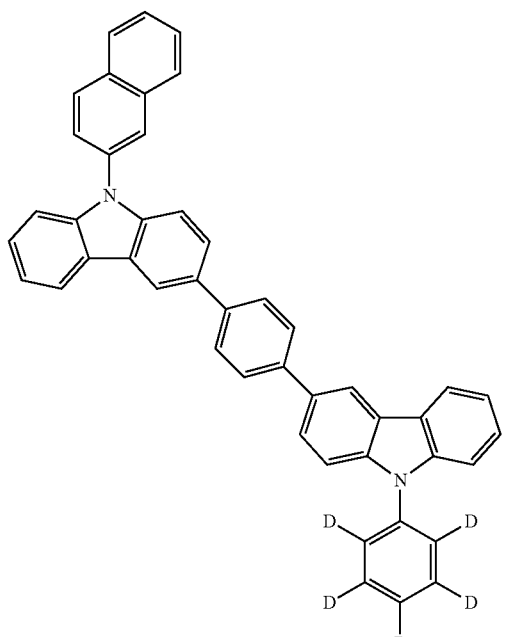
H-15
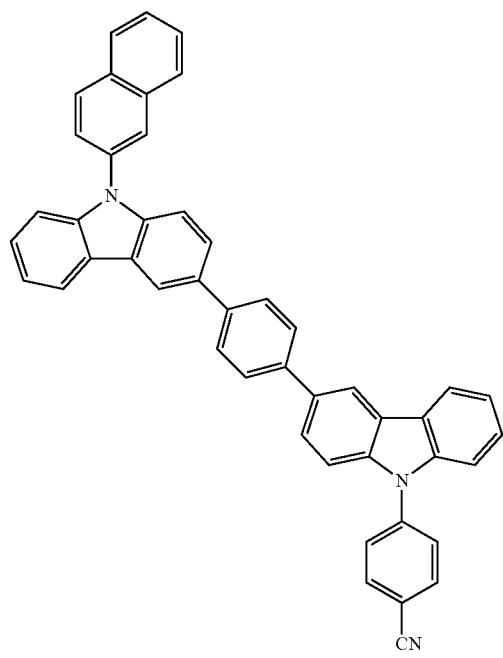
H-14
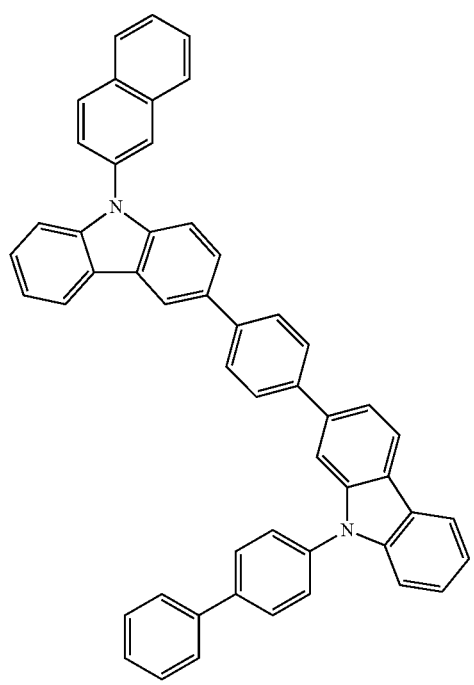
H-17

267
-continued
H-18
H-19
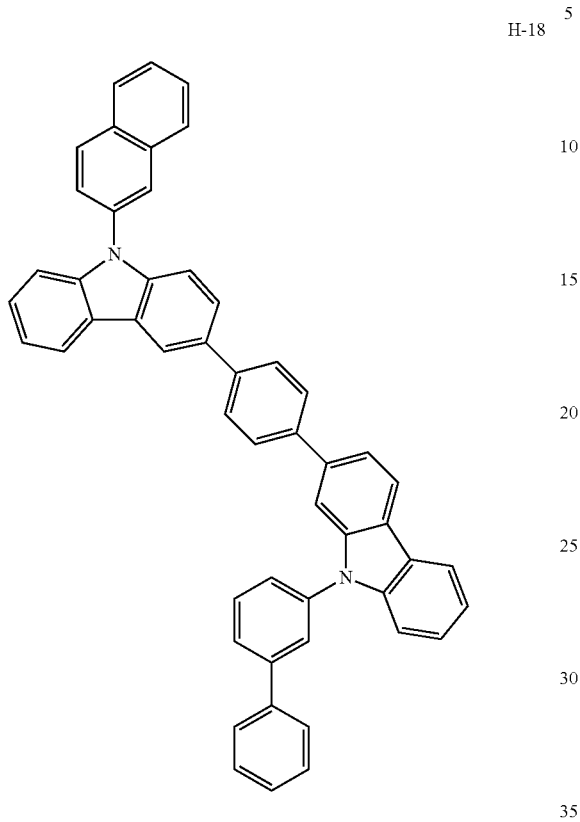
268
-continued
H-20
H-22
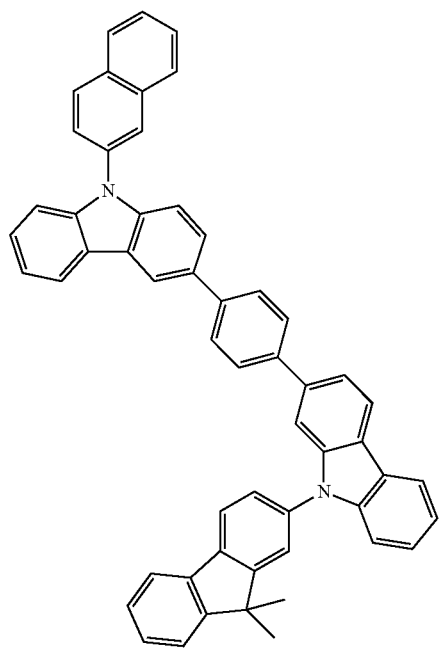

-continued
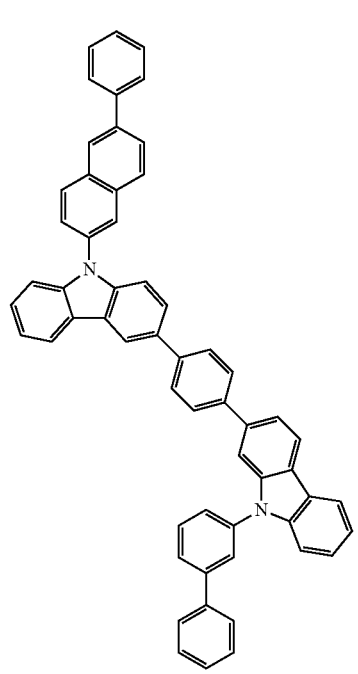
H-23
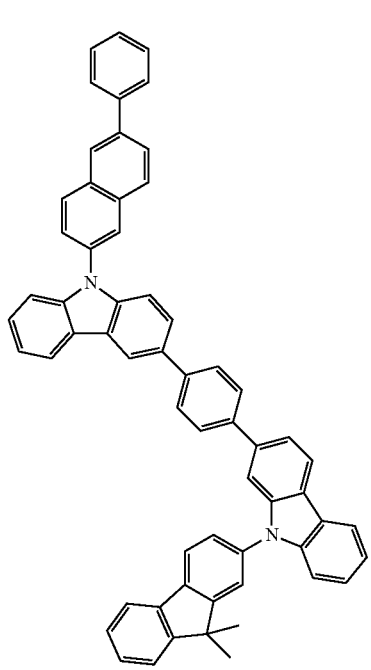
H-25
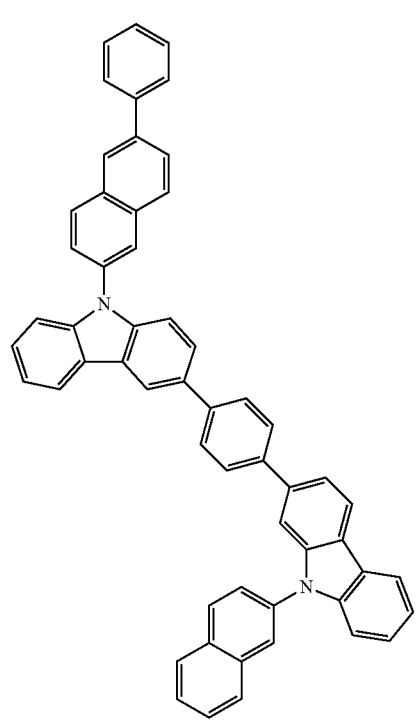
H-24
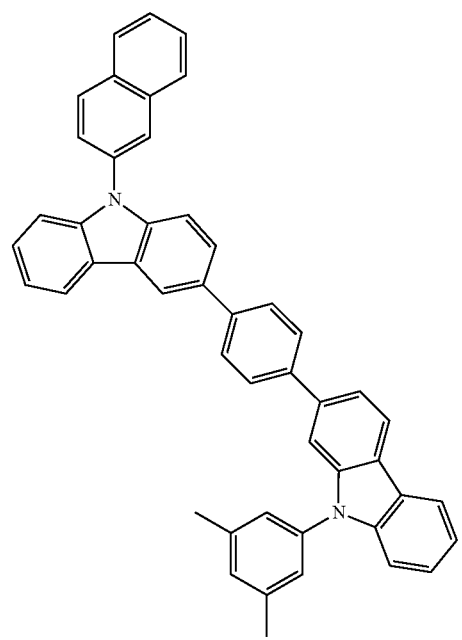
H-26

H-27
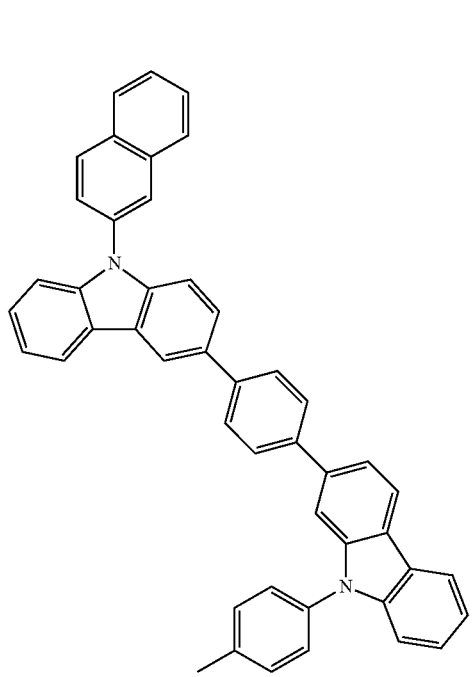
H-28
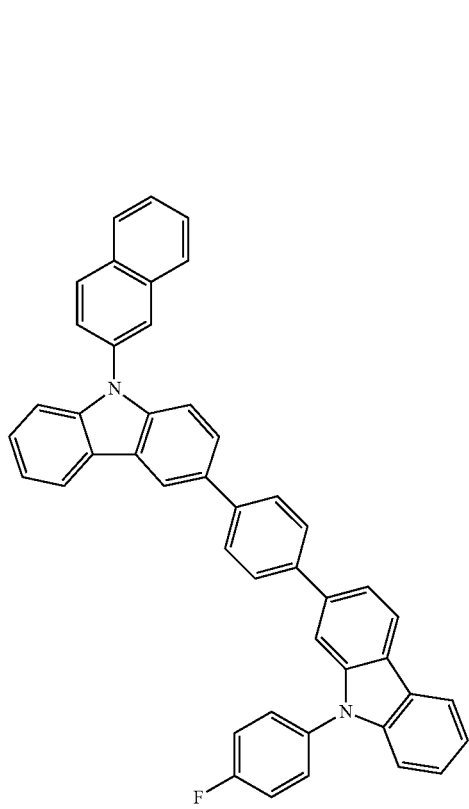
H-29
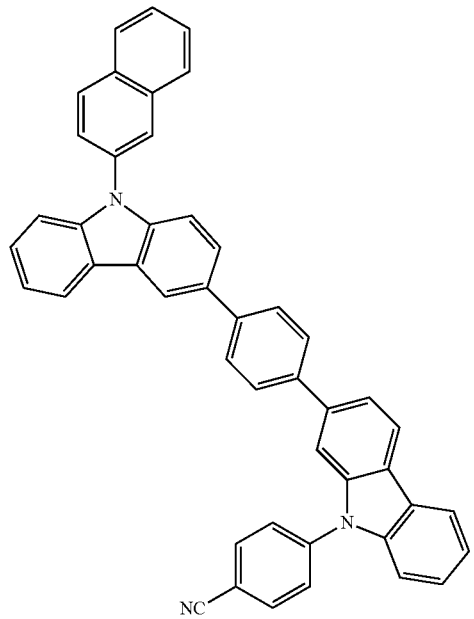
H-30
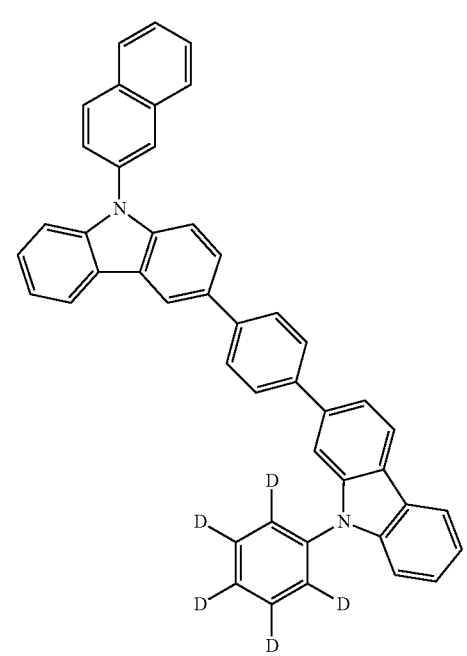

H-32
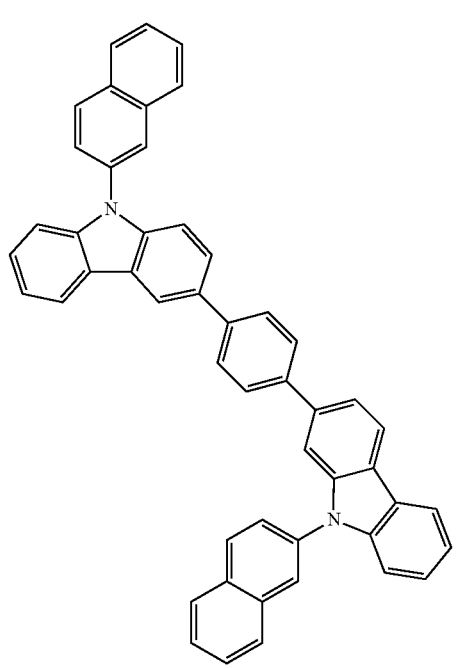
H-34
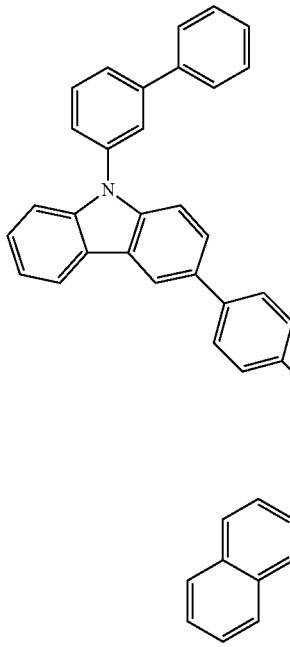
H-33
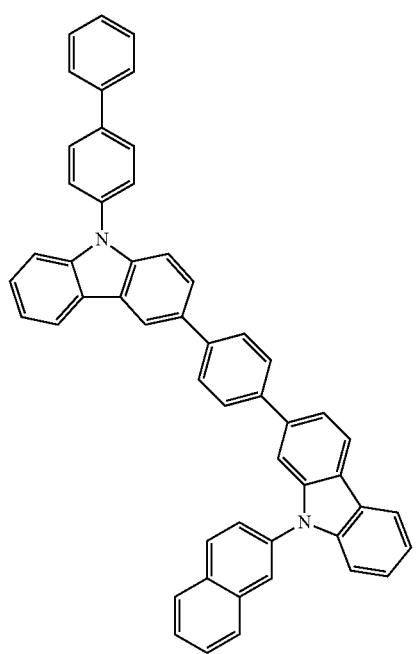
H-35
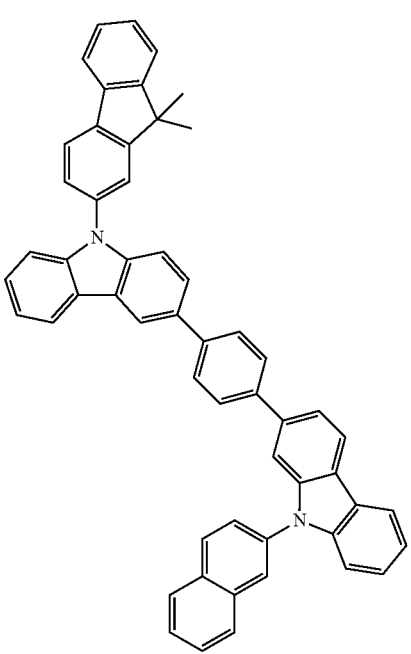

-continued
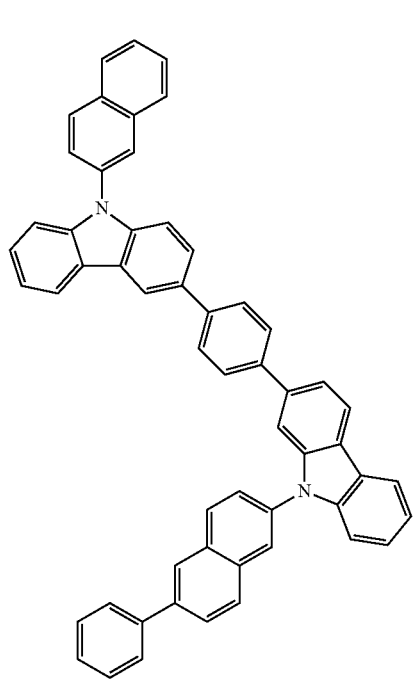
H-37
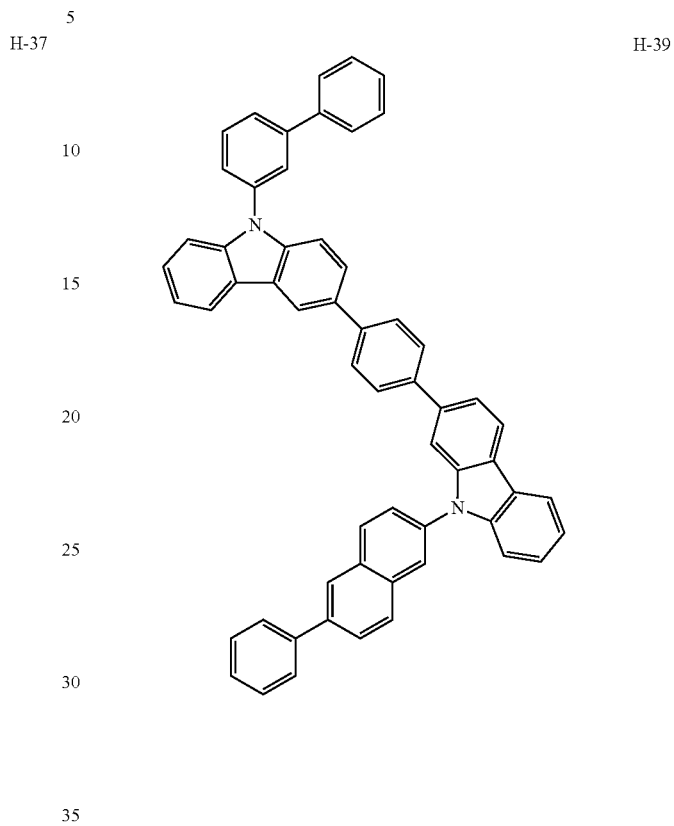
H-39
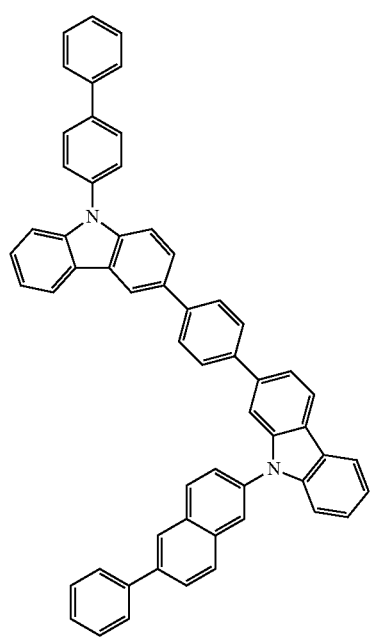
H-38
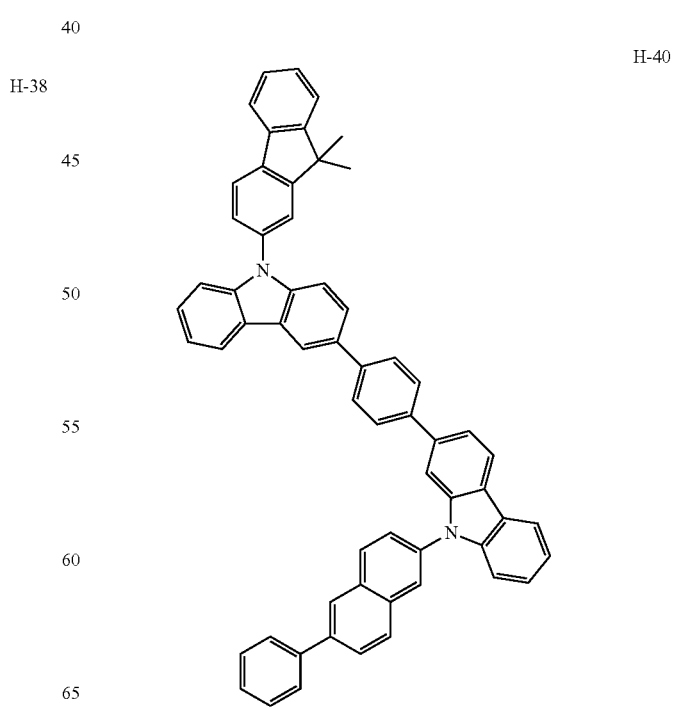
H-40

-continued
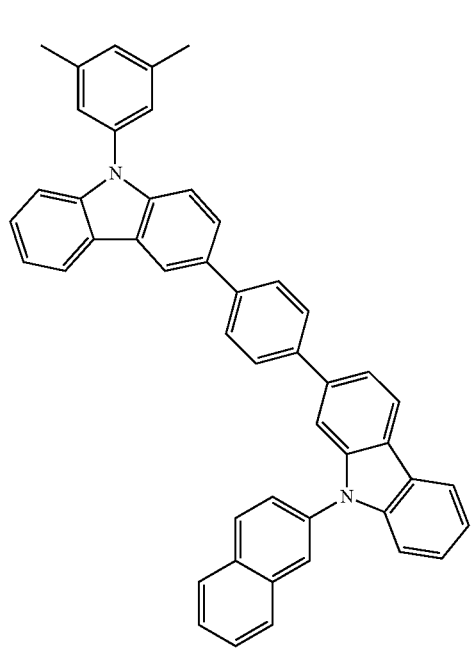
H-41
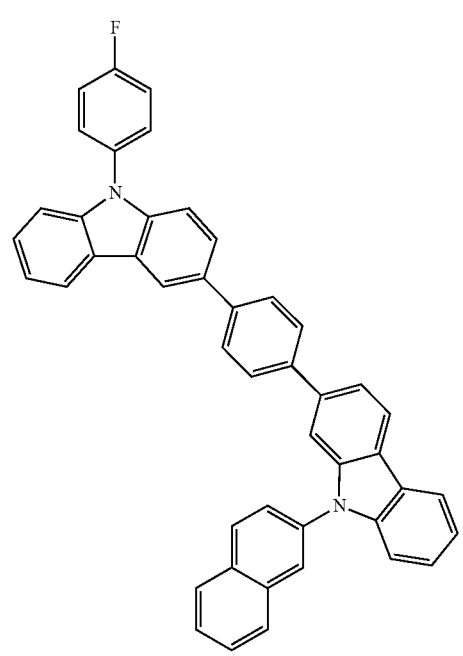
H-42
-continued
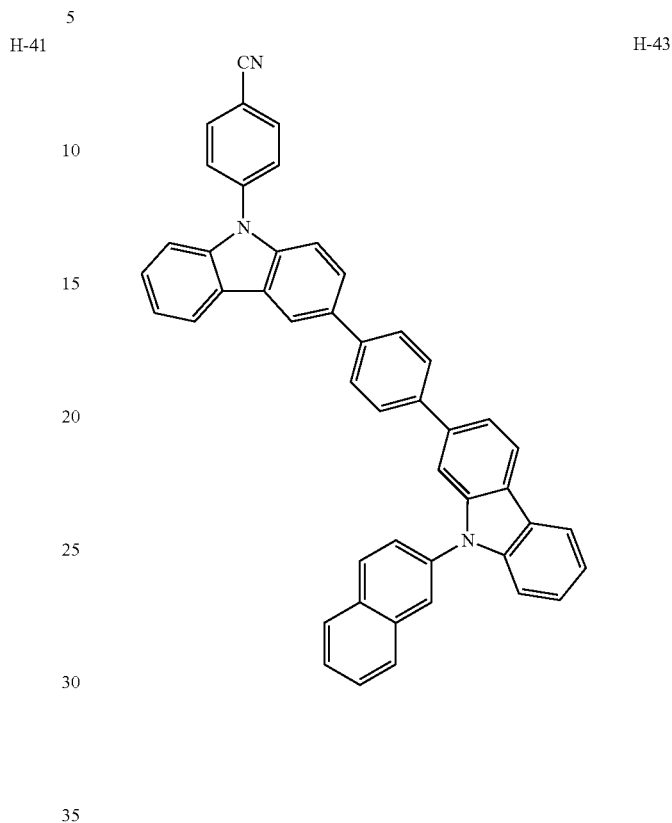
H-43
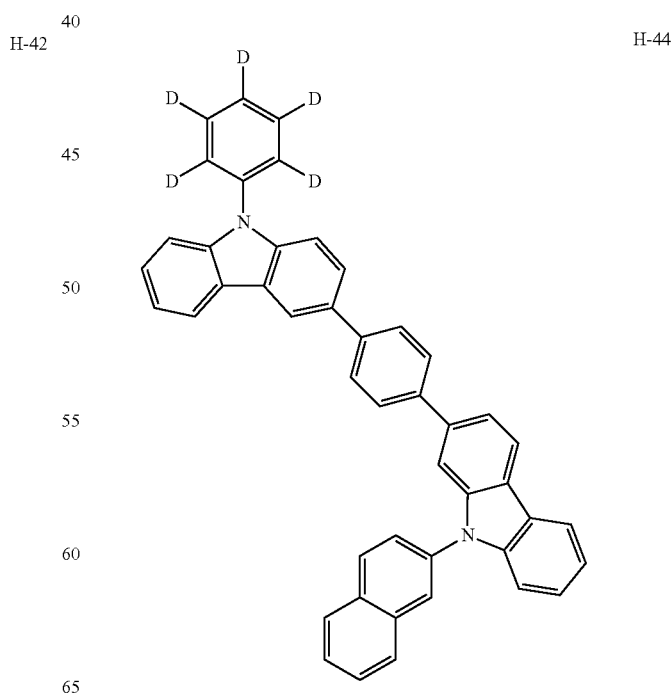
H-44

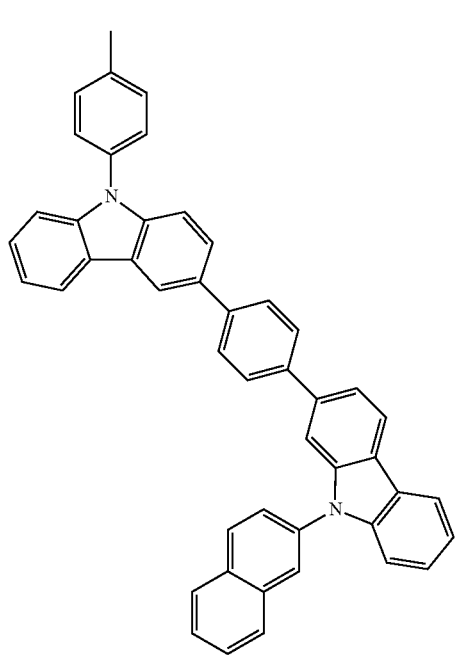
H-45
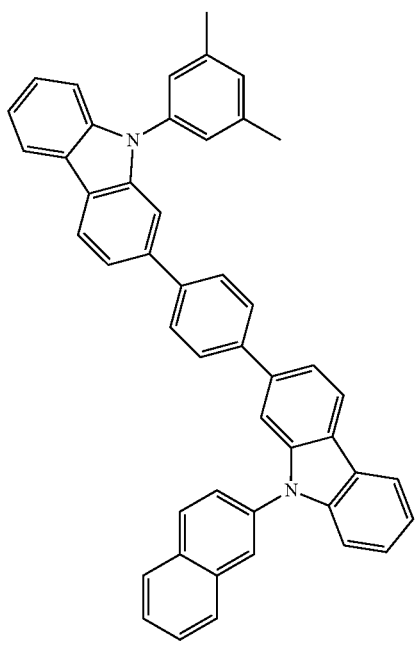
H-56
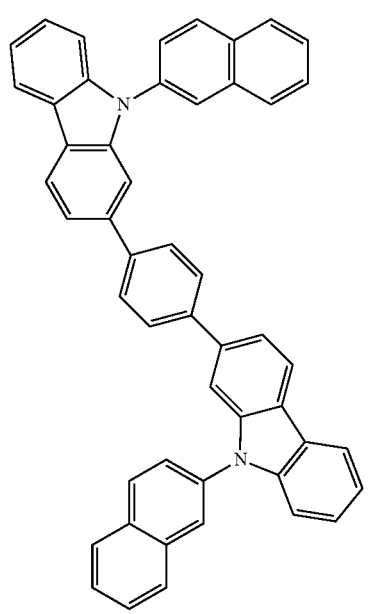
H-47
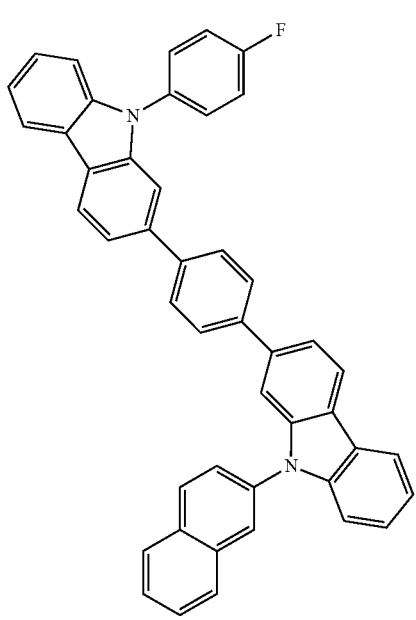
H-57

H-58
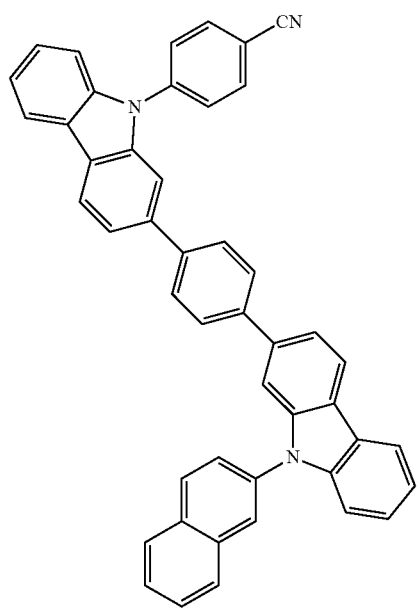
H-60
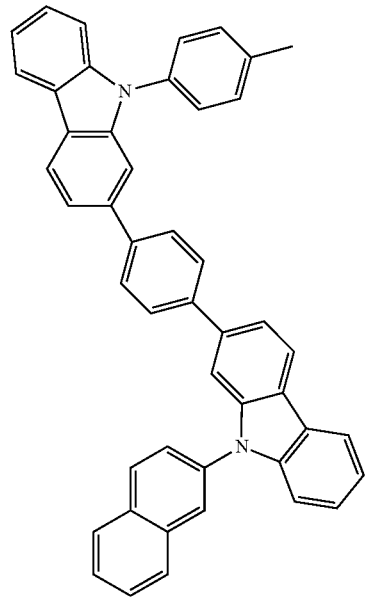
H-59
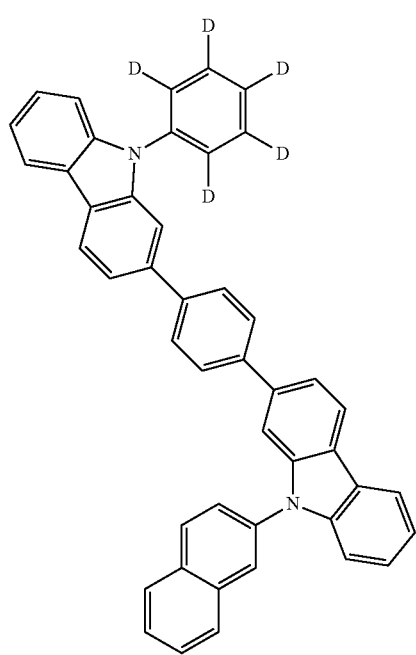
H-61
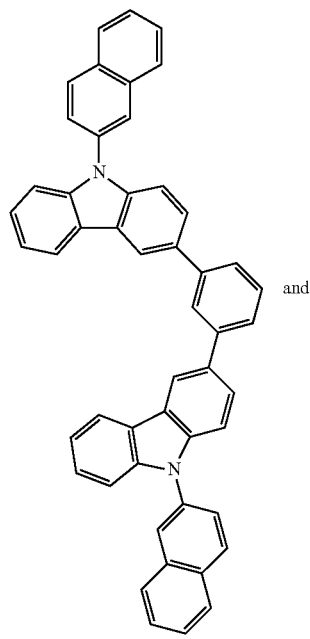
and

H-62
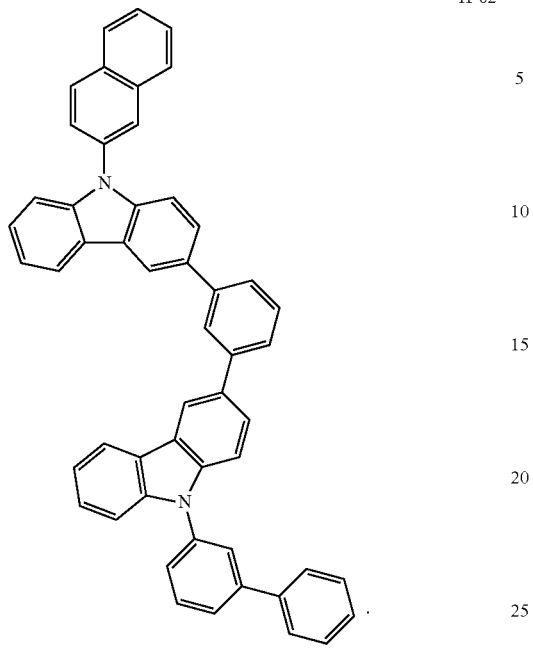
6. An organic electroluminescent device comprising the compound according to claim 1.
* * * * *